United States Patent [19]
Stephens et al.

[11] Patent Number: 6,127,119
[45] Date of Patent: Oct. 3, 2000

[54] NUCLEIC ACID LIGANDS OF TISSUE TARGET

[75] Inventors: Andrew Stephens; Larry Gold, both of Boulder, Colo.; Ulrich Speck, Berlin, Germany

[73] Assignee: NeXstar Pharmaceuticals, Inc., Boulder, Colo.

[21] Appl. No.: 08/976,413

[22] Filed: Nov. 21, 1997

Related U.S. Application Data

[63] Continuation-in-part of application No. 08/433,124, May 3, 1995, Pat. No. 5,750,342, which is a continuation-in-part of application No. 07/714,131, Jun. 10, 1991, Pat. No. 5,475,096, which is a continuation-in-part of application No. 07/536,428, Jun. 11, 1990, abandoned, and a continuation-in-part of application No. 07/964,624, Oct. 21, 1992, Pat. No. 5,496,938.

[51] Int. Cl.$^7$ .............................. C12Q 1/68; C12P 19/34; C07H 21/02; C07H 21/04
[52] U.S. Cl. ........................... 435/6; 435/91.2; 536/24.3; 536/24.31; 536/25.4
[58] Field of Search ..................... 435/6, 91.2; 536/24.3, 536/24.31, 25.4; 514/44; 424/1.73; 935/77, 78

[56] References Cited

U.S. PATENT DOCUMENTS

| | | | |
|---|---|---|---|
| 5,270,163 | 12/1993 | Gold et al. | 435/6 |
| 5,614,503 | 3/1997 | Chaudhary et al. | 524/44 |
| 5,688,935 | 11/1997 | Stephens et al. | 536/23.1 |
| 5,750,342 | 5/1998 | Stephens et al. | 435/6 |

FOREIGN PATENT DOCUMENTS

| | | |
|---|---|---|
| 2 183 661 | 6/1987 | United Kingdom . |
| WO 89/06694 | 7/1989 | WIPO . |
| WO 92/14843 | 9/1992 | WIPO . |
| WO 94/06934 | 3/1994 | WIPO . |

OTHER PUBLICATIONS

Davis et al. (1978) The Lancet 1:1185.
Davis et al. (1980) Circulation 61:982.
Ellington and Szostak (1900) Abstract of papers presented at the 1990 meeting on RNA Processing, Cold Spring Harbor Laboratory, Cold Spring Harbor, NY, p. 226.
Fischman et al. (1989) J. Nucl. Med. 30:1095.
Ginsberg et al. (1990) Arteriosclerosis 10:256.
Isaacsohn et al. (1986) Metabolism 35:364.
Joyce (1989) Gene 82:83.
Joyce and Inoue (1989) Nucleic Acids Research 17:711.
Kinzler and Vogelstein (1989) Nucleic Acids Research 17:3645.
Kramer et al. (1974) J. Mol. Biol. 89:719.
Lees et al. (1988) Arteriosclerosis 8:461.
Lees et al. (1983) J. Nucl. Med. 24:154.
Levisohn and Spiegelman (1969) Proc. Natl. Acad. Sci. USA 63:805.
Levisohn and Spiegelman (1968) Proc. Natl. Acad. Sci. USA 60:866.
Mettinger et al. (1978) The Lancet 1:242.
Minar et al. (1989) Stroke 20:27.
Moerlein et al. (1991) J. Nuc. Med. 32:300.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Ord et al. (1992) Circulation 85:288.
Roberts et al. (1983) J. Lipid Research 24:1160.
Robertson and Joyce (1900) Nature 344:467.
Seelig and Jaschke (1997) Tetrahedron Letters 38:7729.
Thiesen and Bach (1990) Nucleic Acids Research 18:3203.
Tsai and Keene (1993) J. Immunol. 150:1137.
Szostak, "Structure and Activity of Ribozymes," in *Redesigning the Molecules of Life*, (S.A. Benner ed.) Springer–Verlag Berlin Heidelberg, pp. 87–113, (1988).

*Primary Examiner*—Stephanie Zitomer
*Attorney, Agent, or Firm*—Swanson & Bratschun LLC

[57] ABSTRACT

This invention discloses high-affinity oligonucleotide ligands to complex tissue targets, specifically nucleic acid ligands having the ability to bind to complex tissue targets, and the methods for obtaining such ligands. Tissue targets comprise cells, subcellular components, aggregates or cells, collections of cells, and higher ordered structures. Specifically, nucleic acid ligands to blood vessels are described.

21 Claims, 24 Drawing Sheets

Carotid SELEX-Schematic

SEQ ID NO: 242

```
                          a          a g              a 10  12  42         A      A
     |   |   |                     CG
    gaa    UCCC  CUG  UU   GGGCCUU  Cu
           ||||  |||  ||   |||||||  ||
    a      aggg  gac  aa   cucggag  ga
                    |              |
                   50             70
                        A
                       |
                      60 a   cag           ca
              5' 3'   |
                     80
```

SEQ ID NO: 259

Figure 4

SEQ ID NO: 355

LIGAND =
5'-gggagacaagaauaaacgcucaaUCAAUCUCGGACUAGACUAACGACCUUGGUUGACGCUCAuucgacgacaggaggcucacaacagga-3'

Full-length transcript   SEQ ID NO: 268
gggagacaagaauaaacgcucaaUCAAUCUCGGACUAGACUAACGACCUUGGUUGACGCUCAuucgacaggaggcucacaacaggc

5' and 3' fixed region removed   SEQ ID NO: 356
UCAAUCUCGGACUAGACUAACGACCUUGGUUGACGCUCA

5' fixed region removed   SEQ ID NO: 357
UCAAUCUCGGACUAGACUAACGACCUUGGUUGACGCUCAuucgacaggaggcucacaacaggc

3' fixed region removed   SEQ ID NO: 358
gggagacaagaauaaacgcucaaUCAAUCUCGGACUAGACUAACGACCUUGGUUGACGCUCA

SEQ ID NO: 359
```

Figure 17

SEQ ID NO: 360

LIGAND = UCAAUCAAUCUCGGACUAGACUAACGACCUUGGUUGA-3'-3'-dT

| Ligand | SEQ ID NO: | |
|---|---|---|
| ``````U  C            AmC  U  Am``````<br>``````u cmama U CmAmA    U CmGmG      G``````<br>``````mAmG U UmGmG U U   mAmG CmA    Am``````<br>``````        C C            AmU C``````<br><br>Tr153 | 369 | FIG. 20A |
| ``````U  C            AmC  U  Am``````<br>``````u cmama U CmAmA    U CmGmG      Gm``````<br>``````mAmG U UmGmG U U   mAmG CmA     A``````<br>``````        C C           A U C``````<br><br>Tr154 | 370 | FIG. 20B |
| ``````U  C            AmC  U  Am``````<br>``````u cmama U CmAmA    U CmGmG      G``````<br>``````mAmG U UmGmG U U   mAmG CmA     A``````<br>``````        C C           A U C``````<br><br>Tr155 | 371 | FIG. 20C |
| ``````U  C            AmC  U  A``````<br>``````u cmama U CmAmA    U CmGmG      G``````<br>``````mAmG U UmGmG U U   mAmG CmA     Am``````<br>``````        C C            AmU C``````<br><br>Tr156 | 372 | FIG. 20D |
| ``````U  C            AmC  U  A``````<br>``````u cmama U CmAmA    U CmGmG      Gm``````<br>``````mAmG U UmGmG U U   mAmG CmA     A``````<br>``````        C C            AmU C``````<br><br>Tr157 | 373 | FIG. 20E |

| Ligand | SEQ ID NO: | |
|---|---|---|

```
               U C            AmC U Am
u cmama U CmAmA    U CmGmG            G          374      FIG. 20F
mAmG U UmGmG U U    mAmG CmA          A
               C C            AmU C
            Tr158

U C            AmC U A
u cmama U CmAmA    U CmGmG            Gm         375      FIG. 20G
mAmG U UmGmG U U    mAmG CmA          Am
               C C            AmU C
            Tr159

U C            AmC U Am
u cmama U CmAmA    U CmGmG            Gm         376      FIG. 20H
mAmG U UmGmG U U    mAmG CmA          A
               C C            AmU C
            Tr160
```

NUCLEIC ACID LIGANDS OF TISSUE TARGET

RELATED APPLICATIONS

This application is a Continuation-in-Part of U.S. patent application Ser. No. 08/433,124, filed May 3, 1995, entitled "Nucleic Acid Ligands of Tissue Target", now U.S. Pat. No. 5,750,342 which is a Continuation-in-Part of U.S. patent application Ser. No. 07/714,131, filed Jun. 10, 1991, entitled "Nucleic Acid Ligands", now U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment", now abandoned, and U.S. patent application Ser. No. 07/964,624, filed Oct. 21, 1992, entitled "Methods of Producing Nucleic Acid Ligands", now U.S. Pat. No. 5,496,938.

FIELD OF THE INVENTION

Described herein are methods for identifying and preparing nucleic acid ligands to tissues. Tissues are described herein as a collection of macromolecules in a heterogeneous environment. According to this definition, tissues encompass a single cell type, a collection of cell types, an aggregate of cells or an aggregate of macromolecules. The method utilized herein for identifying such nucleic acid ligands is called SELEX, an acronym for Systematic Evolution of Ligands by EXponential enrichment. Specifically disclosed herein are high-affinity nucleic acid ligands which bind to various tissues.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in United States Patent Application Serial No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Nucleic Acid Ligands", now U.S. Pat. No. 5,270,163 (see also PCT Publication WO 91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", now U.S. Pat. No. 5,567,588 describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands", now U.S. Pat. No. 5,496,938, describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459, and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Without question, the SELEX process is very powerful. However, to date the process has been successfully demonstrated primarily with pure, simple targets, such as proteins or small molecules. The present invention provides the first demonstration that complex targets are also compatible with the SELEX process.

It is desirable to be able to obtain nucleic acid ligands to complex tissue targets for various reasons. First, tissue SELEX can be useful to obtain nucleic acid ligands when a distinct target is unknown but a general mode of action of the desired ligand is suggested. Second, tissue SELEX can be useful when nucleic acid ligands are desired based on functional results. Third, it can be desirable to obtain nucleic acid ligands to a complex tissue target when it is unclear which single target would be effective. It is also useful to obtain nucleic acid ligands to a complex tissue target if the purified target is unavailable or unstable in its purified form (i.e., a membrane protein).

BRIEF SUMMARY OF THE INVENTION

The present invention includes methods of identifying and producing nucleic acid ligands to complex targets such as tissues and the nucleic acid ligands so identified and produced. More particularly, nucleic acid ligands are provided that are capable of binding specifically to tissues which are macromolecules in a heterogeneous environment, such as whole cells or substructures thereof, aggregates of cells, collections of cells, aggregates of macromolecules and the like.

Further included in this invention is a method of identifying nucleic acid ligands to tissues comprising the steps of (a) preparing a candidate mixture of nucleic acids, (b) partitioning between members of said candidate mixture on the basis of affinity to tissue, and (c) amplifying the selected molecules to yield a mixture of nucleic acids enriched for nucleic acid sequences with a relatively higher affinity for binding to tissue. Also included are nucleic acid ligands identified according to such method.

Another embodiment of the invention includes methods wherein a negative selection is performed in order to perfect the discrimination between subtle differences of similar tissue types. In this embodiment, the resulting ligands are specific not only for a particular tissue type, but can discriminate between subtly different tissues of the same type. For example, this method can discriminate between normal and abnormal tissue types, between induced and uninduced tissue types, etc.

In another embodiment of the invention, a method is provided for identifying previously unknown or uncharacterized epitopes which are components of a larger unknown macromolecule on the tissue target. The ligands that are evolved by the present invention are capable of binding to previously unknown epitopes and the macromolecule which comprises the unknown epitope can then be identified by standard methods. For example, ligands can be evolved to a previously unknown protein found in the context of a complex tissue target. The ligand of the invention can be used to purify the protein away from the tissue target by standard protein purification and identification methods. These standard methods include affinity purification, microsequencing and cDNA databank searches. In this aspect, the newly identified epitopes which are components of a larger unknown macromolecule, such as new or previously uncharacterized proteins, are provided by the invention. These new epitopes and the macromolecules of which they are a component will be useful as diagnostic and therapeutic agents as well as the ligands that helped identify them.

More specifically, the present invention includes nucleic acid ligand(s) to peripheral blood mononuclear cells (PBMC), clots, arterial cells and blood vessel(s), including arteries, including those ligands shown in Tables 2, 5, 8, 10, 12 and 13, respectively. Also included are nucleic acid ligands to the above-described tissues that are substantially homologous to any of the given ligands and that have substantially the same ability to bind the above-described tissues. Further included in this invention are nucleic acid ligands to the above-described tissues that have substantially the same structural form as the ligands presented herein.

BRIEF DESCRIPTION OF THE FIGURES

FIG. 4 shows the predicted secondary structure of truncate 12.2t55L (SEQ ID NO: 259). Residues are numbered to match their positions in FIG. 3. Arrows indicate deleted residues #13–41 and #86–87 of clone 12.2. The UCGAC loop of the 3' stem-loop of clone 12.2 has been substituted with the sequence GAAA.

(unevolved library; SEQ ID NO: 40) in human atherosclerotic artery segments.

Figure 9:
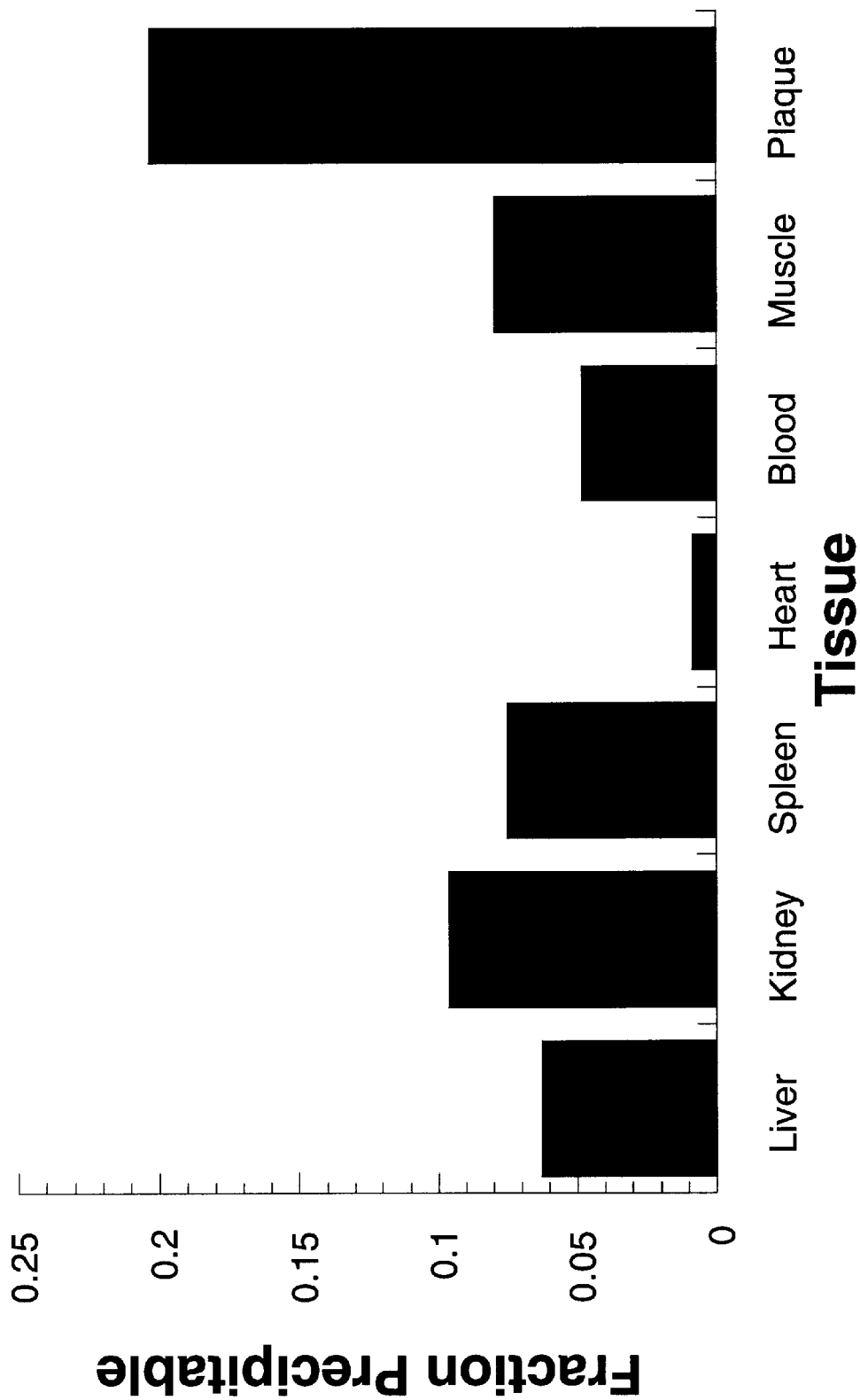

FIG. 9 illustrates the fraction of $^{32}P$ ethanol precipitable counts for various tissues after intravenous injection into a WHHL rabbit.

Figure 10:
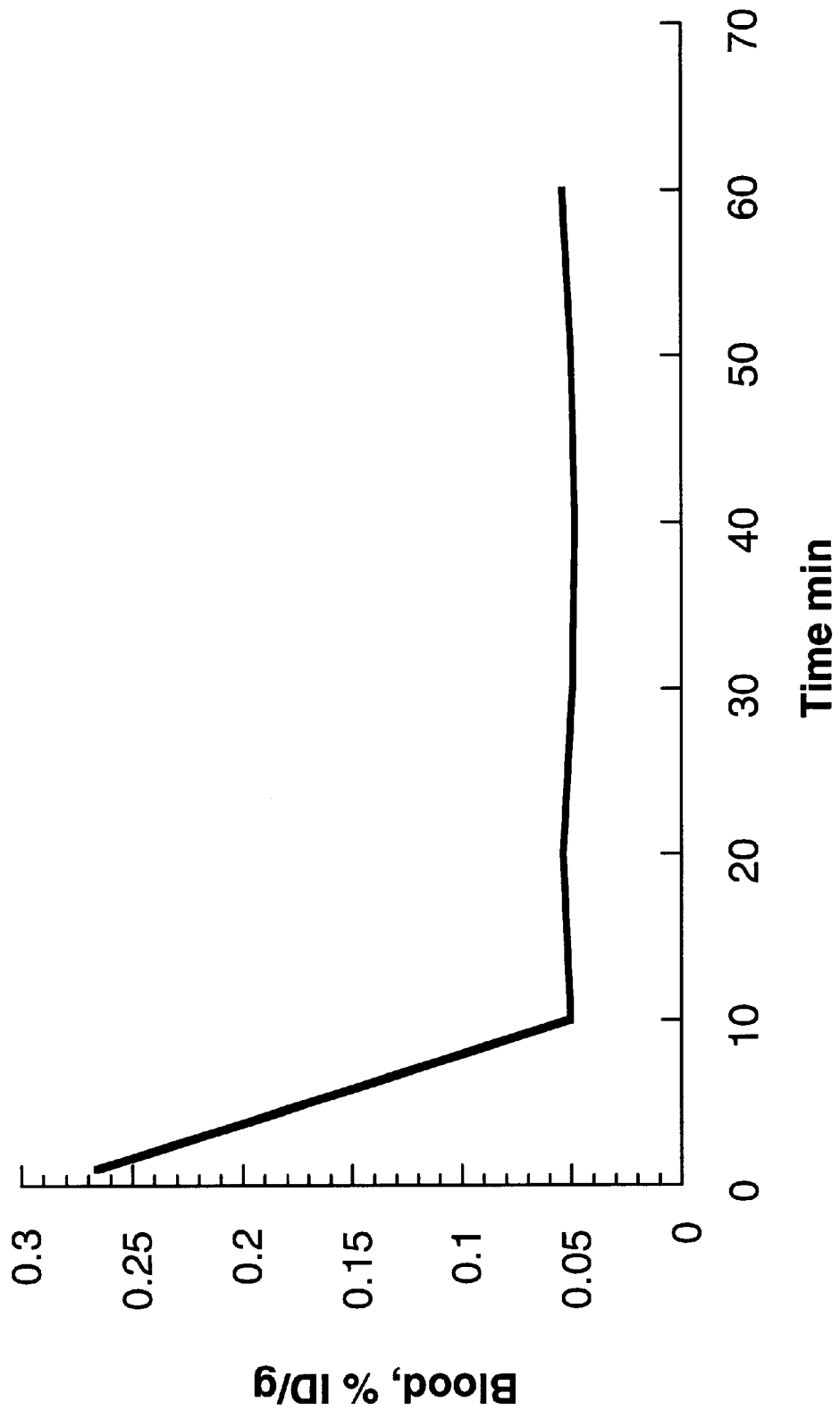

FIG. 10 summarizes the data of the concentration of 99mTc-10.31 (SEQ ID NO: 355) in WHHL blood presented as % ID/g as a function of time.

Figure 11A:
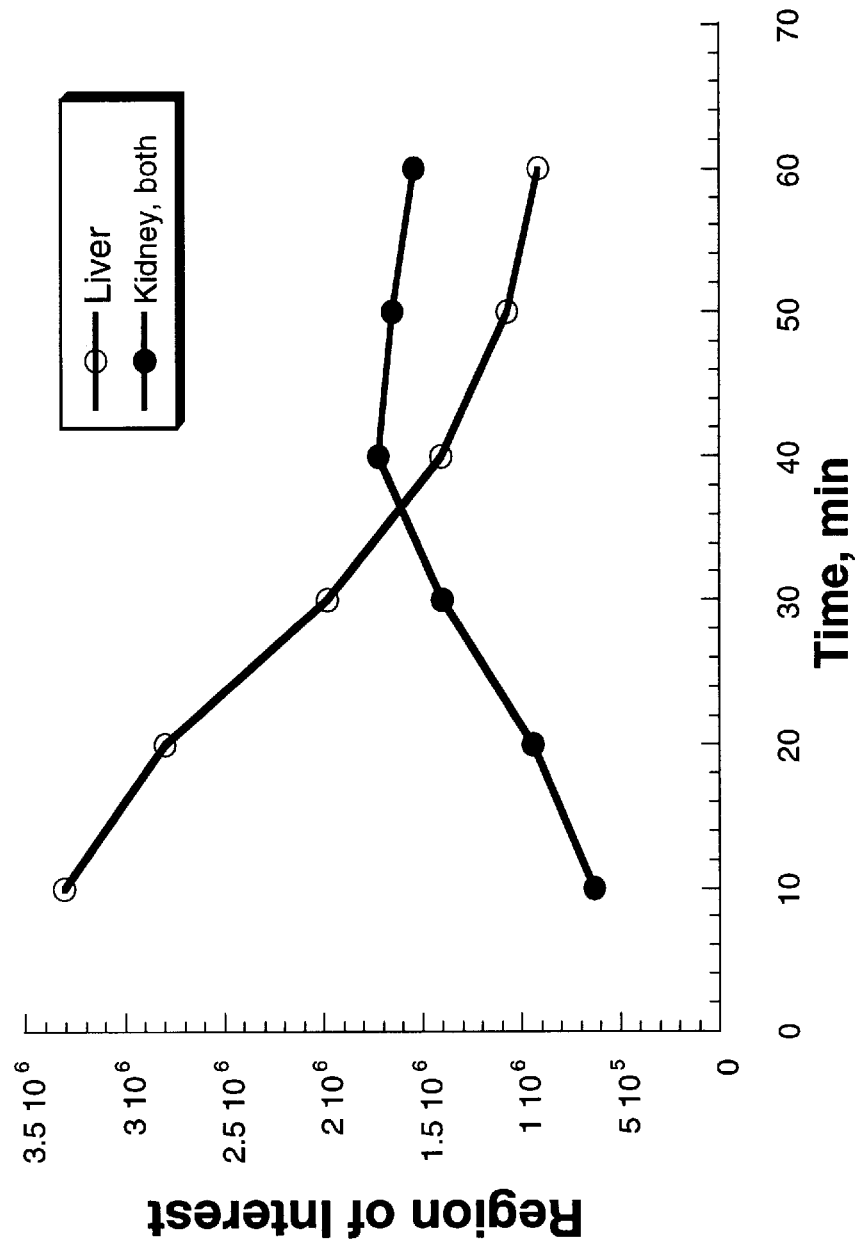

FIG. 11A illustrates a Region of Interest (ROI) analysis of liver (open circle) and kidney (closed circle) accumulation of 99mTc-10.31 (SEQ ID NO: 355) over time.

Figure 11B:
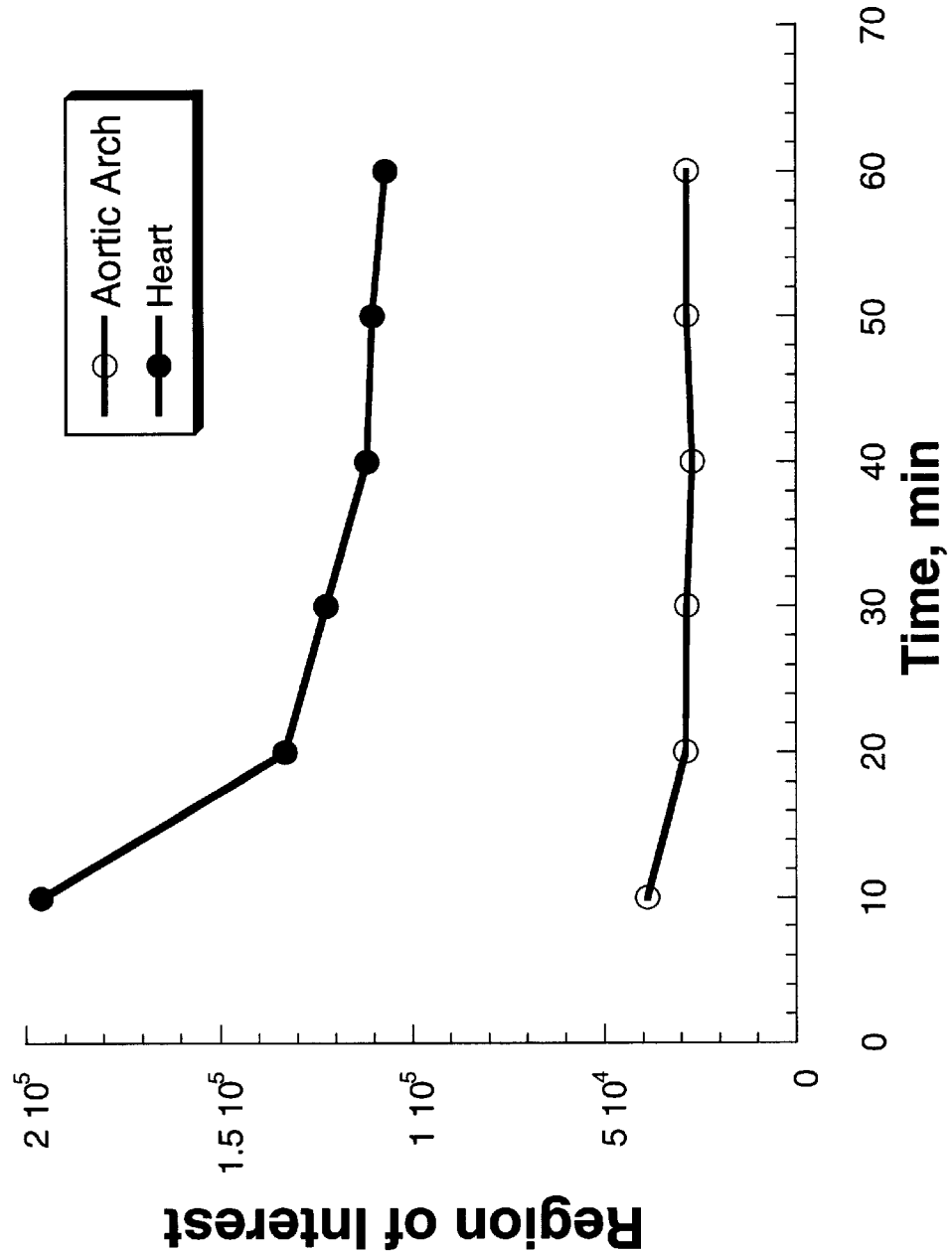

FIG. 11B illustrates a Region of Interest (ROI) analysis of aortic arch (open circle) and heart (closed circle) accumulation of 99mTc-10.31 (SEQ ID NO: 355) over time.

Figure 12:
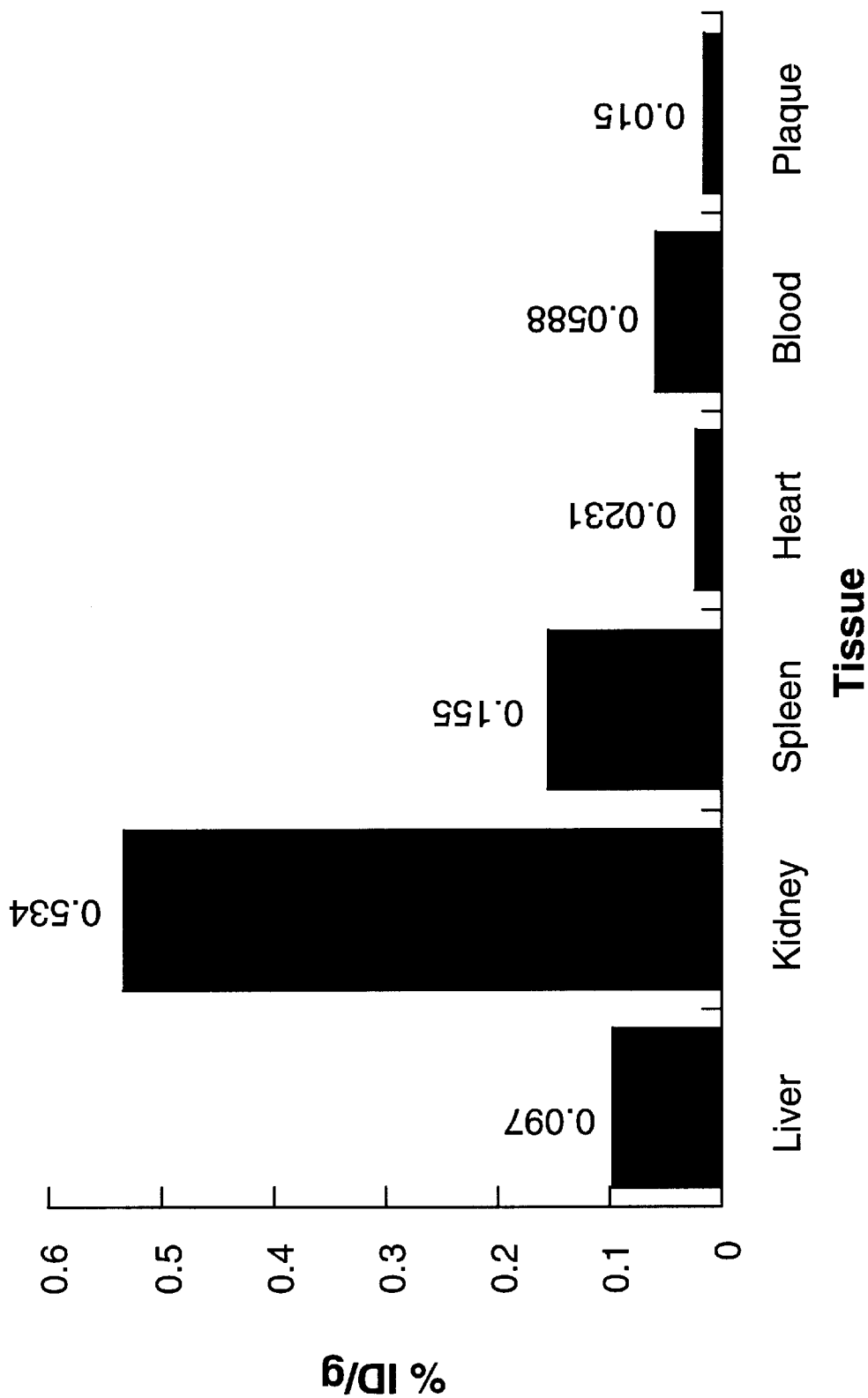

FIG. 12 summarizes the biodistribution data of 99mTc-10.31 (SEQ ID NO: 355) in various WHHL rabbit tissues sixty minutes after i.v. injection presented as % ID/g.

Figure 13:
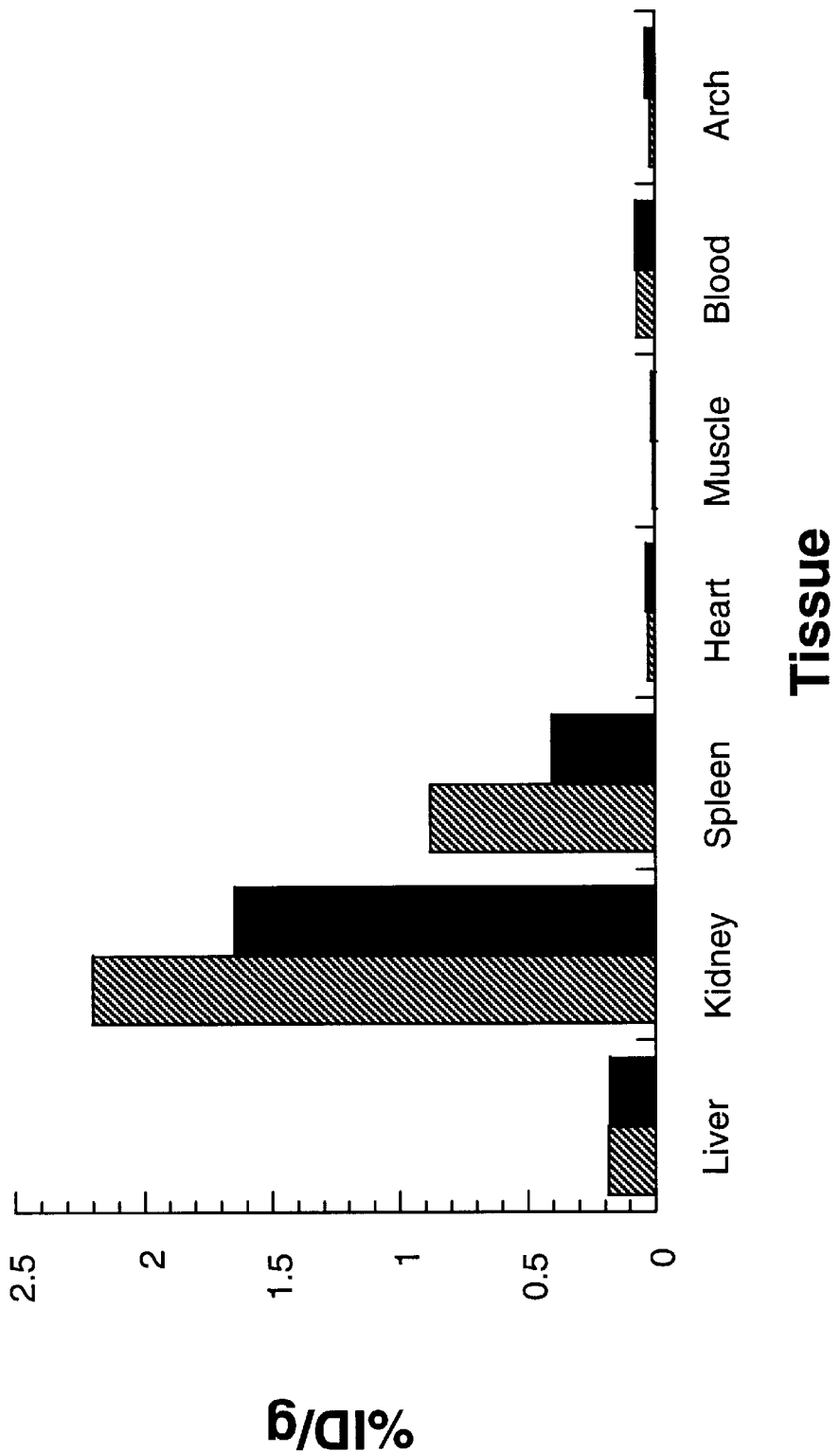

FIG. 13 summarizes the biodistribution of 99m-Tc-10.31 (SEQ ID NO: 355) of selected WHHL (solid bars) and NZW (dashed bars) rabbit tissues sixty minutes after i.v. injection presented as % ID/g.

Figure 14:
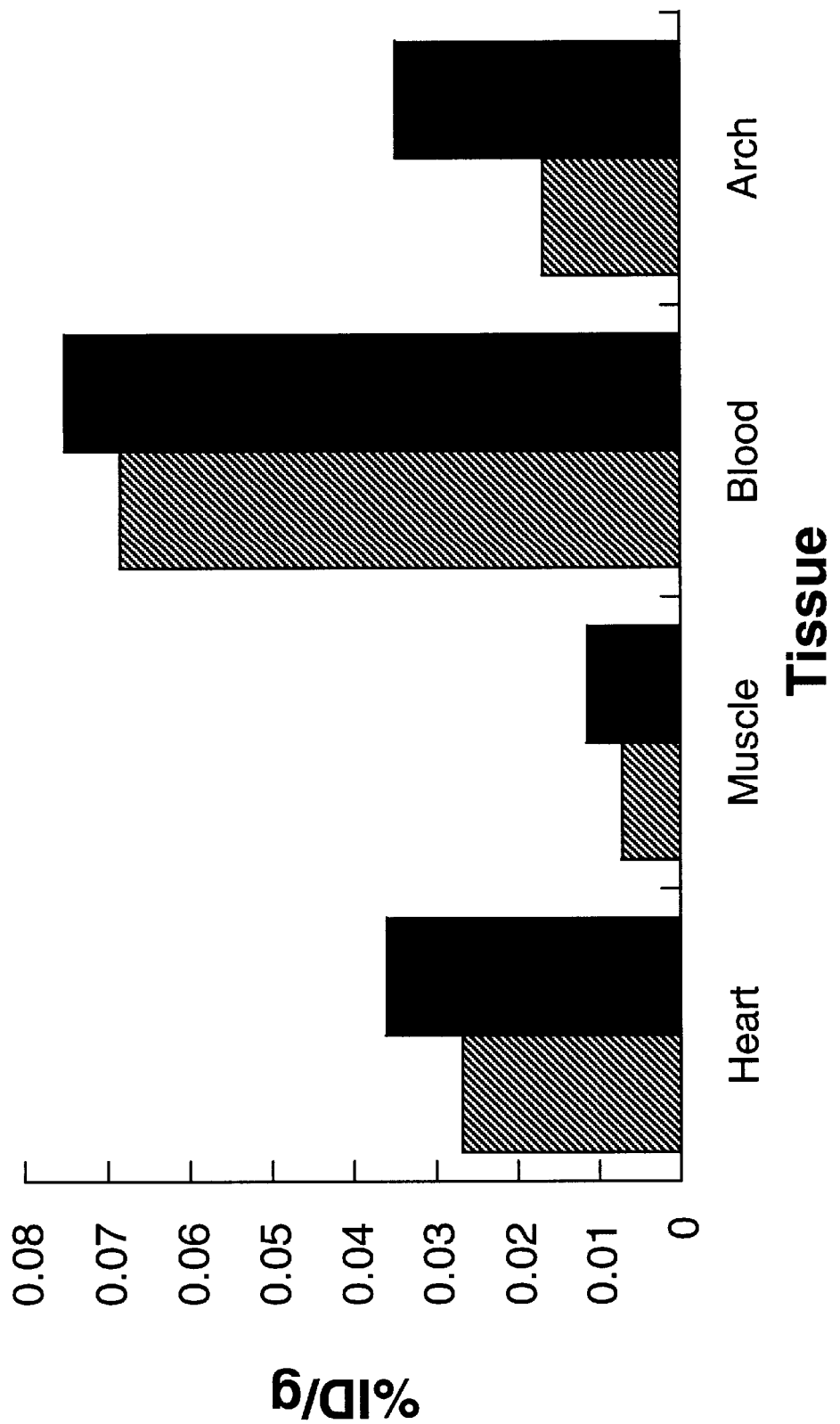

FIG. 14 summarizes the biodistribution of 99m-Tc-10.31 (SEQ ID NO: 355) in various WHHL (solid bars) and NZW (dashed bars) rabbit tissues sixty minutes after i.v. injection presented as % ID/g.

Figure 15:
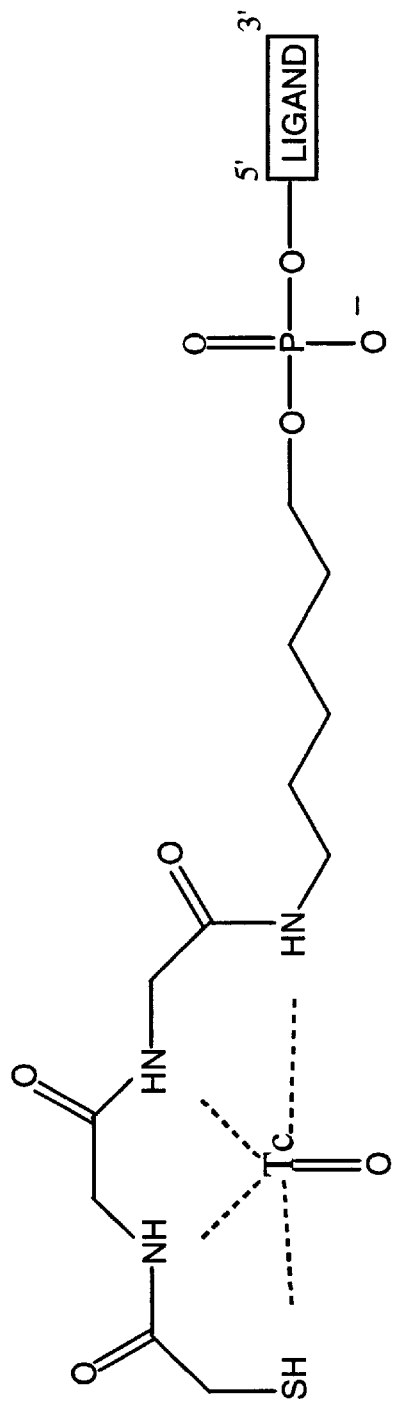

FIG. 15 shows the structure of a Technitium-99-complex of the conjugate 5'-[(mercaptoacetyl-glycyl-glycyl-amidyl)-6-hex-1-yl] phosphoric acid ester of ligand 10.31 (SEQ ID NO: 355). The lower case letters in the ligand sequence represent the fixed sequence regions.

FIG. 16 shows the sequence of clone 10.31 (SEQ ID NO: 268), a truncate of clone 10.31 in which both the 5' and 3' fixed regions have been removed (SEQ ID NO: 356), a truncate of clone 10.31 in which the 5'-fixed region has been removed (SEQ ID NO: 357) and a truncate of clone 10.31 in which the 3'-fixed region has been removed (SEQ ID NO: 358).

FIG. 17 shows a proposed secondary structure of a 37-nucleotide truncate (SEQ ID NO: 359) of clone 10.31 (SEQ ID NO: 268).

Figure 18:
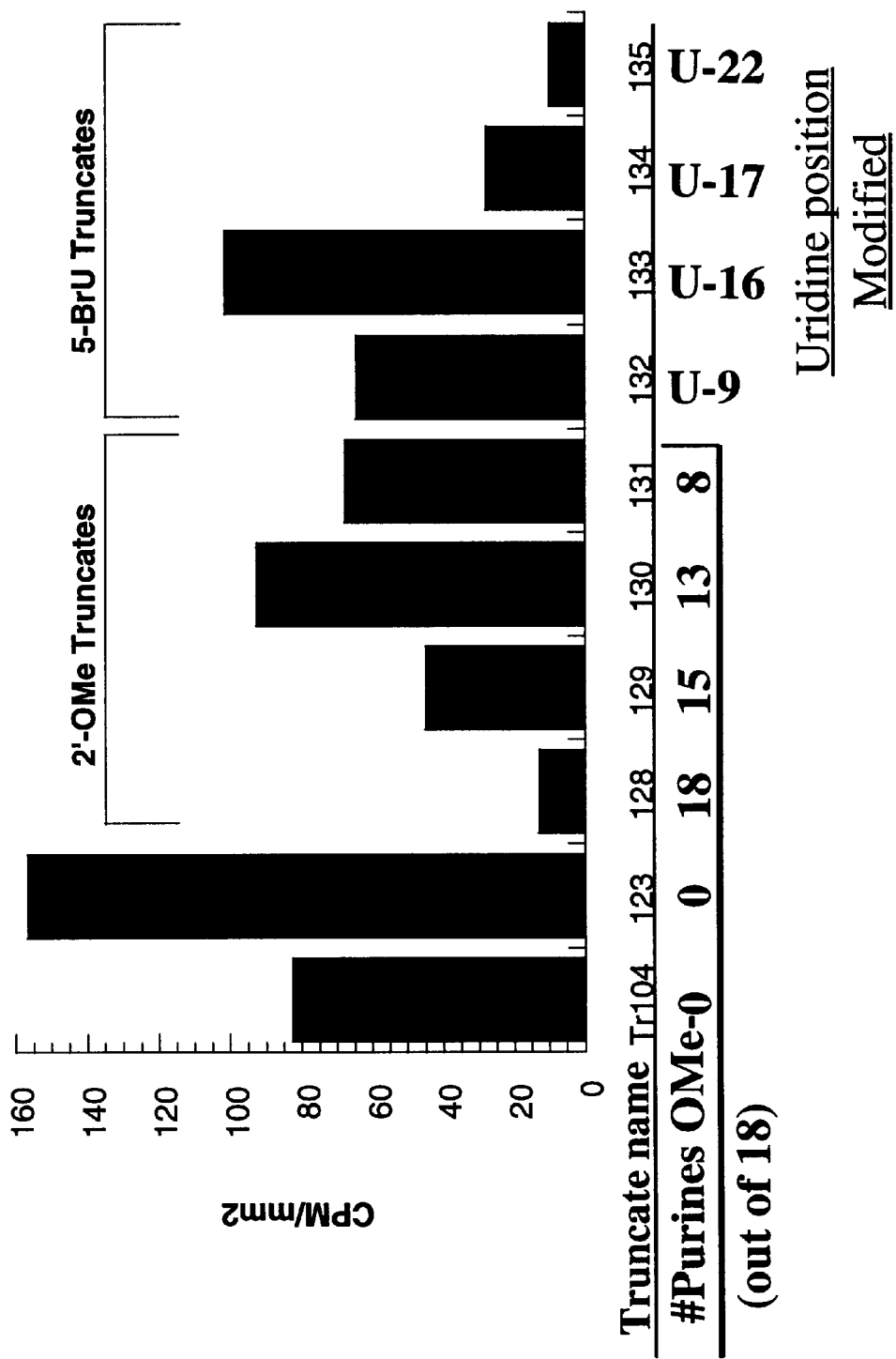

FIG. 18 summarizes the in vitro accumulation assays of analogs of Tr104 (SEQ ID NO: 359), synthesized with increasing numbers of 2'-OH purines substituted with 2'-OMe purines, in WHHL plaque presented as $CMP/mm^2$.

Figure 19:
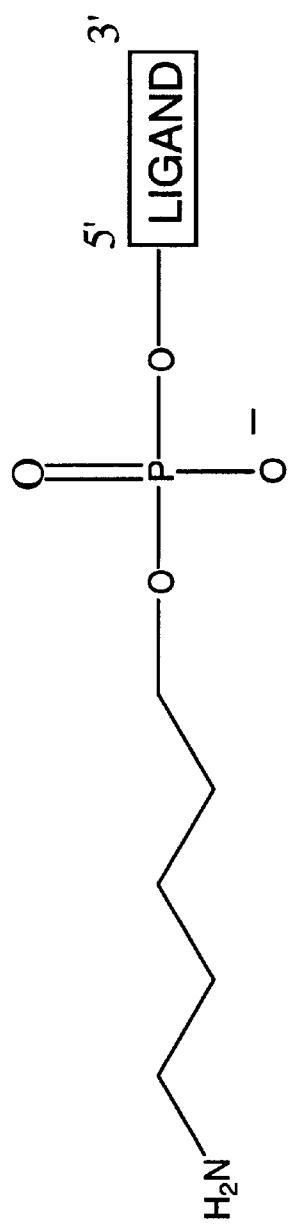

FIG. 19 shows the structure of Tr123 having a 5'-pentyl amine and a 3'-3' thymidine (SEQ ID NO: 360).

FIGS. 20A–H show the structures of 2'-OMe analogs of Tr130, where mG represents 2'-O-methoxy guanosine and mA represents 2'-O-methoxy adenosine.

Figure 21:
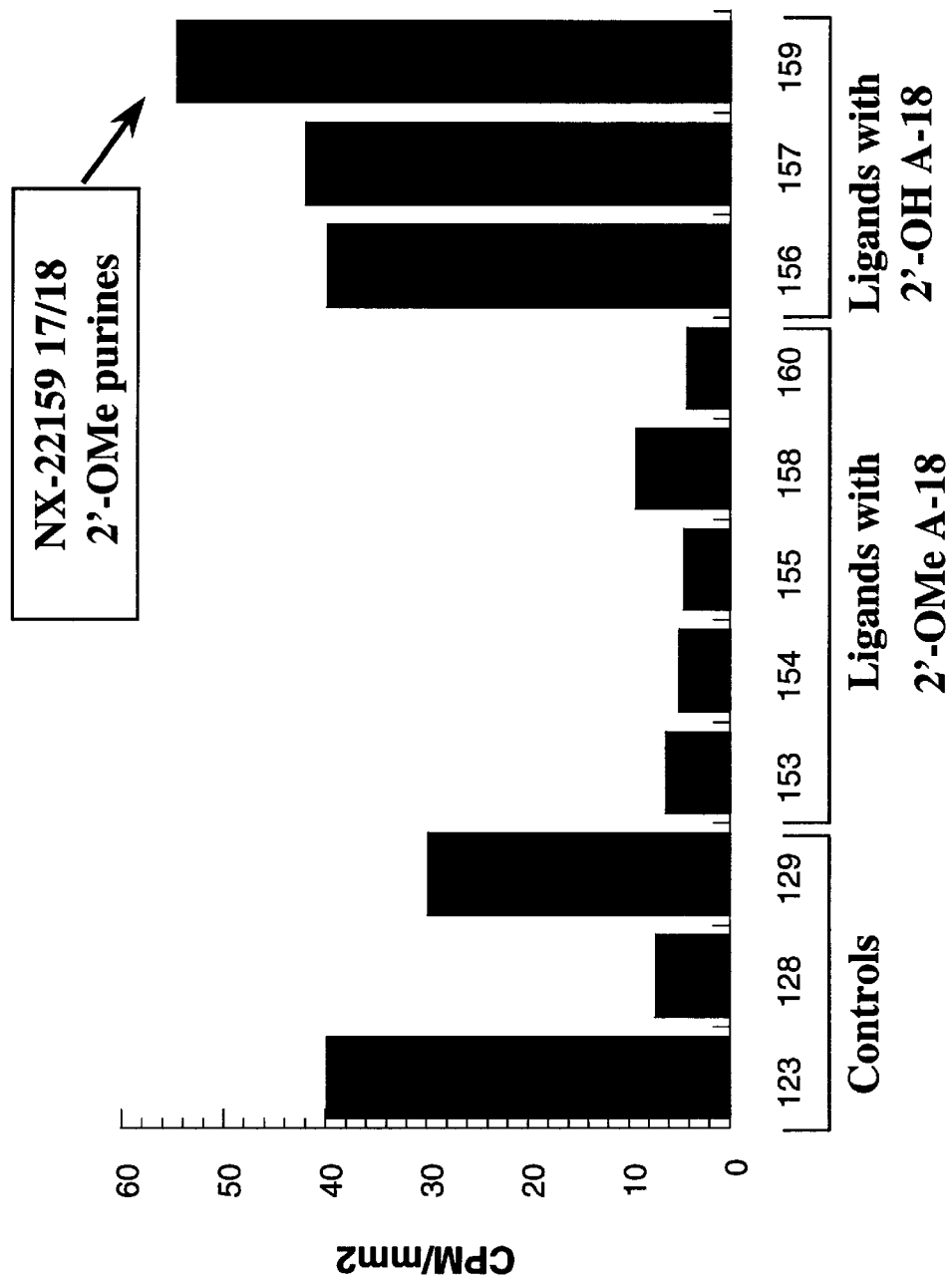

FIG. 21 summarizes the in vitro accumulation assays of various 2'-OMe analogs of Tr130, presented as $CPM/mm^2$.

Figure 22:
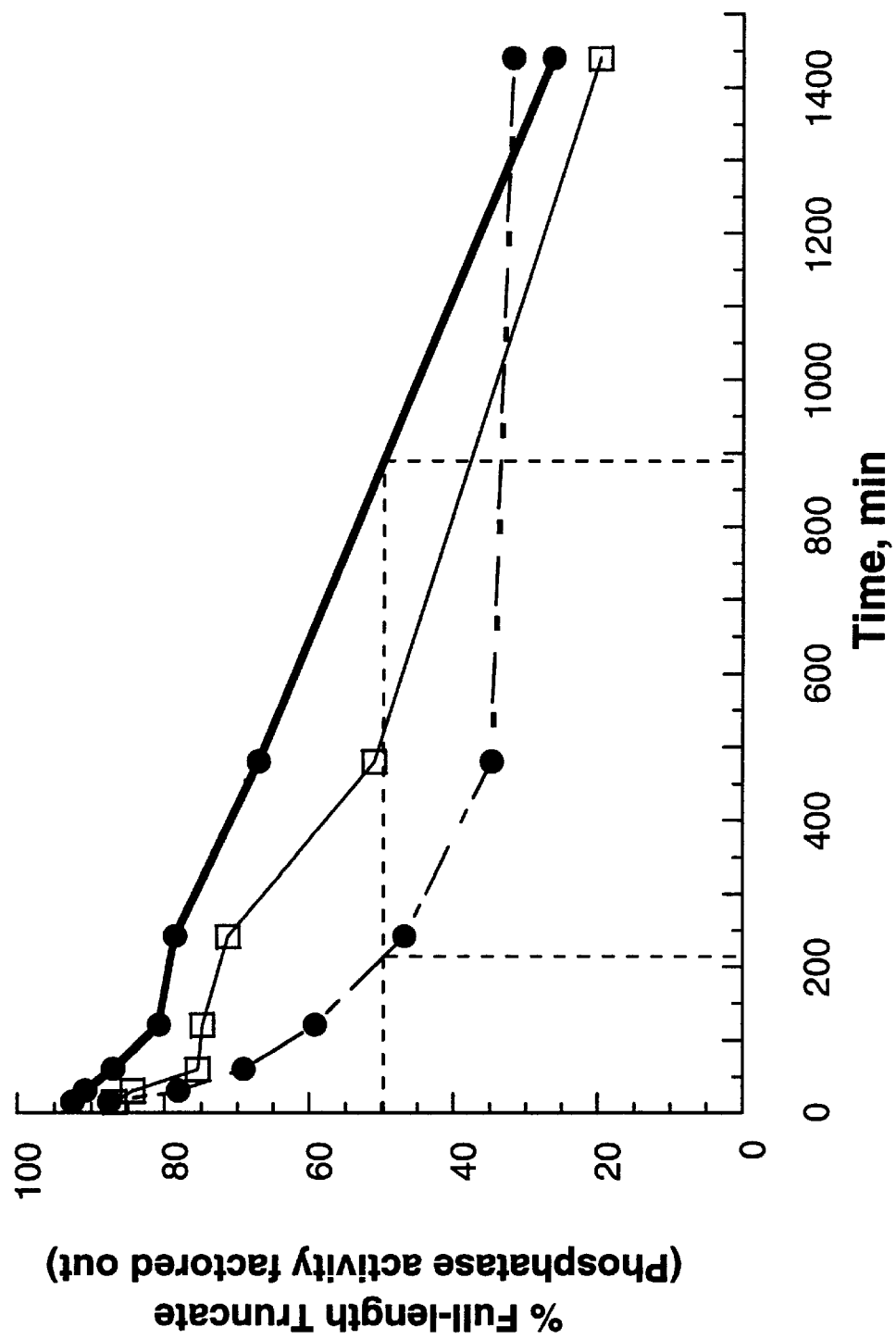

FIG. 22 is a graph summarizing the effect of O-methylation on nuclease resistance for three ligands: Tr104 9 (SEQ ID NO: 359; closed circles, dashed line), Tr128 (SEQ ID NO: 361; closed circles, solid line) and Tr129 (SEQ ID NO: 362; open squares), presented as % full-length transcript versus time.

DETAILED DESCRIPTION OF THE INVENTION

This application describes nucleic acid ligands to complex tissue targets identified generally according to the method known as SELEX. As stated earlier, the SELEX technology is described in detail in the SELEX patent applications which are incorporated herein by reference. This method, referred to as Tissue SELEX, incorporates complex targets in contrast to the more simple targets previously used in the SELEX process. Certain terms used to describe the invention herein are defined as follows:

"SELEX" methodology refers to the combination of selection of nucleic acid ligands which interact with a target in a desirable manner, for example binding to a protein, with amplification of those selected nucleic acids as described in detail above and in the SELEX patent applications. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved.

"Tissue SELEX" methodology applies the SELEX methodology to tissue targets. Tissue SELEX has several advantages. First, using Tissue SELEX one can obtain ligands to specific cell types in the absence of a defined understanding of the involved epitope. The epitope against which a ligand is evolved is usually a substructural component of a larger macromolecule The ligands found by this method could also be useful in identifying new proteins or other new macromolecules on the tissue target. The new proteins or other new macromolecules which comprise a newly identified epitope can be purified and characterized using standard procedures. Second, ligands can be obtained to defined epitopes or macromolecules in the context of their physiologic cellular or membrane environment. Third, it is possible to obtain ligands to tissues in a functionally altered phenotype, e.g., activated, migrating, etc. The ligands and the new macromolecules containing the ligand epitopes identified by this process may be useful as diagnostics or therapeutics.

Tissue SELEX is a powerful methodology which allows one to identify nucleic acid ligands that can mediate many different cell behaviors, such as apoptosis, anergy, differentiation, proliferation, etc., without prior knowledge of the identity of the specific tissue targets that control these changes. The sensitivity of the SELEX process may lead to the generation of oligonucleotides that recognize potentially every different epitope on the complex tissue target. Larger numbers of different sequence motifs are expected using the tissue SELEX process, as compared with simple-target SELEX, since it is believed that different motifs will recognize distinct epitopes on the complex tissue target. Some epitopes may lie within the same protein, but many will be directed to various proteins or other molecules on the tissue. Tissue SELEX can be done in vivo or in vitro.

In one embodiment, a negative selection process (termed counter-SELEX) is employed to enhance the possibility that the ligands derived by tissue SELEX have precise specificity and affinity. In this embodiment, ligands are selected for a specific tissue and then a negative selection is done against a related tissue which does not have certain characteristics for which the ligand is desired. The negative selection can be done against a similar cell line or cell type, different cells, normal tissue, plasma or blood, a non-specific antibody or other available ligand. An example of this negative selection would be to first select using a tumor cell target (such as a malignant melanoma) and then counterselect the resulting nucleic acids against a similar cell type which is not tumorogenic (such as normal human melanocytes). Ligands that interact with both normal and neoplastic tissue will be removed by this negative selection and only those nucleic acid ligands that specifically bind the tumor cells will be identified (or retained). The resulting nucleic acid ligand would be specific for tumors. This technique will provide the ability to identify nucleic acid ligands that can discriminate between two closely related targets, i.e., between a cancerous cell and an untransformed cell of the same tissue type. The negative selection can also be done in vivo. Using this method one can not only generate ligands to specific targets on complex tissue surfaces, but also be able to recognize the differences between normal and abnormal tissue of a particular type.

"SELEX Target" or "Target" refers to any compound upon which a nucleic acid can act in a predetermined desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc., without limitation. Virtually any chemical or biological effector would be a suitable SELEX target. Molecules of any size can serve as SELEX targets. A target can also be modified in certain ways to enhance the likelihood of an interaction between the target and the nucleic acid.

"Tissue target" or "Tissue" refers to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the preferred embodiment, tissues are insoluble macromolecules which are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue, and muscle tissue.

Examples of tissues which fall within this definition include, but are not limited to, heterogeneous aggregates of macromolecules such as fibrin clots which are acellular; homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

"Blood vessel" is understood to be any of the vessels through which blood circulates in the body, including the heart, aorta, arteries, veins and capillaries.

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention.

"Nucleic acid test mixture" or "nucleic acid candidate mixture" is a mixture of nucleic acids of differing, randomized sequence. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process. The length of the randomized section of the nucleic acid is generally between 8 and 250 nucleotides, preferably between 8 and 60 nucleotides.

"Nucleic acid ligand" is a nucleic acid which has been isolated from the nucleic acid candidate mixture that acts on a target in a desirable manner. Examples of actions on a target in a desirable manner include, but are not limited to binding of the target, catalytically changing the target, reacting with the target in a way which modifies/alters the target or the functional activity of the target, covalently attaching to the target as in a suicide inhibitor, facilitating the reaction between the target and another molecule. In most, but not all, instances this desirable manner is binding to the target. In the most preferred embodiment, a nucleic acid ligand is a non-naturally occurring nucleic acid ligand having a specific binding affinity for a tissue target molecule, such target molecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule.

Nucleic acid ligand includes nucleic acid sequences that are substantially homologous to the nucleic acid ligands actually isolated by the Tissue SELEX procedures. By substantially homologous, it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. In the past it has been shown that the sequence homologies of various nucleic acid ligands to a specific target shows that sequences with little or no primary homology may have substantially the same ability to bind the target. For these reasons, this invention also includes nucleic acid ligands that have substantially the same ability to bind a target as the nucleic acid ligands identified by the Tissue SELEX process. Substantially the same ability to bind a target means that the affinity is within a few orders of magnitude of the affinity of the ligands described herein. It is well within the skill of those of ordinary skill in the art to determine whether a given sequence—substantially homologous to those specifically described herein—has substantially the same ability to bind a tissue target.

The invention also includes nucleic acid ligands that have substantially the same postulated structure or structural motifs. Substantially the same structure or structural motifs can be postulated by sequence alignment using the Zukerfold program (see Zucker (1989) Science 244:48–52). As would be known in the art, other computer programs can be used for predicting secondary structure and structural motifs. Substantially the same structure or structural motif of nucleic acid ligands in solution or as a bound structure can also be postulated using NMR or other techniques as would be known in the art.

The term "clone" is used interchangeably with the term "nucleic acid ligand".

"Partitioning" means any process for separating nucleic acid ligands from the remainder of the unreacted nucleic acid candidate mixture. Partitioning can be accomplished by various methods known in the art. Filter binding, affinity chromatography, liquid-liquid partitioning, filtration, gel shift, density gradient centrifugation are all examples of suitable partitioning methods. Equilibrium partitioning methods can also be used as described in detail below. Since the tissue targets of the present invention are non-soluble, there are numerous simple partitioning methods which are well suited to this invention. The simple partitioning methods include any method for separating a solid from a liquid, such as, centrifugation with and without oils, membrane separations and simply washing the insoluble tissue target. The ligands can also be specifically eluted from the target with a specific antibody or ligand. The choice of partitioning method will depend on properties of the target and the nucleic acid and can be made according to principles and properties known to those of ordinary skill in the art.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction or the ratio of phosphoramidites in the chemical synthesis. A deliberate bias may be desired, for example, to affect secondary structure, to introduce bias toward molecules known to have facilitating activity, to introduce certain structural characteristics, or based on preliminary results.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX patent applications describe and elaborate on this process in great detail. Included are targets that can be used in the process; methods for partitioning nucleic acids within a candidate mixture; and methods for amplifying partitioned nucleic acids to generate an enriched candidate mixture. The SELEX patent applications also describe ligands obtained to a number of target species, including both protein targets where the protein is and is not a nucleic acid binding protein.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled A Nucleic Acid Complexes." VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes." VEGF Nucleic Acid Ligands that are associated with a Lipophilic Compound, such as a glycerol lipid, or a Non-Immunogenic, High Molecular Weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes." VEGF Nucleic Acid Ligands that are associated with a non-immunogenic, high molecular weight compound or lipophilic compound are also further described in PCT/US 97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

Certain embodiments of the present invention provide a complex comprising one or more nucleic acid ligands to a Tissue Target covalently linked with a non-immunogenic, high molecular weight compound or lipophilic compound. A complex as used herein describes the molecular entity formed by the covalent linking of the nucleic acid ligand of a Tissue Target to a non-immunogenic, high molecular weight compound. A non-immunogenic, high molecular weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the non-immunogenic, high molecular weight compound is a polyalkylene glycol. In the most preferred embodiment, the polyalkylene glycol is polyethylene glycol (PEG). More preferably, the PEG has a molecular weight of about 10–80K. Most preferably, the PEG has a molecular weight of about 20–45K. In certain embodiments of the invention, the non-immunogenic, high molecular weight compound can also be a nucleic acid ligand.

Another embodiment of the invention is directed to complexes comprised of a nucleic acid ligand to a Tissue Target and a lipophilic compound. Lipophilic compounds are compounds that have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipid (and/or other materials or phases with low dielectric constants). Cholesterol, phospholipid, and glycerolipids, such as dialkylglycerol, diacylglycerol, and glycerol amide lipids are further examples of lipophilic compounds. In a preferred embodiment, the lipophilic compound is a glycerolipid.

The non-immunogenic, high molecular weight compound or lipophilic compound may be covalently bound to a variety of positions on the nucleic acid ligand to a Tissue Target, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the nucleic acid ligand to a Tissue Target. In embodiments where the lipophilic compound is a glycerolipid, or the non-immunogenic, high molecular weight compound is polyalkylene glycol or polyethylene glycol, preferably it is bonded to the 5' or 3' hydroxyl of the phosphate group thereof. In the most preferred embodiment, the lipophilic compound or non-immunogenic, high molecular weight compound is bonded to the 5' hydroxyl of the phosphate group of the nucleic acid ligand. Attachment of the non-immunogenic, high molecular weight compound or lipophilic compound to the nucleic acid ligand of the Tissue Target can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be known as a spacer.

The complex comprising a nucleic acid ligand to a Tissue Target and a non-immunogenic, high molecular weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

SELEX provides high affinity ligands of a target molecule. This represents a singular achievement that is unprecedented in the field of nucleic acids research. The present invention applies the SELEX procedure to more complicated tissue targets.

Negative selection (Counter-SELEX) is optionally employed before, during or after the Tissue SELEX process.

The negative selection provides the ability to discriminate between closely related but different tissue types. For example, negative selection can be introduced to identify nucleic acid ligands that have a high specificity for a tumor cell but do not recognize the cognate normal tissue. Similarly, nucleic acid ligands can be identified which specifically recognize atherosclerotic arterial tissue but not normal arterial tissue. Nucleic acid ligands which recognize fibrin, but not fibrinogen can also be identified by this method. Additionally, nucleic acid ligands to a cell type which express a certain receptor can be counter-selected with a cell line engineered not to express the receptor (or other such macromolecule).

One of ordinary skill in the art will readily understand that various mechanisms can be employed to accomplish this negative selection. The following examples are provided mostly for illustrative purposes and are not meant in any way as limiting the procedures of negative selection. Negative selection or Counter-SELEX methods were first described in U.S. patent application Ser. No. 08/134,028, filed Oct. 7, 1993, entitled "High-Affinity Nucleic Acid Ligands that Discriminate Between Theophylline and Caffeine", which is herein incorporated by reference. A particular implementation of negative selection is embodied using equilibrium partitioning. In this method, two cell lines or other tissue types are separated by a semi-permeable membrane (0.45–0.90 $\mu$m pore size) in an equilibrium dialysis chamber; one cell line is the neoplastic target cell line, the other, the normal tissue used for the negative selection. The choice of cell or tissue type for the negative selection will be determined by the specific end results desired and will sometimes consist of a non-malignant cell line of the same tissue type as the neoplastic target. For other experiments, various normal cell types could be combined to create the negative epitope "sink". The random pool of nucleic acids is placed into the dialysis chamber (on the side of the normal cells; this avoids background from high avidity targets which are common to both the tumor and normal cells) and allowed to equilibrate between the two cell lines. Those nucleic acid sequences that remain bound to the target cell line or tissue at equilibrium are selectively recovered and amplified for the next round of SELEX.

This example of negative selection methodology is quite powerful. First, equilibrium dialysis negative selection allows the positive and negative selection to be carried out simultaneously. Second, the stringency of the negative selection can be varied through the alteration of the relative amounts of "positive" and "negative" cells placed on each side of the dialysis membrane. These two characteristics of equilibrium dialysis negative selection allow precise control over the evolution of nucleic acid ligands specific for the target cell or tissue type.

This same type of equilibrium partitioning negative selection can be carried out with adherent cell lines. In this embodiment, monolayers of target and negative cells or tissues are plated in different wells of a multi-welled plate. After adherence, media, along with an oligonucleotide pool, is added such that the wells are connected by the volume of cell media. After equilibration of the oligonucleotide pool, those sequences bound by the target cell line or tissue type would be isolated and amplified for the next round of SELEX.

The equilibrium negative selection strategies above offer a powerful way of generating nucleic acid ligands to tissue targets and especially tumor associated antigens (TAAs).

Additionally, there are several other negative selection methods, which could be classified as "post-SELEX screening procedures". The most simple of these procedures is the testing of individual nucleic acid ligands (those sequences generated by tissue SELEX and demonstrated to be high-affinity ligands for the tissue target) against normal tissue for cross-reactivity. However, this approach is a tedious and time-consuming process.

A more fruitful "post-SELEX" method is to perform a negative selection, for example using a normal tissue as the negative selection target, on a pool that has already been evolved from a SELEX against a desirable complex tissue target, for example a transformed cell line. This example would suggest the performance of two to three negative selections on a normal tissue using a late-round, highly evolved pool from a SELEX of a transformed cell line. The binding of certain sequences to the normal tissue would be used to subtract these sequences from the evolved pool. This method allows one to quickly eliminate from several hundred to several thousand nucleic acid sequences that show a high affinity for those targets common to both the normal and the transformed cell lines.

Another "post-SELEX" screening method is a variation of a photocrosslinking experiment. As an example, it is possible to synthetically incorporate a highly photoreactive nitrine group (which is also iodinatable) on the 5' end of a PCR primer used in the tissue SELEX protocol. Late-round pools from, for example, a tumor cell line SELEX would be amplified with this photoactivatable (and $^{125}$I-labeled) primer, and this sequence pool would then be irradiated in the presence of the tumor cell line, and in the presence of normal tissue. Membrane proteins would be isolated and solubilized for analysis on an SDS gel. One would expect to see many different protein epitopes tagged by specific oligonucleotide sequences, for both the tumor and the normal cell lines. A few tagged targets will be unique to the tumor cell line. Because the oligonucleotides have been photochemically linked to the protein targets in a manner which does not destroy the base sequence of the oligonucleotide, it is possible to isolate a tumor-specific band from an SDS gel, and use PCR to recover a specific sequence motif that recognizes a particular tumor antigen. Thus, in one step, it will be possible to remove from a pool oligonucleotide sequences that recognize possibly hundreds of cell surface antigens, leaving one or a few families of sequences that binds specifically to a single tumor-specific antigen.

As described above, the Tissue SELEX methods can include the identification of macromolecules which comprise new epitopes on the tissue target. The nucleic acid ligand to the new epitope component of the macromolecule can be employed to purify, identify and characterize the macromolecule. The new macromolecule can be a previously unknown protein or peptide, lipid, carbohydrate, etc. Virtually any molecule that is part of the molecular make-up of a tissue can be identified by the Tissue SELEX process.

In order to fully exploit this aspect of the invention, it is important to develop strategies for the purification and identification of new macromolecules which comprise the new epitopes and to determine the roles these new macromolecular components of the tissue play in biological systems. The methods for purifying new macromolecules are well-known, especially in the art of protein purification. These standard purification methods include crosslinking, affinity chromatography, peptide microsequencing, Edman sequencing, mass spectrometry, and cDNA library searches.

The following discussion describes this process as it would be applied to the identification of a new tumor-associated antigen (TAA). For the purposes of this discussion, a TAA is a macromolecule that is expressed on a tumor cell, but not on a similar normal cell. A TAA may or may not be immunogenic. A TAA is merely one example of the kind of macromolecules which can be identified by the Tissue SELEX process and simply used for illustrative purposes. However, it is readily apparent that this process can be extrapolated to any new macromolecule identified by the Tissue SELEX process.

As applied to TAAs, the identification of new TAAs by the Tissue SELEX process is composed of two main parts: one, developing strategies for the purification and identification of new TAAs, and two, the elucidation of the role these tumor antigens play in cancer (i.e., determining the biological significance of each particular TAA in the development and progression of a particular cancer).

The steps of purification and identification of most of the TAAs should be straightforward and understood by one skilled in the art of protein purification. As with antibodies, SELEX provides a reagent—a high-affinity ligand specific for the tumor antigen—that is incredibly useful for the purification of the antigen from whole cells or other tissues. As a non-limiting example, most antigens will be amenable to some type of photo-affinity crosslinking or in the negative selection strategies section above. Specific crosslinking of the TAA, using a photoactivatable oligonucleotide with a 3' biotin conjugate will allow one-pass purification of the TAA target using streptavidin coated beads. An alternative method to this purification strategy is to use a column-bound high-affinity nucleic acid ligand to affinity purify the TAA target from solubilized target cell membrane preparations.

There are many compelling reasons to believe that the method provided herein for identifying macromolecules that comprise new epitopes on tissues offers distinct advantages over traditional methods of new macromolecule discovery. Again, the following discussion will be directed to tumor-associated antigen discovery, but one will readily understand that it can be broadly extrapolated to all new macromolecule discovery.

As applied to tumor-associated antigens, one must fully consider that all that is known about tumor antigens has been derived from the immune system's reaction to particular antigens; science has depended on the particular restrictions of the immune system, and the system's repertoires to distinguish antigenic differences between neoplastic and normal tissue. It is entirely possible that other tumor antigens exist that are not subject to immune response. Some investigators have hypothesized that there may in fact be many antigenic differences between cancer and normal tissue which are, unfortunately, not immunogenic.

The SELEX methodology provides an improved way to identify TAAs that avoids the restrictions posed by the immune system:

a. SELEX can actually provide a deeper search of TAAs than can the entire potential antibody repertoire of an organism—the size of the nucleic acid libraries used in SELEX is unrivaled by any biological system;

b. SELEX provides nucleic acid ligands to targets, including those which are not antigenic to the immune system because of tolerance. Many of the TAAs which have been identified are oncofetal—they are antigens expressed at some point during development or cell differentiation. As prior "self" antigens, they elicit no overt immune response because of earlier immune system tolerization. A SELEX-based search for TAAs avoids the circular nature of using the immune system as a means of identifying tumor antigens;

c. SELEX nucleic acid ligands have been shown to be exquisitely sensitive to target conformation. While most antibodies recognize conformational, or discontinuous epitopes, antibody functional epitopes are composed of only a few amino acids. The potential binding surface of an oligonucleotide ligand is much larger than that of an antibody variable region, and may provide greater conformational discrimination of large targets. Additionally, cross-reactivity for SELEX ligands is substantially less of a problem than for monoclonal antibodies. A considerable set of restrictions also controls T-cell mediated tumor responses. These immune system limitations provide important biological functions; however, they limit the immune system's power for TAA identification.

d. SELEX is possibly more sensitive to small quantities of antigen than the immune system. Although the immune system's threshold for reactivity has been estimated to be 200 copies/cell for an antigenic MHC-presented peptide, a B-cell antibody response (necessary for any antigen that is not a peptide-carbohydrates, lipids or conformational antigens) to a monovalent target requires antigen concentrations of about 100 mM. SELEX can generate ligands to TAA targets with a low representation on the cell surface; and e. SELEX provides a rapid and thorough method of TAA discovery. Screening of monoclonal antibodies to tissue sections and purification and identification of MHC peptides are painstaking processes that set practical limits on the depth and completeness of searches for TAAs. Tissue SELEX experiments take a much abbreviated length of time.

Nucleic acid ligands to tissue targets or the tissue epitopes identified by the method of the invention are useful as diagnostic reagents and as pharmaceuticals. The nucleic acid ligands are also useful for the identification of new macromolecules. The nucleic acid ligands are useful in any application that would be suitable for use of an antibody.

One problem encountered in the therapeutic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the nucleic acid ligands are derived by the SELEX method, the modifications can be pre- or post-SELEX modifications. Pre-SELEX modifications yield nucleic acid ligands with both specificity for it Tissue Target and improved in vivo stability. Post-SELEX modifications made to 2'-OH nucleic acid ligands can result in improved in vivo stability without adversely affecting the binding capacity of the nucleic acid ligands. The preferred modifications of the tissue nucleic acid ligands of the subject invention are 5' and 3' phosphorothioate capping and/or 3'3' inverted phosphodiester linkage at the 3' end. In one preferred embodiment, the preferred modification of the tissue nucleic acid ligand is 3'3' inverted phosphodiester linkage at the 3' end and 2' fluoro (2'-F) and/or, 2' amino (2'-NH$_2$), and/or 2' O methyl (2'-OMe) modification of some or all of the nucleotides.

As diagnostic reagents, the ligands or tissue epitopes can be used in both in vitro diagnostics and in vivo imaging applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek for a diagnostic ligand. Details regarding use of the ligands in diagnostic applications is well known to one of ordinary skill in the art. Nucleic acid ligands that bind specifically to pathological tissues such as tumors may have a role in imaging pathological conditions such as human tumor imaging and even therapeutic delivery of cytotoxic compounds or immune enhancing substances.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labelling tag in order to track the presence of a ligand. Such a tag could be used in a number of diagnostic procedures. For example, in the field of nuclear medicine, radiodiagnostic agents are useful for imaging sites in the body. U.S. patent application Ser. Nos. 08/358,065, filed Dec. 15, 1994, and 08/488,290, filed Jun. 7, 1995, both entitled "Conjugates Made of Metal Complexes and Oligonucleotides, Agents Containing the conjugates, their use in Radiodiagnosis as well as Process for Their Production", which are incorporated herein by reference, describe diagnostic agents comprising oligonucleotides covalently bound to complexing agents which further contain an imaging radioactive isotope such as 99m-Tc.

Specifically, oligonucleotide ligands with high specificity for particular tumor antigens could become as important as monoclonal antibodies for the detection, imaging, and surveillance of cancer. Modified nucleic acid ligands show nuclease resistance in plasma, and the use of 5' and 3' capping structures will provide stability in animals that rivals that of monoclonal antibodies (and without the immunogenicity of animal-derived MAbs). Radionuclides, magnetic compounds, and the like can be conjugated to tumor-specific oligonucleotides for cancer imaging. SELEX tumor ligands can also be used to determine if these tumor antigens are sloughed off tumors, and are detectable in the plasma like PSA.

The nucleic acid ligands to tissue targets or newly identified macromolecules components of tissue are also useful as pharmaceuticals. Therapeutic uses include the treatment or prevention of diseases or medical conditions in human patients. Therapeutic uses also include veterinary applications. The ligands can bind to receptors and be useful as receptor antagonists. Conversely, under certain circumstances the ligands can bind to receptors and cause receptor capping and act as receptor agonists.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

Standard formulations can be used for the nucleic acid ligands of the invention and are known to one of ordinary skill in the art.

The following examples provide a non-limiting description of the present invention. Example One describes obtaining ssDNA ligands to the complex tissue target peripheral blood mononuclear cells (PBMC). Ligands to PBMC have many uses including imaging lymph nodes for cancer screening and flow cytometry uses for AIDS monitoring.

Example Two describes the ability to obtain RNA ligands to human fibrin clots. The pyrimidine residues of these RNA ligands have been modified with fluorine at the 2'-position of the sugar. The fibrin ligands are useful as diagnostic agents as described below.

Circulating fibrinogen is converted to insoluble fibrin by the actions of the common product of the intrinsic and extrinsic coagulation cascade, thrombin. Fibrin provides a fibrous network for the clot allowing platelet deposition and later fibroblast invasion. Fibrin is present in large amounts in all thrombi, relatively less in platelet-rich arterial clots than fibrin-rich venous clots. Fibrin also can provide the nidus for atherosclerotic plaques and restenotic lesions by harboring thrombin and other mitogens which can lead to endothelial activation and smooth muscle cell proliferation.

The noninvasive detection and localization of thrombi remains a major challenge in clinical diagnosis. Deep vein thrombosis (DVT) and pulmonary embolism (PE) carry with them a high rate of mortality and morbidity. Deep-vein thrombosis (DVT) is a major complication of hospitalization and is diagnosed by physical exam less than one third of the time. Patients at risk include those with a major medical illness, malignancy, undergoing general abdominal, thoracic surgery or major orthopaedic surgery. High risk patients carry a 40–80% risk of DVT with a 1–2% risk of fatal pulmonary embolism (PE) (Weinmann, E. E. and Salzman, E. W. (1994) New Engl. J. Med. 331:1630–1641). PE accounts for 50,000 deaths/yr. 90% of PEs are non-fatal but carry significant morbidity: dyspnea, pulmonary infarction, abscess, or hypertension. 95% of PEs arise as a complication of DVT. Diagnosis of these conditions is difficult and has not improved, as noted by the high rate of undiagnosed PE on autopsy, which has not improved over time. Freiman et al. found evidence of subclinical PE in 64% of consecutive autopsies among persons with various causes of death (Freiman, D. G., Suyemoto, J. and Wessler, S., (1965) N. Engl. J. Med., 272, 1278–1280). Arterial thrombus, mostly secondary to atheromatosis, is even more difficult to diagnose non-invasively.

Non-invasive imaging of venous clots has relied on ultrasonic visualization of the deep venous system of the lower extremities. These studies are limited (generally only the thigh region) and are extremely operator dependent. PE diagnosis is generally done by ventilation and perfusion scanning using radioisotopes with the gold-standard being invasive pulmonary angiography. Radiolabeled fibrinogen has been used historically (Lensing, A. W. and Hirsch, J. (1993)). It requires either prospective administration or thrombus extension after it becomes clinically apparent. A number of reports of radiolabeled antibodies to either fibrin or platelets have been reported. These are sensitive but slow, with adequate images appearing 12–48 hours after injection of the tracer. The need for delayed images is due to clearance of the unbound antibody from the vasculature to allow for adequate signal-to-noise ratio. No significant imaging of coronary artery disease has been reported. The conjecture is that the thickness of the blood pool in the left ventricle of the heart significantly obscures the signal from the small overlying epicardial coronary arteries. Arterial imaging has been performed on the larger vessels of the aorta or femoral arteries using either anti-fibrin or anti-platelet antibodies. Both antibodies have problems: the antifibrin Abs bind to epitopes that are poorly accessible and which are constantly changing through clot stabilization and fibrinolysis; the anti-platelet Abs bind to epitopes which exist in circulating blood, thereby increasing their background. Meaningful high resolution detection of disease in small arteries will require high specificity, rapid clearance of unbound material, and probably 3-dimensional tomographic imaging technologies. In many respects, RNA ligands are suitable agents for these diagnostic approaches. A superior non-invasive diagnostic test for pulmonary embolism would be particularly clinically relevant.

Example Three describes the ability to obtain RNA ligands to rat stenotic carotid arteries. The stenotic carotid arteries ligands are useful as diagnostic and pharmaceutical agents as described below.

Atherosclerosis is one of the major causes of mortality in the world. There has been much effort in identifying and targeting both therapeutics and diagnostic agents to this pathological tissue. Experimentally atherosclerosis suffers from the absence of ideal animal models. Rodent vessels are significantly different from the primate especially with respect to the neointima. Primate models are expensive. The pig or 'minipig' provides a model for restenosis but does not provide a good model of primary atherosclerosis. Recently, transgenic mouse models have become available, but they are still poorly defined.

Although mechanisms and components of atherosclerosis are not completely defined, most investigators would agree that smooth muscle cells play an important role. The consensus is that these SMCs proliferate within the intima and are in some form "activated". The rat balloon-injured carotid artery model is one of the best understood models of response to arterial damage. Although there are limits to this model, there is clear evidence that in response to endothelial damage a proliferative response occurs primarily involving the SMCs. Many unique proteins have been identified from this tissue as well as signals responsible for SMC activation, migration and proliferation, as well as, extracellular matrix deposition. As such this remains a viable model of restenosis and less directly, primary atherosclerosis.

The rat balloon-injured carotid (RBIC) model provides a unique model for testing the hypothesis that nucleic acid ligands can be evolved by the SELEX methodology which is capable of recognizing pathological tissue to the exclusion of closely related normal tissue. RBIC are relatively well understood with respect to their composition and structure, are easily and reproducibly produced in a readily available lab animal, and have relevance to human pathologic conditions.

Example 4 describes a second experiment to obtain RNA ligands to rat stenotic carotid arteries involving twelve rounds of ex vivo SELEX followed by twelve rounds of in vivo enrichment, after which a single sequence (clone 12.2; SEQ ID NO: 242) was identified representing 48% of the final enriched library. This sequence accumulated at 1.4±0.4% injected dose/gram (% ID/g) in the balloon injured carotid compared to 0.1±0.05% ID/g in the contralateral control artery one hour after administration. Blood level at one hour was 0.2±0.06% ID/g. Tissue specificity (balloon injured: carotid: normal carotid) was 14, (p<0.05) and the signal to background (balloon injured: carotid: blood) was 7, (p<0.05).

Example 5 describes the ability to obtain RNA ligands to vascular tissue using the Watanabe Heritable Hyperlipidemnic (WHHL) Rabbit model of atherosclerosis. The WHHL rabbit plaque tissue ligands are useful as diagnostic and pharmaceutical agents. The WHHL rabbit model provides a novel technique of identifying a nucleic acid ligand which accumulates specifically at a site of induced vascular pathology and for the development of in vivo imaging agents. In this example, a nucleic acid ligand (clone 10.31; SEQ ID NO: 268) was identified that has a 3.5–10-fold increased affinity for plaqued WHHL vascular tissue over non-plaqued WHHL vascular tissue or vascular tissue.

Example 6 describes the in vitro binding of a nucleic acid ligand to WHHL rabbit atherosclerotic plaque tissue to human atherosclerotic plaque tissue, demonstrating that a WHHL rabbit-derived nucleic acid ligand has cross-reactivity with human atherosclerotic plaque tissue.

Example 7 demonstrates that clone 10.31 (SEQ ID NO: 268), identified in Example 5, accumulates in vascular plaque in rabbits.

Example 8 describes the in vitro binding, in vivo imaging and biodistribution of a 99m-Tc-labelled clone 10.31 identified in Example 5. Phospho-images showed that 15% of the input dose accumulated in the plaqued artery, demonstrating that an in vivo imaging agent can be developed through this method.

Example 9 describes a comparison of in vivo imaging and biodistribution of a WHHL rabbit-derived nucleic acid ligand in both a WHHL rabbit and a non-atherogenic New Zealand White rabbit. The aortic arch was observed in the WHHL rabbit but could not be visualized in the New Zealand rabbit.

Example 10 describes truncation and post-SELEX modifications of WHHL ligand 10.31 (SEQ ID NO: 268) in which purine positions in the truncate were substituted with 2'-OMe to study the effects of these substitutions on the activity of the truncates.

Example 11 describes a tissue SELEX on human atherosclerotic coronary artery segments.

EXAMPLE ONE ssDNA Ligands to Peripheral Blood Mononuclear Cells (PBMC)

This example demonstrates the ability to obtain ssDNA ligands to the complex tissue target human peripheral blood mononuclear cells (PBMC). PBMC are isolated from whole blood as described below and contain a complex mixture of cell types including B-lymphocytes, T-lymphocytes and monocytes. Ligands to PBMC have many uses including imaging lymph nodes for cancer screening and flow cytometry uses for AIDS monitoring.

A. Materials and Methods

Isolation of PBMCs

Fresh human blood was collected in heparinized vacutainers and up to 35 ml of whole blood was layered atop 10 ml of ficoll (Sigma Histopaque-1077®) in a 50 ml polyethylene conical tube. The samples were centrifuged at 400×g for 30 minutes at room temperature to separate the blood into three layers: red blood cells (RBCs) below the ficoll, peripheral blood mononuclear cells (PBMCs, including B lymphocytes, T lymphocytes, and monocytes) immediately above the ficoll, and acellular plasma above the PBMCs. Following centrifugation, the plasma was aspirated with a pasteur pipette to within 0.5 cm of the opaque PBMC interface. The PBMC interface, also referred to as the "buffy coat", was transferred to a 15 ml conical tube with a pasteur pipette, 10 ml of phosphate buffered saline solution (PBS, 137 mM NaCl, 2.7 mM KCl, 10.1 mM $Na_2HPO_4$, 1.8 mM $KH_2PO_4$) was added, and the cells were washed by gentle aspiration. The cells were then centrifuged at 250×g for 10 minutes at room temperature and the supernatant aspirated and discarded. The cell pellet was resuspended in 5 ml PBS, mixed by gentle aspiration, centrifuged at 250×g for 10 minutes at room temperature, and the supernatant aspirated and discarded. This washing step was repeated a third time, and the cells were resuspended in a final volume of 0.3 ml PBS, transferred to a 1.7 ml eppendorf tube, and stored on ice. PBMC yield and viability were measured by diluting the cells 1:50 in PBS, adding an equal volume of 0.4% trypan blue, and counting viable cells with a hemocytometer. Typical yields were $10^6$ cells/ml of whole blood with >95% viability.

Generation of Degenerate ssDNA Library

A library of synthetic DNA oligonucleotides containing 40 random nucleotides flanked by invariant primer annealing sites (oligonucleotide 1,5'-AGGGAGGAC GATGCGG-$[N]_{40}$-CAGACGACTCGCCCGA-3') (SEQ ID NO: 1) was amplified by the Polymerase Chain Reaction (PCR) for three cycles using oligonucleotides 2 (5'-AGGGAGGACGATGCGG-3') (SEQ ID NO: 2) and 3 (5'-(Biotin)$_3$-TCGGGCGAGTCGTCTG-3') (SEQ ID NO: 3) as primers. Oligonucleotide 3 had three biotin phosphoramidites conjugated to its 5' terminus. The 72 nucleotide double stranded product was denatured by adding an equal volume of formamide and heating to 95° C. for 3 minutes, and electrophoresed on an 8% polyacrylamide gel containing 8 M urea. The DNA strand lacking the biotin tag migrates faster than the biotinylated strand, and was isolated by excision from the gel, elution by squashing in 0.4 ml 2 mM EDTA and gentle agitation for 15 minutes, and centrifugation for 5 minutes using a microcentrifuge filter unit (CoStar Spin-X) to partition the ssDNA from the gel slurry. The recovered ssDNA was precipitated with 0.5 M NaCl and 2 volumes of ethanol, pelleted by centrifugation, washed once with 0.4 ml 70% ethanol, dried, and resuspended in deionized, distilled water (dd$H_2O$).

Selection for PBMC Affinity and Amplification

The affinity of the degenerate ssDNA library for PBMCs was determined using a cell-excess nitrocellulose filter binding assay as described in (Carey, et al. (1983) Biochemistry 22:2601–2609. Since the number of possible DNA binding targets on the surface of a PBMC is unknown, affinity values are reported as the concentration of cells (in units of cells/$\mu$l) showing half saturation in this assay. Selections for PBMC affinity were performed under DNA-excess conditions predicted to saturate available target sites, with heparin (Calbiochem, average M.W. 5000) added in excess of DNA to act as a non-amplifiable competitor and to increase stringency. PBMCs, DNA, and heparin were equilibrated for 15 minutes at 37° C. and PBMC:DNA complexes were partitioned from free DNA by filtration. PBMC-independent (background) retention of DNA was measured by filtering a similar reaction lacking PBMCs. Filters were pre-wet with 1 ml of wash buffer (50 mM Tris Acetate, pH 7.4) and following application of the sample, washed with 5 ml of wash buffer to remove unbound DNA. For selections 9–21, 0.5 M urea was added to the wash buffer to further reduce background retention. To minimize the likelihood of enriching for DNA with an affinity for the filter, we alternated among three different filter types: nitrocellulose (Millipore, Type HA, 0.45 $\mu$m), acrylic-coated nylon (Gelman Sciences, Versapor-450, 0.45 $\mu$m) and glass microfibre (Whatman, GF/C).

For the first selection, 1.4 $\mu$M DNA (70 pmoles or about $4\times10^{13}$ molecules) was equilibrated with 100 $\mu$M heparin and PBMCs at final concentrations of 40,000, 20,000, 10,000, 5,000, and 2,500 cells in 50 $\mu$l PBS. The fraction of total DNA complexed to PBMCs and retained by the filters was calculated by measuring Cerenkov radiation in a scintillation counter. A plot of fraction of DNA bound as a function of total DNA gives a linear relationship with a slope equal to the number of DNA molecules bound per cell (an estimate of the number of DNA binding targets per cell). For each subsequent selection, 5–9 PBMC concentrations were tested and plotted in this fashion and the DNA/cell value recorded. In an additional effort to reduce enrichment for filter binders each selection, the filter with the cell concentration retaining between 1% and 10% of total DNA, and if possible, at least 10 times more DNA than PBMC-independent (background) retention, was chosen for further amplification and enrichment. The selected DNA was harvested from the filter as described in Tuerk and Gold ((1990) Science 249:505–510), amplified by PCR, and size-purified by electrophoresis on an 8% polyacrylamide, 8 M urea gel as described above. As enrichment progressed through successive selections, stringency was increased by decreasing the DNA concentration, increasing the heparin concentration, and for selections #12–21, performing the selections in fresh human plasma instead of PBS. Performing selections in plasma adds an element of specificity, as PBMC-binding DNA molecules with a higher affinity for a plasma component will be depleted from the library. The DNA, PBMC, and heparin concentrations, as well as other relevant selection data, are summarized in Table 1.

Cloning and Sequencing Isolates

Following selection #21, 2 pmol of the selected library was amplified by PCR using oligonucleotide 4 (5'-CCGAAGCTTAATACGACTCACTATAGGGAGGAC GATGCGG-3', containing a Hind III restriction endonuclease cleavage site, underlined) (SEQ ID NO: 4) and oligonucleotide 5 (5'-GCCGGATCCTCGGGCGAGTCGTCTG-3', containing a Bam HI site, underlined) (SEQ ID NO: 5) as primers. The double-stranded product was size-purified on an 8% polyacrylamide gel and recovered as described above. Fifteen pmol of the PCR product was digested with Hind III and BamHI, along with 1 pmol pUC19 (all from New England Biolabs) for 3 hours at 37° C. Following digestion, the sample was extracted once each with one volume of phenol and chloroform and recovered by precipitation as described above. The selected library was ligated into pUC19 with DNA ligase (New England Biolabs) for 3 hours at 37° C. and the ligation product introduced into *E. coli* DH1α cells by electroporation transformation. Vectors from successful transformations were isolated using a standard plasmid mini-prep protocol and sequenced by dideoxy extension of end-labeled oligonucleotide 6 (5'-TTCACAC AGGAAACAG-3') (SEQ ID NO: 6) with Sequenase T7 DNA Polymerase (U.S. Biochemical). For a detailed description of these techniques, refer to Schneider, et al.

(1993) FASEB 7:201–207. Larger quantities of individual ligands (>20 pmol) were prepared by amplifying the vector inserts by PCR using oligonucleotides 2 and 3 as primers and denaturing and size-purifying the product as described above.

Competition Assay Measuring Disruption of PBMC:DNA Complexes

In a 20 µl reaction containing 100 µM heparin in PBS, 10 nM end-labeled DNA was equilibrated with a saturating concentration of PBMCs (10,000 cells/µl) for 10 minutes at 37° C. 5 µl of unlabeled competitor DNA was then added to a final concentration ranging from 1.25 nM to 3.2 µM and allowed to equilibrate for 10 minutes at 37° C. Reactions were filtered and the percent of total labeled DNA retained on the filter was recorded.

B. Results

Affinity for PBMCs was Enriched 40-Fold, and is Heparin Dependent

Following 21 rounds of enrichment by selection and amplification, the affinity of the DNA library for PBMCs was enriched by a factor of 40. In a cell-excess titration in PBS and 100 µM heparin, the degenerate library (DNA-0) showed half saturation at 43,500 cells/µl, while the fully enriched library (DNA-21) showed half saturation at 1,000 cells/µl. The difference in affinity between DNA-0 and DNA-21 is heparin dependent and most sensitive in the range of 10–100 µM. Below 10 µM, binding of the random library approaches that of the selected library, while above 100 µM, binding of the selected library begins to decrease and approach that of the random library. The relationship between heparin concentration and DNA binding demonstrates the ability of heparin to effectively compete for non-specific binding sites on PBMCs.

Enriched Library Consists of Families with Conserved Elements

From the enriched library, 34 members were isolated and sequenced as shown in Table 2 (SEQ ID NOs: 7–39). Of these 34 sequences, 33 were unique, and 29 contained the sequence TAGGG (or a variation one base removed) in two locations within the 40 nucleotide random cassette. When aligned by the TAGGG pentamers, additional conserved elements emerged and were used to classify the isolates into families as shown in Table 2. The sequences of the 34 isolates from the enriched library are aligned by their conserved TAGGG elements (boldface) and classified into families sharing other conserved elements. Only the sequence of the evolved 40 nucleotide cassette is shown in the alignment. The sequences of the invariant flanking regions are shown in the box and are the same as those from SEQ ID NO: 1. Runs of 2 or more G residues are underlined. The 10 isolates chosen for further characterization are indicated with a bullet. Computer algorithms were unable to identify any stable secondary structures for the selected ligands, possibly due to an overall lack of pyrimidine residues (particularly C residues) in the random cassette. However, conservation of a complex higher-order structure cannot be ruled out, as a large number of GG elements (underlined in Table 2 and consistent with the formation of G-quartet motifs) were selected for in the random region and exist upstream in the invariant flanking region.

Isolates from the Enriched Library Bind PBMCs with High Affinity

To compare the affinity of the selected families for PBMCs, one member of each was chosen for a binding assay (indicated with a bullet in Table 2). The affinities of the chosen ligands in PBS and 100 µM heparin ranged from 400–3,000 cells/µl except ligand L9, which lacked the conserved TAGGG elements and showed half saturation at 15,400 cells/µl as shown in Table 3.

The Enriched Library Binds PBMCs but not RBCs

A DNA ligand is most useful if it not only shows high affinity binding to PBMCs, but also shows specific binding to PBMCs. Using the cell-excess binding assay described above, the affinities of DNA-0 and DNA-21 for human PBMCs, rat PBMCs, and human red blood cells (RBCs) were compared. In PBS and 2.5 mM heparin, rat PBMCs mimic human PBMCs in their interaction with each DNA library. In PBS and 100 µM heparin, DNA-21 binds better than DNA-0 to human RBCs, but even at cell concentrations as high as $10^5$/µl (saturation conditions for PBMC binding to DNA-21), RBCs show only 5% binding to DNA-21 and less than 1% binding to DNA-0.

DNA:PBMC Complexes are Disrupted by DNA Competitor

A characteristic of dead cells is an inability to pump out internalized DNA. To demonstrate that the DNA binding seen in the binding assays is a measure of complex formation on the surface of viable cells rather than internalization by dead cells, we pre-bound a saturating concentration of PBMCs with radiolabeled DNA-21 and followed with a chase of excess unlabeled DNA-21 at various concentrations. When the data is plotted as the percent of labelled DNA bound as a function of competitor concentration, a sigmoidal relationship is seen showing one-half saturation at approximately 20 nM competitor and approaching zero as the competitor concentration increases. When this data is plotted as a scatchard, two types of interactions are seen: a high affinity interaction with a $K_d$ value of 8 nM and a stoichiometry of $3 \times 10^5$ DNA/cell, and a low affinity interaction with a $K_d$ value of 460 nM and a stoichiometry of $3 \times 10^6$ DNA/cell. Internalization of DNA by dead PBMCs is inconsistent with these results, as all of the pre-bound DNA-21 is competed off at concentrations of unlabeled DNA-21 above 1000 nM.

EXAMPLE TWO

2'-F RNA Ligands to Human Fibrin Clots

This example describes the ability to obtain RNA ligands to human fibrin clots. The pyrimidine residues of these RNA ligands have been modified with fluorines at the 2'-position o of the sugar. The fibrin ligands are useful as diagnostic agents as described previously.

A. Methods

Clot formation

Human blood was collected in EDTA Vacutainer tubes (Becton-Dickenson), spun at 4° C. in a clinical centrifuge. Plasma was removed and stored at −70° C. Clots were generated in glass tubes by the addition of $CaCl_2$ to a final concentration of 20 mM, incubated for 12–16 hr at 37° C.

For the SELEX protocol, the clots were generated in the presence of a glass hanger. Clots were washed 2 hr at 20° C. by continuous exchange of 125 ml 0.01M HEPES, 0.125 M NaCl, 2 mM $MgCl_2$, pH 7.5 (Fibrin buffer).

For the in vitro assays, clots were generated by recalcification of 50 ml plasma in 96-well microtiter dishes. After 12–16 hr in a humidified chamber at 37° C, the clots were washed by 4×200 µl buffer changes at 15 min each.

For the in vivo pulmonary embolism assay, clots were generated from recalcified plasma as above. Clots from 2 ml plasma were rimmed and centrifuged for 10 min in a clinical centrifuge. They were washed with 2 ml buffer with centrifugation. Clots were then homogenized for 1 min at low speed with a Tissue-Tearor (Biospec Products). Homogenate was washed 3×2 ml buffer followed by passage through 18, 20, 21, 22, and 23 Ga needles respectively. Homogenate was resuspended in 0.5 volumes buffer relative to initial plasma volume.

Generation of RNA Pool

2'F-pyrimidine, 2'OH-purine RNA was used for this SELEX. The initial DNA template, 40N8, was synthesized on a solid-phase automated DNA synthesizer by standard techniques and had the sequence gggagauaagaauaaacgcucaa-40N-uucgacaggaggcucacaacaggc (SEQ ID NO: 40). All subsequent PCR rounds utilized the primers 5'-taatacgactcactatagggagauaagaauaaacgcucaa (SEQ ID NO: 41) and 5'-gcctgttgtgagcctcctgtcgaa (SEQ ID NO: 42) as the 5' and 3' primers, respectively. PCR, reverse transcription and generation of RNA with T7 RNA polymerase was performed as previously described. Transcription of 2'F RNA was performed in the presence of 1 mM each ATP and GTP (in the presence or absence of $\alpha$-$^{32}$P-ATP), and 3 mM each 2'F UTP and 2'F CTP. Transcription proceeded for 5–14 hr at 37° C. followed by gel electrophoretic purification in the presence of formamide and 7 M urea.

SELEX Protocol

The general protocol used for this SELEX is outlined in Table 4. Clots from 0.5 ml plasma were immersed in a 1–4 mM solution of 2'F RNA pool in fibrin buffer for 1 hr at 20° C. Clots were washed by immersion with 4×1 ml buffer for 30 min each. The clot was then macerated with a sharp blade and shaken vigorously for 1 hr in 0.6 ml phenol and 0.45 ml 7M urea. 0.4 ml CHCl$_3$ is added to elicit a phase separation, followed by centrifugation at 14,000 RPM. The aqueous phase was extracted with equal volumes 1:1 phenol:CHCl$_3$, then CHCl$_3$, and precipitated with 1.5 ml 1:1 isopropanol:ethanol in the presence of NaOAc and tRNA as a carrier. Generally 0.5–10 pmoles RNA was recovered from a SELEX round.

Stringency and specificity were added to the SELEX after the pool showed signs of increased binding in buffer. Initially, after seven rounds of SELEX, the SELEX binding reaction was done in heparin-anticoagulated plasma. Subsequent washes were done in buffer. At later rounds, washes were also performed in heparinized plasma. No attempt was made to alter the clot size or RNA concentration. A first SELEX performed in this manner yielded a significant amount of fibrinogen cross-reactivity. A second SELEX was performed which diverged from the first at round six, at which time a fibrinogen 'Counter-SELEX' was added. 1–4 nmoles of a 1 mM transcribed pool RNA was premixed with human fibrinogen to a final concentration of 25 µM. After 15 min incubation at 37° C., the solution was filtered two times through three 1 cm diameter, 0.45 micron, nitrocellulose filters. This resulted in the removal of 80–90% of the protein. The filtered RNA was requantitated and added to clot SELEX reaction.

Sequence Alignment

CLUSTER Algorithm CLUSTER is a program that performs multiple sequence alignment with reoptimization of gap placement within the growing consensus. The algorithm consists of two parts: sequence alignment and clustering. Sequence alignment uses the dynamic programming algorithm of Altschul and Erickson (Altschul and Erickson (1986) Bulletin of Mathematical Biology 48:603–616) with a weight vector selected on an a priori statistical basis, namely, a match=1.0, mismatch=−1/3, gap opening=−1.0 and gap extension=−1/3. The total cost of alignment is the sum of each pairwise alignment within the consensus, utilizing the quasinatural gap costs of Altschul (Altschul (1989) J. Theoretical Biology 138: 297–309). Normalization of alignment costs allows for comparison between alignments that contain different numbers of sequences. The normalization used in CLUSTER compares an alignment to the best possible one in which every position matches. A normalized score is the cost of alignment divided by the cost of the best possible alignment. The K-Means algorithm clusters sequences into families. Here, the algorithm is modified slightly from the original version (Tou and Gonzales (1974) *Pattern recognition principles* (Addison-Wesley Publishing Company)) to accommodate cost of alignment as the distance measure. Convergence occurs when there is only one family, or the cost to combine any two clusters is beyond a threshold. Optimization (Step 3) pulls out subsets of sequences and realigns them as described by (Subbiah and Harrison (1989) J. Mol. Biol. 209:539–548).

Fibrinogen binding

Fibrinogen binding was determined by standard nitrocellulose filter binding assays as described in the SELEX patent applications.

In vitro clot assay

To 50 µl clot in microtiter wells was added 5,000 or 25,000 CPM (~0.5 or 2.5 pmoles) in 100 µl. Clots were incubated for 1 hr followed by 4×200 µl buffer washes at 15 min each. Microtiter wells were counted directly in the presence of scintillant.

In vivo pulmonary embolism assay

Clot homogenate prepared as above from 200 µl plasma was admixed with 100 pmoles (~1×10$^6$ CPM) for 15 min at 22° C. just prior to injecting suspension via a 23-ga needle into the tail vein of a 200–250 gm Sprague-Dawley male rat. At predetermined times, the animal was sacrificed by exsanguination followed by removal of the lungs. The left lung, which consists of only one lobe, was pressed onto Whatman one paper and then dried on a gel dryer at 80° C. for 2 hr and subjected to autoradiography. The multi-lobar right lung was homogenized in 1 ml buffer and quantitated in scintillant.

Histologic autoradiography

To visualize clot-bound RNA, histologic autoradiography was employed. RNA was 5'-end-labeled with γ-$^{33}$P-ATP. Binding was performed as described for the SELEX reactions or for the in vivo pulmonary embolism assay. Tissues were fixed at least 24 hours in 10% neutral buffered formalin, processed to paraffin, and made into 5 µm sections on poly-L-lysine slides. After drying in 60° C. oven, they were deparaffinized and rehydrated prior to exposure. Lungs were perfused with normal saline via the right atrium and inflated with 10% formalin prior to removal, fixation and imbedding. Slides were dipped in melted nuclear emulsion (Amersham LM-1), allowed to dry, and exposed at 4° C. Slides were developed in Dektol developer (Kodak), fixed (Kodak Fixer), and stained in Giemsa (Sigma).

B. Results

Two separate SELEX experimentals were performed on fibrin clot as outlined in Table 4. The two SELEX experimentals differed in the degree and method of counter-SELEX. In the first SELEX experiment (termed FC), eleven total rounds were performed. The binding reaction was performed in buffer for the first seven rounds. The binding was done in human heparinized plasma for rounds eight and nine. The final rounds were done in whole human heparinized blood. In all rounds, the clot was washed with Fibrin buffer. The second SELEX experiment (termed FCN) diverged from the first at round six when there was a first indication of enrichment. A 25 µM fibrinogen counter-SELEX was added to each round beginning at round six. In addition, the binding reactions were done in heparinized human plasma and the clots were washed with plasma instead of physiologic buffer for rounds 7–14. The final round pools bound 2.5% and 6.4%, respectively, in the presence of heparinized plasma. The round twelve and fourteen pools for the first and second SELEX experiments, respectively, were sequenced. In both cases RNA sequencing indicated considerable nonrandomness. The pools were amplified with new primers containing EcoR1 and Hind III sites on the 5' and 3' end, respectively, and cloned into pUC 18.

Visualization of clot binding

The round eleven pool from the initial SELEX was 5'-end labeled with $^{33}$P. The pool was admixed with clot in an identical manner to a SELEX in Fibrin buffer. After washing the clot was fixed in formalin, imbedded, sectioned and overlaid with autoradiography emulsion. Development of the sections showed the RNA (visualized as black grains) were coating the outside of the clot with some diffusion into the interstices of the clot. In another experiment, the rat PE model was performed with $^{33}$P kinased ligand. The pool was pre-bound to the homogenized clot and injected into the tail vein of a rat. At fifteen minutes the rat pulmonary bed was perfused with saline via the right atrium. The lungs were inflated and fixed by injection of 10% formalin into the trachea prior to removal and placement in formalin. Tissues were processed as above. Tissues showed black grains only in close association with intravascular clots. There was no evidence of RNA pooling downstream of occluded vessels. Furthermore, when the study was run with a non-evolved round 0 pool no black grains were visualized within the lung.

Sequence analysis and activity screening

Seventy-two clones of each were sequenced (SEQ ID NOS: 43–130). Eighty-eight unique clones were seen and 15 clones differed by only one nucleotide. The sequences were combined for analysis and grouped into sequence motifs by the application of CLUSTER and visual inspection as shown in Table 5. Only the sequence of the evolved 40 nucleotide cassette is shown in the alignment. The sequences of the invariant flanking regions are included in each clone and are the same of those in SEQ ID NO:40. When the unique clones from both SELEXes were combined for CLUSTER analysis they formed 17 separate motifs. 27/88 clones (31%) were grouped into two major motifs. Motif I and II had 15 and 12 members, respectively. A third motif (Motif III) contained 9 members primarily from the first SELEX and had properties similar to Motif I. Four of the motifs had only two members each.

78/88 (89%) clones were screened for binding in the qualitative in vitro microtiter plate assay. These clones were grouped into high, medium and low affinity with 37, 10, and 31 members in each group, respectively. 46/78 clones screened were further screened for fibrinogen-binding activity. The screen was a standard nitrocellulose binding assay employing a four-point curve from 0.1–10 μM fibrinogen concentration. Sixteen of the clones were further screened for clot binding in the in vivo rat pulmonary embolism assay. Results for each of these assays are shown in Table 5.

Of the 27 clones in the major two sequence motifs, 24 were evaluated by the initial screen for binding in the microtiter plate assay. Of those, 15/24 (63%) were characterized as high-affinity or moderate-affinity clot binders. The fibrinogen-binding screen was also divided into high, moderate and low affinity groups with 14, 6, and 26 in each group, respectively. In the fibrinogen-binding screen, high-affinity binders were included if the Kd<1 mM, while low-affinity binders included those clones with a Kd>1 mM. In Motif I, 10/11 (91%) were in the high- or moderate-affinity for fibrinogen binding while, in Motif II, 0/9 (0%) fell in the high- or moderate affinity fibrinogen binding groups. Eleven members of Motifs I, 11 were tested in the in vivo PE assay. The clones from Motif I had on average 40% increase in clot binding over Motif II when the binding reaction was performed in buffer. However, when the binding reaction was performed in heparinized plasma, Motif I had a binding decrease by 90% while Motif II had a decrease of only 10%. There was a clear distinction between Motif I and II in the degree of fibrinogen binding. Motif I bound clots with a slightly greater degree than Motif II but had a significant degree of crossreactivity. More definitive fibrinogen binding curves indicated that Motif I clones had Kd of 200–600 nM. The Kd(fibrinogen) of Motif II is too high to be quantitated accurately. 1–3% binding was seen at the highest fibrinogen concentration of 10 μM. One can extrapolate a Kd of greater than 100 μM.

Binding Quantitation

The two best binders in the PE model which had the lowest affinity for fibrinogen were pursued. Both of these clones resided in Motif II. Clone 69 (SEQ ID NO: 55) was analyzed for binding in vitro homogenized clot. By adding a fixed amount of radiolabeled clone 69 (2 nM) to a fixed amount of clot (200 μliters plasma equivalent) with increasing amount of non-radiolabeled ligand, binding could be quantitated. Analyzing data in a Scatchard format yield a two-component curve with high and low affinity binding components. There were 200 nM high affinity sites per 200 μliters plasma equivalent. The ligand bound these sites with a Kd of 10–20 nM. These sites were saturable. Furthermore, if the ligand was pre-bound to the clot homogenate, it could be competed off the clot by the addition of 3 μM unlabeled clone FC 69 with a half-life of 37 min. The labeled ligand did not diffuse off the clot homogenate to any significant degree over 4 hours in the presence of buffer alone or 3 mM of a 2'-F clone which had no measurable affinity for clots. As such it appears that the binding of a specific ligand to clots is specific and stable.

Clone Truncation

Boundary experiments were performed in which the ligand was radiolabeled on either the 5' or 3' end. The ligand was subjected to partial cleavage by modest alkaline hydrolysis and bound to fibrin. Binding RNAs were purified and sequenced. The results are shown in Table 6. Typically a ladder was seen until a region critical to binding was lost, at which point there is a step-off on the sequencing gel. Duplicating the reaction with both ends labeled allowed the determination of both the 5' and 3' boundary. Boundary studies were performed on one clone from Motif I and two clones from Motif II. All clones could be folded into a putative secondary structure which was consistent with the boundaries. The Motif I could be folded into a 'dumbbell' structure. Motif II used a significant amount of the 3'-fixed region. It could be folded into a stem-loop/bulge structure. Based on the boundaries and the structure potentials four nested synthetic 2'F oligonucleotides of clone FC 69 (SEQ ID NO: 55) were synthesized by automated solid-phase synthesizer ranging from 25–41 nucleotides in length (SEQ ID NOS: 131–134). These were tested for binding to homogenized clot by competition with full-length material both in vitro and in the rat PE model. In the in vitro assay, qualitatively binding was seen with all four clones, 69.4 (SEQ ID NO: 134) (the longest) being the best. In the rat PE model, again, all four truncates bound clot. The two truncates with four additional nucleotides past the boundary on the 3'-end showed 3-fold increased binding over those whose sequence ended exactly at the 3'-boundary. The binding to clots in the lung as normalized to full-length material was 32, 118, 36, and 108% for each of the four truncates, respectively. Furthermore, the binding of the best truncate in this assay, 69.2 (SEQ ID NO: 133)(29-nucleotides), was partially inhibited by the addition of 1 μM unlabeled full-length clone FC 69.

EXAMPLE THREE

RNA Ligands to Stenotic Carotid Arteries

This example describes the ability to obtain RNA ligands to rat stenotic carotid arteries. The stenotic carotid arteries ligands are useful as diagnostic and pharmaceutical agents as described previously.

A. Methods

Generation of RNA Pool

2'F-pyrimidine, 2'OH-purine RNA was used for this SELEX. The initial DNA template, 40N8, was synthesized on a solid-phase automated DNA synthesizer by standard techniques and had the sequence gggagauaagaauaaacgcucaa-40N-uucgacaggaggcucacaacaggc (SEQ ID NO: 40). All subsequent PCR rounds utilized the primers: 5'-taatacgactcactatagggagauaagaauaaacgcucaa (SEQ ID NO: 41) and 5'-gcctgttgtgagcctcctgtcgaa (SEQ ID NO: 42) as the 5' and 3' primers, respectively. PCR, reverse transcription and generation of RNA with T7 RNA polymerase was performed as previously described. Transcription of 2'F RNA was performed in the presence of 1 mM each ATP and GTP (in the presence or absence of α-$^{32}$P-ATP), and 3 mM each 2'-F UTP and 2'-F CTP. Transcription proceeded for 5–14 hr at 37° C. followed by gel electrophoretic purification in the presence of formamide and 7 M urea.

SELEX Protocol 250 gm male Sprague-Dawley were subjected to either unilateral or bilateral balloon-injury of the carotids. Rats were anesthetized with isoflorane. The carotids exposed by a 1 cm midline incision. The common, internal, and external carotid were identified. A #2 French Fogarty catheter was inserted into the external carotid just above the bifurcation and advanced to the aortic arch. The balloon was inflated and pulled back to the bifurcation. This was repeated six times. The catheter was removed, and the external carotid was ligated. The skin was closed by cyanoacrylate glue. Injuries were allowed to develop for 10–14 days.

Figure 1:
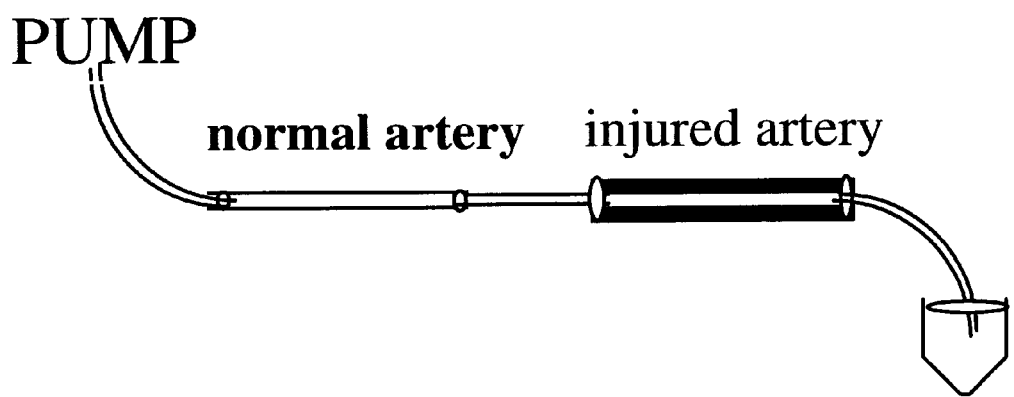
FIG. 1 shows a schematic representation used in the carotid artery SELEX procedures.

At the time of SELEX, animals were sacrificed under anesthesia by exsanguination. Both carotid arteries were dissected from the bifurcation to the aortic arch. The arteries were gently stripped of any associated connective tissue. Twelve rounds of SELEX were performed ex vivo as indicated in Table 7. The first three rounds were done by simply immersing two arteries in 0.5 ml of a 2 μM RNA solution. The binding reaction was rotated at 20° C. Carotid segments were then washed with four 1 ml buffer washes for 15 min each prior to harvesting the bound RNA. Subsequently, two carotid arteries were ligated together in series with a small length of polyethylene tubing. The distal ends were also canulated with tubing for attachment to a syringe pump and collection of eluent. These procedures were done with minimal disruption to the arterial segments. For the SELEX, 0.75–2.3 nmoles in one ml physiologic buffer was passed through the arterial segments at 4 ml/hr. This was followed by washing the segments with an additional 1 ml of buffer at 4 ml/hr. The segments were taken out of line, counted by Cherenkov radiation, and processed for RNA extraction. Rounds 4–7 were performed in this manner with both artery segments having been balloon-injured. All tissue was processed for RNA extraction. In rounds 8–12, an uninjured artery was ligated upstream from an injured artery as shown in FIG. 1. Perfusion proceeded as above. Both artery segments were counted, but only the injured segment was processed for RNA extraction. Rounds 8–12 were done to 'counter-SELEX' against the evolved RNA binding normal arterial endothelium. In a subsequent control, it was shown that the uninjured artery had an intact monolayer of intimal endothelium by Factor VIII immunohistochemistry.

Tissue Extraction of 2'-F-RNA

Carotid segments were minced with a scalpel and homogenized with 1 ml TRIZOL Reagent (Gibco). Homogenate was clarified by centrifugation, phase-separated with CHCl$_3$, and the aqueous phase precipitated with isopropanol, all according the manufacturers protocol. Purified RNA was resuspended in H$_2$O, and digested for 15 min at 37° C. with 0.1 U/μL DNAse I (Pharmacia) and 100 μg/ml RNAse A (Sigma) in reverse transcription buffer. 2'-F-pyrimidine, 2'-OH-purine RNA is stable to RNAse A digestion. The digest was phenol, phenol/CHCl$_3$ extracted and EtOH precipitated out of sodium acetate. The RNA was then subjected to RT/PCR under standard conditions to generate a template for T7 RNA polymerase. After twelve rounds the pool was cloned and sequenced. The sequences identified as C# in Table 8 were obtained by this protocol.

In Vivo SELEX

In a subsequent SELEX, 3–5 nmoles of the Round twelve pool was injected directly into the tail vein of a rat with a 14 day unilateral lesion. After 15 min, the animal was sacrificed and the carotids processed. RNA was amplified as before. Four Rounds of in vivo SELEX were done as indicated in Table 7. This pool was cloned and sequenced and the sequences from both cloning steps were combined for sequence analysis. The sequences identified as Civ# in Table 8 were obtained by this protocol.

Binding Analysis

Binding of RNA either as a pool or individual clones was performed by comparing $^{32}$P counts bound to normal versus injured carotid artery segments. Binding was visualized by histologic autoradiography in either the ex vivo perfusion system or by overlaying RNA onto fresh-frozen carotid artery slices.

Histologic autoradiography

To visualize carotid-bound RNA, histologic autoradiography was employed. RNA was 5'-end-labeled with γ-$^{33}$P-ATP. Binding was performed as described for the SELEX reactions. Tissues were fixed at least 24 hours in 10% neutral buffered formalin, processed to paraffin, and made into 5 mm sections on poly-L-lysine slides. After drying in 60° C. oven, they were deparaffinized and rehydrated prior to exposure. Slides were dipped in melted nuclear emulsion (Amersham LM-1), allowed to dry, and exposed at 4° C. Slides were developed in Dektol developer (Kodak), fixed (Kodak Fixer), and stained in Giemsa (Sigma).

Fresh-frozen carotid sections were prepared by imbedding normal or injured carotid artery segments in OCT™ (Optimal Cutting Temperature, 10.24% polyvinyl alcohol, 4.26% polyethylene glycol and 85.5% non-reactive proprietary ingredients, Sakura Finetek USA, Inc., Torrance, Calif. distributed through Allegiance Scientific Products or Van Walters & Rogers Scientific Sources) and freezing at −20° C. 5 μm sections were cut on a cryostat, placed on a slide (typically a normal and injured section were juxtaposed on a single slide), and stored frozen at −5° C. Slides were warmed to room temperature, the paired sections were encircled with a grease pencil, and pre-bound with 30 ml PBS, 0.5% Tween-20, 1 mM low molecular weight heparin (Calbiochem). After 15 min the solution is removed and 30 µl of the same solution containing 10,000 CPM (~1 pmol) $^{33}$P-labeled RNA is added for 30 min. Slides were washed twice with PBS/Tween-20, twice with PBS. Slides were fixed in 10% neutral buffered formalin, then rinsed in distilled water prior to exposure.

Sequence Alignment

CLUSTER Algorithm. CLUSTER is a program that performs multiple sequence alignment with reoptimization of gap placement within the growing consensus. The algorithm consists of two parts: sequence alignment and clustering. Sequence alignment uses the dynamic programming algorithm of Altschul and Erickson (Altschul and Erickson (1986) Bulletin of Mathematical Biology 48:603–616) with a weight vector selected on an a priori statistical basis, namely, a match=1.0, mismatch=−1/3, gap opening=−1.0 and gap extension=−1/3. The total cost of alignment is the sum of each pairwise alignment within the consensus, utilizing the quasi-natural gap costs of Altschul (Altschul (1989) J. Theoretical Biology 138:297–309). Normalization of alignment costs allows for comparison between alignments that contain different numbers of sequences. The normalization used in CLUSTER compares an alignment to the best possible one in which every position matches. A normalized score is the cost of alignment divided by the cost of the best possible alignment. The K-Means algorithm clusters sequences into families. Here, the algorithm is modified slightly from the original version (Tou and Gonzales (1974) *Pattern recognition principles* (Addison-Wesley Publishing Company)) to accommodate cost of alignment as the distance measure. Convergence occurs when there is only one family, or the cost to combine any two clusters is beyond a threshold. Optimization (Step 3) pulls out subsets of sequences and realigns them as described by (Subbiah and Harrison (1989) J. Mol. Biol. 209:539–548).

B. Results

SELEX

Twelve rounds of ex vivo RBIC SELEX was performed followed by four rounds of in vivo SELEX as indicated in Table 7. Pools were cloned and sequenced after the ex vivo SELEX and the ex vivo/in vivo SELEX; the sequences are provided in Table 8. Only the sequence of the evolved 40 nucleotide cassette is shown in the alignment of Table 8. The sequences of the invariant flanking regions are included in each clone and are the same as those of SEQ ID NO: 40. The last five rounds of the ex vivo SELEX were done with a normal carotid artery as a negative selection (Counter-SELEX). Evaluation of these rounds indicated that over the last five rounds the injured carotid bound between 0.07–0.5% without a trend towards increased binding in the later rounds. The discrimination between normal and injured was 3.2–4.5, again without a trend toward increased discrimination. At round twelve, the RNA pool was sequenced and shown to be significantly non-random.

The pool was then taken forward in the in vivo SELEX. Very little RNA was recovered from the injured carotid arteries (0.2–0.6 pmoles). Comparing CPM in the normal versus injured yielded discrimination values of 2.61–3.54. At the first round of in vivo SELEX, equal amounts of Round 12 RNA and Round 0 RNA were injected into two different animals both with unilateral balloon injuries. There was no discrimination for the Round 0 RNA (i.e. the same number of counts bound the normal as the injured artery), whereas in the round 12 pool, 2.61 times more RNA bound the injured carotid as compared to the uninjured. At Round 15, the evolved pool was injected into the animal or perfused through an ex vivo apparatus exactly as had been done for rounds 8–12. The discrimination of the Round 15 RNA was 4.61, which was higher than had ever been seen during the ex vivo SELEX.

Seventy-two clones from the ex vivo SELEX were sequenced, of which 50 were unique as shown in Table 8. The striking finding was that of the seventy-two clones, two were present in multiple copies. One clone (clone C33; SEQ ID NO: 146) had nine identical or one base difference copies, while another (clone C37;SEQ ID NO: 186) had ten copies. Thus nineteen of twenty-two copies in the initial sequencing arose from two sequences. Sequences stemming from those two persisted after the in vivo SELEX with clones related to C33 generating the largest single family in the combined analysis (Motif I).

Analysis of Clone Binding

Of the ninety-four unique clones from the two SELEX methods, twenty-eight were screened for binding to fresh-frozen rat carotid artery sections. These were qualitatively graded by intensity of staining (+, ++, +++) and specificity (s, ns) as shown in Table 8. Clones were seen with a variety of patterns from no visible binding to strong binding of all tissue components. Specificity was graded based on relative intensity of binding to neointimal tissue over normal or injured media or adventia. Early on C33 (SEQ ID NO: 146) was found to have both increased intensity and specificity over both unevolved Round 0 or Round 12 pool RNA. Further screening uncovered three other clones with better binding characteristics: C59 (SEQ ID NO: 150), Civ45 (SEQ ID NO: 202), and Civ37 (SEQ ID NO: 210). Civ41 (SEQ ID NO: 158) was of interest because it was of the same Motif as C33 and C59, but had very intense staining and little specificity: staining neointima, as well as normal an injured media. Civ45 in three independent binding experiments had the most intense staining in a specifically neointimal distribution. This clone also showed an slight increase in binding to injured media over normal media. If smooth muscle cells migrate from the media to the neointima in the injured artery, then it may not be surprising that whatever this clone is binding exists within the injured media. Of the four clones noted with high specificity, two of them are from Motif I and are closely related. Three of the four contain the sequence GUUUG (underlined in Table 8). Putative secondary structures are shown in Table 9. It is unknown at this time whether these structure correlate to the true structure. In the absence of boundary experiments they provide a basis for truncation studies.

Clone C33 and C59 were $^{33}$P-labeled and perfused in an ex vivo manner. Although not quantitated, they showed dramatic binding to the lumenal wall of the damage artery but not to the normal vessel.

C59 was used to stain fresh-frozen section of RBIC of different ages. Carotids were harvested at 1, 2, 4, 6, 8, 16 weeks after balloon injury. The neointimal signal was greatest at 2–6 weeks. It was minimally present at one week and disappeared after six weeks. The pattern of staining neointima in the highly specific clones is diffusely granular. Silver grains are not obviously associated with smooth muscle cell bodies. One hypothesis is that the RNAs are binding to components of the extracellular matrix (ECM). It is known that SMCs require an ECM scaffold to migrate. They have been shown to lay down unique proteoglycans in the course neointimal proliferation. The presence and disappearance of these unique proteoglycans corresponds temporally to the binding of RNAs to neointima. As such one viable possibility is that the RNAs are binding specifically to these proteoglycans.

EXAMPLE 4

RNA Ligands to Stenotic Carotid Arteries

This Example describes the identification of RNA ligands to rat stenotic carotid arteries using a similar method to that described in Example 3 but with a few modifications.

The method used to generate the 2'-F-pyrimidine, 2'-OH-purine RNA pool in this Example was identical to the method described in Example 3.

A. Methods

SELEX Protocol 250 gm Sprague-Dawley were subjected to either unilateral or bilateral balloon-injury of the carotids as described in Example 3.

Initial selections were performed ex vivo. Rat carotid arteries were balloon-denuded with a #2 Fogarty catheter introduced into the external carotid artery and advanced to the aortic arch. After fourteen days the carotid artery was harvested, carefully stripped of excess connective tissue and ligated in line to polyethylene tubing (FIG. 1). The arterial segment was placed at 25° C. in a phosphate-buffered saline (PBS) bath. $^{32}$P body-labeled transcript (0.75 mM) in PBS was passed through the artery once, over a fifteen minute period (4 ml/hr). The arterial segment was then washed in the same manner with PBS. The segment was disconnected, minced, and the RNA extracted as described in Example 3. The RNA was then subjected to RT/PCR under standard conditions to generate a template for T7 RNA polymerase. This set of procedures constituted one round of SELEX. After six rounds, 0.62% of the RNA was bound to the artery. At round seven an uninjured carotid arterial segment from the same rat was ligated in series upstream of the balloon denuded segment to "counter-SELEX" against the evolved RNA binding normal (uninjured) arterial endothelium.

In Vivo SELEX

Figure 2:
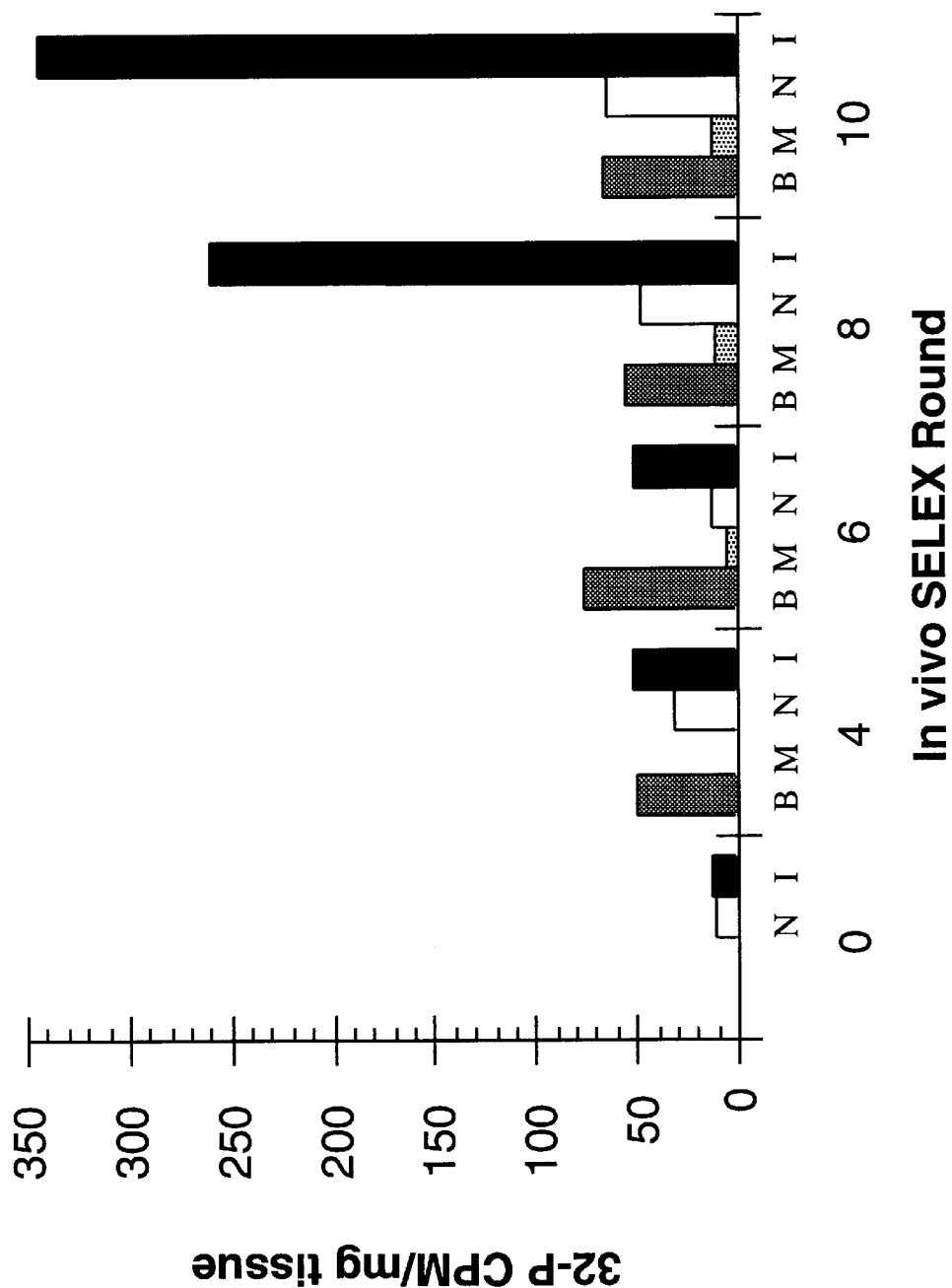
FIG. 2 illustrates the progression of the in vivo rat balloon injured carotid SELEX displayed as the accumulation of radioactive RNA bound per wet weight of tissue (CPM/mg) as a function of the number of SELEX rounds. Four to six nmol $^{32}$P body-labeled 2'-F RNA (10–15 $\mu$M in PBS, 0.1% (w/v) human serum albumin) was injected into a 14-day balloon injured rat via the tail vein. At specific times (between 15 and 60 min) the animal was exsanguinated, perfused with normal saline via heart cannulation until fluid from the inferior vena cava was clear, dissected, and tissues were taken for RNA extraction and quantitation. Blood (B), intercostal muscle (M), normal (N) and balloon denuded carotid artery (I) were harvested for comparison at each round. Shown are the biodistribution profiles of in vivo round 0 (15 min.), 4 (15 min.), 6 (30 min.), 8 (60 min.), and 10 (60 min.).

After twelve rounds of ex vivo SELEX, in vivo SELEX was initiated. Four to six nmoles of the ex vivo enriched library was injected into the tail vein of a rat with a unilateral 14-day balloon injured carotid lesion. Animals were sacrificed at 15 min (in vivo round 1–4), 30 min (round 5–6), 40 min (round 7) or 60 min (round 8–12). Tissue was removed and extracted for RT/PCR as described in Example 3. FIG. 2 shows the progression of the in vivo SELEX displayed as the amount of RNA bound per wet weight of tissue (CPM/mg) as a function of the number of SELEX rounds. After twelve rounds of in vivo SELEX the enriched library was cloned.

Binding Analysis

Clones were screened for binding neointimal tissue in vitro by histologic autoradiography. Histological autoradiography was performed either by perfusing RNA that was 5-end-labeled with gamma-$^{33}$P-labeled through the vessel as in FIG. 1, or by cutting fresh frozen sections and applying the ligands to the cut surface as described in Example 3.

B. Results

Twelve rounds of ex vivo RBIC SELEX were performed followed by twelve rounds of in vivo SELEX. Pools were cloned and sequenced after the in vivo SELEX; the sequences are provided in Table 10 (SEQ ID NOS: 242–258). The sequences shown are the random regions of the sequences; the 3' and 5' sequences of the invariant flanking regions, which are not included in the clones, are same as shown in SEQ ID NOS: 139 and 140, respectively. The last six rounds of the ex vivo SELEX were done with a normal carotid artery as a negative selection (Counter-SELEX). Evaluation of these rounds indicated that over the last six rounds, the injured carotid bound initially led to a decrease in binding to the balloon injured segment (0.02%), with increased binding in the last five rounds. At the twelfth and final ex vivo round, the binding to the normal and balloon injured segment was 0.1% and 0.34%, respectively.

The pool was then taken forward in the in vivo SELEX for twelve rounds. The round twelve in vivo SELEX was cloned and sequenced. Forty-four clones were sequenced and aligned into two motifs (Table 10). Forty-eight percent of the sequenced library was represented by sequences containing one highly conserved motif, of which clone 12.2 (SEQ ID NO: 242) was the most prevalent member.

Analysis of Clone Binding

Autoradiography after perfusion indicated intense uptake on the lumenal surface with little penetration into the neointima. Autoradiography after application of clones to the fresh frozen section showed substantial neointimal binding of the enriched library compared to the random library. The uniform granular silver grain distribution, was not clearly cell-associated, and is suggestive of an extracellular matrix target. Comparison of perfusion and fresh frozen autoradiography led to the conclusion that the clones are binding a neointimal component which is both displayed on the lumenal surface of the lesion and, in addition, is widely distributed throughout the neointimal matrix.

Representative clones from both sequence families were able to specifically compete with clone 12.2 for binding by histologic autoradiography. Radiolabeled clone 12.2 was competed off the fresh frozen section by unlabeled clone 12.2 (SEQ ID NO: 242), 12.13 (SEQ ID NO: 246), 12.15 (SEQ ID NO: 248) and 12.37 (SEQ ID NO: 250) in a dose dependent manner with complete competition by a 30-fold molar excess of the unlabeled clones. However, there was no diminution of signal by the addition of a 300-fold molar excess of a sequence scrambled version of clone 12.2. It is interesting to note that the two sequence families which have no discernible sequence similarities are able to compete with each other for target binding.

Secondary structure analysis

Figure 3:
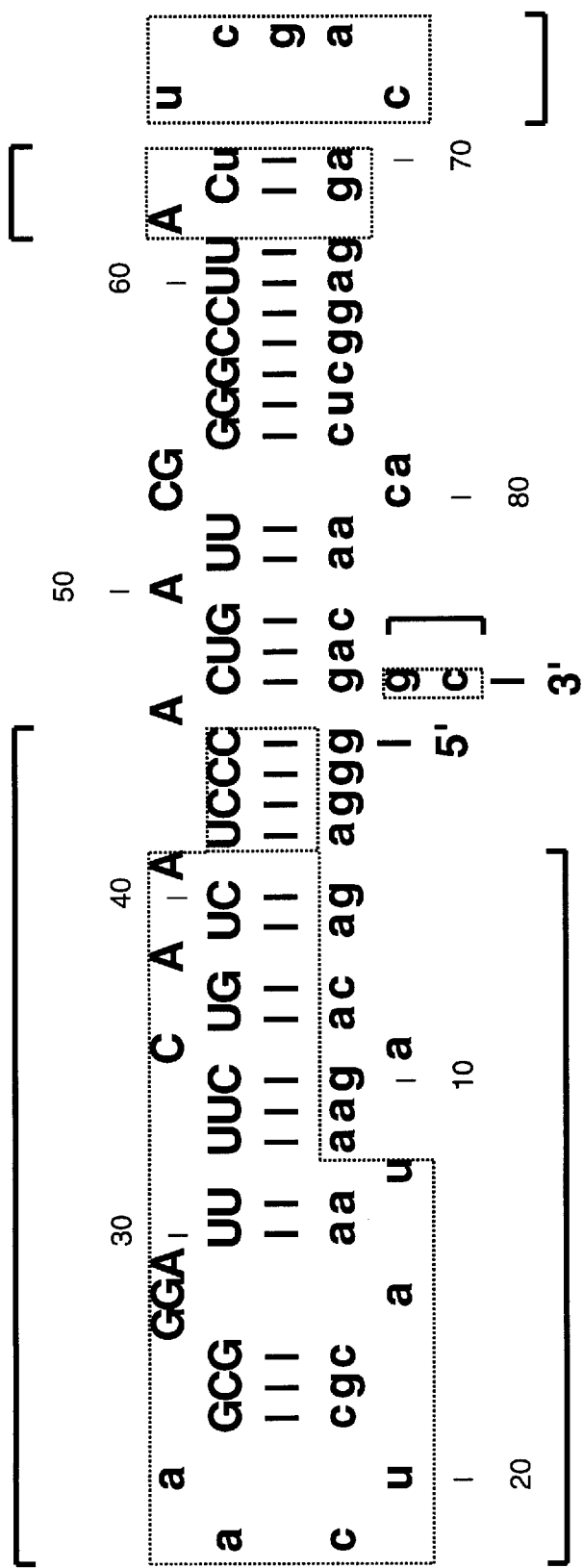
FIG. 3 shows the predicted secondary structure of clone 12.2 (SEQ ID NO: 242) identified in Example 4. Lower case letters represent the fixed regions and upper case letters represent the randomized region. Nucleotide position numbers begin at the 5'-end. Truncation analysis was performed by deleting or substituting regions of clone 12.2 (boxed with a dashed line) and assaying activity in vitro. Alterations that reduce or eliminate activity are bracketed above the structure, and those that have no effect on activity are bracketed below the structure.

The secondary structure of clone 12.2 (FIG. 3) was predicted using an RNA folding algorithm (Zuker, M. (1989) *Science* 244: 48–52) and further supported by structure-specific endonuclease and truncation analyses. Computer-assisted structure predictions were supported experimentally by endonuclease probing. Digests were performed under non-denaturing conditions (4° C., 10 min. in PBS) with single-strand specific endonucleases T$_1$ (Gp↓N, Boehringer Mannheim, 1×10$^{-3}$ U/ml), U$_2$ (Ap↓N, USB, 10 U/ml), S$_1$ (N↓pN, Boehringer Mannheim, 4×10$^{-4}$ U/ml) and P$_1$ (N↓pN, Boehringer Mannheim, 3 U/ml) and double-strand specific endonuclease V$_1$ (N↓pN, Pharmacia, 7 U/ml). Partial cleavage ladders were generated and visualized by denaturing PAGE to identify reactive nucleotides. Truncation analysis was performed by deleting or substituting regions of clone 12.2 (boxed with a dashed line) and assaying activity in vitro. Alterations that reduce or eliminate activity are bracketed above the structure, and those that have no effect on activity are bracketed below the structure.

The motif consists of two stem loops forming a "dumbbell" shape with the 5' and 3' termini juxtaposed. Truncated versions of clone 12.2 were transcribed in vitro, each containing the first twelve bases of clone 12.2, which are required for efficient transcription of 2'-F pyrimidine RNAs. Truncates were tested qualitatively in the in vitro histologic autoradiography assay and selected truncates were assayed for balloon injured carotid tissue accumulation in vivo. Results of the truncation analysis are summarized in FIG. 3. Most of the 5' stem-loop nucleotides (#13–41) can be removed with no loss of activity. The two 3'-terminal nucleotides (#86–87) can also be removed. The sequence of the loop (nucleotides #65–69) is not important as it can be replaced with a GAAA tetraloop (Uhlenbeck, O. C. (1990) Nature 346:613–614) without affecting activity. In contrast, small deletions in the 3' stem critically affect activity. Removal of residue #62 and the two loop-closing base pairs (#63–64 and #70–71) abolishes activity. While loss of residues #13–41 is tolerated, removal of residues #13–46 eliminates activity. The most interesting finding is that there appears to be a requirement that the two juxtaposed guanosines (#1 and #85) not be linked by aphosphodiester bond. A synthetic oligonucleotide consisting of nucleotides #42–85 linked to #1–4 does not have activity, while a transcribed oligonucleotide 12.2t55L (FIG. 4; SEQ ID NO: 259) lacking most of the 5' stem-loop (#13–41) but containing the transcription leader sequence (#1–12), has full activity (FIG. 4). Flexibility at the "hinge" (residue #46) between the two stem loops appears to be important for high affinity binding. Furthermore, removal of the 5'-terminal GGG (#1–3) in a synthetic truncate of 12.2t55L abolishes activity, consistent with the structure proposed in FIG. 4. The 55 nucleotide oligonucleotide 12.2t55L is currently the shortest truncate with identical tissue accumulation as the full length clone 12.2 in vitro.

Biodistribution studies

Figure 5:
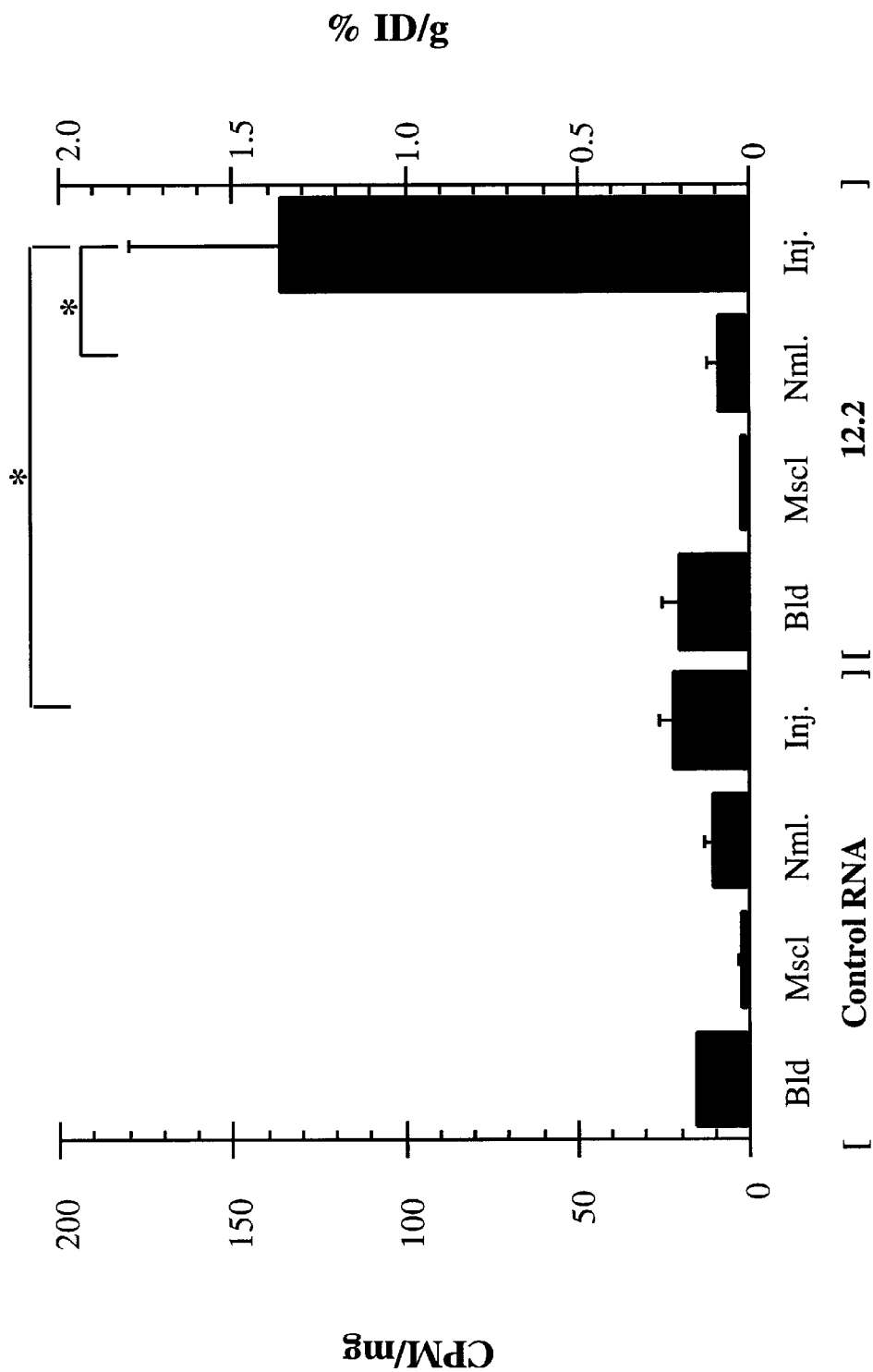
FIG. 5 illustrates the accumulation of radioactive clone 12.2 (SEQ ID NO: 242) and control RNA bound per wet weight of blood (Bld), muscle (Mscl), normal (Nml) and balloon injured (Inj) carotid artery tissue presented as CPM-lmg and % injected dose/g (% ID/g).
Figure 6:
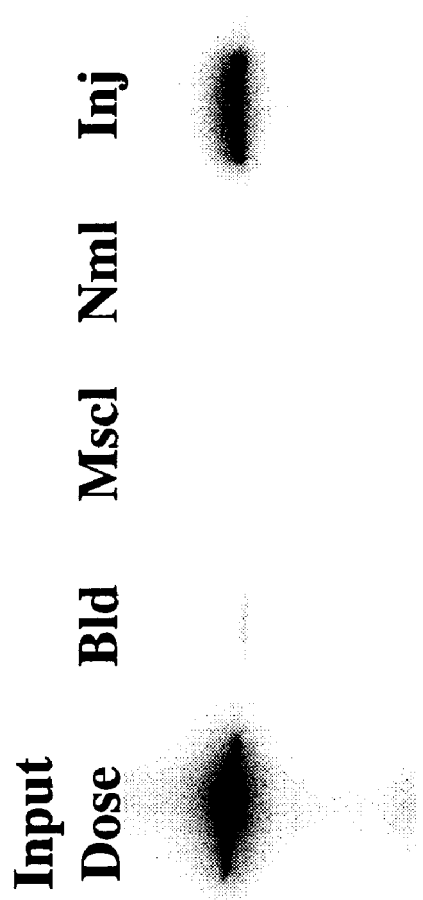
FIG. 6 shows a phosphoimage of a gel obtained by the following procedure: 20 mg of blood, muscle and balloon injured carotid artery tissue and 15 mg of normal carotid artery were extracted and applied to an 8% polyacrylamide, 7M Urea denaturing gel, visualized with a phosphor capture screen (Fuji). Lane 1 is the injected does; lane 2 is blood (Bld), lane 3 is muscle (Mscl), lane 4 is normal artery (Nml) and lane 5 is balloon injured artery (Inj).

A limited biodistribution study was performed in rats (FIG. 5). Sixty min after a bolus injection of 2 nmoles (10 mCi) $^{32}$P-α-ATP-labeled clone 12.2, radioactivity accumulated in blood to 0.2±0.05% ID/g (±s.e.), in intercostal muscle to 0.05±0.02% ID/g, in normal carotid to 0.1±0.05% ID/g, and in injured carotid to 1.4±0.4% ID/g. The ratio of balloon injured to normal carotid for clone 12.2 was 14 (p<0.05). An 87-nucleotide 2'-F transcript control with the same terminal invariant regions was used as a non-specific control. The ratio of clone 12.2 to non-specific oligonucleotide binding injured carotid was 7 (p<0.05). These values compare very favorably to those previously reported for vascular imaging agents (Lees, A. M., et al. (1988) Arteriosclerosis 8:461–470; Hardoff, R, et al. (1993) J. Clin. Pharmacol. 33:1039–1047). Clone 12.2 is cleared primarily in the liver, kidney and spleen accumulating to 3–4% ID/g in each of these tissues at 60 min. Sequence-independent accumulation in these organs is routinely observed. Blood, muscle, normal and balloon injured carotid artery tissue were extracted, normalized to wet tissue weight, and applied to a denaturing gel (FIG. 6).

The accumulation of full length transcript into the injured artery was evaluated. RNA extraction with Trizol (Calbiochem) yielded 60–70% of the radiolabel in the aqueous phase after phase separation. If a 2'-F transcript was added to tissue ex vivo just prior to extraction, >90% of the radiolabel was precipitated as full-length RNA. In the first round (15 min in the rat), 47% of the extracted radiolabel from the injured artery was isopropanol precipitable as full length material. By the twelfth round (60 min in the rat) 85% of the extracted label was precipitable as full length. In contrast, radioactivity extracted from the blood at the twelfth round was only 15% precipitable.

Full length material was easily visualized from the injured carotid tissue but only faintly present in the other tissues. To visualize the binding of clone 12.2, in another animal, the aortic arch and both carotid arteries were dissected in one piece. The vessels were visualized on a phosphor capture screen (Fuji). The image indicated a seven-fold increased uptake per unit area of clone 12.2 in the balloon injured artery compared to the control artery or the aortic arch region.

Binding kinetics

Binding kinetics were studied. Binding of clone 12.2 was rapid and approached 3% ID/g at the earliest time point (15 minutes), and was lost from the injured carotid with a $t_{1/2}$=50 min. In this case, the ratio of clone 12.2 present in injured carotid vs. blood peaked at 40 to 60 min. It is interesting to note that the signal to noise is the highest at 60 min, the time used for the last rounds of in vivo SELEX.

EXAMPLE 5

RNA Ligands to Watanabe Heritable Hyperlipidemic Rabbit Arteries

This example describes the ability to obtain RNA ligands to Watanabe Heritable Hyperlipidemic Rabbit (WHHL) arteries. The Watanabe Heritable Hyperlipidemic Rabbit (WHHL) is an extensively used model of atherosclerosis in which the rabbit has a homozygous deficiency for the low density lipoprotein receptor. These animals maintain very high cholesterol levels and develop atherosclerotic lesions spontaneously.

A. Methods

Generation of RNA Pool

2'-F pyrimidine, 2'-OH purine RNA was used for this SELEX. The initial DNA template, 40N8, was synthesized on a solid-phase automated DNA synthesizer by standard techniques and had the sequence gggagauaagaauaaacgcucaa-40N-uucgacaggaggcucacaacaggc (SEQ ID NO: 40). All subsequent PCR rounds utilized the primers: 5'-taatacgactcactatagggagauaagaauaaacgcucaa (SEQ ID NO: 41) and 5'-gcctgttgtgagcctcctgtcgaa (SEQ ID NO: 42) as the 5' and 3' primers, respectively. PCR, reverse transcription and generation of RNA with T7 RNA polymerase was performed as previously described. Transcription of 2'-F RNA was performed in the presence of 1 mM each ATP and GTP (in the presence or absence of α-$^{32}$P-ATP), and 3mM each 2'-F UTP and 2'-F CTP. Transcription proceeded for 5–14 hr at 37° C. followed by gel electrophoretic purification in the presence of formamide and 7 M urea.

SELEX Protocol

A WHHL or control New Zealand white (NZW) rabbit was anaesthetized with isoflorane. The animal was exsanguinated and the aorta from the arch to the diaphragm was dissected. The arterial segment was placed at 37° C. in Hanks solution buffered with 25 mM HEPES (H/H), pH 7.3. The $^{32}$P body-labeled transcript (0.25–1.0 mM) in H/H was incubated with the arterial segment for 45 minutes at 37° C. with gentle agitation. The arterial segment was then washed in the same manner four times with increasing wash buffer volumes as the SELEX continued to increase stringency (Table 11). Wash volumes increased from a total of 4 mL in Round I to 160 mL in Rounds 9 and 10. The plaque-containing segment was then weighed, minced, and the RNA extracted. For rounds 1–3 (in vitro SELEX), regions containing plaque, which was readily apparent by visual inspection, were isolated as a full thickness including the intima, media, and adventitia. The RNA was reverse transcribed, amplified by the polymerase chain reaction (PCR), and transcribed to RNA. This set of procedures constituted one round of SELEX. Five rounds of in vitro SELEX were performed, as indicated in Table 11 (Rounds 1, 2, 3, 9 and 10).

In vivo SELEX

U.S. Pat. No. 60/034,651, filed Jan. 8, 1997, entitled "Bioconjugation by Diels-Alder Cycloaddition", which is incorporated herein by reference, describes RNA polymerase catalyzed transcriptions of DNA templates initiated with a nucleoside or nucleotide bearing a group other than a triphosphate at the 5'-position. In Rounds 4–8 a SELEX the pool was transcribed in the presence of a five-fold excess guanosine aminohexyl phosphate (guanosine 5' monophosphate with a hexyl amine moiety on the 5' position) over guanosine triphosphate in order to efficiently place a unique primary amine on the 5'-end of the transcript. The transcript pool was conjugated with a tripeptidyl 99m-Tc chelate moiety (mercaptoacetyl-glycyl-glycyl-amidyl)-6-hex-1-yl), as described in U.S. patent application Ser. Nos. 08/358,065 and 08/488,290, supra, via N-hydroxy succinamide chemistry. Five nmole of the conjugated pool was labeled with 99m-Tc (radiochemical yield after purification 90–95%) to a specific activity of 1,000 Ci/mmole. The labelled pool was injected into the marginal ear vein of an anaesthetized WHHL rabbit. Ten minute images of the rabbit in the left lateral position were obtain with a Siemans LEM DIFI-TRAC ZLC 10" FOV gamma camera. After 15–65 min the animal was exsanguinated, as indicated in Table 11. The thoracic aorta and arch were isolated and the plaque harvested. For rounds 4–6 (in vivo SELEX), regions containing plaque, which was readily apparent by visual inspection, were isolated as a full thickness including the intima, media, and adventitia. For rounds 7–8 (in vivo SELEX, Table 11) the intima and plaque were stripped from the media and adventitia for processing.

Two additional rounds of in vitro SELEX (rounds 9–10) were performed as described above. The pool was incubated with the arterial segment and the arterial segment was then washed as indicated in Table 11. The plaque-containing segment was then weighed, minced, and the RNA extracted. For rounds 9–10 (in vitro SELEX) the intima and plaque were stripped from the media and adventitia for processing.

B. Results

Figure 7:
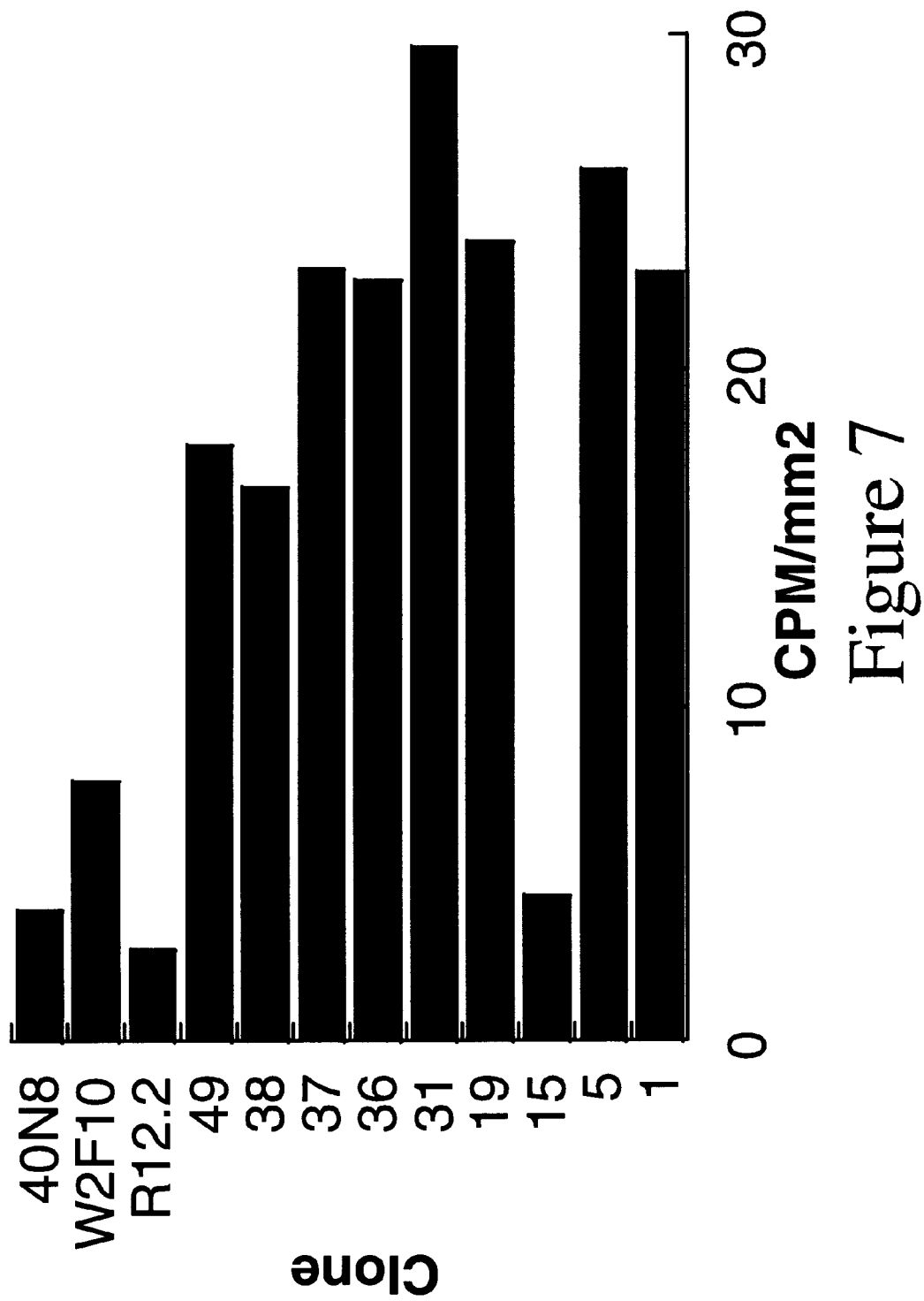
FIG. 7 illustrates the accumulation of radioactive clones from round 10 of a WHHL in vivo SELEX after in vitro incubation with plaque-containing arterial segments presented as CPM/mm$^2$.

The Phospho-Imager images of the aortas from a WHHL rabbit and a New Zealand White (NZW) rabbit after the injection of 5 mCi of Round nine into the marginal ear vein 40 min prior to harvesting, in concert with corroborating in vitro incubation data and RNA pool sequencing data (not shown), supported the conclusion that the initial library had evolved and was ready to sequence. The Round 5 and 10 pools were cloned and sequenced; the sequences from round 10 are provided in Table 12 (SEQ ID NOS: 260–354). From the Round 10 pool, 28% of the sequences were highly related, most likely resulting from a single clone (Family 1; SEQ ID NOS: 260–287). In addition a second family (Family 2; SEQ ED NOS: 288–294) wasidentified containing 7 highly related sequences. None of the remaining 65% of the sequences (Orphans; SEQ ID NOS: 295–354) have been placed into families or, as yet, screened for activity. Members of the Family 1 were screened by in vitro incubation with plaque-containing arterial segments. The aortic segments were incubated with 50 nM of the clone for 30 min at 37° C., followed by 3×40 min washes at 37° C. FIG. 7 shows the results of the screen. All but one of the screened clones had high affinity for the plaque. The non-binding clone was determined to be unrelated to the other clones. Clone 10.31 (SEQ ID NO: 268) was chosen as the lead clone for further analysis.

EXAMPLE 6

In vitro binding of Clones 10.5 and 10.31 to Human Atherosclerotic Plaque Tissue Clones 10.5 (SEQ ID NO: 260) and 10.31 (SEQ ID NO: 268) from Example 5 were assayed in two separate experiments for in vitro binding to human atherosclerotic plaque tissue. Human tissues were obtained from recipients of heart transplants. The vessels were used within three hours of removal from the recipients and were kept oxygenated in Tyrodes buffer until use. In each experiment the arterial segment was placed at 37° C. in Hanks solution buffered with 25 mM HEPES (H/H), pH 7.3. The transcripts were incubated with the arterial segment for 30 minutes, and the arterial segment was washed with 3×40 minute washes.

Figure 8:
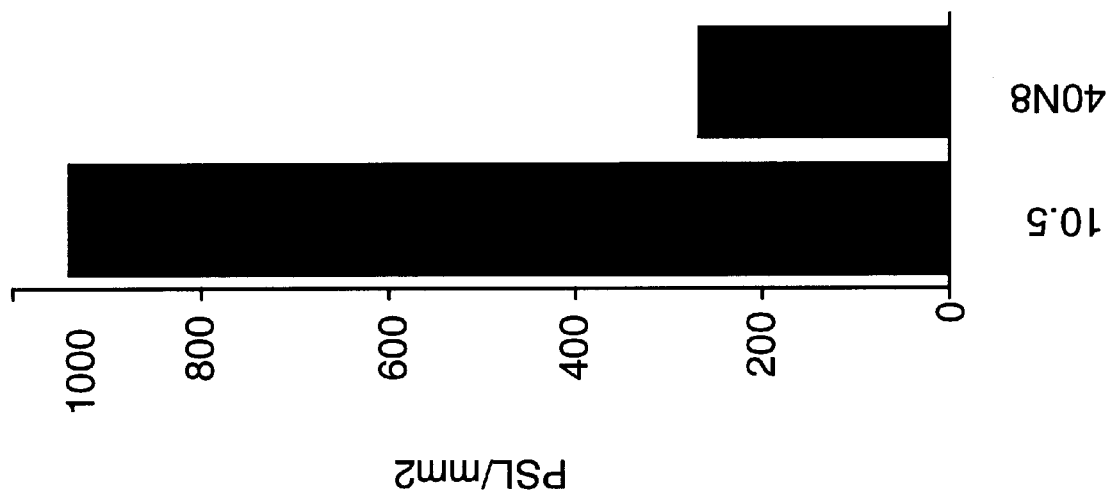
FIG. 8 illustrates accumulation of WHHL clone 10.5 (SEQ ID NO: 260) and the negative control 40N8

In the first experiment, clone 10.5 was compared to 40N8 (the initial unevolved library; SEQ ID NO: 40). FIG. 8 shows binding of family member 10.5 to human plaque-containing coronary artery with 40N8 as the negative control. Clone 10.5 bound ~3.5 times better than the unevolved library.

In a separate experiment with an independently harvested artery from a second subject, 10.31 clone was $^{33}$P labeled. This allowed for higher spatial resolution on the Phospo-Imager and in addition histologic autoradiographic analysis of the binding. Histologic autoradiography of an ex vivo incubation with clone 10.31 and a negative control 10.15 (SEQ ID NO: 348) indicated patchy intense binding at the level of the endothelium or subendothelial matrix with very little diffusion into the tissue. No histological structures could be identified to which 10.31 was binding. This experiment demonstrated that a WHHL Rabbit derived nucleic acid ligand has cross-reactivity to human atherosclerotic tissue.

EXAMPLE 7

Analysis of Clone 10.31 for Plaque Accumulation in WHHL Rabbits after Intravenous Injection Clone 10.31 (SEQ ID NO: 268) from Example 5 was analyzed for plaque accumulation in rabbits. Previous incubation studies indicated that 10–20% of input dose could accumulate in plaque. 3.5 nmole (50 uCi) of clone 10.31 was $^{32}$P body-labeled and injected into a WHHL rabbit via the marginal ear vein. The animal was sacrificed at 60 min and the thoracic aorta was harvested, the arch was removed and the aorta was Phospho-Imaged. The images showed that there was clear accumulation of 10.31 in the plaque areas, which stained red after Oil Red O staining. The ratio of plaqued to non-plaqued vessel accumulation is 5. In one part of the study, tissues were Trizol extracted, isopropanol precipitated, counted and applied to a PAGE gel. FIG. 9 shows the fraction of $^{32}$P ethanol precipitable counts for various tissues after Trizol extraction. Much of the radioactivity is in the form of non-precipitable counts, indicating degradation of clone 10.31. The amount of degradation of 10.31 in the plaque is surprising. Of the radioactivity recovered from the tissue after injection, only 20% is precipitable, but all of this is full-length.

EXAMPLE 8

In vitro Binding, In Vivo Imaging and Biodistribution of 99m-Tc-Labelled 10.31

Clone 10.31 (SEQ ID NO: 268) was transcribed in the presence of a five-fold excess guanosine aminohexyl phosphate over guanosine triphosphate and then conjugated with a tripeptidyl 99m-Tc chelate moiety as described in Example 5 via N-hydroxy succinamide chemistry to give transcripts which were >90% conjugated to the chelate moiety. In this example, the conjugated transcripts were then labeled with 99m-Tc to a specific activity of 5000 mCi/mmole transcript.

In one part of the experiment, 50 nM (0.5 mCi) of 99m-Tc labeled 10.31 (FIG. 15; SEQ ID NO: 355) was incubated in vitro with a WHHL arterial segment for 30 min at 37° C., followed by 3×30 min wash at 37° C. Phospho-Imager images of the arterial segment showed that 15% of the input dose was found in the plaqued artery.

In a second part of the experiment, on the same day, the 99m-Tc labeled 10.31 was injected into another WHHL rabbit for in vivo imaging and biodistribution. The WHHL rabbit was catheterized in the contralateral ear prior to injection of 10.31. 7.5 mCi of 99m-Tc-10.31 was injected into the marginal ear vein. At specific times blood was withdrawn from the catheter and 99m-Tc was quantitated. The rapid clearance of radiolabel from the blood can be seen in FIG. 10. Radiolabel dropped rapidly by 10 min and then stayed constant, not dropping to zero. From the previous Trizol extraction data (Example 7) this basal level does not represent full-length material For the in vivo imaging, ten minute images were obtained until sacrifice at 60 min. The images showed that the uptake of clone 10.31 in the liver is very rapid. The rabbit is different from rats and mice in that over time the liver clears the radiolabel. In the final gamma camera image (50–60 min), the kidney, spleen and bladder had significantly more radiolabel than the liver. In a darker exposure the aortic knob could be visualized. Region of Interest analysis (FIGS. 11A and 11B) indicated that the radiolabel accumulated in the arch very rapidly (within 10 min) and remains for the remainder of the hour. FIG. 12 shows the formal biodistribution data. The accumulation of clone 10.31 in the plaque was 0.015% ID/g.

After the in vivo imaging studies were complete, the animal was sacrificed and the aorta was removed for in vitro imaging. The intact aorta was place on the gamma camera. A strong signal was seen with highest intensity in the arch and a second focus of activity distally. These foci of nuclide accumulation were confirmed to be plaque by Oil Red O and delineated more clearly by the Phospho-Imager.

EXAMPLE 9

Comparison of In vivo Imaging and Biodistribution of 10.31 in WHHL and New Zealand Rabbits A second set of imaging experiments were performed in order to obtain biodistribution data and to assess whether the aortic knob could be seen in the NZW rabbit. This experiment was performed as described in Example 8, except that 5 mCi (1 nmole) 99m-Tc-labelled 10.31 (SEQ ID NO: 355) was injected into both a WHHL and a NZW rabbit. Again a catheter was placed in the contralateral ear vein of the WHHL rabbit prior to injection for withdrawal of blood samples. The overall biodistributions of the radiolabeled 10.31 in the WHHL and NZW rabbits were similar to the Example 8. In the Phospho-Imager images of the thorax of the NZW rabbit, blood is seen early on in the heart which dissipates. At no time is the aortic arch in the NZW rabbit visualized. Phospho-Imager images of the WHHL rabbit showed that more label was retained in the heart. The aortic arch and retrocardiac fullness representing the descending aorta were observed throughout the 60 min. The results of this experiment showed that the region of the aortic arch was clearly visible in the WHHL rabbit but not in the NZW rabbit.

Sixty minutes after IV injection the animals were sacrificed and the aortas were removed for in vitro imaging. The aortas were placed on the gamma camera. The image of the WHHL rabbit aorta showed intense uptake in the arch of the WHHL rabbit. FIGS. 13 and 14 show the biodistribution of 99m-Tc labelled 10.31 in the WHHL (solid bars) and NZW (dashed bars) rabbits. Again, the highest accumulation at 60 min was in the kidneys. 0.038% ID/g label was found in the WHHL arch as compared to half that in the NZW arch. These numbers are higher than seen in the previous example. The differential between normal and diseased artery is less than what was seen in the rat restenotic arteries (Example 4, FIG. 5). Subsequently, the plaque was dissected out. The plaque did not contain more counts on a per gram basis than normal vessel but did show increased accumulation over normal vessel on a per area basis.

EXAMPLE 10

Truncation and Post-SELEX Modifications of WHHL Ligand 10.31

In the progression of development of nucleic acid ligands for clinical applications it is desirable to transform a transcript from an enzymatically generated species to a chemically synthesized one. The first part of this exercise is to reduce the transcript to its minimal binding component, termed truncation. Initially, three truncated analogs of 10.31 (SEQ ID NO: 268) were synthesized by standard techniques on a solid phase automated synthesizer removing the 5'-fixed region (SEQ ID NO: 357), the 3' fixed region (SEQ ID NO: 358), or both the 5'- and the 3'-fixed regions (SEQ ID NO: 356) as shown in FIG. 16. In vitro accumulation of $^{32}P$ radiolabeled polyacrylamide gel electrophoresis purified truncates on WHHL aortic segments by methods described in Example 8 indicated that the 3'-fixed region was not required for binding activity but that some or all of the 5'-fixed region was required. Secondary structure predictions of the truncate without the 3'-fixed region indicated a strong possible structure of 37-nucleotides (FIG. 17). Synthesis and assaying of this molecule, termed alternatively 10.31.37 or Tr104 (SEQ ID NO: 359), confirmed that this was the core binding motif. FIG. 17 details putative secondary structure of the core binding Motif. The 8 base pair stem has been confirmed by NMR with NOSY.

In preparation for in vivo studies, Tr123 (FIG. 19; SEQ ID NO: 360) was synthesized by adding a 5'-pentyl amine and a 3'-3' thymidine cap to Tr104. The 5'-amine is to allow coupling of the 99m-Tc cage as well as pharmacokinetic modulating molecules, while the 3' cap was added to stabilize the molecule from 3'-exonucleases found in vivo. This ligand also bound WHHL plaque as well or better than Tr104 (FIG. 18).

It has previously been shown that post -SELEX modifications of the 2' positions of purines increases the nuclease resistance of an nucleic acid ligand (Green, L. S. et al *Current Biology* 2:683–695, 1995). A set of Tr104 analogs was synthesized in which increasing numbers of the 2'-OH purines were substituted with 2'-OMe purines: Tr128 (SEQ ID NO: 361) has 18 out of 18 purines modified with 2'-OMe. Tr129 (SEQ ID NO: 362) has 15 out of 18 purines modified with 2'-OMe. Tr130 (SEQ ID NO: 363) has 13 out of 18 purines modified with 2'-OMe. Tr131 (SEQ ID NO: 364) has 8 out of 18 purines modified with 2'-OMe. Based on the results shown in FIG. 18 it appeared that at least 13 out of 18 purines (Tr130) could be substituted with 2'-OMe without affecting activity (FIG. 18).

Tr130 became the basis for further 2'-O-methylation studies (FIGS. 20A–H, SEQ ID NOS: 369–376). In vitro accumulation assays indicated that seventeen out of eighteen 2' purine sites could be O-methylated without loss of activity (FIG. 21; Tr159; SEQ ID NO: 375). O-methylating all eighteen sites (Tr128; SEQ ID NO: 360) rendered the aptamer inactive. Further studies indicated that the adenosine at position eighteen required a 2'-OH for the nucleic acid ligand to retain binding activity (FIG. 21).

In order to test the effect of O-methylation on nuclease resistance, selected nucleic acid ligands were $^{32}$P end-labeled and incubated in the presence of fresh heparinized WHHL rabbit plasma. At specified times over a 24 hr period aliquots were removed, diluted and run on a 8% polyacrylamide, 7 M urea gel. Full-length material was quantitated on a Phospho-imager. FIG. 22 shows a plot of three truncates, Tr104, Tr128 and Tr129 (from FIG. 18). After factoring out phosphatase activity (which is not effected by O-methylation) it can be seen that full O-methylation increased the $t_{1/2}$ by 4.2-fold while the partially O-methylated species has 2.5-fold longer $t_{1/2}$. The O-methylated species in which only A-18 is unsubstituted (Tr159; SEQ ID NO: 375) is expected to have intermediate stability between 2.5 and 4.2 times longer than the parent nucleic acid ligand.

In another experiment, selected uridines in truncate Tr104 were substituted with 5-Br-deoxy uridine (5-BrdU). Tr132 (SEQ ID NO: 365) has a 5-BrdU at position 9, Tr133 (SEQ ID NO: 366) has a BrdU at position 16, Tr134 (SEQ ID NO: 367) has a BrdU at position 17, and Tr135 (SEQ ID NO: 368) has a BrdU at position 22. These truncates were radiolabeled and assayed in a manner analogous to the O-methylated nucleic acid ligand truncates. Again it can be seen that the activity of Tr104 is sensitive to modifications in the terminal loop region. BrdU substitution at positions 17 and 22 had significant effects on binding while substitutions at positions 9 and 16 did not.

EXAMPLE 11

Tissue SELEX on human atherosclerotic coronary artery segments

Human coronary arteries were harvested from heart transplant recipients. Heart were transported on ice in oxygenated Tyrodes buffer and used within 3 hr of harvest. 1–3 cm coronary artery segments were canulated with PE tubing in a similar manner to Example 3. A 0.25 to 2.0 micromolar solution of the RNA library 40 N8 in Hanks/HEPES was perfused through the artery in a recirculating mode at 1 ml/min for 30 min, at 25 C. The artery was then perfused with buffer alone without recirculation for an addition 30 min. The artery was opened longitudinally. Plaque containing regions were excised and stripped of media and adventitia. The RNA library was extracted from the plaque in a manner analogous to the rabbit plaque (Example 8). The library was cloned and sequenced after Round 5. Of 64 clones sequenced 19% (12/64) represented the WHHL Family I (Table 12), 1.5% (1/64) represented WHHL Family 2, 11% (7/64) represented a new family, designated huart. 1, 2 sequences were found to exist 3.1% of the time (2/64), and the rest were unique and not grouped into families. Table 13 shows the human artery sequences (SEQ ID NOS: 377–440).

TABLE 1

Summary of Selection Parameters and Data for PBMC SELEX

| Selection | [DNA] nM | [PBMC] cells/µl | [heparin] µM | Filter Type | % PBMC retention | % bkgd retention | DNA/cell |
|---|---|---|---|---|---|---|---|
| 1 | 1,400 | 40,000 | 100 | NC | 3.1 | 0.1 | $6.0 \times 10^5$ |
| 2 | 900 | 120,000 | 100 | NC | 4.7 | 0.3 | $2.0 \times 10^5$ |
| 3 | 800 | 92,000 | 100 | GF | 3.5 | 0.8 | $9.0 \times 10^4$ |
| 4 | 480 | 60,800 | 100 | AN | 1.8 | 0.08 | $8.7 \times 10^4$ |
| 5 | 500 | 52,500 | 500 | NC | 4.6 | 0.3 | $2.2 \times 10^5$ |
| 6 | 990 | 18,300 | 500 | NC | 1.3 | 0.05 | $5.0 \times 10^5$ |
| 7 | 750 | 14,400 | 2,500 | NC | 1.6 | 0.09 | $2.2 \times 10^5$ |
| 8 | 560 | 47,800 | 2,500 | AN | 4.0 | 0.2 | $2.8 \times 10^5$ |
| 9* | 100 | 11,200 | 2,500 | NC | 7.2 | 0.5 | $9.3 \times 10^4$ |
| 10* | 100 | 12,600 | 2,500 | AN | 3.1 | 0.6 | $1.0 \times 10^5$ |
| 11* | 100 | 5,100 | 2,500 | NC | 5.7 | 0.7 | $7.3 \times 10^4$ |
| 12* | 50 | 37,500 | 2,500 + plasma | NC | 2.2 | 0.1 | $2.3 \times 10^4$ |
| 13* | 50 | 75,000 | 2,500 + plasma | AN | 4.9 | 0.3 | $2.2 \times 10^4$ |
| 14* | 10 | 32,000 | 2,500 + plasma | NC | 0.9 | 0.2 | $1.6 \times 10^3$ |
| 15* | 10 | 32,000 | plasma | NC | 3.1 | 0.3 | $2.3 \times 10^3$ |
| 16* | 10 | 112,000 | plasma | AN | 5.6 | 0.5 | $3.1 \times 10^3$ |
| 17* | 10 | 65,000 | plasma | NC | 3.0 | 0.6 | $3.1 \times 10^3$ |
| 18* | 10 | 87,300 | plasma | AN | 4.8 | 0.5 | $4.2 \times 10^3$ |
| 19* | 10 | 118,560 | plasma | AN | 6.0 | 0.5 | $3.3 \times 10^3$ |
| 20* | 10 | 94,560 | plasma | NC | 4.0 | 0.3 | $3.1 \times 10^3$ |
| 21* | 10 | 48,000 | plasma | AN | 7.3 | 0.7 | $5.8 \times 10^3$ |

TABLE 2

PBMC SEQUENCES
Degenerate SsDNA Library
5'-AGGGAGGACGATGCGG-[N]$_{40}$-CAGACGACTCGCCCGA-3' (SEQ ID NO: 1)
  5' fixed         random      3'fixed
   region          region       region

| Ligand | Random region (fixed regions are provided as described above) | SEQ ID NO: |
|---|---|---|
| L49 | GGGGTCGGTTCGGGCATA TAGGG TATTCTTCGTA GAGGG | 7 |
| L8  | GGGGTCGGTTCGGGCATA TAGGG TATTCTTCGTA AAGGG | 8 |
| L35 | GGGGTCGGTTCGGGCATA TAGGG TATCCTTCGTA GAGGG | 9 |
| L1,L34 | CACGT TAGTAGGAT TAGGA TTATTCAGGTTG TAGGG AACA | 10 |
| L29 | CACGTTCAGCAGGAT TAGGG TTGTTTNGGTTG TAGGG ACACA | 11 |
| L18 | CACGG TAGTAAGTAG TAGGG TATTATA AT TAGGG GATCCA | 12 |
| L21 | CACGG CAGTATTATT CAGGG GTCTTAGATAT TAGGG GGCA | 13 |
| L42 | CACGGTAGGTTTTAGA TAGGG ATATTTGGTG TAGGG AGCA | 14 |
| L5  | CACGGTAGGTTATAGA TAGGG ATATTTNTTG TAGGG AACA | 15 |
| L11 | CACGGTAGGTTTTAGA TAGGG ATATTTGATG TAGGG AGCA | 16 |
| L25 | CACGGTAGGTTTTAGA TAGGG ATATTTGGTA TAGGG AGCA | 17 |
| L36 | CACGGTAGGCTTTAGA TAGGG ATATTTGATG TAGGG AGCA | 18 |
| L26 | GGGGAG TAGGG TATTTAAAAATGT TAGGG TAAGTTTCCTC | 19 |
| L10 | GGGGAG TAGGG TATTTAAAAGTGT CAGGG TAAGTTTCCTC | 20 |
| L7  | CGTAGTAAGAAGTATTAT TAGGG ATATTG TAGGG GCGCTA | 21 |
| L22 | CGTAGTAAGAAGTATTAT TAGGG ATATTG CAGGG GCGCTA | 22 |
| L43 | GGCAGCAAGA GTTTGAT TAGGG TATAGT TAGGG GCGCTG | 23 |
| L19 | GCAGCAAGA GTTTGAT TAGGG TATAGT TAGGG GCGCTGC | 24 |
| L41 | GCAGTAAGG GTTTGAT TAGGG TATAGT TAGGG GCGCTGC | 25 |
| L46 | GCAGCAAGAGG TTGAT TAGGG TATAGT TAGGG GCGCTG | 26 |
| L20 | CGGCAAGATGATTGAA TAGGG GATCTAAAGT TAGGG GCGC | 27 |
| L6  | GCAGCAGG TG TAGGG GTATAGATGGA TAGGG ATTTCTTCT | 28 |
| L28 | CACA TAGGG GAAATGA GAATAG TAGGG TATTAATACAGTG | 29 |
| L38 | CACA TAGGG GAAATGA GAAGAA TAGGG TATTAATACAGTG | 30 |
| L50 | CAGGT TAGGG GAAAGGTTTAATAAT TAGGG TATAAAT GTG | 31 |
| L14 | CAGGTAGAGA TAGGG AAGTTTTATG TAGGG GACAATTCGT | 32 |
| L44 | CAGGTAGAGA TAGGG AAGTTTTATG TAGGG GACAATTCGT | 33 |
| L31 | CACAA TAGGG AAATTT GTTGTTATAGT TAGGG ATACTGGA | 34 |
| L40 | GGCCGAA TAGGG AAATTTA TTATTACT AACAGTAATCCCC | 35 |
| L48 | CAGGACT TAGGG ATTTAGTTGTTT TAGGG GTTATGTAGT | 36 |
| L9  | GGGGGGATGAGAGATGTAATCCACATGTCACTTATTAAGTCC | 37 |
| L12 | CAGGGGATGGATGTAATCCTCATGTCACTTATTAAGTCC | 38 |
| L13 | TACGACTACGATTGAGTATCCGGCTATAATATTACCATTG | 39 |

TABLE 3

Sequences and Affinities of Selected PBMC Ligands

| LIGAND | SEQUENCE OF RANDOM REGION | AFFINITY (PBMC/ml) | SEQ ID NO: |
|---|---|---|---|
| DNA-0 | Degenerate DNA Library | 43,500 | 1 |
| DNA-21 | Enriched DNA Library | 1,000 | |
| L1  | CACGTTAGTAGGATTAGGATTATTCAGGTTGTAGGGAACA | 3,000 | 10 |
| L7  | CGTAGTAAGAAGTATTATTAGGGATATTGTAGGGGCGCTA | 700 | 21 |
| L14 | CAGGTAGAGATAGGGAAGTTTTATGTAGGGGACAATTCGT | 1,200 | 32 |
| L26 | GGGGAGTAGGGTATTTAAAAATGTTAGGGTAAGTTTCCTC | 800 | 19 |
| L28 | CACATAGGGGAAATGAGAATAGTAGGGTATTAATACAGTG | 2,400 | 29 |
| L31 | CACAATAGGGAAATTTGTTGTTATAGTTAGGGATACTGGA | 1,800 | 34 |
| L42 | CACGGTAGGTTTTAGATAGGGATATTTGGTGTAGGGAGCA | 1,100 | 14 |

TABLE 3-continued

Sequences and Affinities of Selected PBMC Ligands

| LIGAND | SEQUENCE OF RANDOM REGION | AFFINITY (PBMC/ml) | SEQ ID NO: |
|---|---|---|---|
| L43 | GGCAGCAAGAGTTTGAT<u>TAGGG</u>TATAGT<u>TAGGG</u>GCGCTG | 700 | 23 |
| L49 | GGGGTCGGTTCGGGCATA<u>TAGGG</u>TATTCTTCGTA<u>GAGGG</u> | 400 | 7 |
| L9 | GGGGGGATGAGATGTAATCCACATGTCACTTATTAAGTCC | 15,400 | 37 |

TABLE 4

Serum Clot SELEX 2'F-40N8-RNA

| Round | Method | [Clot] | [RNA] | [NaCl] | Wash | Volume, ml | % bound | Yield, pm | Background |
|---|---|---|---|---|---|---|---|---|---|
| FC | | | | | | | | | |
| 1 | clot incubation | 500 ul plasma | 4.00E-06 | 125 mM | Buffer | 0.5 | 1 | 26 | |
| 2 | clot incubation | 500 ul plasma | 4.00E-06 | 125 mM | " | " | 0.66 | 12.3 | |
| 3 | clot incubation | 500 ul plasma | 1.90E-06 | 125 mM | " | " | 0.18 | 1.6 | |
| 4 | clot incubation | 500 ul plasma | 4.00E-06 | 125 mM | " | " | 0.18 | 3.5 | |
| 5 | clot incubation | 500 ul plasma | 4.00E-06 | 125 mM | " | " | 0.37 | 7.8 | |
| 6 | clot incubation | 500 ul plasma | 4.00E-06 | 125 mM | " | " | 2.9 | 50 | |
| 7 | clot incubation | 500 ul plasma | 4.00E-06 | 125 mM | " | " | 6.2 | 81 | |
| 8 | clot incubation | 500 ul plasma | 3.00E-06 | Hep. Plasma | " | " | 9 | 67 | |
| 9 | clot incubation | 500 ul plasma | 4.00E-06 | Hep. Plasma | " | " | 4 | 53 | long wash |
| 10 | clot incubation | 500 ul plasma | 2.90E-06 | Hep. Blood | " | " | 7.9 | 70 | |
| 11 | clot incubation | 500 ul plasma | 4.00E-06 | Hep. Blood | " | " | 2.5 | 46 | |
| FCN | | | | | | | | | Counter-SELEX |
| 7 | clot incubation | 500 ul plasma | 5.40E-06 | Hep. Plasma | Hep. Plasma | 0.5 | 0.7 | 20 | 0.025 mM fibrinogen |
| 8 | clot incubation | 500 ul plasma | 1.93E-06 | " | " | " | 1.3 | 8.6 | " |
| 9 | clot incubation | 500 ul plasma | 2.47E-06 | " | " | " | 1.4 | 15 | " |
| 10 | clot incubation | 500 ul plasma | 6.00E-07 | " | " | " | 2.3 | 4.7 | " |
| 11 | clot incubation | 500 ul plasma | 2.00E-06 | " | " | " | 2.6 | 20 | " |
| 12 | clot incubation | 500 ul plasma | 3.80E-07 | " | " | " | 1.8 | 14 | " |
| 13 | clot incubation | 500 ul plasma | 1.80E-06 | " | " | " | 1.9 | 12 | " |
| 14 | clot incubation | 500 ul plasma | 2.10E-06 | " | " | " | 5.1 | 41 | " |

TABLE 5

Fibrin-Binding Clones

| FINAL CLUSTERS | | SEQ ID NO | In Vitro Clot Binding | Fibrinogen Affinity | Bindin PE Assay |
|---|---|---|---|---|---|
| FC1 | AGGGCUCGUGUGCCAAAUCGCUAACAAC-AAGCUAGCUGAU | 43 | o | | |
| FCN54 | CUGGGCUCAUCCGGCGAAU-GAUG-CAAGGAAGAUUUCACAU | 44 | o | | % | score 0.365079

TABLE 5-continued

Fibrin-Binding Clones

| FINAL CLUSTERS | | SEQ ID NO | In Vitro Clot Binding | Fibrino- gen Affinity | Bindin PE Assay |
|---|---|---|---|---|---|
| FC3 | AAGGA-UAG-UGUGCU--CCUGUA--CCAAAUUUCCAAAGCGAUAU | 45 | ○ | | |
| FC73 | AAAGAGUAA---AGCG--CG-GAA--CAGGAUUCACGUUGCGCUCUU | 46 | ○ | | |
| FC75 | AAAGAGUAA---AGCG--CG-GAA--CAGGAUUCACGUUGCGCUCA | 47 | ○ | | |
| FCN6 | CAACGAUUAUCUUUUCGGCCGUGAAACCCAAACUGACGCC | 48 | ○ | % | |
| score 0.292824 | | | | | |
| FC4 | CGCGAGGAUAGGGUG--CAGCUUCUGUUCCAAAUACGUGA-AU | 49 | * | | |
| FC12 | UAAGUCGAAGAGCUCCUGAUCCAAACCAUCGA-AAG-GACGU | 50 | ○ | | |
| FC28 | GG-UAAGUUG--GAGCUCCUUAUCCAAGCACGCAAUAAGUGAC | 51 | ○ | | |
| MOTIF II score 0.355556 | | | | | |
| FC6 | UUUGGCGU-GG-GAU-CCUGGA-CUGAAGG--AUUUGACGAUGC | 52 | ○ | | |
| FC45 | AUUCAAGACA-GA-GAC-UUUCCU-U-GAA--U-GCUCUGUCCCAUAA | 53 | | | |
| FC54 | ACAAAUGU-GC-GAC-CUUGGA-C-GAAGUUAACUCGGACGGUUC | 54 | ○ | | |
| FC69 | ACAAAUGU-GC-GCC-CUUGGA-C-GAAGUUAACUCGGACGGUUC | 55 | * | % | $ |
| FC72 | ACAAAUGU-GC-GCC-CUUGGA-C-GAAGUUAACUCGGACGGUUG | 56 | * | % | |
| FCN16 | ACAAAUGU-GC-GCC-CUUGGA-C-GAAGUUAACUCGGACGGUUC | 57 | ○ | % | |
| FCN19 | AAGUCU-GA-GACUCCUGGA-CUGAA-UUAGCUAGGACGGCUG | 58 | • | % | $ |
| FCN30 | UAGGAGCCUAGCAGCC-CCUGCAUC-GA----UCACUAGGAUGGUU | 59 | * | % | $ |
| FCN38 | AAAGUGUAGC-CUU-CCUGGA-CUGUAGGU-ACUAGGACGGUCC | 60 | * | % | @ |
| FCN44 | ACAAAUGU-GC-UCC-CUUGGA-C-GAAGUUAACUCGG-CGG | 61 | * | % | $ |
| FCN55 | AAGAAGCUG-GC-GAC-AGGCGA---AAAGCAGACU-UGAGGGAA | 62 | ○ | % | @ |
| FCN72 | AGUAG-GU-GA-GGCUUCUGGA-CUGAAG-UAACUAGGUCGGUUC | 63 | * | % | @ |
| score 0.339752 | | | | | |
| FC8 | CAUGA-GCUGCUGGACCAAA-CAGAUG-GAGG---AACCA-CCGUGU | 64 | * | | |
| FC39 | GA-GCU-CUUGACGAAAACCUAUGCGAGAUGGAUACU-CGGUU | 65 | | | |
| FC40 | GA-GCU-CUUGACGAAAACCUAUGCGAGAAGGAUACU-CGGUU | 66 | | | |
| FC41 | GA-GCU-CUAGACGAAAACCUAUGCGAGAUG-AUACU-CGGUC | 67 | ○ | | |
| FC55 | UGA-GCU-CUUGAAGAAGUCC-----GAAC---AUUCUCCUUUCUGCGACU | 68 | ○ | | |
| FC64 | GA-GCUCCGGGAUCCAAGCG--UGCAACA---ACACU-AUGCCCAC | 69 | ○ | | |
| FC65 | AAUAC-CCU-CGGGAACCAAUCC-----GACCCU-AUUUUGCAGUUUG | 70 | * | | |
| FCN59 | AUGAUGCU-CCUGAAGUAAUCACCAG-GAC----AUCCU-CGGCAU | 71 | ○ | % | |
| FC9 | GCAAU--CU-CGGACUAGACCAACGACCUUCGUUUGACGCUC-A | 72 | ○ | % | @ |
| FC18 | CCGAUUU--CU-AGGACG-GAUUUACG---GAGAAUUGAGUCGC-AAG | 73 | ○ | | |
| MOTIF I score 0.262803 | | | | | |
| FC38 | A-CGG-CGAGAAUGACAAU-GUUAUUCUACGAGCGAAGGAUUA | 74 | | | |
| FC50 | GCAAU--CU-CGGACUAGACUAACGACCUUGGUUUGACGCUA-A | 75 | * | # | $ |
| FC51 | GCAAU--CU-CGGACUAGACUAACGACCUUCGUUUGACGCUC-A | 76 | * | # | $ |
| FC60 | AGAGCAGCCGGAGGUGUGAGCUCUGACUCUG-AACAGCUG | 77 | ○ | | |

TABLE 5-continued

Fibrin-Binding Clones

| FINAL CLUSTERS | Sequence | SEQ ID NO | In Vitro Clot Binding | Fibrinogen Affinity | Bindin PE Assay |
|---|---|---|---|---|---|
| FC76 | CGGGAUUU--CU-CGGAAAAGACUAACGAC--UAAUUCCAGAACC | 78 | ○ | | |
| FCN11 | GCAAU--CU-CGGACUAGGCUAACGACCUUUGUUUGACGCUC-A | 79 | * | # | |
| FCN14 | GCAAU--CU-CGGACUAGACUAACGACCUUCGUUUGACGCUU-A | 80 | * | # | $ |
| FCN26 | UC--CA-AGGACCAAACGGGUGUUCGGCAGUGGACU-UU-AGCAA | 81 | ○ | # | |
| FCN28 | UGGGCUAC--AU-GUGAGUACACCAGCGUGAGAGUUCUUAGG | 82 | ○ | # | |
| FCN29 | CUGUGCAGUAACUGCGGAUGAGACCAACCGG-AUGGCUCAAC | 83 | • | # | |
| FCN57 | ACAAU--CU-CGGACUAGACUAACGACCUUCGUUUGACGCUU-A | 84 | * | # | |
| FCN61 | GCAAU--CU-CGGACGAGACUAACGACCUUCGUUUGACGCUU-A | 85 | * | # | |
| FCN65 | AGCGCUAGAUGGACGAGAGACUUUUAAGUAGC-AAGCGGUA | 86 | * | # | |
| score 0.274690 | | | | | |
| FC10 | CAGACUCAGAGCGCCGUGAGCUUCUGAAG-CAA--UCGCAGGU | 87 | * | # | |
| FC53 | G-CGGGGAGCUCCUCGAGAAACUGAGUUCAACUUCCCAGGU | 88 | ○ | # | |
| MOTIF III score 0.387597 | | | | | |
| FC14 | GUGUUGGAGCUCUUGAUUGGAAAAG--UAGA--ACAAAUCGAAA | 89 | * | # | $ |
| FC30 | GUGUUGGAGCUCUUGAUUGGAAAAU--UAGA--GCAAAUCGAAA | 90 | * | # | $ |
| FC49 | CAAUCCGAGCUCUUGAA-GCAAUCC--UUGAUUGCAAGAUGAU | 91 | ○ | | |
| FC52 | UCGGAUG-AGCUCUUGAA-GCAGUUC--AAGG--ACAGACAUAAAG | 92 | * | | |
| FC59 | UUCCAGGU-UAGCGGCCAAACC--UCGA-CUUGAACAGACUUUA | 93 | ○ | | |
| FC70 | GUGUUGGAGCUCUUGAUUGGAAAAG--UAGA--GCAAAACGAAA | 94 | * | # | $ |
| FC74 | GUGUUGGAGCUCUUGAUUGGAAAAG--UAGA--GCAAAUCGAAA | 95 | * | # | $ |
| FCN2 | GUGGUGCUGCAAUUGCUCGGUCGGC--GUGCUCUCUACUUGA | 96 | | | |
| FCN3 | GCUCAAGAGACUGAA-GGAAAAGCUUAGAGCUCAAAGC-AUA | 97 | | | |
| score 0.306520 | | | | | |
| FC22 | CGUGUUGGGUUCAAAGACCAGCUUACGGUACACAGUACGA | 98 | ○ | | |
| FCN31 | UC-UGUUGG-UUCAAAGACUUGCUAAGGGGUCGAAGCACCCU | 99 | * | / | |
| score 0.492063 | | | | | |
| FC24 | GAC-GACAAAG-AGUCCGUUC-CAAACCUC-UGAGACAGGGU | 100 | ○ | | |
| FCNB | U-AGCAAGUCCCACAUCCCAGACGGG-CUAAAAAGAGGUGGA | 101 | ○ | % | |
| FCN18 | AUGAAC--GACCGCGG--GCAGUCGCGU-UCAAAUGAG-UGGUUUU | 102 | • | % | |
| FCN24 | AUGAGUA-GACCGAGGAAGCACCCGGCUCUCAAAUGAG-UGA | 103 | * | / | |
| FCN64 | AUGAGUA-GACCGAGGAAGCACCCGGCUCUCAAAUGAC-UGA | 104 | ○ | / | |
| score 0.294667 | | | | | |
| FC25 | AAGGCC-AU--CAGGGCAAAGACCUCCUAGGUACUGA-CGCUUA | 105 | ○ | | |
| FC34 | AAGGCCGAA--CAACGAAGUUUGAUUC-AGGUACUCAGCG-UUC | 106 | ○ | % | |
| FC35 | AAGGCCGAA--CAACGAAGAUUGAUUC-AGGUACUCAGCG-UUC | 107 | ○ | | |
| FCN34 | AAGGCGGAGGGCAAGCAAGA-ACCU-C-ACGAACAGA-CG-UUAA | 108 | • | | |
| score 0.428395 | | | | | |

TABLE 5-continued

Fibrin-Binding Clones

| FINAL CLUSTERS | | SEQ ID NO | In Vitro Clot Binding | Fibrino-gen Affinity | Bindin PE Assay |
|---|---|---|---|---|---|
| FC33 | AGCCUGAGGUAUAGUU---ACG-CU-AUAUGGGA--GGUAGGCUUUA | 109 | * | | |
| FCN13 | CGUGAUG-ACAGCUCGGACGGCUCAU-UGCGCGGAGUAG-CUA | 110 | * | % | @ |
| FCN56 | CGGCUCGAUG-CUAGCUGGGACGGCUCAU-UGAGACUGGUUG | 111 | • | % | |
| score 0.324074 | | | | | |
| FC42 | AGUGCAACCU-GAACCAAACCAAACUAGCGCGCAGUUGGGU | 112 | o | | |
| FCN36 | AGCAGAUGGUGCUGAGGUAU-CAU-GAAGACGCUGAC-GCUUA | 113 | • | / | |
| FCN49 | GAAUGGAGCCAAGAAAGACAGCGAUGUCUCGGAC-GAUGAG | 114 | o | % | |
| FCN50 | GAAUGGAGCCAGGAAAGACAGCGAUGUCUCGGAC-GAUGAG | 115 | * | / | |
| FCN58 | GGAUGGAGCCAAGAAAGACAGCGAUGUCUCGGAC-GAUGAG | 116 | o | % | |
| FCN67 | CGUG-AGAUUCCCCUGCGUAAGACCA-GAAGACUAUCAG-GCU | 117 | | | |
| score 0.335225 | | | | | |
| FC43 | AGGGUUGAGGCUUAUCCUUCUUUCGUUCGUGACACGAUCG | 118 | * | | |
| FCN69 | GAUUGACACGCA--CUCCAAUGGCUC-UGAAGUGUUCGUGUGC | 119 | • | % | |
| score 0.296296 | | | | | |
| FC46 | AAAUUCAAUGCUCUGAUGGGUUUAUGAGUUAAUGCGU-GGAC | 120 | o | | |
| FC61 | AAAGGCCCU-UUCAGCAGGGAUC--GAGGUACUGGAU-GGAUA | 121 | o | | |
| FCN27 | AAAGUCG-UGUGC-GAGAGGCUCA-GAUUUAAUGCGGAGGA | 122 | o | % | |
| score 0.343669 | | | | | |
| FCN9 | CGUU-GAAAUCGCUCCUCAGU-G-UGAGUUGAAUCAGCUGACC | 123 | • | % | |
| FCN21 | AGUUUGGAUUCG-GCAGGUGCUG-AGACUUUGAU-AGCC-ACUA | 124 | • | % | |
| FCN22 | GUGAGAAAU-G-UCGGGGC-GAUGACUUGGA-CGGUCCACCG | 125 | • | | % |
| FCN60 | CGUU-GAAAUCGCUCCUCAGC-G-UGAGUUGAAUCAGCUGACC | 126 | | | |
| score 0.376263 | | | | | |
| FCN12 | AGAGAGGAACUGCGAUUCAGACCAAAACGGA--AAUGGCUGU | 127 | • | % | |
| FCN25 | GAUAUACUAACUUUCUUUGAAAGCCAAAAGUAUUAAUG-CG | 128 | * | % | |
| FCN48 | GAUAUACUAACUUUGUUUGAAAGCCAAAAGUAUUAAUG-CG | 129 | * | / | $ |
| FCN52 | AGCCGAGCUAAUCCCGAAAGUGACCCGGAACGACG-CGGCA | 130 | o | % | |
| score 0.363636 | | | | | |

TABLE 5 KEY
o-low in vitro clot binding
•-moderate in vitro clot binding
*-high in vitro clot binding
%-low fibrinogen affinity, Kd > 1 mM
/-moderate fibrinogen affinity
-high fibrinogen affinity, Kd < 1 mM
@-low binding PE assay
$-high binding PE assay

TABLE 6

| Truncation Analysis | SEQ ID NO: |
|---|---|
| FC #69                                                                boundary | |
| gggagacaagaauaaacgcucaaACAAAUGUGCGCCCUUGGA<u>CGAAGUUAACUCGGACGGUUC</u>uucgacaggaggcucacaacaggc | 55 |
| 69.1 (25)                              CGAAGUUAACUCGGACGGUUCuucg | 131 |
| 69.2 (29)                              CGAAGUUAACUCGGACGGUUCuucgacag | 132 |
| 69.3 (29)                         UGGACGAAGUUAACUCGGACGGUUCuucg | 133 |
| 69.4 (41)                    CCCUUGGACGAAGUUAACUCGGACGGUUCuucgacaggagg | 134 |
| FCN #30                                                               boundary | |
| gggagacaagaauaaacgcucaaUAGGAGCCUAGCAGCCCCUGCA<u>UCGAUCACUAGGAUGGUU</u>uucgaaggaggcucacaacaggc | 59 |
| N30.1 (23)                              UCGAUCACUAGGAUGGUUuucga | 135 |
| N30.2 (30)                              UCGAUCACUAGGAUGGUUuucgacaggagg | 136 |
| N30.3 (31)                          CCCCUGCAUCGAUCACUAGGAUGGUUuucga | 137 |
| N30.4 (38)                          CCCCUGCAUCGAUCACUAGGAUGGUUuucgacaggagg | 138 |

```
                    A-C                                    C-U
5'-C-G-A-A-G--U-U-A     U           U-C-G-A--U-C-A     A
3'-g-c-u-u-C  G-G-C     C           a-g-c-u  G-G-U     G
              UU      A-G                   uUu      A-G
              69.1(25)                      N30.1 (23)
```

TABLE 7

Rat Carotid Artery SELEX

| Round | Method | Buffer | [2'F40N8], uM | % bound | Discrimination injured/norm |
|---|---|---|---|---|---|
| Ex Vivo | | | | | |
| 1 | minced | Ringers lact. | 5 | 6.7 | n.a. |
| 2 | minced | Ringers lact. | 2 | 2.7 | n.a. |
| 3 | minced | Ringers lact. | 3.4 | 6.9 | n.a. |
| 4 | perfused. inj. | Ringers lact. | 2.5 | 0.2 | n.a. |
| 5 | perfused. inj. | Ringers lact. | 5.9 | 0.6 | n.a. |
| 6 | perfused. inj. | Ringers lact. | 2.3 | 0.62 | n.a. |
| 7 | perfused. inj. | Ringers lact. | 2.3 | 0.7 | n.a. |
| 8 | perf. normal | Ringers lact. | 0.75 | 0.54 | |
|   | injured | Ringers lact. | 0.75 | 1.04 | 1.9 |
| 9 | perf. normal | PBS | 0.75 | 0.02 | |
|   | injured | PBS | 0.75 | 0.07 | 3.3 |
| 10 | perf. normal | PBS | 0.75 | 0.1 | |
|    | injured | PBS | 0.75 | 0.5 | 4.5 |
| 11 | perf. normal | PBS | 0.75 | 0.1 | |
|    | injured | PBS | 0.75 | 0.35 | 3.4 |
| 12 | perf. normal | PBS | 0.75 | 0.1 | |
|    | injured | PBS | 0.75 | 0.34 | 3.4 |
| In Vivo | | | amount injected, nmoles | | |
| 13 | in vivo | PBS | 3 | 0.01 | 2.61 |
| 40N8(control) | in vivo | PBS | 3 | n.a. | 1.16 |
| 14 | in vivo | PBS | 3 | 0.02 | 4.06 |
| 15 | in vivo | PBS | 3.8 | 0.02 | |
| 15 | ex vivo | PBS | 3.8 uM | n.a. | 0.94 (not flushed) 4.61 |
| 16 | in vivo | PBS | 3.9 | 0.005 | 3.54 |

TABLE 8

| MOTIF I | FINAL CLUSTERS | SEQ ID NO | INTENSITY OF STAINING | BINDING SPECIFICITY |
|---|---|---|---|---|
| p3 | gggagauaaga-auaa-acgcu-caa | 139 | | |
| p5 | uucgacaggaggcucacaacaggc | 140 | | |

TABLE 8-continued

| MOTIF I | FINAL CLUSTERS | SEQ ID NO | INTENSITY OF STAINING | BINDING SPECIFICITY |
|---|---|---|---|---|
| C4 | ACCA-CUGGGC-CCAG-UUUAG-AAA---CU-CAUU---GCCCAAAUCCGG | 141 | | |
| C13 | AAG--AAGA-AUCG-AAAAAUCUAC--CUUGUUC-GGAGCCUGCUCU | 142 | + | ns |
| C15 | U-CUAG-AC-AG-CGAAGGCUGAGCUAUGACACUGAACUUCUUA | 143 | − | |
| C22 | GCAAUCU-GGA-CUAG-ACUAA-CGAC--CUUC<u>GUU-UG</u>ACGCUCA | 144 | | |
| C26 | GCAAUCUCGGA-CUAG-ACUAA-CGAC--CUUC<u>GUU-UG</u>ACGC--AAU | 145 | | |
| C33 | GCAAUCUCGGA-CUAG-ACUAA-CGAC--CUUC<u>GUU-UG</u>ACGCUCA | 146 | ++ | s |
| C38 | GCAAUCUCGGA-CUCG-ACUAA-CGAC--CUUCGUU-UGACGCUCA | 147 | | |
| C53 | GACAAUAACCGC-----ACCAA-CGUU--CU---GUU-CUUCGCUUGCACGU | 148 | − | |
| C57 | CAAU-UCCCA-CU-G-AUUCG-GGGC--GGUCCUUGCGAUGGCGAGA | 149 | | |
| C59 | CUCAGA-CAACCAACAG-CA-C--GUUC-UC-UGUU-UUCGUC<u>GUUUG</u> | 150 | +++ | s |
| C60 | GCAAUCUCGGA-CUAG-ACUAA-CGAC--CUUC<u>GUU-UG</u>ACGCUUA | 151 | | |
| C72 | GCAAUCUCGGA-CUAG-ACUAA-CGAC--CUUC<u>GUU-UG</u>ACGCUCG | 152 | | |
| Civ3 | CGCU-CAUG-ACCAGGCGCUA-CUGACUG-AGAUGUUGAACUUA | 153 | − | |
| Civ14 | GCAAUCUCGGA-CUAG-ACUAA-CGAC--CCUC<u>GUU-UG</u>ACGCUCA | 154 | | |
| Civ27 | AUAAGAUCAAC-AUUGG-CG----GUU--UA-UGUUAUUCGUCCGUUUG | 155 | | |
| Civ30 | GCAAUCUCGGA-CUAG-ACUAA-CGAC--CUUC<u>GUU-UG</u>ACGCUUA | 156 | | |
| Civ34 | CACGCGAGAG-CU---UCUAA-AGCU--GCUGAAU-CGA-GCUCCACGA | 157 | | |
| Civ41 | ACAAUCUCGGA-CUAG-ACUAA-CGAC--CUUC<u>GUU-UG</u>ACGCUUA | 158 | +++ | ns |
| Civ42 | GCAAUCUCGGA-UUAG-ACUAA-CGAC--CUUU<u>GUU-UG</u>ACGCUCA | 159 | | |
| Civ48 | GCAAUCUCGGA-CUAG-ACUAA-CGAC--CUUCGUA-UGACGCUUA | 160 | | |
| Civ50 | GCAAUCUCGGA-CUAG-ACUAA-CGAC--CUUCGCU-UGACGCUCA | 161 | | |
| Civ53 | GGAGAUCCUCGA-GGAA-ACU---CGAA--CUUCUUCCCGACGUUGA | 162 | | |
| Civ59 | ACAGCUCGGA-UAAG-ACUAA-CGAC--CU-A<u>GUU-UG</u>--GCUAAGCAA | 163 | ++ | ns |
| Civ65 | GCAAUCUCGGA-CUAG-ACUAA-CGAC--CUUC<u>GUU-UG</u>ACGCUCA | 164 | | |
| score 0.268867 | | | | |
| C1 | ACAAGGGAGUCGGUUUAU-UCAGCCUG-UUCGGAACCUGACU | 165 | + | ns |
| C44 | AUCCAAGACGCUUAGU---UCUUGCUC-UUCGGGGCUUC-CUA-CG | 166 | | |
| C45 | AAGUAAACUCGAGACCGUUCUGGCUGAUUCGGGGC-ACUCU | 167 | | |
| C55 | ACUUGACAA-UCCCCCUGAUUCGGGGCCUGACUAUCACGA | 168 | ++ | ns |
| C58 | ACACGACA-UCGAAGUUA-UCCCCCUGAUUCGGAGCCAG-CUG | 169 | − | |
| C65 | AGCUGGAAA-UCCAAAUGC-UUUGUCUAGUU-GGGGC--CACUU | 170 | | |
| C67 | AGACUCUUGAUCA-UCCCCCUAGUUCGGGGC-UGACUG-CACU | 171 | | |
| Civ6 | ACUUGACAA-UCCCCCUGAUUCGGGGCCUGACUAUCACGAU | 172 | | |
| Civ24 | GGAGCGAAAUUCUUGAAUA-UCC-ACUGAUUCGGACCGUC-CU | 173 | − | |
| Civ29 | GCGGGAUUUUCCUGAUCA-UCCCACUGAUUCGGGGCCUUAG | 174 | | |
| Civ31 | AGUUUCUCCUUGGCAA-UCCCCCUAUUCGGGGCUUCAUUG | 175 | | |
| Civ55 | GAGCGAAAUUCUUGAAUA-UCC-ACUGAUUCGGAGCGUC-CU | 176 | | |

TABLE 8-continued

| MOTIF I | FINAL CLUSTERS | SEQ ID NO | INTENSITY OF STAINING | BINDING SPECIFICITY |
|---|---|---|---|---|
| Civ56 | ACGGCAUUCUAAACAU-UCCCCCUUGUUCGGAGCCACUCU | 177 | | |
| Civ62 | GCGGA-UUUUGAUCA-UCCCCCUGAUUCGGAGAC-CUCUUAC | 178 | − | |
| score 0.286720 | | | | |
| C3 | GGGAACGAAUCGUCCAAAA--GA-CCUCGCGGAAUCGGC-G-UUA | 179 | + | ns |
| C17 | GCGAGCUCUU-GCACAAAACCGAUCCUCGC--AUACAGCAGGU | 180 | − | |
| C30 | GGGAACGAAUCGUUCAAAA- -GA-CCACGCG-AAUCGGC-GCUUA | 181 | | |
| score 0.441975 | | | | |
| C10 | GAGCUGUUGACGAAAACUUAUGCGGAGAU--GGAUA-CUCGGU | 182 | + | s |
| C27 | GAGCUCUUGACGAAAACCUAUUCG-AGAU--GGAUA-CUCGGUU | 183 | | |
| C35 | GGAGCCGAUUG-UACAACCUAGGUG-AGCU----CAAU-CACCUCGC | 184 | | |
| C36 | GGGCCCUCUGCUACAACUUCGGCA-AGGA----CAUU-UUCCGGAC | 185 | | |
| C37 | GAGCUCUUGACGAAAACCUAUGCG-AGAU--GGAUA-CUCGGUU | 186 | + | ns |
| C49 | GAAAGC-CAUGUUGAAAGUUUCACCC-AGAUUCGGA---GUCGUUG | 187 | ++ | ns |
| C62 | ACUGAGCUCGUGU--ACAA--UGUUAG-GGAA--GGACAUCUCGAUA | 188 | | |
| C66 | GAGCUCUUGACGAAAACCUAUGCG-AGAA--GGAUA-CUCGGUU | 189 | | |
| C69 | GAGCUCUUGACGAAAACCUACGCG-AGAU--GGAAA-CUCGGUU | 190 | | |
| Civ32 | CACAGGGGUUUC---AAACCUCCCCC-UGAUUCGGAGC-UUC | 191 | | |
| Civ38 | AACCUCGCCAGGAAUAACU-UGCG-ACUUUCGGAUC-GUCUUA | 192 | + | ns |
| Civ54 | GAGCUCUUGACGAAAACCUAUGCG-AGAU--GGAUA-CUCGGUU | 193 | | |
| Civ64 | CUUUGGAGCUCCUGG----AACGAAAGCG-GAAU---UAAC-UUCCUUA | 194 | | |
| score 0.303419 | | | | |
| C11 | ACAAUUCAGGACGGGG---UUUCUU---GAAUG--GGUUCGACCUU-CA | 195 | | |
| C52 | CCAGUA-GAUCAA-CUCCCUGGCAACU---GGUUCGCCGUUAUA | 196 | | |
| Civ5 | A-CCUUGAUGUUCA--CUCCCU---AACUCAAGGUUCGACGUC-UA | 197 | | |
| Civ33 | ACAA-CCUGGACAAGGAAUUUUUCU----AGUGUUCGUUGGACGU | 198 | ++ | s |
| Civ35 | A-CCUUGAUGUUGAA-CUCCCU---AACUCAAGGCUCGACGUC-UA | 199 | ++ | s |
| score 0.301361 | | | | |
| C19 | ACGAAGGCAACUUCA-AACAUUUCCUUACGUUCCG-CGCUCA | 200 | | |
| C51 | ACGGCGCCAACAGCG-AAUGUUCGCCC-CGUUCGGACGCUUA | 201 | | |
| Civ45 | ACCGACACAACCACG--ACGUUCGGUC-GGUUUGUCCGAUUA | 202 | | s |
| Civ63 | ACGGAGGCAACCAAG--AGAUUUCCAU-CGUUCGUUCGAUUGA | 203 | | |
| Civ70 | UCC-AUCCAACGCGGCAAGAUUUGAUG-GACUUUGACGAUCA | 204 | | |
| score 0.326357 | | | | |
| C23 | AA-GCU--CAGC-AGAUCGGGACUUCUGAUCUUCGGGUCGCUUA | 205 | − | |
| Civ67 | CAACGGUAGCGGCUAGAACGCGCCGACUGAU-UUAGG----CUUA | 206 | | |
| score 0.362963 | | | | |
| C28 | UCCUCCUG-UUCG-GAGUCUCAAUGUCGACUCGGCCGGACCU | 207 | | |
| Civ12 | AGA-AAUCCCCUUGAUUCG-GAGUCGUCUUUUCGAG-CGUAGU | 208 | + | ns |

TABLE 8-continued

| MOTIF I | FINAL CLUSTERS | SEQ ID NO | INTENSITY OF STAINING | BINDING SPECIFICITY |
|---|---|---|---|---|
| Civ26 | AGA-AAUCCCCUUGAUUCG-GAGUCGUCUUUUCGAG-CGAAGG | 209 | | |
| Civ37 | GAGAGUCAAC-UG---CGAGAAUGG-CUUUCCCAA-CGGCACCUUU | 210 | | s |
| Civ40 | AGAUAAUCCCCCGGAUUCG-GAGUCCUCUUGACGAA-CUUCC | 211 | | |
| score 0.356944 | | | | |
| C29 | C-GGA-ACAAACGGAAAUGGCACACAGG-AGAAAGACGAGACC | 212 | | |
| C34 | CAGGAGAUUAA-GGAACAGGC-CACAGAUAGAGACACG-GAGC | 213 | | |
| score 0.426357 | | | | |
| C31 | AACUGGACGAGAGGAGCUAGCGUCCAAGUUCGGAGCUA | 214 | + | ns |
| Civ44 | ACUGAUUCUCAGCGGCUAGCGCUGAAGUUCG-A-CUAGUUCA | 215 | | |
| score 0.410853 | | | | |
| C39 | GGCCACAAGCAG-AGAACAGAACAA-CAGAGCGAUGGAG-AGA | 216 | | |
| C50 | GGAG-CAUCCAGGAUAACAGGCUAAACACCGCAA-GGACCAG | 217 | | |
| score 0.333333 | | | | |
| C46 | CGGAGGAAGGAAGAGG--AACCUUCGC-CUCUGAUUUAGCUUA | 218 | | |
| C68 | CGUGGGCAAACUGAGG-CAUUCCCCGCGCUCAGAGAUUCAU | 219 | | |
| C71 | CAAUGGCAACUAGGCCACAAAGUUC-C-CACUGAUUCGACGU | 220 | | |
| Civ19 | GCAAUCGGACCGAAAGG----CCUUACC-GAUUUCUCGACCUUUC | 221 | +++ | ns |
| Civ43 | CGGAGGAAGGAAGAGG--AACCUUUGC-CUCUGAUUUAGCUUA | 222 | | |
| Civ47 | CGGAGGAAGGAAGAGG--AACCUUCGC-CUCUGAUUUAGCUUA | 223 | | |
| Civ57 | AGUCGAGUUUCAAGG--AUCAUCCCC-CUCUUCGGAGCCUUUC | 224 | | |
| Civ58 | CGGAGGAAGGAAGAGG--AGCCUUCGC-CUCUGAUUUAGCUUA | 225 | | |
| score 0.347884 | | | | |
| C56 | CGAGGCCACCGACAAGGAAGUCG---ACCG-GAGUUGAAGUAAA | 226 | | |
| Civ39 | GGCC-CCUAGCGGGAUGCCGCUAAUCGCGAAUCGAGGUUUA | 227 | | |
| score 0.348485 | | | | |
| Civ7 | UCGAUGCU--AUC-GAGUUCU-ACUCGGAAGGUUC-AACGUUUAA | 228 | ++ | s |
| Civ9 | CCCAUACU-GAGA-AAGAACAGACUUCUCAGGUUCGAACGU | 229 | | |
| Civ13 | CCUGAGACG-GUAC-GAGUUCGGACUC---AGGAUUUAACGCUUU | 230 | | |
| Civ15 | CUUACUCAACCU-GCGA-ACGCACAG-GUU---AG-UUC-ACCGUUUA | 231 | | |
| Civ17 | ACCCACACU-GAGA-AAGAACAGACUCCACAGGUUCGAACGU | 232 | | |
| Civ36 | AAACUCAUUCU-GAGCUAAGCUCA-AGUUC-----UUGCAACGUUUG | 233 | | |
| Civ49 | ACCGAUUCUCGAAG-CAGCACG--CUCC--AGG-UCUGACGUUUU | 234 | | |
| Civ66 | ACCUAUACU-GAGA-AAGAACAGACUUCUCAGGUUCGAACGU | 235 | | |
| score 0.316084 | | | | |
| Civ8 | AGGAACUUAUUCGAC---AUCAG-UCGGUUCCCUGGACGGGUUG | 236 | | |
| Civ51 | GAACCUAUUCAACCGGAUUAGGUUGGUUCUC-GGAUGUCUA | 237 | | |
| score 0.439394 | | | | |

TABLE 9

Carotid Truncates and Putative Structures

```
         A
  GA   UC       C    Cu ga
    CCU GUUUG AGCU  uc  c
    ggа caaacucgg  ag  a
                    c
                         g
    C12.1
    (C33 truncate)
    (SEQ ID NO: 238)

GA   UC       C       A
    CCU GUUUG AGCU Uuu c
                         a
    gga caaacucggaggac
                  c
    (Civ41 truncate)
    (SEQ ID NO: 239)
```

TABLE 9-continued

Carotid Truncates and Putative Structures

```
           U
    GC       G       C
  CG   G  G        UGU  A
    UUC  GUUUG  AU Uuuc g a
    gg   a caaac  uggagg  a c
                     c    c
    (Civ45 truncate)
    (SEQ ID NO: 240)

G
    GUC UUUG u u c
    cgggg aca  g
              a
    (C59 truncate)
    (SEQ ID NO: 241)
```

TABLE 10

| CLONE | COPIES | SEQUENCE OF RANDOM REGION | SEQ ID NOS: |
|---|---|---|---|
| 12.2 | 8 | GCGGGAUUUUCCUGAUCAUCCCACUGAUUCGGGCCUUAC | 242 |
| 12.10 | 8 | GGAGCGAUAUUCUUGAACAUCCACUGAUUCGGAGCGUCCU | 243 |
| 12.11 | 4 | CGCUGACUUGUUUAUUCCCACUGGUUCGGAGUCUUGCUGU | 244 |
| 12.18 | 1 | ACCGUCUUCUUACAUCCCACUGAUUUGGAGUCUCGUUGUA | 245 |
| 12.13 | 4 | CACUGAAGCAAAGUUACCUUUCUCAGAUGU UUAGCGCCUA | 246 |
| 12.8 | 3 | CGGAGGAAGGAAGAGGAACCUUCGCCUCUGAU UUAGC UUA | 267 |
| 12.15 | 3 | CGAAGGACGCGAUGCAAUCGGCCUUUGAAU UUAGCGUUCA | 248 |
| 12.9 | 2 | CUGAAGGAUGCAGCCAAGGCCGCCCUUCUAGU UUAGC UUA | 249 |
| 12.37 | 2 | CUAAGAACGAAGCCACCGUUUCGCCUUAGUAUUAGCC UUA | 250 |
| 12.42 | 2 | CUUUAGUUGUCGCAGGAGCCAAACUAAAGUAUUAGCU UUA | 251 |
| 12.17 | 1 | CAACGGUAGCGGCCAGAACGCGCCGACUGAU UUAGGC UUA | 252 |
| 12.23 | 1 | UGCGAAGUACAAGACAAACUUGUUUCGACAU UUAGCA UUG | 253 |
| 12.5 | 1 | CGCCGUCACGAGGAUGACCUCAGCGGAAGGU UUAACG AUA | 254 |
| 12.12 | 1 | CGCAGAUAACGGUCUUUCCGUGUCUGAUGU UUAACGAAGA | 255 |
| 12.36 | 1 | CGCGGAACAAUAGAGGAUUGGGUCGGCGAU UUAACGUUCA | 256 |
| 12.46 | 1 | CACUAGAUGGGAGAUCCUCAGGCUAGGUGU UUAGG UUCA | 257 |
| 12.31 | 1 | AUCCAGAUUGGAAGCAAUCCUGCUGGAUUAUUAGCC UUA | 258 |
| | | 5'-gggagauaagaauaaacgcuaaa-[4 0N]-uucgacaggaggcucaaaacaggc-3' | 40 |

TABLE 11

WHHL SELEX Conditions

| Round # | In Vitro/In Vivo | RNA | Incubation Time, min | Wash Time, min |
|---|---|---|---|---|
| 1 | In Vitro | 0.54 uM | 45 | 4 × 1 ml, 15 min |
| 2 | In Vitro | 1.6 uM | 55 | 2 × 3 ml, 15 min |
|   |          |         |    | 1 × 50 ml, 20 min |
| 3 | In Vitro | 1.47 uM | 60 | 3 × 125 ml, 20 min |
| 4 | In Vivo | 18.3 uM | 15 |  |
| 5 | In Vivo | 5.0 uM | 30 |  |
| 6 | In Vivo | 13.3 uM | 50 |  |
| 7 | In Vivo | 7.0 uM | 65 |  |
| 8 | In Vivo | N.A. | 60 |  |
| 9 | In Vitro | 0.50 uM | 55 | 4 × 40 ml, 30 min |
| 10 | In Vitro | 0.27 uM | 45 | 4 × 40 ml, 30 min |

TABLE 12

Round 10 Clones from Watanabe Heritable Hyperlipidemic Rabbit Atherosclerotic Plaque SELEX

| | | | SEQ. ID NOS. |
|---|---|---|---|
| Family I | | | |
| 10.5 | gggagacaagaauaaacgcucaa | GCAACCUCGGACUAGACUAACGACCUU GUUUGACACUUA | uucgacaggaggcucacaacaggc | 260 |
| 10.1 | gggagacaagaauaaacgcucaa | UCAAUCUCGGACUAGACUAACGACUUUCGUUUGACGCUUA | uucgacaggaggcucacaacaggc | 261 |
| 10.12 | gggagacaagaauaaacgcucaa | GCAAUCUCGGACUAGACUAACGACCUU GUUUGACGCUGA | uucgacaggaggcucacaacaggc | 262 |
| 10.14 | agacaagaauaaacgcuca | ACAAUCUCGGACUAGACUAACGACCUUGGUUUGACGCUCA | uucgacaggaggcucacaacaggc | 263 |
| 10.19 | gggagacaagaauaaacgcucaa | GCAACCUCGGACUAGACUAACGACCUUCGUUUGACGCUUA | uucgacaggaggcucacaacaggc | 264 |
| 10.23 | gggagacaagaauaaacgcucaa | CCANNCUCGGACUANACUACCCANCUUCGUUNNACCCUUA | uucgacaggaggcucacaacaggc | 265 |
| 10.36 | gggagacaagaauaaacgcucaa | GCAAUCUCGGACUAGACUAACGA CUUCGUUUGACGCUUA | uucgacaggaggcucacaacaygc | 266 |
| 10.37 | gggagacaanaauaaacgcucaa | GCAAUCUCGGAUUAGACUAACKA CUUCGUUUGACACUUA | uucgacaggaggcucacaacaggc | 267 |
| 10.31 | gggagacaagaauaaacgcucaa | UCAAUCUCGGACUAGACUAACGACCUUGGUU GACGCUCA | uucgacaggaggcucacaacaggc | 268 |
| 10.49 | gggagacaagaauaaacgcucaa | GCAACCUCGGACUAGACUAACGACCUU GUUUGGCACUUA | uucgacaggaggcucacaacaggc | 269 |
| 10.38 | gggagacaagaauaaacgcucaa | GCAAUCUCGGACUAAACUAACGACUUUCGUUCGACGCUUA | uucgacaggaggcucacaacaggc | 270 |
| 10.53 | gggagacaagaauaaacgcucaa | GCAACCUCGGAUCAGACUAACGACCUUGGUU GACGCUUA | uucgacaggaggcucacaacaggc | 271 |
| 10.55 | gggagacaagaauaaacncucaa | GCAACCUCGGAUUANACUAACGACCUUCNUUUGACGCUUA | uucgacaggaggcucacaacaggc | 272 |
| 10.56 | gggagacaagaauaaacgcucaa | GCAAUCUCGGACUAGACUAACGACCUUCGUUUGACGCUUA | uucgacaggaggcucacaacaggc | 273 |
| 10.64 | gggagacaagaauaaacgcucaa | GCAAUCUCGGACUARACUAACGACCUUCGUUUGACGCUUA | uucgacaggaggcucacaacaggc | 274 |
| 10.65 | gggagacaagaauaaacgcucaa | GCAACCUCGGACUAAACUAACGACCUUCGUUUGACGCUUA | uucgacaggaggcucacaacaggc | 275 |
| 10.68 | gggagacaagaauaaacgcucaaGCAAACCUCGGACUAAACUAACGACCUUCGUUUGACGCUUA | | uucgacaggaggcucacaacaggc | 276 |
| 10.72 | gggagacaakaauaaacgcucaa | GCKAUCCCGGUACUANACUAACGACCUUGUUUGACGCUUA | uucgacaggaggcucacaacaggc | 277 |
| 10.73 | gggagacaagaauaaacucucaa | GCAAUCUCGGACUAGACUAACGACCUUCGUUUGACGCUUA | uucgacaggaggcucacaacaggc | 278 |
| 10.76 | gggagacaagaauaaacgcucaa | UCAAUCUCGGACUAGACUAACGACUUUCGUUUGACGCUUA | uucgacaggaggcucacaacaggc | 279 |
| 10.77 | gggagacaagaauaaacgcucaa | KCAAUCUCGGACUAAACUAACKACUUCBUUUGACGCUUA | uucnacaggaggcucacaacaggc | 280 |
| 10.81 | gggagauaagaauaaacgcucaa | KCAAUCUCGGACUAAACUAACGACCUUGUUUGACSCUUA | uucgacaggaggcucacaucaggc | 281 |
| 10.84 | gggagacaagaauaaacgcucaa | GCAAACCUCGGACUAAACUAACGACCUUCGUUUGACGCUUAuucgacaggaggcucacaacangc | | 282 |
| 10.95 | gggagacaagaauaaacgcucaa | GCGAUCUCGGACUAAACUAACGACUUCGUUUGACGCUCA | uucgacaggaggcucacaacaugc | 283 |

TABLE 12-continued

Round 10 Clones from Watanabe Heritable Hyperlipidemic Rabbit Atherosclerotic Plaque SELEX

| | | | | SEQ. ID NOS. |
|---|---|---|---|---|
| 10.99 | gggagacaagaauaaacgcucaa | GCAAUCUCGGACUANACUAACNACYUUCGUUUAACCCCC | uuncaanngaaggncccnannnggc | 294 |
| 10.000 | gggagacaaaaauaaacgcucaa | GCAACCUCGGACUAAACUAACGACCUUCGUUUGACGCUUA | uucgacaggaggcucacaacaggc | 285 |
| 10.101 | gggagacaagaauaaacgcucaa | GCAAUCUCGGACUANACUAACGACCUUCGUUUGACGCUUA | uucgacaggaggcucacaacaggc | 286 |
| 10.104 | gggagacaagaauaaacgcucaa | GCAACCUCGGACUAGACUAACNACCUUGUUUGACGCUA | uucgacaggaggcucacaacaggc | 287 |
| 10.70 | gggagacaagaauaaacgcucaa | CGACCCUGGCUCUAGAGUUCUCGUAUUCGCUGUCGCAUGA | uucgacaggaggcucacaacaggc | 288 |
| 10.86 | gggagacaagaauaaacgcucaa | CGCACAUGACCAGGCGCUACUGACUGARAUGUUGAACUUA | uucgacaggaggcucacaacaggc | 289 |
| 10.97 | gggagacaagaauaaacgcucaa | CGACCCUGGCUCUAAARUUCUCGUAUUCGCUGUCGCCUGA | uucgacaggaggcucacaacaggc | 290 |
| 10.45 | gggagacaagaauaaacgcucaa | CUACCCAMGCCUCUAGAGUUCUCGUAUUCGCUGUCGCAUGA | uucgacaggaggcucacaacaggc | 291 |
| 10.78 | gggagacaacaauaaacgcucaa | CGACCCUGGCCCUARAGUUCUCGUAUUCSCUGUCGCAUGA | uucgacaggaggcucacaacaggc | 292 |
| 10.79 | gggagacaagaauaaacgcucaa | CGACCCUGGCUCUARAGUUCUCGUAUUCGCUGUCGCAUGA | uucgacaggaggcucacaacaggc | 293 |
| 10.108 | gggagacaagaauaaacgcucaa | CNACCCUGGCUCUAGAGUUCUCGUAUUCGCUGUCGCAUGA | uucgacaggaggcucacaacaggc | 294 |
| Orphans | | | | |
| 10.41 | gggagacaagaauaaacgcucaa | AACUCGUUCAGCAUCUACAAACUACUACAUUGAAGCACCC | ucgaacagggaaggcucacaacaggc | 295 |
| 10.46 | | AAGACACCWCWCCAAUUCUAAUAUACAGCACUACAUGGCC | uucgacaggaggcucacaacaggc | 296 |
| 10.83 | gggagacaagaauaaacgcucaa | AAGUACGGUGUCUACCAAACCGCAUCCAUCACCGAUA | uucgacaggaggcucacaacaggc | 297 |
| 10.30 | gggagacaagaauaaacgcucaa | AAUUUCACCGAGGCAGACGAACAUCAAKUGCAGCUGCUAA | uucgacaggaggcucacaacaggc | 298 |
| 10.90 | gggagacaacaauaaacgcucaa | ACAAAUUCGUACWCACUUCKCGGAGGCMGGGGUAYAUC | uucnacaggaggcucacaacaggc | 299 |
| 10.54 | gggagacaagaauaaacgcucaa | ACACUCAUAGAGUCCAAUUCAACGCGCCAUUAUCUCAARA | uucgacaggaggcucacaacaggc | 300 |
| 10.80 | gggagacaagaauaaacgcucaa | ACUCCYCUGCUAGACAARCGGMCAKUGCACNUCAACAAAU | uucgacaggaggcucacaacaggc | 301 |
| 10.57 | ugagacaagaauaaacgcucaa | AGAGCCAUCCCUUAAACGCAGCUACGGAGGUCGUUCUUAU | uucgacaggaggcucacaacaggc | 302 |
| 10.75 | gggagacaagaauaaacgcucaa | AKCAAACAUUCUCAUAUAAAKAGCCAAAAUAGACAACCAC | uucgacaggaggcucacaacaggc | 303 |
| 10.59 | ugagacaacaauaaacgcucaa | AGGCAUGCASCAAAAGCACACCGAAAUAUCUCCAAUCCCU | uucgacaggaggcucacaacaggc | 304 |
| 10.47 | gggagacaagaauaaacgcucaa | AGGCAUGAGUCCGCACAUAUGUGAACGUGAGCACAUAAAU | uucgacaggaggcucacaacaggc | 305 |
| 10.87 | gggagacaagaauaaacgcucaa | AGUCGUCGCGCAUAUUGACACAAUAAUCGUGUCAUAACCU | uucgacaggaggcucacaacaggc | 306 |
| 10.71 | gggagacaaaaauaaacgcucaa | AUACUCGCGAUCGCAGCAUCAUCCCGCCUCCUUGAAACAC | uucgacaggaggcucacaacaggc | 307 |
| 10.16 | gggagacaagaauaaacgcucaa | AUAGGAUGCCGCAUCGGUGUACACUCACACGCUAACCAU | uucgacaggaggcucacaacaggc | 308 |
| 10.33 | gggagacacaauaawcgcucaa | AUCCUUUAACGAUAGCACAAUAGAAUUAGACUCCAACAAG | uucgacaggaggcucacaacaggc | 309 |
| 10.88 | gggagacaagaauaaacgcucaa | AUGUCGACAUACAUAAAAUACGUCAAGCUUGCGAUCGAU | uucgacaggaggcucacaacaggc | 310 |
| 10.4 | gggagacaagaauaaacgcucaa | CAAGCCAUGCGUUAGUGCCCCUUCCAGUUCCCA | uucgacaggaggcucacaacaggc | 311 |
| 10.96 | gggagacaauaaacgcucaa | CAACCCGGGCUCNANANUUCUCGUAUCCCCUGUCNCNUUA | uucgacuggangcucacaacaggn | 312 |
| 10.22 | gggagacaagaauaaacgcucaa | CAUGAAAAACUUUCUAUUCCGUAAAUCACGUGAGUCGCUAG | uucgacaggaggcucacaacaggc | 313 |
| 10.62 | gggagacaagaauaaacgcucaa | CAUUGGCAGYWAABCMUCCAYCCAUARACRCUCAACAAGU | uucgacaggaggcucacaacaggc | 314 |
| 10.13 | gggagacaagaauaaacgcucaa | CCAAGGAGCUUCCUGGCACCGUACCUACAUCGACCUGUUA | uucnaacaggaaggcucacaacaggc | 315 |
| 10.51 | gggagacaagaauaaacgcucaa | CCAWYCUCUSAYCAGACUAACCACCYYGUAUGAMCCUYA | uuccaamggaagsycmcaacarggv | 316 |
| 10.25 | agacaagaauaaacgcucaa | CCCAAUAUCAGUUGUCUCAAACUGCGCUACUUCAUGCUUG | uucgacaggaggcucacaacaggc | 317 |
| 10.50 | agacaagaauaaacncucaa | CCCCAAACCUACCCCUCUAUAUUCCUUCUCGUAACCCAA | uucgacaggaggcucacaacaggc | 318 |

TABLE 12-continued

Round 10 Clones from Watanabe Heritable Hyperlipidemic Rabbit Atherosclerotic Plaque SELEX

| | | | | SEQ. ID NOS. |
|---|---|---|---|---|
| 10.89 | gggagacaagaauaaacgcucaa | CCCCUCYYRGACUCCAUCAACAAMUCCCCYCCUGACUCG | uucgacaggaggacgcacaacaggc | 319 |
| 10.103 | gggagacaagaauaaacgcucaa | MCCGGUGCAUGUGCUAWAAUAACAUUCGGCCAUUAUCCMA | uucuacaggaggcucanaacungc | 320 |
| 10.27 | gggagacaagaauaaacgcucaa | CCGUCCUCASAYYCCACUWACGUCCAUKWAUGAAAUWCAC | -uccaacagyaggcucacaacaggc | 321 |
| 10.24 | gggagacaagaauaaacgcucaa | CCUAUCGUCGUCCUACAUAGAGCUAUCCCUCGCUUCGC | uucgacaggaggcucacaacaggc | 322 |
| 10.82 | gggagacaagaauaaacgcucaa | RCAAUCUCSGAAWMUCACUACCCACUCCCKUCUGACNCUCA | uucgacaggaggcucacaacaggc | 323 |
| 10.18 | gggagacaagaauaaacgcucaa | GCAUCAGAACUCAAUUUCUUCAGCCAGCGUGCUUACGACA | uucgacaggaggcucacaacaggc | 324 |
| 10.40 | gggagacaagaauaaacgcucaa | GCAUUCACAGUCGAUCCAAUUCCGGAACCUUAUCCAACAA | uucgacaggaggcucacaacaggc | 325 |
| 10.8 | gggagacaagaauaaacgcucaa | GCCCCUUCUGGACGCCGCUAA GAUCUCCCCAACCCGAUA | uucgacaggaggcucacaacaggc | 326 |
| 10.107 | gggagacaagaauaaacgcucaa | GCGGGAUUUUCCNGAUCAUCCCACUGAUUCGGGGCCUUAC | uucgacaggaggcucacaacaggc | 327 |
| 10.102 | gggagacaagaauaaacgcucaa | GCGUAAUGAGCUGUGCCCGCGUUUAUGAUCUAUAUCCUAA | uucgacaggaggcucacaacaggc | 328 |
| 10.17 | gggagacaagaauaaacgcucaa | GCUAGUCAUCUGCCUAACUCCUCACGAGACCCAGCCGUAC | uucgacaggaggcucacaacaggc | 329 |
| 10.35 | gggagacaagaauaaacgcucaa | GACAUUAUUUGACAUCUAGGUGUAGCAAGUAUAGACCUAA | uu . . . | |
| 10.92 | gggagacaagaauaaacgcucaa | GGAUGAACAAUACCCCAUGCAGUCCAAGUCCUGCUUUCAC | uucgacaggaggcucacaacaggc | 330 |
| 10.39 | gggagacaagaauaaacgcucaa | GUGUACACRAAGUCAGUUAGCGGACAGUUUGCGCAGCCCGU | uuCGACAGGAGGCUCACAACAGGC | 331 |
| 10.3 | gggagacaagaauaaacgcucaa | GUSCaGGUSUGACCACCUGWASgACCCUGCCCACCCGUCA | uucgacaggaggcucacaacaggc | 332 |
| 10.94 | gggagacaaaauaaacgcucaa | GUUGCCCUCGCGAAUGUACCCAUCGUACAGAACGGUCUAA | uucgacaggaggcucacaacaggc | 333 |
| 10.85 | gggagacaagaauaaacgcucaa | UAACACCCACCACUCRCGCAUGGCAUUGUCVCCAAAUAAC | uucgacaggaggcucacaacaggc | 334 |
| 10.67 | gggagacaagaauaaacgcucaa | UACCGGGCGAKCUACCCUGUACUGCCUCUUCCUUCACAGC | uucgacaggaggcucacaacaggc | 335 |
| 10.6 | gggagacaagaauaaacgcucaa | UACGAACAAAGGAACUCAGUCAAAAACAGCAGUGUACCA | uucgacaggaggcucacaacaggc | 336 |
| 10.26 | gggagacaagaauaaacgcucaa | UCAAC | uucgacaggaggcucacaacaggc | 337 |
| 10.11 | gggagacaagaauaaacgcucaa | UCACGGUAAGGACCCAGAUUCUCCUCUUCCCAACCUCGCA | uucgacaggagg | 338 |
| 10.20 | gggagacaagaauaaacgcucaa | UCAUGCUCACGACUAUUGCCAUAACGCUAUCCACACAACA | uucgacaggaggcucacaacaggc | 339 |
| 10.9 | gggagacaagaauaaacgcucaa | UCCAUGCAUGAUCGUAAGCUAUAAAGGUGCGCAAACCUUG | uucgacaggaggcucacaacaggc | 340 |
| 10.52 | gggagacaagaauaaacgcucaa | UCGGUCUCAACCUACCCACCCCAGUAAGCAUGAGGCUACA | uucgacaggaggcucacaacaggc | 341 |
| 10.21 | gggagacaagaauaaacgcucaa | UCGGCAAAGUCCUCUUAUAUACAGUCUGCAAUCACUCAUU | uucgacaggaggcucacaacaggc | 342 |
| 10.106 | gggagacaagaauaaacgcucaa | UCUAUGCAACAACGANCAUUCACUCCANCUAGGUWCAGG | uucgacaggaggcucanaacaggc | 343 |
| 10.10 | gggagacaagaauaaacgcucaa | UGCCCGGUACAAAUCUUUCUACACCACGAUCUCCCCUAUC | uucgacaggaggcucacaacaggc | 344 |
| 10.74 | gggagacaagaauaaacgcucaa | UGGGAUUGGGUCUUACACGUUCACUCGCUUAUCCUCCCAA | uucgacaggaggcucacaacaggc | 345 |
| 10.2 | gggagacaagaauaaac—cucaa | UGUUACAAAACACAGACGCCGCGCUAAGGUAUAUCCGCUG | uucgacaggaggcucacaacaggc | 346 |
| 10.44 | gggagacaagaauaaacgcucaa | UGUUAAUCAACUACAAUGCACUUGAGCCAAACAACCGACU | uucgacaggaggcucacaacaggc | 347 |
| 10.15 | gggagacaagaauaaacgcucaa | UUCCAUUGGUUUGCCCUAUCGAGACCCGUCCGCUGUUCCU | uucgacaggaggcucacaacaggc | 348 |
| 10.48 | ggagacaagaauaaacgcucaa | UUUCUUGUGAUGUCAGAAUGACCCUAGACUUACGUCCAAA | uucgacaggaggcucacaacaggc | 349 |
| 10.7 | gggagacaagaauaaacgcucaa | UUGACGCACCCAUCGGCCCGUCCACUGCUCCCCACCUAGU | uucgacaggaggcucacaacaggc | 350 |
| 10.28 | gggagacaagaauaaacgcucaa | CRGUAUCAUGAACUCCCACGAACRCCACUGUUUUAAUU | uucgacaggaggcucacaacwggc | 351 |
| 10.43 | gggagacaagaauaaacgcucaa | GCGGGAUUUUCCUGAUCAUCCCACUGAWUCGGGGCCUUAC | uucgacaggaggcucacaacaggc | 352 |

TABLE 12-continued

Round 10 Clones from Watanabe Heritable Hyperlipidemic Rabbit Atherosclerotic Plaque SELEX

| | | | SEQ. ID NOS. |
|---|---|---|---|
| 10.93 | gggagacaagaauaaacgcucaa NAGUGGAUAACGUAUAGCCAAUUUUCUCACUCGCCUCGUU uucgacaggaggcucacaacaggc | | 353 |
| 10.98 | gggagacaaaaauaacgcucaa RAAAACCUACCUUCGUACAUUGGAUARAAAACGGCUCUU uucgacaggaggcucacaacaggc | | 354 |

TABLE 13

Sequences from Round 5 Human Artery Perfusion Selex

SEQ ID NOS:

Family I from Watanabe Heritable Hyperlipidemic Rabbit
Atherosclerotic Plaque SELEX NOS:

| 81 | GGGAGACAAGAAUAAACGCUCAA AAACAACCUCGGACUAGACUAACGACCUUGUUCGACGCUUA | 377 |
|---|---|---|
| 5 | GGGAGACAAGAAUAAACGCUCAA GCAAUCUCGGACUAGACUAACGACCUUCGUUUGACGCUUA | 378 |
| 9 | GGGAGACAAGAAUAAACGCUCAA GCAACCUCGGACUAGACUAACGACCUUAGUUUGACGCUUA | 379 |
| 14 | GGGAGACAAGAAUAAACGCUCAA GCAACCUCGGACUAGACUAACGACCUUCGUUUGACGCUUA | 380 |
| 37 | GGGAGACAAGAAUAAACGCUCAA GCAAUCUCGGACUAGACUAACGACCUCGUUUGACGCUUA | 381 |
| 45 | GGGAGACAAGAAUAAACGCUCAA GCAACCUCGGAUUAGACUAACGACCUUCGUUUGACGCUUA | 382 |
| 54 | GGGAGACAAGAAUAAACGCUCAA GCAACCUCGGACUAGACUAACGACCUUGUUCGACGCUUA | 383 |
| 68 | GGGAGACAAGAAUAAACGCUCAA GCAACCUCGGACUAGGCUAACGACCUUGUUUGACACUUA | 384 |
| 69 | GGGAGACAAGAAUAAACGCUCAA GCAACCUCGGACUAGACUAACGACCUUCGUUUGACGCUUA | 385 |
| 71 | GGGAGACAAGAAUAAACGCUCAA GCAAUCUCGGACUAGACUAACGACUUCGCUUGACGCUCA | 386 |
| 78 | GGGAGACAAGAAUAAACGCUCAA GCAAUCUCGGACUAGACUAACGACCUUGUUUGACGCCUA | 387 |
| 95 | GGGAGACAAGAAUAAACGCUCAA GCAAUCUCGGACUAGACUAACGACCUUCGUUUGACGCUUA | 388 |

Family II from Watanabe Heritable Hyperlipidemic Rabbit
Atherosclerotic Plaque SELEX

| 43 | GGGAGACAAGAAUAAACGCUCAA CGACCCUGGCUCUAGAGUUCUCGUAUUCGCUGUCGCAUGA | 389 |
|---|---|---|

Family I from Round 5 Human Perfusion Selex

| 1 | GGGAGACAAGAAUAAACGCUCAA GGCUAGAUCUACAGAAGGACUAGAACCCCAAAAGCGACAA | 390 |
|---|---|---|
| 11 | GGGAGACAAGAAUAAACGCUCAA GGCUAGAUCUACAGACGGACUAGAACCCCAAAAGCGACAA | 391 |
| 13 | GGGAGACAAGAAUAAACGCUCAA GGCUAGAUCUACAGACGGACUAGAACCCCAAAAGCGACAA | 392 |
| 35 | GGGAGACAAGAAUAAACGCUCAA UUCGACAGGAGGCUCACAACAGGCAAGCUU | 393 |
| 41 | GGGAGACAAGAAUAAACGCUCAA GGCUAGAUCUACAGACGGACUAGAACCCCAAAAGCGACAA | 394 |
| 62 | GGGAGACAAGAAUAAACGCUCAA GGCUAGAUCUACAGACGGACUAGAACCCCAAAAGCGACAA | 395 |
| 72 | GGGAGACAAGAAUAAACGCUCAA GGNUAGAUCUACAGACAGACUAGAACCCCAAAAGUGACAA | 396 |

Sequences Present in Round 5 Human Artery Perfusion
Selex in More Than One Copy Number

| 25 | GGGAGACAAGAAUAAACGCUCAA CGUUGAGAGCAACCUGUCGAUCCCGGAGCAGACUAACGAU | 397 |
|---|---|---|
| 40 | GGGAGACAAGAAUAAACGCUCAA CGUUCAGAGCAACCUGUCGAUCCCGGAGCAGACUAACGAU | 398 |
| 23 | GGGAGACAAGAAUAAACGCUCAA GUGUUGGAGCUCUUGAUUGGAAAAGUAGAGCAAAUCGAAA | 399 |
| 85 | GGGAGACAAGAAUAAACGCUCAA GUGUUGGAGCUCUUGAUUGGAAAAGUAGAGCAAAUCGAAA | 400 |

TABLE 13-continued

Sequences from Round 5 Human Artery Perfusion Selex

| | | SEQ ID NOS: |
|---|---|---|

Orphans

| | | SEQ ID NOS: |
|---|---|---|
| 38 | GGGAGACAAGAAUAAACGCUCAA AAAAUCGUCACCCCUCCGGUCCUCACAUGACAGCAUGAACA | 401 |
| 86 | GGGAGACAAGAAUAAACGCUCAA AAAGCUAGAUCAGCAGUGAACGACUACAAGUGCAUAGUA | 402 |
| 19 | GGGAGACAAGAAUAAACGCUCAA AACCGGAGAGCCCGAACCACCGGUAGCAUCCGCAUCAUAC | 403 |
| 29 | GGGAGACAAGAAUAAACGCUCAA AAUAUAGCCCUGCGAUCUUAGCCCAACUUCCUCAAAGCUU | 404 |
| 82 | GGGAGACAAGAAUAAACGCUCAA ACCAGAAAAGAAGCUCAAAACCUUUGCUUGAUCGACACA | 405 |
| 91 | GGGAGACAAGAAUAAACGCUCAA ACCGAUCGAUAUGACUCGACAUGUCGAUGCACAAAGUAAC | 406 |
| 76 | GGGAGACAAGAAUAAACGCUCAA ACCUUAUACCAUCCUGUCUCAACCAUACUCUGAUACACAA | 407 |
| 77 | GGGAGACAAGAAUAAACGCUCAA AGAUGAAUAAUGACCCACAACUGACCCAGCGAUACUAUAA | 408 |
| 65 | GGGAGACAAGAAUAMCGCUCAA AGCUGCCAGACACAAUCCGGUGGCAGUCCGAUAAAUACAC | 409 |
| 12 | GGGAGACAAGAAUAAACGCUCAA AGGCCCAAGAUGUACACACGGUCACGUCCUACAUACUACA | 410 |
| 79 | GGGAGACAAGAAUAAACGCUCAA AGUCCACGCUGCGUGUGCUCCAGCAUACGACUCUUAAGCU | 411 |
| 22 | GGGAGACAAGAAUAAACGCUCAA AGUGUGAACUCCUAAACCCCUCCGGACAGAUAACACGGAC | 412 |
| 3 | GGGAGACAAGAAUAAACGCUCAA AUCUCGACCUCGGUCGGCCCUUCCCGAAGCCGUGUAUAUC | 413 |
| 16 | GGGAGACAAGAAUAAACGCUCAA AUGAAGCUGAUGCACCAUUAUCAACACCACCCUACGUUAC | 414 |
| 20 | GGGAGACAAGAAUAAACGCUCAA AUUAUGGAUAUACGAGACCCACCCUCCUCUCUAGCGUACA | 415 |
| 2 | GGGAGACAAGAAUAAACGCUCAA CAACUAAUACCGCUAAAAGACUGCAGCCUCAGUACACAAA | 416 |
| 15 | GGGAGACAAGAAUAAACGCUCAA CAACAUACUCAACUACCACGAAGCAAACUGCGUAAACCAC | 417 |
| 34 | GGGAGACAAGAAUAAACGCUCAA CACACCCUAAAUCACCAUCCACUGGCCGUCACCAAUAAC | 418 |
| 28 | GGGAGACAAGAAUAAACGCUCAA CCCCAAUGUACGAGCCAGUACCAAGCCACCACGAUAUGU | 419 |
| 73 | GGGAGACAAGAAUAAACGCUCAA CCCCGUAUCUCUUCGACAGCCCCCUCUUCCUCCAACCACA | 420 |
| 80 | GGGAGACAAGAAUAAACGCUCAA CUCAACUGGAAACCACGGGAUGACAACCGUCCAUUGCAAU | 421 |
| 6 | GGGAGACAAGAAUAAACGCUCAA GACCUAUUUCAACCUGUGCCUGAUCACCUAAAGUUUGCCU | 422 |
| 83 | GGGAGACAAGAAUAAACGCUCAA GAGACUCAUUAAGCGCCCGCCGUUGAACGUCACCCCUAUC | 423 |
| 70 | GGGAGACAAGAAUAAACGCUCAA GCACCCCAGCAAAAAUCCGAUCCAAACCACACUCCCAAAAC | 424 |
| 61 | GGGAGACAAGAAUAAACGCUCAA GGAUCUUACUCAGCCCCUGUUUCAACAAUCCAUGCUCCAG | 425 |
| 89 | NGGAGACACGAGUANACGCUCAA GGNUNUGCACACAUAGCCAACCNGACCNUUGNUUAAUUCA | 426 |
| 74 | GGGAGACAAGAAUAAACGCUCAA GGGAUCAAAAUCCAAACGCGUUAACCGUUAAUACACUUAU | 427 |
| 10 | GGGAGACAAGAAUAAACGCUCAA GUCCUGACUACUAACAUUGCCCGUGACCCAUUGCCUUAC | 428 |
| 92 | GGGAGACAAGAAUAAACGCUCAA UAACACAAUGUAAGUCCUUCGAUCACACCUAAUUAGAUCA | 429 |
| 32 | GGGAGACAAGAAUAAACGCUCAA UACCCACACUCCUGAUCACCCCAUUACUUUCUAUAUAC | 430 |
| 55 | GGGAGACAAGAAUAAACGCUCAA UAGGGACUAACGCUGUGUGCUACAGGCCCCCAAACAUCA | 431 |
| 49 | GGGAGACAAGAAUAAACGCUCAA UCAAACAGCCUGGAUACCUCUCUCCCUAUCCCCUCACUUA | 432 |
| 87 | GGGAGACAAGAAUAAACGCUCAA UCGAUACUAGAUCCUAUUGCAGACGUAACGUUGCUUUAAG | 433 |
| 96 | GGGAGACAAGAAUAAACGCUCAA UCGGCCAGCAUCAAGGACAUCACUUACACCUAGUACCUAC | 434 |
| 90 | GGGAGACAAGAAUAAACGCUCAA UCUACCACACGCUUCCCGAACGACCUCCCAAUUAACUCGA | 435 |
| 93 | GGGAGACAAGAAUAAACGCUCAA UCUCACAGUUGAAGUAAUCACCAUCGCCAUACAAACUA | 436 |

TABLE 13-continued

Sequences from Round 5 Human Artery Perfusion Selex

| | | SEQ ID NOS: |
|---|---|---|
| 7 | GGGAGACAAGAAUAAACGCUCAA UGAUAGAAGCCAAAAGCGCCGUUUGCGACGAUCACCUUAU | 437 |
| 17 | GGGAGACAAGAAUAAACGCUCAA UGAUGUGCCGCGGCCCAACCACAAUAAUCGCACUCUUACA | 438 |
| 94 | GGGAGACAAGAAUAAACGCUCAA UUAGCAACCAAGCAUCCGUUAAUAAGCGGAAAAGACACGA | 439 |
| 66 | GGGAGACAAGAAUAAACGCUCAA NGNUAACGCUUUACCUCUCCCAANCNUCAAACAGGAAUUA | 440 |

Family I from Watanabe Heritable Hyperlipidemic Rabbit Atherosclerotic Plaque SELEX

| | | |
|---|---|---|
| 81 | UUCGACAGGAGGCUCACAACAGGCAAGCUU | 377 |
| 5 | UUCGACAGGAGGCUCACAACAGGCAAGCUU | 378 |
| 9 | UUCGACAGGAGGCUCACAACAGGCAAGCUU | 379 |
| 14 | UUCGACAGGAGGCUCACAACAGGCAAGCUU | 380 |
| 37 | UUCGACAGGAGGCUCACAACAGGCAAGCUU | 381 |
| 45 | UUCGACAGGAGGCUCACAACAGGCAAGCUU | 382 |
| 54 | UUCGACAGGAGGCUCACAACAGGCAAGCUU | 383 |
| 68 | UUCGACAGGAGGCUCACAACAGGCAAGCUU | 384 |
| 69 | UUCGACAGGAGGCUCACAACAGGCAAGCUU | 385 |
| 71 | UUCGACAGGAGGCUCACAACAGGCAAGCUU | 386 |
| 78 | UUCGACAGGAGGCUCACAACAGGCAAGCUU | 387 |
| 95 | UUCGACAGGAGGCUCACAACAGGCAAGCUU | 388 |

Family II from Watanabe Heritable Hyperlipidemic Rabbit Atherosclerotic Plaque SELEX

| | | |
|---|---|---|
| 43 | UUCGACAGGAGGCUCACAACAGGCAAGCUU | 389 |

Family I from Round 5 Human Perfusion Selex

| | | |
|---|---|---|
| 1 | UUCGACAGGAGGCUCACAACAGGCAAGCUU | 390 |
| 11 | UUCGACAGGAGGCUCACAACAGGCAAGCUU | 391 |
| 13 | UUCGACAGGAGGCUCACAACAGGCAAGCUU | 392 |
| 35 | | 393 |
| 41 | UUCGACAGGAGGCUCACAACAGGCAAGCUU | 394 |
| 62 | UUCGACAGGAGGCUCACAACAGGCAAGCUU | 395 |
| 72 | UUCGACAGGAGGCUCACAACAGGCAAGCUU | 396 |

Sequences Present in Round 5 Human Arter Perfusion Selex in More Than One Copy Number

| | | |
|---|---|---|
| 25 | UUCGACAGGAGGCUCACAACAGGCAAGCUU | 397 |
| 40 | UUCGACAGGAGGCUCACAACAGGCAAGCUU | 398 |
| 23 | UUCGACAGGAGGCUCACAACAGGCAAGCUU | 399 |
| 85 | UUCGACAGGAGGCUCACAACAGGCAAGCUU | 400 |

TABLE 13-continued

Sequences from Round 5 Human Artery Perfusion Selex

|  | SEQ ID NOS: |
|---|---|
| Orphans | |
| 38 UUCGACAGGAGGCUCACAACAGGCAAGCUU | 401 |
| 86 UUCGACAGGAGGCUCACAACAGGCAAGCUU | 402 |
| 19 UUCGACAGGAGGCUCACAACAGGCAAGCUU | 403 |
| 29 UUCGACAGGAGGCUCACAACAGGCAAGCUU | 404 |
| 82 UUCGACAGGAGGCUCACAACAGGCAAGCUU | 405 |
| 91 UUCGACAGGAGGCUCACAACAGGCAAGCUU | 406 |
| 76 UUCGACAGGAGGCUCACAACAGGCAAGCUU | 407 |
| 77 UUCGACAGGAGGCUCACAACAGGCAAGCUU | 408 |
| 65 UUCGACAGGAGGCUCACAACAGGCAAGCUU | 409 |
| 12 UUCGACAGGAGGCUCACAACAGGCAAGCUU | 410 |
| 79 UUCGACAGGAGGCUCACAACAGGCAAGCUU | 411 |
| 22 UUCGACAGGAGGCUCACAACAGGCAAGCUU | 412 |
| 3 UUCGACAGGAGGCUCACAACAGGCAAGCUU | 413 |
| 16 UUCGACAGGAGGCUCACAACAGGCAAGCUU | 414 |
| 20 UUCGACAGGAGGCUCACAACAGGCAAGCUU | 415 |
| 2 UUCGACAGGAGGCUCACAACAGGCAAGCUU | 416 |
| 15 UUCGACAGGAGGCUCACAACAGGCAAGCUU | 417 |
| 34 UUCGACAGGAGGCUCACAACAGGCAAGCUU | 418 |
| 28 UUCGACAGGAGGCUCACAACAGGCAAGCUU | 419 |
| 73 UUCGACAGGAGGCUCACAACAGGCAAGCUU | 420 |
| 80 UUCGACAGGAGGCUCACAACAGGCAAGCUU | 421 |
| 6 UUCGACAGGAGGCUCACAACAGGCAAGCUU | 422 |
| 83 UUCGACAGGAGGCUCACAACAGGCAAGCUU | 423 |
| 70 UUCGACAGGAGGCUCACAACAGGCAAGCUU | 424 |
| 61 UUCGACAGGAGGCUCACAACAGGCAAGCUU | 425 |
| 89 UUCGACAGGAGGCUCACAACAGGCAAGCUU | 426 |
| 74 UUCGACAGGAGGCUCACAACAGGCAAGCUU | 427 |
| 10 UUCGACAGGAGGCUCACAACAGGCAAGCUU | 428 |
| 92 UUCGACAGGAGGCUCACAACAGGCAAGCUU | 429 |
| 32 UUCGACAGGAGGCUCACAACAGGCAAGCUU | 430 |
| 55 UUCGACAGGAGGCUCACAACAGGCAAGCUU | 431 |
| 49 UUCGACAGGAGGCUCACAACAGGCAAGCUU | 432 |
| 87 UUCGACAGGAGGCUCACAACAGGCAAGCUU | 433 |
| 96 UUCGACAGGAGGCUCACAACAGGCAAGCUU | 434 |
| 90 UUCGACAGGAGGCUCACAACAGGCAAGCUU | 435 |
| 93 UUCGACAGGAGGCUCACAACAGGCAAGCUU | 436 |

TABLE 13-continued

Sequences from Round 5 Human Artery Perfusion Selex

| | | SEQ ID NOS: |
|---|---|---|
| 7 | UUCGACAGGAGGCUCACAACAGGCAAGCUU | 437 |
| 17 | UUCGACAGGAGGCUCACAACAGGCAAGCUU | 438 |
| 94 | UUCGACAGGAGGCUCACAACAGGCAAGCUU | 439 |
| 66 | UUCGACAGGAGGCUCACAACAGGCAAGCUU | 440 |

---

SEQUENCE LISTING (1) GENERAL INFORMATION:

(iii) NUMBER OF SEQUENCES: 440

(2) INFORMATION FOR SEQ ID NO:1:

(i) SEQUENCE CHARACTERISTICS:
      (A) LENGTH: 72 base pairs
      (B) TYPE: nucleic acid
      (C) STRANDEDNESS: single
      (D) TOPOLOGY: linear (xi) SEQUENCE DESCRIPTION: SEQ ID NO:1:

AGGGAGGACG ATGCGGNNNN NNNNNNNNNN NNNNNNNNNN NNNNNNNNNN    50

NNNNNNCAGA CGACTCGCCC GA    72

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:2:

AGGGAGGACG ATGCGG    16

(2) INFORMATION FOR SEQ ID NO:3:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:3:

TCGGGCGAGT CGTCTG    16

(2) INFORMATION FOR SEQ ID NO:4:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:4:

CCGAAGCTTA ATACGACTCA CTATAGGGAG GACGATGCGG    40

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY:linear (xi) SEQUENCE DESCRIPTION: SEQ ID NO:5:

```
GCCGGATCCT CGGGCGAGTC GTCTG                                             25
```

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY:linear (xi) SEQUENCE DESCRIPTION: SEQ ID NO:6:

```
TTCACACAGG AAACAG                                                       16
```

(2) INFORMATION FOR SEQ ID NO:7:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:7:

```
AGGGAGGACG ATGCGGGGGG TCGGTTCGGG CATATAGGGT ATTCTTCGTA                  50

GAGGGCAGAC GACTCGCCCG A                                                 71
```

(2) INFORMATION FOR SEQ ID NO:8:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:8:

```
AGGGAGGACG ATGCGGGGGG TCGGTTCGGG CATATAGGGT ATTCTTCGTA                  50

AAGGGCAGAC GACTCGCCCG A                                                 71
```

(2) INFORMATION FOR SEQ ID NO:9:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:9:

```
AGGGAGGACG ATGCGGGGGG TCGGTTCGGG CATATAGGGT ATCCTTCGTA                  50

GAGGGCAGAC GACTCGCCCG A                                                 71
```

(2) INFORMATION FOR SEQ ID NO:10:

(i) SEQUENCE CHARACTERISTICS:
        (A) LENGTH: 72 base pairs
        (B) TYPE: nucleic acid
        (C) STRANDEDNESS: single
        (D) TOPOLOGY:linear

```
    (xi) SEQUENCE DESCRIPTION: SEQ ID NO:10:

AGGGAGGACG ATGCGGCACG TTAGTAGGAT TAGGATTATT CAGGTTGTAG          50

GGAACACAGA CGACTCGCCC GA                                        72

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: single
        (D) TOPOLOGY:linear (xi) SEQUENCE DESCRIPTION: SEQ ID NO:11:

AGGGAGGACG ATGCGGCACG TTCAGCAGGA TTAGGGTTGT TTNGGTTGTA          50

GGGACACACA GACGACTCGC CCGA                                      74

(2) INFORMATION FOR SEQ ID NO:12:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:12:

AGGGAGGACG ATGCGGCACG GTAGTAAGTA GTAGGGTATT ATAATTAGGG          50

GATCCACAGA CGACTCGCCC GA                                        72

(2) INFORMATION FOR SEQ ID NO:13:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:13:

AGGGAGGACG ATGCGGCACG GCAGTATTAT TCAGGGGTCT TAGATATTAG          50

GGGGCACAGA CGACTCGCCC GA                                        72

(2) INFORMATION FOR SEQ ID NO:14:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:14:

AGGGAGGACG ATGCGGCACG GTAGGTTTTA GATAGGGATA TTTGGTGTAG          50

GGAGCACAGA CGACTCGCCC GA                                        72

(2) INFORMATION FOR SEQ ID NO:15:

(i) SEQUENCE CHARACTERISTICS:
        (A) LENGTH: 72 base pairs
        (B) TYPE: nucleic acid
        (C) STRANDEDNESS: single
        (D) TOPOLOGY:linear
```

(xi) SEQUENCE DESCRIPTION: SEQ ID NO:15:

AGGGAGGACG ATGCGGCACG GTAGGTTATA GATAGGGATA TTTNTTGTAG          50

GGAACACAGA CGACTCGCCC GA                                        72

(2) INFORMATION FOR SEQ ID NO:16:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:16:

AGGGAGGACG ATGCGGCACG GTAGGTTTTA GATAGGGATA TTTGATGTAG          50

GGAGCACAGA CGACTCGCCC GA                                        72

(2) INFORMATION FOR SEQ ID NO:17:

(i) SEQUENCE CHARACTERISTICS:
        (A) LENGTH:  72 base pairs
        (B) TYPE: nucleic acid
        (C) STRANDEDNESS: single
        (D) TOPOLOGY:linear (xi) SEQUENCE DESCRIPTION: SEQ ID NO:17:

AGGGAGGACG ATGCGGCACG GTAGGTTTTA GATAGGGATA TTTGGTATAG          50

GGAGCACAGA CGACTCGCCC GA                                        72

(2) INFORMATION FOR SEQ ID NO:18:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:18:

AGGGAGGACG ATGCGGCACG GTAGGCTTTA GATAGGGATA TTTGATGTAG          50

GGAGCACAGA CGACTCGCCC GA                                        72

(2) INFORMATION FOR SEQ ID NO:19:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:19:

AGGGAGGACG ATGCGGGGGG AGTAGGGTAT TTAAAAATGT TAGGGTAAGT          50

TTCCTCCAGA CGACTCGCCC GA                                        72

(2) INFORMATION FOR SEQ ID NO:20:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:20:

AGGGAGGACG ATGCGGGGGG AGTAGGGTAT TTAAAAGTGT CAGGGTAAGT    50

TTCCTCCAGA CGACTCGCCC GA    72

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:21:

AGGGAGGACG ATGCGGCGTA GTAAGAAGTA TTATTAGGGA TATTGTAGGG    50

GCGCTACAGA CGACTCGCCC GA    72

(2) INFORMATION FOR SEQ ID NO:22:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:22:

AGGGAGGACG ATGCGGCGTA GTAAGAAGTA TTATTAGGGA TATTGCAGGG    50

GCGCTACAGA CGACTCGCCC GA    72

(2) INFORMATION FOR SEQ ID NO:23:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:23:

AGGGAGGACG ATGCGGGGCA GCAAGAGTTT GATTAGGGTA TAGTTAGGGG    50

CGCTGCAGAC GACTCGCCCG A    71

(2) INFORMATION FOR SEQ ID NO:24:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:24:

AGGGAGGACG ATGCGGGCAG CAAGAGTTTG ATTAGGGTAT AGTTAGGGGC    50

GCTGCCAGAC GACTCGCCCG A    71

(2) INFORMATION FOR SEQ ID NO:25:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:25:

AGGGAGGACG ATGCGGGCAG TAAGGGTTTG ATTAGGGTAT AGTTAGGGGC           50

GCTGCCAGAC GACTCGCCCG A                                         71

(2) INFORMATION FOR SEQ ID NO:26:

(i) SEQUENCE CHARACTERISTICS:
        (A) LENGTH: 70 base pairs
        (B) TYPE: nucleic acid
        (C) STRANDEDNESS: single
        (D) TOPOLOGY:linear (xi) SEQUENCE DESCRIPTION: SEQ ID NO:26:

AGGGAGGACG ATGCGGGCAG CAAGAGGTTG ATTAGGGTAT AGTTAGGGGC           50

GCTGCAGACG ACTCGCCCGA                                           70

(2) INFORMATION FOR SEQ ID NO:27:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:27:

AGGGAGGACG ATGCGGCGGC AAGATGATTG AATAGGGGAT CTAAAGTTAG           50

GGGCGCCAGA CGACTCGCCC GA                                        72

(2) INFORMATION FOR SEQ ID NO:28:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:28:

AGGGAGGACG ATGCGGGCAG CAGGTGTAGG GGTATAGATG GATAGGGATT           50

TCTTCTCAGA CGACTCGCCC GA                                        72

(2) INFORMATION FOR SEQ ID NO:29:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:29:

AGGGAGGACG ATGCGGCACA TAGGGGAAAT GAGAATAGTA GGGTATTAAT           50

ACAGTGCAGA CGACTCGCCC GA                                        72

(2) INFORMATION FOR SEQ ID NO:30:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:30:

AGGGAGGACG ATGCGGCACA TAGGGGAAAT GAGAAGAATA GGGTATTAAT            50

ACAGTGCAGA CGACTCGCCC GA            72

(2) INFORMATION FOR SEQ ID NO:31:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:31:

AGGGAGGACG ATGCGGCAGG TTAGGGGAAA GGTTTAATAA TTAGGGTATA            50

AATGTGCAGA CGACTCGCCC GA            72

(2) INFORMATION FOR SEQ ID NO:32:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:32:

AGGGAGGACG ATGCGGCAGG TAGAGATAGG GAAGTTTTAT GTAGGGGACA            50

ATTCGTCAGA CGACTCGCCC GA            72

(2) INFORMATION FOR SEQ ID NO:33:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:33:

AGGGAGGACG ATGCGGCAGG TAGAGATAGG GAAGTTTTAT GTAGGGGACA            50

ATTCGTCAGA CGACTCGCCC GA            72

(2) INFORMATION FOR SEQ ID NO:34:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:34:

AGGGAGGACG ATGCGGCACA ATAGGGAAAT TTGTTGTTAT AGTTAGGGAT            50

ACTGGACAGA CGACTCGCCC GA            72

(2) INFORMATION FOR SEQ ID NO:35:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:35:

AGGGAGGACG ATGCGGGGCC GAATAGGGAA ATTTATTATT ACTAACAGTA          50

ATCCCCCAGA CGACTCGCCC GA                                       72

(2) INFORMATION FOR SEQ ID NO:36:

(i) SEQUENCE CHARACTERISTICS:
        (A) LENGTH: 71 base pairs
        (B) TYPE: nucleic acid
        (C) STRANDEDNESS: single
        (D) TOPOLOGY:linear (xi) SEQUENCE DESCRIPTION: SEQ ID NO:36:

AGGGAGGACG ATGCGGCAGG ACTTAGGGAT TTAGTTGTTT TAGGGGTTAT          50

GTAGTCAGAC GACTCGCCCG A                                        71

(2) INFORMATION FOR SEQ ID NO:37:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:37:

AGGGAGGACG ATGCGGGGGG GGATGAGATG TAATCCACAT GTCACTTATT          50

AAGTCCCAGA CGACTCGCCC GA                                       72

(2) INFORMATION FOR SEQ ID NO:38:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:38:

AGGGAGGACG ATGCGGCAGG GGATGGGATG TAATCCTCAT GTCACTTATT          50

AAGTCCCAGA CGACTCGCCC GA                                       72

(2) INFORMATION FOR SEQ ID NO:39:

(i) SEQUENCE CHARACTERISTICS:
        (A) LENGTH: 72 base pairs
        (B) TYPE: nucleic acid
        (C) STRANDEDNESS: single
        (D) TOPOLOGY:linear (xi) SEQUENCE DESCRIPTION: SEQ ID NO:39:

AGGGAGGACG ATGCGGTACG ACTACGATTG AGTATCCGGC TATAATATTA          50

CCATTGCAGA CGACTCGCCC GA                                       72

(2) INFORMATION FOR SEQ ID NO:40:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine

```
    (ix) FEATURE:
         (D) OTHER INFORMATION: All U's are 2'-F uracil (xi) SEQUENCE DESCRIPTION: SEQ ID NO:40:

GGGAGAUAAG AAUAAACGCU CAANNNNNNN NNNNNNNNNN NNNNNNNNNN                50

NNNNNNNNNN NNNUUCGACA GGAGGCUCAC AACAGGC                              87

(2) INFORMATION FOR SEQ ID NO:41:

(i) SEQUENCE CHARACTERISTICS:
        (A) LENGTH: 40 base pairs
        (B) TYPE: nucleic acid
        (C) STRANDEDNESS: single
        (D) TOPOLOGY:linear (xi) SEQUENCE DESCRIPTION: SEQ ID NO:41:

TAATACGACT CACTATAGGG AGAUAAGAAU AAACGCUCAA                           40

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY:linear (xi) SEQUENCE DESCRIPTION: SEQ ID NO:42:

GCCTGTTGTG AGCCTCCTGT CGAA                                            24

(2) INFORMATION FOR SEQ ID NO:43:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:43:

GGGAGAUAAG AAUAAACGCU CAAAGGGCUC GUGUGCCAAA UCGCUAACAA                50

CAAGCUAGCU GAUUUCGACA GGAGGCUCAC AACAGGC                              87

(2) INFORMATION FOR SEQ ID NO:44:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:44:

GGGAGAUAAG AAUAAACGCU CAACUGGGCU CAUCCGGCGA AUGAUGCAAG                50

GAAGAUUUCA CAUUUCGACA GGAGGCUCAC AACAGGC                              87
```

(2) INFORMATION FOR SEQ ID NO:45:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:45:

```
GGGAGAUAAG AAUAAACGCU CAAAAGGAUA GUGUGCUCCU GUACCAAAUU           50

UCCAAAGCGA UAUUUCGACA GGAGGCUCAC AACAGGC                         87
```

(2) INFORMATION FOR SEQ ID NO:46:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:46:

```
GGGAGAUAAG AAUAAACGCU CAAAAAGAGU AAAGCGCGGA ACAGGAUUCA           50

CGUUGCGCUC UUUUCGACAG GAGGCUCACA ACAGGC                          86
```

(2) INFORMATION FOR SEQ ID NO:47:

(i) SEQUENCE CHARACTERISTICS:
        (A) LENGTH: 85 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:47:

```
GGGAGAUAAG AAUAAACGCU CAAAAAGAGU AAAGCGCGGA ACAGGAUUCA           50

CGUUGCGCUC AUUCGACAGG AGGCUCACAA CAGGC                           85
```

(2) INFORMATION FOR SEQ ID NO:48:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:48:

GGGAGAUAAG AAUAAACGCU CAACAACGAU UAUCUUUUCG GCCGUGAAAC         50

CCAAACUGAC GCCUUCGACA GGAGGCUCAC AACAGGC                      87

(2) INFORMATION FOR SEQ ID NO:49:

(i) SEQUENCE CHARACTERISTICS:
         (A) LENGTH: 87 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:49:

GGGAGAUAAG AAUAAACGCU CAACGCGAGG AUAGGGUGCA GCUUCUGUUC         50

CAAAUACGUG AAUUCGACA GGAGGCUCAC AACAGGC                       87

(2) INFORMATION FOR SEQ ID NO:50:

(i) SEQUENCE CHARACTERISTICS:
         (A) LENGTH: 87 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:50:

GGGAGAUAAG AAUAAACGCU CAAUAAGUCG AAGAGCUCCU GAUCCAAACC         50

AUCGAAAGGA CGUUUCGACA GGAGGCUCAC AACAGGC                      87

(2) INFORMATION FOR SEQ ID NO:51:

(i) SEQUENCE CHARACTERISTICS:
         (A) LENGTH: 87 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:51:

GGGAGAUAAG AAUAAACGCU CAAGGUAAGU UGGAGCUCCU UAUCCAAGCA         50

CGCAAUAAGU GACUUCGACA GGAGGCUCAC AACAGGC                      87

(2) INFORMATION FOR SEQ ID NO:52:

(i) SEQUENCE CHARACTERISTICS:
         (A) LENGTH: 86 base pairs
         (B) TYPE: nucleic acid
         (C) STRANDEDNESS: single
         (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:52:

GGGAGAUAAG AAUAAACGCU CAAUUUGGCG UGGGAUCCUG GACUGAAGGA           50

UUUUGACGAU GCUUCGACAG GAGGCUCACA ACAGGC                          86

(2) INFORMATION FOR SEQ ID NO:53:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:53:

GGGAGAUAAG AAUAAACGCU CAAAUUCAAG ACAGAGACUU UCCUUGAAUG           50

CUCUGUCCCA UAAUUCGACA GGAGGCUCAC AACAGGC                         87

(2) INFORMATION FOR SEQ ID NO:54:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:54:

GGGAGAUAAG AAUAAACGCU CAAACAAAUG UGCGACCUUG GACGAAGUUA           50

ACUCGGACGG UUCUUCGACA GGAGGCUCAC AACAGGC                         87

(2) INFORMATION FOR SEQ ID NO:55:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:55:

GGGAGAUAAG AAUAAACGCU CAAACAAAUG UGCGCCCUUG GACGAAGUUA           50

ACUCGGACGG UUCUUCGACA GGAGGCUCAC AACAGGC                         87

(2) INFORMATION FOR SEQ ID NO:56:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:56:

GGGAGAUAAG AAUAAACGCU CAAACAAAUG UGCGCCCUUG GACGAAGUUA            50

ACUCGGACGG UUGUUCGACA GGAGGCUCAC AACAGGC                         87

(2) INFORMATION FOR SEQ ID NO:57:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:57:

GGGAGAUAAG AAUAAACGCU CAAACAAAUG UGCGCCCUUG GACGAAGUUA            50

ACUCGGACGG UUCUUCGACA GGAGGCUCAC AACAGGC                         87

(2) INFORMATION FOR SEQ ID NO:58:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:58:

GGGAGAUAAG AAUAAACGCU CAAAAGUCUG AGACUCCUGG ACUGAAUUAG            50

CUAGGACGGC UGUUCGACAG GAGGCUCACA ACAGGC                          86

(2) INFORMATION FOR SEQ ID NO:59:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil

```
    (xi) SEQUENCE DESCRIPTION: SEQ ID NO:59:

GGGAGAUAAG AAUAAACGCU CAAUAGGAGC CUAGCAGCCC CUGCAUCGAU            50

CACUAGGAUG GUUUUCGACA GGAGGCUCAC AACAGGC                         87

(2) INFORMATION FOR SEQ ID NO:60:

(i) SEQUENCE CHARACTERISTICS:
         (A) LENGTH: 87 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:60:

GGGAGAUAAG AAUAAACGCU CAAAAAGUGU AGCCUUCCUG GACUGUAGGU            50

ACUAGGACGG UCCUUCGACA GGAGGCUCAC AACAGGC                         87

(2) INFORMATION FOR SEQ ID NO:61:

(i) SEQUENCE CHARACTERISTICS:
         (A) LENGTH: 83 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:61:

GGGAGAUAAG AAUAAACGCU CAAACAAAUG UGCUCCCUUG GACGAAGUUA            50

ACUCGGCGGU UCGACAGGAG GCUCACAACA GGC                             83

(2) INFORMATION FOR SEQ ID NO:62:

(i) SEQUENCE CHARACTERISTICS:
         (A) LENGTH: 86 base pairs
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:62:

GGGAGAUAAG AAUAAACGCU CAAAAGAAGC UGGCGACAGG CGAAAAGCAG            50

ACUUGAGGGG AAUUCGACAG GAGGCUCACA ACAGGC                          86

(2) INFORMATION FOR SEQ ID NO:63:

(i) SEQUENCE CHARACTERISTICS:
         (A) LENGTH: 87 base pairs
         (B) TYPE: nucleic acid
         (C) STRANDEDNESS: single
         (D) TOPOLOGY:linear
```

(ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:63:

GGGAGAUAAG AAUAAACGCU CAAAGUAGGU GAGGCUUCUG GACUGAAGUA      50

ACUAGGUCGG UUCUUCGACA GGAGGCUCAC AACAGGC      87

(2) INFORMATION FOR SEQ ID NO:64:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:64:

GGGAGAUAAG AAUAAACGCU CAACAUGAGC UGCUGGACCA AACAGAUGGA      50

GGAACCACCG UGUUUCGACA GGAGGCUCAC AACAGGC      87

(2) INFORMATION FOR SEQ ID NO:65:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:65:

GGGAGAUAAG AAUAAACGCU CAAGAGCUCU UGACGAAAAC CUAUGCGAGA      50

UGGAUACUCG GUUUCGACA GGAGGCUCAC AACAGGC      87

(2) INFORMATION FOR SEQ ID NO:66:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:66:

GGGAGAUAAG AAUAAACGCU CAAGAGCUCU UGACGAAAAC CUAUGCGAGA      50

AGGAUACUCG GUUUCGACA GGAGGCUCAC AACAGGC      87

```
(2) INFORMATION FOR SEQ ID NO:67:

(i) SEQUENCE CHARACTERISTICS:
        (A) LENGTH: 85 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:67:

GGGAGAUAAG AAUAAACGCU CAAGAGCUCU AGACGAAAAC CUAUGCGAGA              50

UGAUACUCGG UCUUCGACAG GAGGCUCAAA CAGGC                              85

(2) INFORMATION FOR SEQ ID NO:68:

(i) SEQUENCE CHARACTERISTICS:
        (A) LENGTH: 88 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:68:

GGGAGAUAAG AAUAAACGCU CAAUGAGCUC UUGAAGAAGU CCGAACAUUC              50

UCCUUUCUGC GACUUUCGAC AGGAGGCUCA CAACAGGC                           88

(2) INFORMATION FOR SEQ ID NO:69:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:69:

GGGAGAUAAG AAUAAACGCU CAAGAGCUCC GGGAUCCAAG CGUGCAACAA              50

CACUAUGCCC ACUUCGACAG GAGGCUCACA ACAGGC                             86

(2) INFORMATION FOR SEQ ID NO:70:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil
```

(xi) SEQUENCE DESCRIPTION: SEQ ID NO:70:

GGGAGAUAAG AAUAAACGCU CAAAAUACCC UCGGGAACCA AUCCGACCCU          50

AUUUUGCAGU UUGUUCGACA GGAGGCUCAC AACAGGC          87

(2) INFORMATION FOR SEQ ID NO:71:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:71:

GGGAGAUAAG AAUAAACGCU CAAAUGAUGC UCCUGAAGUA AUCACCAGGA          50

CAUCCUCGGC AUUUCGACAG GAGGCUCACA ACAGGC          86

(2) INFORMATION FOR SEQ ID NO:72:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:72:

GGGAGAUAAG AAUAAACGCU CAAGCAAUCU CGGACUAGAC CAACGACCUU          50

CGUUUGACGC UCAUUCGACA GGAGGCUCAC AACAGGC          87

(2) INFORMATION FOR SEQ ID NO:73:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:73:

GGGAGAUAAG AAUAAACGCU CAACCGAUUU CUAGGACGGA UUUACGGAGA          50

AUUGAGUCGC AAGUUCGACA GGAGGCUCAC AACAGGC          87

(2) INFORMATION FOR SEQ ID NO:74:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:74:

GGGAGAUAAG AAUAAACGCU CAAACGGCGA GAAUGACAAU GUUAUUCUAC        50

GAGCGAAGGA UUAUUCGACA GGAGGCUCAC AACAGGC                     87

(2) INFORMATION FOR SEQ ID NO:75:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:75:

GGGAGAUAAG AAUAAACGCU CAAGCAAUCU CGGACUAGAC UAACGACCUU        50

GGUUUGACGC UAAUUCGACA GGAGGCUCAC AACAGGC                     87

(2) INFORMATION FOR SEQ ID NO:76:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:76:

GGGAGAUAAG AAUAAACGCU CAAGCAAUCU CGGACUAGAC UAACGACCUU        50

CGUUUGACGC UCAUUCGACA GGAGGCUCAC AACAGGC                     87

(2) INFORMATION FOR SEQ ID NO:77:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:77:

GGGAGAUAAG AAUAAACGCU CAAAGAGCAG CCGGAGGUGU GAGCUCUGAC        50

UCUGAACAGC UGUUCGACAG GAGGCUCACA ACAGGC                      86

(2) INFORMATION FOR SEQ ID NO:78:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:78:

```
GGGAGAUAAG AAUAAACGCU CAACGGGAUU UCUCGGAAAA GACUAACGAC          50

UAAUUCCAGA ACCUUCGACA GGAGGCUCAC AACAGGC                        87
```

(2) INFORMATION FOR SEQ ID NO:79:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:79:

```
GGGAGAUAAG AAUAAACGCU CAAGCAAUCU CGGACUAGGC UAACGACCUU          50

UGUUUGACGC UCAUUCGACA GGAGGCUCAC AACAGGC                        87
```

(2) INFORMATION FOR SEQ ID NO:80:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:80:

```
GGGAGAUAAG AAUAAACGCU CAAGCAAUCU CGGACUAGAC UAACGACCUU          50

CGUUUGACGC UUAUUCGACA GGAGGCUCAC AACAGGC                        87
```

(2) INFORMATION FOR SEQ ID NO:81:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:81:

GGGAGAUAAG AAUAAACGCU CAAUCCAAGG ACCAAACGGG UGUUCGGCAG           50

UGGACUUUAG CAAUUCGACA GGAGGCUCAC AACAGGC                         87

(2) INFORMATION FOR SEQ ID NO:82:

(i) SEQUENCE CHARACTERISTICS:
                (A) LENGTH: 86 base pairs
                (B) TYPE: nucleic acid
                (C) STRANDEDNESS: single
                (D) TOPOLOGY:linear (ix) FEATURE:
                (D) OTHER INFORMATION:   All C's are 2'-F cytosine (ix) FEATURE:
                (D) OTHER INFORMATION:   All U's are 2'-F uracil (xi) SEQUENCE DESCRIPTION: SEQ ID NO:82:

GGGAGAUAAG AAUAAACGCU CAAUGGGCUA CAUGUGAGUA CACCAGCGUG           50

AGAGUUCUUA GGUUCGACAG GAGGCUCACA ACAGGC                          86

(2) INFORMATION FOR SEQ ID NO:83:

(i) SEQUENCE CHARACTERISTICS:
                (A) LENGTH: 88 base pairs
                (B) TYPE: nucleic acid
                (C) STRANDEDNESS: single
                (D) TOPOLOGY:linear (ix) FEATURE:
                (D) OTHER INFORMATION:   All C's are 2'-F cytosine (ix) FEATURE:
                (D) OTHER INFORMATION:   All U's are 2'-F uracil (xi) SEQUENCE DESCRIPTION: SEQ ID NO:83:

GGGAGAUAAG AAUAAACGCU CAACUGUGCA GUAACUGCGG AUGAGACCAA           50

CCGGAUGGCU CAACUUCGAC AGGAGGCUCA CAACAGGC                        88

(2) INFORMATION FOR SEQ ID NO:84:

(i) SEQUENCE CHARACTERISTICS:
                (A) LENGTH: 87 base pairs
                (B) TYPE: nucleic acid
                (C) STRANDEDNESS: single
                (D) TOPOLOGY:linear (ix) FEATURE:
                (D) OTHER INFORMATION:   All C's are 2'-F cytosine (ix) FEATURE:
                (D) OTHER INFORMATION:   All U's are 2'-F uracil (xi) SEQUENCE DESCRIPTION: SEQ ID NO:84:

GGGAGAUAAG AAUAAACGCU CAAACAAUCU CGGACUAGAC UAACGACCUU           50

CGUUUGACGC UUAUUCGACA GGAGGCUCAC AACAGGC                         87

(2) INFORMATION FOR SEQ ID NO:85:

(i) SEQUENCE CHARACTERISTICS:
                (A) LENGTH: 87 base pairs
                (B) TYPE: nucleic acid
                (C) STRANDEDNESS: single
                (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:85:

GGGAGAUAAG AAUAAACGCU CAAGCAAUCU CGGACGAGAC UAACGACCUU          50

CGUUUGACGC UUAUUCGACA GGAGGCUCAC AACAGGC                       87

(2) INFORMATION FOR SEQ ID NO:86:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:86:

GGGAGAUAAG AAUAAACGCU CAAAGCGCUA GAUGGACGAG AGACUUUUAA          50

GUAGCAAGCG GUAUUCGACA GGAGGCUCAC AACAGGC                       87

(2) INFORMATION FOR SEQ ID NO:87:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:87:

GGGAGAUAAG AAUAAACGCU CAACAGACUC AGAGCGCCGU GAGCUUCUGA          50

AGCAAUCGCA GGUUUCGACA GGAGGCUCAC AACAGGC                       87

(2) INFORMATION FOR SEQ ID NO:88:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:88:

GGGAGAUAAG AAUAAACGCU CAAGCGGGGA GCUCCUCGAG AAACUGAGUU          50

CAACUUCCCA GGUUUCGACA GGAGGCUCAC AACAGGC                       87

(2) INFORMATION FOR SEQ ID NO:89:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:89:

GGGAGAUAAG AAUAAACGCU CAAGUGUUGG AGCUCUUGAU UGGAAAAGUA        50

GAACAAAUCG AAAUUCGACA GGAGGCUCAC AACAGGC                     87

(2) INFORMATION FOR SEQ ID NO:90:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:90:

GGGAGAUAAG AAUAAACGCU CAAGUGUUGG AGCUCUUGAU UGGAAAAUUA        50

GAGCAAAUCG AAAUUCGACA GGAGGCUCAC AACAGGC                     87

(2) INFORMATION FOR SEQ ID NO:91:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:91:

GGGAGAUAAG AAUAAACGCU CAACAAUCCG AGCUCUUGAA GCAAUCCUUG        50

AUUGCAAGAU GAUUUCGACA GGAGGCUCAC AACAGGC                     87

(2) INFORMATION FOR SEQ ID NO:92:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:92:

GGGAGAUAAG AAUAAACGCU CAAUCGGAUG AGCUCUUGAA GCAGUUCAAG          50

GACAGACAUA AAGUUCGACA GGAGGCUCAC AACAGGC                       87

(2) INFORMATION FOR SEQ ID NO:93:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:93:

GGGAGAUAAG AAUAAACGCU CAAUUCCAGG UUAGCGGCCA AACCUCGACU          50

UGAACAGACU UUAUUCGACA GGAGGCUCAC AACAGGC                       87

(2) INFORMATION FOR SEQ ID NO:94:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:94:

GGGAGAUAAG AAUAAACGCU CAAGUGUUGG AGCUCUUGAU UGGAAAAGUA          50

GAGCAAAACG AAAUUCGACA GGAGGCUCAC AACAGGC                       87

(2) INFORMATION FOR SEQ ID NO:95:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:95:

GGGAGAUAAG AAUAAACGCU CAAGUGUUGG AGCUCUUGAU UGGAAAAGUA          50

GAGCAAAUCG AAAUUCGACA GGAGGCUCAC AACAGGC                       87

(2) INFORMATION FOR SEQ ID NO:96:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:96:

GGGAGAUAAG AAUAAACGCU CAAGUGGUGC UGCAAUUGCU CGGUCGGCGU           50

GCUCUCUACU UGAUUCGACA GGAGGCUCAC AACAGGC                        87

(2) INFORMATION FOR SEQ ID NO:97:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:97:

GGGAGAUAAG AAUAAACGCU CAAGCUCAAG AGACUGAAGG AAAAGCUUAG           50

AGCUCAAAGC AUAUUCGACA GGAGGCUCAC AACAGGC                        87

(2) INFORMATION FOR SEQ ID NO:98:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:98:

GGGAGAUAAG AAUAAACGCU CAACGUGUUG GGUUCAAAGA CCAGCUUACG           50

GUACACAGUA CGAUUCGACA GGAGGCUCAC AACAGGC                        87

(2) INFORMATION FOR SEQ ID NO:99:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:99:

GGGAGAUAAG AAUAAACGCU CAAUCUGUUG GUUCAAAGAC UUGCUAAGGG           50

GUCGAAGCAC CCUUUCGACA GGAGGCUCAC AACAGGC                        87

(2) INFORMATION FOR SEQ ID NO:100:

(i) SEQUENCE CHARACTERISTICS:
        (A) LENGTH: 85 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:100:

GGGAGAUAAG AAUAAACGCU CAAGACGACA AAGAGUCCGU UCCAAACCUC         50

UGAGACAGGG UUUCGACAGG AGGCUCACAA CAGGC                         85

(2) INFORMATION FOR SEQ ID NO:101:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:101:

GGGAGAUAAG AAUAAACGCU CAAUAGCAAG UCCCACAUCC CAGACGGGCU         50

AAAAAGAGGU GGAUUCGACA GGAGGCUCAC AACAGGC                       87

(2) INFORMATION FOR SEQ ID NO:102:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:102:

GGGAGAUAAG AAUAAACGCU CAAAUGAACG ACCGCGGGCA GUCGCGUUCA         50

AAUGAGUGGU UUUUCGACA GGAGGCUCAC AACAGGC                        87

(2) INFORMATION FOR SEQ ID NO:103:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:103:

GGGAGAUAAG AAUAAACGCU CAAAUGAGUA GACCGAGGAA GCACCCGGCU                50

CUCAAAUGAG UGAUUCGACA GGAGGCUCAC AACAGGC                              87

(2) INFORMATION FOR SEQ ID NO:104:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:104:

GGGAGAUAAG AAUAAACGCU CAAAUGAGUA GACCGAGGAA GCACCCGGCU                50

CUCAAAUGAC UGAUUCGACA GGAGGCUCAC AACAGGC                              87

(2) INFORMATION FOR SEQ ID NO:105:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:105:

GGGAGAUAAG AAUAAACGCU CAAAAGGCCA UCAGGGCAAA GACCUCCUAG                50

GUACUGACGC UUAUUCGACA GGAGGCUCAC AACAGGC                              87

(2) INFORMATION FOR SEQ ID NO:106:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:106:

GGGAGAUAAG AAUAAACGCU CAAAAGGCCG AACAACGAAG UUUGAUUCAG                50

GUACUCAGCG UUCUUCGACA GGAGGCUCAC AACAGGC                              87

(2) INFORMATION FOR SEQ ID NO:107:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
            (D) OTHER INFORMATION:   All C's are 2'-F cytosine (ix) FEATURE:
            (D) OTHER INFORMATION:   All U's are 2'-F uracil (xi) SEQUENCE DESCRIPTION: SEQ ID NO:107:

GGGAGAUAAG AAUAAACGCU CAAAAGGCCG AACAACGAAG AUUGAUUCAG          50

GUACUCAGCG UUCUUCGACA GGAGGCUCAC AACAGGC                        87

(2) INFORMATION FOR SEQ ID NO:108:

(i) SEQUENCE CHARACTERISTICS:
            (A) LENGTH: 87 base pairs
            (B) TYPE: nucleic acid
            (C) STRANDEDNESS: single
            (D) TOPOLOGY:linear (ix) FEATURE:
            (D) OTHER INFORMATION:   All C's are 2'-F cytosine (ix) FEATURE:
            (D) OTHER INFORMATION:   All U's are 2'-F uracil (xi) SEQUENCE DESCRIPTION: SEQ ID NO:108:

GGGAGAUAAG AAUAAACGCU CAAAAGGCGG AGGGCAAGCA AGAACCUCAC          50

GAACAGACGU UAAUUCGACA GGAGGCUCAC AACAGGC                        87

(2) INFORMATION FOR SEQ ID NO:109:

(i) SEQUENCE CHARACTERISTICS:
            (A) LENGTH: 87 base pairs
            (B) TYPE: nucleic acid
            (C) STRANDEDNESS: single
            (D) TOPOLOGY:linear (ix) FEATURE:
            (D) OTHER INFORMATION:   All C's are 2'-F cytosine (ix) FEATURE:
            (D) OTHER INFORMATION:   All U's are 2'-F uracil (xi) SEQUENCE DESCRIPTION: SEQ ID NO:109:

GGGAGAUAAG AAUAAACGCU CAAAGCCUGA GGUAUAGUUA CGCUAUAUGG          50

GAGGUAGGCU UUAUUCGACA GGAGGCUCAC AACAGGC                        87

(2) INFORMATION FOR SEQ ID NO:110:

(i) SEQUENCE CHARACTERISTICS:
            (A) LENGTH: 87 base pairs
            (B) TYPE: nucleic acid
            (C) STRANDEDNESS: single
            (D) TOPOLOGY:linear (ix) FEATURE:
            (D) OTHER INFORMATION:   All C's are 2'-F cytosine (ix) FEATURE:
            (D) OTHER INFORMATION:   All U's are 2'-F uracil (xi) SEQUENCE DESCRIPTION: SEQ ID NO:110:

GGGAGAUAAG AAUAAACGCU CAACGUGAUG ACAGCUCGGA CGGCUCAUUG          50

CGCGGAGUAG CUAUUCGACA GGAGGCUCAC AACAGGC                        87

(2) INFORMATION FOR SEQ ID NO:111:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:111:

GGGAGAUAAG AAUAAACGCU CAACGGCUCG AUGCUAGCUG GGACGGCUCA        50

UUGAGACUGG UUGUUCGACA GGAGGCUCAC AACAGGC                     87

(2) INFORMATION FOR SEQ ID NO:112:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:112:

GGGAGAUAAG AAUAAACGCU CAAAGUGCAA CCUGAACCAA ACCAAACUAG        50

CGCGCAGUUG GGUUUCGACA GGAGGCUCAC AACAGGC                     87

(2) INFORMATION FOR SEQ ID NO:113:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:113:

GGGAGAUAAG AAUAAACGCU CAAAGCAGAU GGUGCUGAGG UAUCAUGAAG        50

ACGCUGACGC UUAUUCGACA GGAGGCUCAC AACAGGC                     87

(2) INFORMATION FOR SEQ ID NO:114:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:114:

GGGAGAUAAG AAUAAACGCU CAAGAAUGGA GCCAAGAAAG ACAGCGAUGU         50

CUCGGACGAU GAGUUCGACA GGAGGCUCAC AACAGGC                      87

(2) INFORMATION FOR SEQ ID NO:115:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:115:

GGGAGAUAAG AAUAAACGCU CAAGAAUGGA GCCAGGAAAG ACAGCGAUGU         50

CUCGGACGAU GAGUUCGACA GGAGGCUCAC AACAGGC                      87

(2) INFORMATION FOR SEQ ID NO:116:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:116:

GGGAGAUAAG AAUAAACGCU CAAGGAUGGA GCCAAGAAAG ACAGCGAUGU         50

CUCGGACGAU GAGUUCGACA GGAGGCUCAC AACAGGC                      87

(2) INFORMATION FOR SEQ ID NO:117:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:117:

GGGAGAUAAG AAUAAACGCU CAACGUGAGA UUCCCCUGCG UAAGACCAGA         50

AGACUAUCAG GCUUUCGACA GGAGGCUCAC AACAGGC                      87

(2) INFORMATION FOR SEQ ID NO:118:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:118:

GGGAGAUAAG AAUAAACGCU CAAAGGGUUG AGGCUUAUCC UUCUUUCGUU         50

CGUGACACGA UCGUUCGACA GGAGGCUCAC AACAGGC                      87

(2) INFORMATION FOR SEQ ID NO:119:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:119:

GGGAGAUAAG AAUAAACGCU CAAGAUUGAC ACGCACUCCA AUGGCUCUGA         50

AGUGUUCGUG UGCUUCGACA GGAGGCUCAC AACAGGC                      87

(2) INFORMATION FOR SEQ ID NO:120:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:120:

GGGAGAUAAG AAUAAACGCU CAAAAAUUCA AUGCUCUGAU GGGUUUAUGA         50

GUUAAUGCGU GGACUUCGAC AGGAGGCUCA CAACAGGC                     88

(2) INFORMATION FOR SEQ ID NO:121:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:121:

GGGAGAUAAG AAUAAACGCU CAAAAAGGCC CUUUCAGCAG GGAUCGAGGU         50

ACUGGAUGGA UAUUCGACAG GAGGCUCACA ACAGGC                       86

(2) INFORMATION FOR SEQ ID NO:122:

(i) SEQUENCE CHARACTERISTICS:
        (A) LENGTH: 85 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:122:

```
GGGAGAUAAG AAUAAACGCU CAAAAAGUCG UGUGCGAGAG GCUCAGAUUU          50

AAUGCGGAGG AUUCGACAGG AGGCUCACAA CAGGC                          85
```

(2) INFORMATION FOR SEQ ID NO:123:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:123:

```
GGGAGAUAAG AAUAAACGCU CAACGUUGAA AUCGCUCCUC AGUGUGAGUU          50

GAAUCAGCUG ACCUUCGACA GGAGGCUCAC AACAGGC                        87
```

(2) INFORMATION FOR SEQ ID NO:124:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:124:

```
GGGAGAUAAG AAUAAACGCU CAAAGUUUGG AUUCGGCAGG UGCUGAGACU          50

UUGAUAGCCA CUAUUCGACA GGAGGCUCAC AACAGGC                        87
```

(2) INFORMATION FOR SEQ ID NO:125:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:125:

GGGAGAUAAG AAUAAACGCU CAAGUGAGAA AUGUCGGGGG CGAUGACUUG         50

GACGGUCCAC CGUUCGACAG GAGGCUCACA ACAGGC                        86

(2) INFORMATION FOR SEQ ID NO:126:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:126:

GGGAGAUAAG AAUAAACGCU CAACGUUGAA AUCGCUCCUC AGCGUGAGUU         50

GAAUCAGCUG ACCUUCGACA GGAGGCUCAC AACAGGC                       87

(2) INFORMATION FOR SEQ ID NO:127:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:127:

GGGAGAUAAG AAUAAACGCU CAAAGAGAGG AACUGCGAUU CAGACCAAAA         50

CGGAAAUGGC UGUUUCGACA GGAGGCUCAC AACAGGC                       87

(2) INFORMATION FOR SEQ ID NO:128:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:128:

GGGAGAUAAG AAUAAACGCU CAAGAUAUAC UAACUUUCUU UGAAAGCCAA         50

AAGUAUUAAU GCGUUCGACA GGAGGCUCAC AACAGGC                       87

(2) INFORMATION FOR SEQ ID NO:129:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:129:

GGGAGAUAAG AAUAAACGCU CAAGAUAUAC UAACUUUGUU UGAAAGCCAA          50

AAGUAUUAAU GCGUUCGACA GGAGGCUCAC AACAGGC                         87

(2) INFORMATION FOR SEQ ID NO:130:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:130:

GGGAGAUAAG AAUAAACGCU CAAAGCCGAG CUAAUCCCGA AAGUGACCCG          50

GAACGACGCG GCAUUCGACA GGAGGCUCAC AACAGGC                         87

(2) INFORMATION FOR SEQ ID NO:131:

(i) SEQUENCE CHARACTERISTICS:
              (A) LENGTH: 25 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:131:

CGAAGUUAAC UCGGACGGUU CUUCG                                      25

(2) INFORMATION FOR SEQ ID NO:132:

(i) SEQUENCE CHARACTERISTICS:
              (A) LENGTH: 29 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:132:

CGAAGUUAAC UCGGACGGUU CUUCGACAG                                  29

(2) INFORMATION FOR SEQ ID NO:133:

(i) SEQUENCE CHARACTERISTICS:
              (A) LENGTH: 29 base pairs
              (B) TYPE: nucleic acid
              (C) STRANDEDNESS: single
              (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:133:

UGGACGAAGU UAACUCGGAC GGUUCUUCG                                              29

(2) INFORMATION FOR SEQ ID NO:134:

(i) SEQUENCE CHARACTERISTICS:
        (A) LENGTH: 41 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:134:

CCCUUGGACG AAGUUAACUC GGACGGUUCU UCGACAGGAG G                                41

(2) INFORMATION FOR SEQ ID NO:135:

(i) SEQUENCE CHARACTERISTICS:
        (A) LENGTH: 23 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:135:

UCGAUCACUA GGAUGGUUUU CGA                                                    23

(2) INFORMATION FOR SEQ ID NO:136:

(i) SEQUENCE CHARACTERISTICS:
        (A) LENGTH: 30 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:136:

UCGAUCACUA GGAUGGUUUU CGACAGGAGG                                             30

(2) INFORMATION FOR SEQ ID NO:137:

(i) SEQUENCE CHARACTERISTICS:
        (A) LENGTH: 31 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
    (D) OTHER INFORMATION: All U's are 2'-F uracil (xi) SEQUENCE DESCRIPTION: SEQ ID NO:137:

CCCCUGCAUC GAUCACUAGG AUGGUUUUCG A                                31

(2) INFORMATION FOR SEQ ID NO:138:

(i) SEQUENCE CHARACTERISTICS:
        (A) LENGTH: 38 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:138:

CCCCUGCAUC GAUCACUAGG AUGGUUUUCG ACAGGAGG                         38

(2) INFORMATION FOR SEQ ID NO:139:

(i) SEQUENCE CHARACTERISTICS:
        (A) LENGTH: 23 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:139:

GGGAGAUAAG AAUAAACGCU CAA                                         23

(2) INFORMATION FOR SEQ ID NO:140:

(i) SEQUENCE CHARACTERISTICS:
        (A) LENGTH: 24 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:140:

UUCGACAGGA GGCUCACAAC AGGC                                        24

(2) INFORMATION FOR SEQ ID NO:141:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:141:

GGGAGAUAAG AAUAAACGCU CAAACCACUG GGCCCAGUUU AGAAACUCAU          50

UGCCCAAAUC CGGUUCGACA GGAGGCUCAC AACAGGC                        87

(2) INFORMATION FOR SEQ ID NO:142:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:142:

GGGAGAUAAG AAUAAACGCU CAAAGAAGA AUCGAAAAAU CUACCUUGUU           50

CGGAGCCUGC UCUUUCGACA GGAGGCUCAC AACAGGC                        87

(2) INFORMATION FOR SEQ ID NO:143:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:143:

GGGAGAUAAG AAUAAACGCU CAAUCUAGAC AGCGAAGGCU GAGCUAUGAC          50

ACUGAACUUC UUAUUCGACA GGAGGCUCAC AACAGGC                        87

(2) INFORMATION FOR SEQ ID NO:144:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:144:

GGGAGAUAAG AAUAAACGCU CAAGCAAUCU GGACUAGACU AACGACCUUC          50

GCUUGACGCU CAUUCGACAG GAGGCUCACA ACAGGC                         86

(2) INFORMATION FOR SEQ ID NO:145:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:145:

GGGAGAUAAG AAUAAACGCU CAAGCAAUCU CGGACUAGAC UAACGACCUU          50

CGUUUGACGC AAUUCGACA GGAGGCUCAC AACAGGC                         87

(2) INFORMATION FOR SEQ ID NO:146:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:146:

GGGAGAUAAG AAUAAACGCU CAAGCAAUCU CGGACUAGAC UAACGACCUU          50

CGUUUGACGC UCAUUCGACA GGAGGCUCAC AACAGGC                        87

(2) INFORMATION FOR SEQ ID NO:147:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:147:

GGGAGAUAAG AAUAAACGCU CAAGCAAUCU CGGACUCGAC UAACGACCUU          50

CGUUUGACGC UCAUUCGACA GGAGGCUCAC AACAGGC                        87

(2) INFORMATION FOR SEQ ID NO:148:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:148:

GGGAGAUAAG AAUAAACGCU CAAGACAAUA ACCGCACCAA CGUUCUGUUC          50

UUCGCUUGCA CGUUUCGACA GGAGGCUCAC AACAGGC                        87

(2) INFORMATION FOR SEQ ID NO:149:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:149:

```
GGGAGAUAAG AAUAAACGCU CAACAAUUCC CACUGAUUCG GGGCGGUCCU          50

UGCGAUGGCG AGAUUCGACA GGAGGCUCAC AACAGGC                        87
```

(2) INFORMATION FOR SEQ ID NO:150:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:150:

```
GGGAGAUAAG AAUAAACGCU CAACUCAGAC AACCAACAGC ACGUUCUCUG          50

UUUUCGUCGU UUGUUCGACA GGAGGCUCAC AACAGGC                        87
```

(2) INFORMATION FOR SEQ ID NO:151:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:151:

```
GGGAGAUAAG AAUAAACGCU CAAGCAAUCU CGGACUAGAC UAACGACCUU          50

CGUUUGACGC UUAUUCGACA GGAGGCUCAC AACAGGC                        87
```

(2) INFORMATION FOR SEQ ID NO:152:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:152:

GGGAGAUAAG AAUAAACGCU CAAGCAAUCU CGGACUAGAC UAACGACCUU        50

CGUUUGACGC UCGUUCGACA GGAGGCUCAC AACAGGC        87

(2) INFORMATION FOR SEQ ID NO:153:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:153:

GGGAGAUAAG AAUAAACGCU CAACGCUCAU GACCAGGCGC UACUGACUGA        50

GAUGUUGAAC UUAUUCGACA GGAGGCUCAC AACAGGC        87

(2) INFORMATION FOR SEQ ID NO:154:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:154:

GGGAGAUAAG AAUAAACGCU CAAGCAAUCU CGGACUAGAC UAACGACCCU        50

CGUUUGACGC UCAUUCGACA GGAGGCUCAC AACAGGC        87

(2) INFORMATION FOR SEQ ID NO:155:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:155:

GGGAGAUAAG AAUAAACGCU CAAAUAAGAU CAACAUUGGC GGUUUAUGUU        50

AUUCGUCCGU UUGUUCGACA GGAGGCUCAC AACAGGC        87

(2) INFORMATION FOR SEQ ID NO:156:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:156:

GGGAGAUAAG AAUAAACGCU CAAGCAAUCU CGGACUAGAC UAACGACCUU           50

CGUUUGACGC UUAUUCGACA GGAGGCUCAC AACAGGC                        87

(2) INFORMATION FOR SEQ ID NO:157:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:157:

GGGAGAUAAG AAUAAACGCU CAACACGCGA GAGCUUCUAA AGCUGCUGAA           50

UCGAGCUCCA CGAUUCGACA GGAGGCUCAC AACAGGC                        87

(2) INFORMATION FOR SEQ ID NO:158:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:158:

GGGAGAUAAG AAUAAACGCU CAAACAAUCU CGGACUAGAC UAACGACCUU           50

CGUUUGACGC UUAUUCGACA GGAGGCUCAC AACAGGC                        87

(2) INFORMATION FOR SEQ ID NO:159:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:159:

GGGAGAUAAG AAUAAACGCU CAAGCAAUCU CGGAUUAGAC UAACGACCUU           50

UGUUUGACGC UCAUUCGACA GGAGGCUCAC AACAGGC                        87

(2) INFORMATION FOR SEQ ID NO:160:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:160:

GGGAGAUAAG AAUAAACGCU CAAGCAAUCU CGGACUAGAC UAACGACCUU            50

CGUAUGACGC UUAUUCGACA GGAGGCUCAC AACAGGC                         87

(2) INFORMATION FOR SEQ ID NO:161:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:161:

GGGAGAUAAG AAUAAACGCU CAAGCAAUCU CGGACUAGAC UAACGACCUU            50

CGCUUGACGC UCAUUCGACA GGAGGCUCAC AACAGGC                         87

(2) INFORMATION FOR SEQ ID NO:162:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:162:

GGGAGAUAAG AAUAAACGCU CAAGGAGAUC CUCGAGGAAA CUCGAACUUC            50

UUCCCGACGU UGAUUCGACA GGAGGCUCAC AACAGGC                         87

(2) INFORMATION FOR SEQ ID NO:163:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:163:

GGGAGAUAAG AAUAAACGCU CAAACAGCUC GGAUAAGACU AACGACCUAG          50

UUUGGCUAAG CAAUUCGACA GGAGGCUCAC AACAGGC                        87

(2) INFORMATION FOR SEQ ID NO:164:

(i) SEQUENCE CHARACTERISTICS:
      (A) LENGTH: 87 base pairs
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:164:

GGGAGAUAAG AAUAAACGCU CAAGCAAUCU CGGACUAGAC UAACGACCUU          50

CGUUUGACGC UCAUUCGACA GGAGGCUCAC AACAGGC                        87

(2) INFORMATION FOR SEQ ID NO:165:

(i) SEQUENCE CHARACTERISTICS:
      (A) LENGTH: 87 base pairs
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:165:

GGGAGAUAAG AAUAAACGCU CAAACAAGGG AGUCGGUUUA UUCAGCCUGU          50

UCGGAACCUG ACUUCGACA GGAGGCUCAC AACAGGC                         87

(2) INFORMATION FOR SEQ ID NO:166:

(i) SEQUENCE CHARACTERISTICS:
      (A) LENGTH: 87 base pairs
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:166:

GGGAGAUAAG AAUAAACGCU CAAAUCCAAG ACGCUUAGUU CUUGCUCUUC          50

GGGGCUUCCU ACGUUCGACA GGAGGCUCAC AACAGGC                        87

(2) INFORMATION FOR SEQ ID NO:167:

(i) SEQUENCE CHARACTERISTICS:
      (A) LENGTH: 87 base pairs
      (B) TYPE: nucleic acid
      (C) STRANDEDNESS: single
      (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:167:

GGGAGAUAAG AAUAAACGCU CAAAAGUAAA CUCGAGACCG UUCUGGCUGA          50

UUCGGGGCAC UCUUUCGACA GGAGGCUCAC AACAGGC                       87

(2) INFORMATION FOR SEQ ID NO:168:

(i) SEQUENCE CHARACTERISTICS:
              (A) LENGTH: 86 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:168:

GGGAGAUAAG AAUAAACGCU CAAACUUGAC AAUCCCCCUG AUUCGGGGCC          50

UGACUAUCAC GAUUCGACAG GAGGCUCACA ACAGGC                        86

(2) INFORMATION FOR SEQ ID NO:169:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:169:

GGGAGAUAAG AAUAAACGCU CAAACACGAC AUCGAAGUUA UCCCCCUGAU          50

UCGGAGCCAG CUGUUCGACA GGAGGCUCAC AACAGGC                       87

(2) INFORMATION FOR SEQ ID NO:170:

(i) SEQUENCE CHARACTERISTICS:
              (A) LENGTH: 86 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:170:

GGGAGAUAAG AAUAAACGCU CAAAGCUGGA AAUCCAAAUG CUUUGUCUAG          50

UUGGGGCCAC UUUUCGACAG GAGGCUCACA ACAGGC                        86

(2) INFORMATION FOR SEQ ID NO:171:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:171:

GGGAGAUAAG AAUAAACGCU CAAAGACUCU UGAUCAUCCC CCUAGUUCGG            50

GGCUGACUGC ACUUCGACA GGAGGCUCAC AACAGGC                          87

(2) INFORMATION FOR SEQ ID NO:172:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:172:

GGGAGAUAAG AAUAAACGCU CAAACUUGAC AAUCCCCCUG AUUCGGGGCC            50

UGACUAUCAC GAUUUCGACA GGAGGCUCAC AACAGGC                         87

(2) INFORMATION FOR SEQ ID NO:173:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:173:

GGGAGAUAAG AAUAAACGCU CAAGGAGCGA AAUUCUUGAA UAUCCACUGA            50

UUCGGACCGU CCUUUCGACA GGAGGCUCAC AACAGGC                         87

(2) INFORMATION FOR SEQ ID NO:174:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:174:

GGGAGAUAAG AAUAAACGCU CAAGCGGGAU UUUCCUGAUC AUCCCACUGA          50

UUCGGGGCCU UAGUUCGACA GGAGGCUCAC AACAGGC                        87

(2) INFORMATION FOR SEQ ID NO:175:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:175:

GGGAGAUAAG AAUAAACGCU CAAAGUUUCU CCUUGGCAAU CCCCCCUAUU          50

CGGGGCUUCA UUGUUCGACA GGAGGCUCAC AACAGGC                        87

(2) INFORMATION FOR SEQ ID NO:176:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:176:

GGGAGAUAAG AAUAAACGCU CAAGAGCGAA AUUCUUGAAU AUCCACUGAU          50

UCGGAGCGUC CUUUCGACAG GAGGCUCACA ACAGGC                         86

(2) INFORMATION FOR SEQ ID NO:177:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:177:

GGGAGAUAAG AAUAAACGCU CAAACGGCAU UCUAAACAUU CCCCCUUGUU          50

CGGAGCCACU CUUUCGACAG GAGGCUCACA ACAGGC                         86

(2) INFORMATION FOR SEQ ID NO:178:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
              (D) OTHER INFORMATION:  All C's are 2'-F cytosine (ix) FEATURE:
              (D) OTHER INFORMATION:  All U's are 2'-F uracil (xi) SEQUENCE DESCRIPTION: SEQ ID NO:178:

GGGAGAUAAG AAUAAACGCU CAAGCGGAUU UUGAUCAUCC CCCUGAUUCG                    50

GAGACCUCUU ACUUCGACAG GAGGCUCACA ACAGGC                                  86

(2) INFORMATION FOR SEQ ID NO:179:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION:  All C's are 2'-F cytosine (ix) FEATURE:
              (D) OTHER INFORMATION:  All U's are 2'-F uracil (xi) SEQUENCE DESCRIPTION: SEQ ID NO:179:

GGGAGAUAAG AAUAAACGCU CAAGGGAACG AAUCGUCCAA AAGACCUCGC                    50

GGAAUCGGCG UUAUUCGACA GGAGGCUCAC AACAGGC                                 87

(2) INFORMATION FOR SEQ ID NO:180:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION:  All C's are 2'-F cytosine (ix) FEATURE:
              (D) OTHER INFORMATION:  All U's are 2'-F uracil (xi) SEQUENCE DESCRIPTION: SEQ ID NO:180:

GGGAGAUAAG AAUAAACGCU CAAGCGAGCU CUUGCACAAA ACCGAUCCUC                    50

GCAUACAGCA GGUUUCGACA GGAGGCUCAC AACAGGC                                 87

(2) INFORMATION FOR SEQ ID NO:181:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION:  All C's are 2'-F cytosine (ix) FEATURE:
              (D) OTHER INFORMATION:  All U's are 2'-F uracil (xi) SEQUENCE DESCRIPTION: SEQ ID NO:181:

GGGAGAUAAG AAUAAACGCU CAAGGGAACG AAUCGUUCAA AAGACCACGC                    50

GAAUCGGCGC UUAUUCGACA GGAGGCUCAC AACAGGC                                 87

(2) INFORMATION FOR SEQ ID NO:182:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:182:

| | |
|---|---|
| GGGAGAUAAG AAUAAACGCU CAAGAGCUGU UGACGAAAAC UUAUGCGGAG | 50 |
| AUGGAUACUC GGUUUCGACA GGAGGCUCAC AACAGGC | 87 |

(2) INFORMATION FOR SEQ ID NO:183:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:183:

| | |
|---|---|
| GGGAGAUAAG AAUAAACGCU CAAGAGCUCU UGACGAAAAC CUAUUCGAGA | 50 |
| UGGAUACUCG GUUUUCGACA GGAGGCUCAC AACAGGC | 87 |

(2) INFORMATION FOR SEQ ID NO:184:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:184:

| | |
|---|---|
| GGGAGAUAAG AAUAAACGCU CAAGGAGCCG AUUGUACAAC CUAGGUGAGC | 50 |
| UCAAUCACCU CGCUUCGACA GGAGGCUCAC AACAGGC | 87 |

(2) INFORMATION FOR SEQ ID NO:185:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:185:

GGGAGAUAAG AAUAAACGCU CAAGGGCCCU CUGCUACAAC UUCGGCAAGG　　　　　50

ACAUUUCCG GACUUCGACA GGAGGCUCAC AACAGGC　　　　　　　　　　　　87

(2) INFORMATION FOR SEQ ID NO:186:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:186:

GGGAGAUAAG AAUAAACGCU CAAGAGCUCU UGACGAAAAC CUAUGCGAGA　　　　　50

UGGAUACUCG GUUUUCGACA GGAGGCUCAC AACAGGC　　　　　　　　　　　　87

(2) INFORMATION FOR SEQ ID NO:187:

(i) SEQUENCE CHARACTERISTICS:
        (A) LENGTH: 88 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:187:

GGGAGAUAAG AAUAAACGCU CAAGAAAGCC AUGUUGAAAG UUUCACCCAG　　　　　50

AUUCGGAGUC GUUGUUCGAC AGGAGGCUCA CAACAGGC　　　　　　　　　　　88

(2) INFORMATION FOR SEQ ID NO:188:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:188:

GGGAGAUAAG AAUAAACGCU CAAACUGAGC UCGUGUACAA UGUUAGGGAA　　　　　50

GGACAUCUCG AUAUUCGACA GGAGGCUCAC AACAGGC　　　　　　　　　　　　87

(2) INFORMATION FOR SEQ ID NO:189:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:189:

GGGAGAUAAG AAUAAACGCU CAAGAGCUCU UGACGAAAAC CUAUGCGAGA           50

AGGAUACUCG GUUUUCGACA GGAGGCUCAC AACAGGC                        87

(2) INFORMATION FOR SEQ ID NO:190:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:190:

GGGAGAUAAG AAUAAACGCU CAAGAGCUCU UGACGAAAAC CUACGCGAGA           50

UGGAAACUCG GUUUUCGACA GGAGGCUCAC AACAGGC                        87

(2) INFORMATION FOR SEQ ID NO:191:

(i) SEQUENCE CHARACTERISTICS:
              (A) LENGTH: 84 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:191:

GGGAGAUAAG AAUAAACGCU CAACACAGGG GUUUCAAACC UCCCCCUGAU           50

UCGGAGCUUC UUCGACAGGA GGCUCACAAC AGGC                           84

(2) INFORMATION FOR SEQ ID NO:192:

(i) SEQUENCE CHARACTERISTICS:
              (A) LENGTH: 87 base pairs
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:192:

GGGAGAUAAG AAUAAACGCU CAAAACCUCG CCAGGAAUAA CUUGCGACUU           50

UCGGAUCGUC UUAUUCGACA GGAGGCUCAC AACAGGC                        87

```
(2) INFORMATION FOR SEQ ID NO:193:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:193:

GGGAGAUAAG AAUAAACGCU CAAGAGCUCU UGACGAAAAC CUAUGCGAGA          50

UGGAUACUCG GUUUUCGACA GGAGGCUCAC AACAGGC                       87

(2) INFORMATION FOR SEQ ID NO:194:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:194:

GGGAGAUAAG AAUAAACGCU CAACUUUGGA GCUCCUGGAA CGAAAGCGGA          50

AUUAACUUCC UUAUUCGACA GGAGGCUCAC AACAGGC                       87

(2) INFORMATION FOR SEQ ID NO:195:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:195:

GGGAGAUAAG AAUAAACGCU CAAACAAUUC AGGACGGGGU UUCUUGAAUG          50

GGUUCGACCU UCAUUCGACA GGAGGCUCAC AACAGGC                       87

(2) INFORMATION FOR SEQ ID NO:196:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil
```

(xi) SEQUENCE DESCRIPTION: SEQ ID NO:196:

GGGAGAUAAG AAUAAACGCU CAACCAGUAG AUCAACUCCC UGGCAACUGG             50

UUCGCCGUUA UAUUCGACAG GAGGCUCACA ACAGGC                            86

(2) INFORMATION FOR SEQ ID NO:197:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:197:

GGGAGAUAAG AAUAAACGCU CAAACCUUGA UGUUCACUCC CUAACUCAAG             50

GUUCGACGUC UAUUCGACAG GAGGCUCACA ACAGGC                            86

(2) INFORMATION FOR SEQ ID NO:198:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:198:

GGGAGAUAAG AAUAAACGCU CAAACAACCU GGACAAGGAA UUUUUCUAGU             50

GUUCGUUGGA CGUUUCGACA GGAGGCUCAC AACAGGC                           87

(2) INFORMATION FOR SEQ ID NO:199:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:199:

GGGAGAUAAG AAUAAACGCU CAAACCUUGA UGUUGAACUC CCUAACUCAA             50

GGCUCGACGU CUAUUCGACA GGAGGCUCAC AACAGGC                           87

(2) INFORMATION FOR SEQ ID NO:200:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:200:

GGGAGAUAAG AAUAAACGCU CAAACGAAGG CAACUUCAAA CAUUUCCUUA                50

CGUUCCGCGC UCAUUCGACA GGAGGCUCAC AACAGGC                             87

(2) INFORMATION FOR SEQ ID NO:201:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:201:

GGGAGAUAAG AAUAAACGCU CAAACGGCGC CAACAGCGAA UGUUCGCCCC                50

GUUCGGACGC UUAUUCGACA GGAGGCUCAC AACAGGC                             87

(2) INFORMATION FOR SEQ ID NO:202:

(i) SEQUENCE CHARACTERISTICS:
              (A) LENGTH: 86 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:202:

GGGAGAUAAG AAUAAACGCU CAAACCGACA CAACCACGAC GUUCGGUCGG                50

UUUGUCCGAU UAUUCGACAG GAGGCUCACA ACAGGC                              86

(2) INFORMATION FOR SEQ ID NO:203:

(i) SEQUENCE CHARACTERISTICS:
              (A) LENGTH: 87 base pairs
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:203:

GGGAGAUAAG AAUAAACGCU CAAACGGAGG CAACCAAGAG AUUUCCAUCG                50

UUCGUUCGAU UGAUUCGACA GGAGGCUCAC AACAGGC                             87

(2) INFORMATION FOR SEQ ID NO:204:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:204:

```
GGGAGAUAAG AAUAAACGCU CAAUCCAUCC AACGCGGCAA GAUUUGAUGG          50

ACUUUGACGA UCAUUCGACA GGAGGCUCAC AACAGGC                        87
```

(2) INFORMATION FOR SEQ ID NO:205:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:205:

```
GGGAGAUAAG AAUAAACGCU CAAAAGCUCA GCAGAUCGGG ACUUCUGAUC          50

UUCGGGUCGC UUAUUCGACA GGAGGCUCAC AACAGGC                        87
```

(2) INFORMATION FOR SEQ ID NO:206:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:206:

```
GGGAGAUAAG AAUAAACGCU CAACAACGGU AGCGGCUAGA ACGCGCCGAC          50

UGAUUUAGGC UUAUUCGACA GGAGGCUCAC AACAGGC                        87
```

(2) INFORMATION FOR SEQ ID NO:207:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:207:

GGGAGAUAAG AAUAAACGCU CAAUCCUCCU GUUCGGAGUC UCAAUGUCGA        50

CUCGGCCGGA CCUUUCGACA GGAGGCUCAC AACAGGC                     87

(2) INFORMATION FOR SEQ ID NO:208:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:208:

GGGAGAUAAG AAUAAACGCU CAAAGAAAUC CCCUUGAUUC GGAGUCGUCU        50

UUUCGAGCGU AGUUUCGACA GGAGGCUCAC AACAGGC                     87

(2) INFORMATION FOR SEQ ID NO:209:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:209:

GGGAGAUAAG AAUAAACGCU CAAAGAAAUC CCCUUGAUUC GGAGUCGUCU        50

UUUCGAGCGA AGGUUCGACA GGAGGCUCAC AACAGGC                     87

(2) INFORMATION FOR SEQ ID NO:210:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:210:

GGGAGAUAAG AAUAAACGCU CAAGAGAGUC AACUGCGAGA AUGGCUUUCC        50

CAACGGCACC UUUUCGACA GGAGGCUCAC AACAGGC                      87

(2) INFORMATION FOR SEQ ID NO:211:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:211:

GGGAGAUAAG AAUAAACGCU CAAAGAUAAU CCCCCGGAUU CGGAGUCCUC        50

UUGACGAACU UCCUUCGACA GGAGGCUCAC AACAGGC        87

(2) INFORMATION FOR SEQ ID NO:212:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:212:

GGGAGAUAAG AAUAAACGCU CAACGGAACA AACGGAAAUG GCACACAGGA        50

GAAAGACGAG ACCUUCGACA GGAGGCUCAC AACAGGC        87

(2) INFORMATION FOR SEQ ID NO:213:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:213:

GGGAGAUAAG AAUAAACGCU CAACAGGAGA UUAAGGAACA GGCCACAGAU        50

AGAGACACGG AGCUUCGACA GGAGGCUCAC AACAGGC        87

(2) INFORMATION FOR SEQ ID NO:214:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:214:

GGGAGAUAAG AAUAAACGCU CAAAACUGGA CGAGAGGAGC UAGCGUCCAA        50

GUUCGGAGCU AUUCGACAGG AGGCUCACAA CAGGC        85

(2) INFORMATION FOR SEQ ID NO:215:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:215:

```
GGGAGAUAAG AAUAAACGCU CAAACUGAUU CUCAGCGGCU AGCGCUGAAG            50

UUCGACUAGU UCAUUCGACA GGAGGCUCAC AACAGGC                          87
```

(2) INFORMATION FOR SEQ ID NO:216:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:216:

```
GGGAGAUAAG AAUAAACGCU CAAGGCCACA AGCAGAGAAC AGAACAACAG            50

AGCGAUGGAG AGAUUCGACA GGAGGCUCAC AACAGGC                          87
```

(2) INFORMATION FOR SEQ ID NO:217:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:217:

```
GGGAGAUAAG AAUAAACGCU CAAGGAGCAU CCAGGAUAAC AGGCUAAACA            50

CCGCAAGGAC CAGUUCGACA GGAGGCUCAC AACAGGC                          87
```

(2) INFORMATION FOR SEQ ID NO:218:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:218:

GGGAGAUAAG AAUAAACGCU CAACGGAGGA AGGAAGAGGA ACCUUCGCCU          50

CUGAUUUAGC UUAUUCGACA GGAGGCUCAC AACAGGC                        87

(2) INFORMATION FOR SEQ ID NO:219:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:219:

GGGAGAUAAG AAUAAACGCU CAACGUGGGC AAACUGAGGC AUUCCCCGCG          50

CUCAGAGAUU CAUUUCGACA GGAGGCUCAC AACAGGC                        87

(2) INFORMATION FOR SEQ ID NO:220:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:220:

GGGAGAUAAG AAUAAACGCU CAACAAUGGC AACUAGGCCA CAAAGUUCCC          50

ACUGAUUCGA CGUUUCGACA GGAGGCUCAC AACAGGC                        87

(2) INFORMATION FOR SEQ ID NO:221:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:221:

GGGAGAUAAG AAUAAACGCU CAAGCAAUCG GACCGAAAGG CCUUACCGAU          50

UUCUCGACCU UUCUUCGACA GGAGGCUCAC AACAGGC                        87

(2) INFORMATION FOR SEQ ID NO:222:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:222:

GGGAGAUAAG AAUAAACGCU CAACGGAGGA AGGAAGAGGA ACCUUUGCCU          50

CUGAUUUAGC UUAUUCGACA GGAGGCUCAC AACAGGC                       87

(2) INFORMATION FOR SEQ ID NO:223:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:223:

GGGAGAUAAG AAUAAACGCU CAACGGAGGA AGGAAGAGGA ACCUUCGCCU          50

CUGAUUUAGC UUAUUCGACA GGAGGCUCAC AACAGGC                       87

(2) INFORMATION FOR SEQ ID NO:224:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:224:

GGGAGAUAAG AAUAAACGCU CAAAGUCGAG UUUCAAGGAU CAUCCCCUC           50

UUCGGAGCCU UUCUUCGACA GGAGGCUCAC AACAGGC                       87

(2) INFORMATION FOR SEQ ID NO:225:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:225:

GGGAGAUAAG AAUAAACGCU CAACGGAGGA AGGAAGAGGA GCCUUCGCCU          50

CUGAUUUAGC UUAUUCGACA GGAGGCUCAC AACAGGC                       87

(2) INFORMATION FOR SEQ ID NO:226:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:226:

GGGAGAUAAG AAUAAACGCU CAACGAGGCC ACCGACAAGG AAGUCGACCG           50

GAGUUGAAGU AAAUUCGACA GGAGGCUCAC AACAGGC                        87

(2) INFORMATION FOR SEQ ID NO:227:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:227:

GGGAGAUAAG AAUAAACGCU CAAGGCCCCU AGCGGGAUGC CGCUAAUCGC           50

GAAUCGAGGU UUAUUCGACA GGAGGCUCAC AACAGGC                        87

(2) INFORMATION FOR SEQ ID NO:228:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:228:

GGGAGAUAAG AAUAAACGCU CAAUCGAUGC UAUCGAGUUC UACUCGGAAG           50

GUUCAACGUU UAAUUCGACA GGAGGCUCAC AACAGGC                        87

(2) INFORMATION FOR SEQ ID NO:229:

(i) SEQUENCE CHARACTERISTICS:
        (A) LENGTH: 86 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:229:

GGGAGAUAAG AAUAAACGCU CAACCCAUAC UGAGAAAGAA CAGACUUCUC          50

AGGUUCGAAC GUUUCGACAG GAGGCUCACA ACAGGC                         86

(2) INFORMATION FOR SEQ ID NO:230:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:230:

GGGAGAUAAG AAUAAACGCU CAACCUGAGA CGGUACGAGU UCGGACUCAG          50

GAUUUAACGC UUUUUCGACA GGAGGCUCAC AACAGGC                        87

(2) INFORMATION FOR SEQ ID NO:231:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:231:

GGGAGAUAAG AAUAAACGCU CAACUUACUC AACCUGCGAA CGCACAGGUU          50

AGUUCACCGU UUAUUCGACA GGAGGCUCAC AACAGGC                        87

(2) INFORMATION FOR SEQ ID NO:232:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:232:

GGGAGAUAAG AAUAAACGCU CAAACCCACA CUGAGAAAGA ACAGACUCCA          50

CAGGUUCGAA CGUUUCGACA GGAGGCUCAC AACAGGC                        87

(2) INFORMATION FOR SEQ ID NO:233:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:233:

GGGAGAUAAG AAUAAACGCU CAAAAACUCA UUCUGAGCUA AGCUCAAGUU        50

CUUGCAACGU UUGUUCGACA GGAGGCUCAC AACAGGC                     87

(2) INFORMATION FOR SEQ ID NO:234:

(i) SEQUENCE CHARACTERISTICS:
             (A) LENGTH: 86 base pairs
             (B) TYPE: nucleic acid
             (C) STRANDEDNESS: single
             (D) TOPOLOGY:linear (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:234:

GGGAGAUAAG AAUAAACGCU CAAACCGAUU CUCGAAGCAG CACGCUCCAG        50

GUCUGACGUU UUUUCGACAG GAGGCUCACA ACAGGC                      86

(2) INFORMATION FOR SEQ ID NO:235:

(i) SEQUENCE CHARACTERISTICS:
             (A) LENGTH: 87 base pairs
             (B) TYPE: nucleic acid
             (C) STRANDEDNESS: single
             (D) TOPOLOGY:linear (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:235:

GGGAGAUAAG AAUAAACGCU CAAACCUAUA CUGAGAAAGA ACAGACUUCU        50

CAGGUUCGAA CGUUUCGACA GGAGGCUCAC AACAGGC                     87

(2) INFORMATION FOR SEQ ID NO:236:

(i) SEQUENCE CHARACTERISTICS:
             (A) LENGTH: 87 base pairs
             (B) TYPE: nucleic acid
             (C) STRANDEDNESS: single
             (D) TOPOLOGY:linear (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:236:

GGGAGAUAAG AAUAAACGCU CAAAGGAACU UAUUCGACAU CAGUCGGUUC        50

CCUGGACGGG UUGUUCGACA GGAGGCUCAC AACAGGC                     87

(2) INFORMATION FOR SEQ ID NO:237:

(i) SEQUENCE CHARACTERISTICS:
        (A) LENGTH: 87 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:237:

```
GGGAGAUAAG AAUAAACGCU CAAGAACCUA UUCAACCGGA UUAGGUUGGU          50

UCUCGGAUGU CUAUUCGACA GGAGGCUCAC AACAGGC                       87
```

(2) INFORMATION FOR SEQ ID NO:238:

(i) SEQUENCE CHARACTERISTICS:
        (A) LENGTH: 42 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:238:

```
GACCUUCGUU UGACGCUCAU UCGACAGGAG GCUCACAACA GG                  42
```

(2) INFORMATION FOR SEQ ID NO:239:

(i) SEQUENCE CHARACTERISTICS:
        (A) LENGTH: 42 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:239:

```
GACCUUCGUU UGACGCUUAU UCGACAGGAG GCUCACAACA GG                  42
```

(2) INFORMATION FOR SEQ ID NO:240:

(i) SEQUENCE CHARACTERISTICS:
        (A) LENGTH: 46 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:240:

```
CGUUCGGUCG GUUUGUCCGA UUAUUCGACA GGAGGCUCAC AACAGG              46
```

(2) INFORMATION FOR SEQ ID NO:241:

(i) SEQUENCE CHARACTERISTICS:
        (A) LENGTH: 21 base pairs
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:241:

GUCGUUUGUU CGACAGGAGG C                                              21

(2) INFORMATION FOR SEQ ID NO:242:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:242:

GGGAGAUAAG AAUAAACGCU CAAGCGGGAU UUUCCUGAUC AUCCCACUGA               50

UUCGGGGCCU UACUUCGACA GGAGGCUCAC AACAGGC                             87

(2) INFORMATION FOR SEQ ID NO:243:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:243:

GGGAGAUAAG AAUAAACGCU CAAGGAGCGA UAUUCUUGAA CAUCCACUGA               50

UUCGGAGCGU CCUUUCGACA GGAGGCUCAC AACAGGC                             87

(2) INFORMATION FOR SEQ ID NO:244:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:244:

GGGAGAUAAG AAUAAACGCU CAACGCUGAC UUGUUUAUUC CCACUGGUUC        50

GGAGUCUUGC UGUUUCGACA GGAGGCUCAC AACAGGC                     87

(2) INFORMATION FOR SEQ ID NO:245:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:245:

GGGAGAUAAG AAUAAACGCU CAAACCGUCU UCUUACAUCC CACUGAUUUG        50

GAGUCUCGUU GUAUUCGACA GGAGGCUCAC AACAGGC                     87

(2) INFORMATION FOR SEQ ID NO:246:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:246:

GGGAGAUAAG AAUAAACGCU CAACACUGAA GCAAAGUUAC CUUUCUCAGA        50

UGUUUAGCGC CUAUUCGACA GGAGGCUCAC AACAGGC                     87

(2) INFORMATION FOR SEQ ID NO:247:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:247:

GGGAGAUAAG AAUAAACGCU CAACGGAGGA AGGAAGAGGA ACCUUCGCCU        50

CUGAUUUAGC UUAUUCGACA GGAGGCUCAC AACAGGC                     87

(2) INFORMATION FOR SEQ ID NO:248:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:248:

GGGAGAUAAG AAUAAACGCU CAACGAAGGA CGCGAUGCAA UCGGCCUUUG        50

AAUUUAGCGU UCAUUCGACA GGAGGCUCAC AACAGGC                     87

(2) INFORMATION FOR SEQ ID NO:249:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:249:

GGGAGAUAAG AAUAAACGCU CAACUGAAGG AUGCAGCCAA GGCCGCCCUU        50

CUAGUUUAGC UUAUUCGACA GGAGGCUCAC AACAGGC                     87

(2) INFORMATION FOR SEQ ID NO:250:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:250:

GGGAGAUAAG AAUAAACGCU CAACUAAGAA CGAAGCCACC GUUUCGCCUU        50

AGUAUUAGCC UUAUUCGACA GGAGGCUCAC AACAGGC                     87

(2) INFORMATION FOR SEQ ID NO:251:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:251:

GGGAGAUAAG AAUAAACGCU CAACUUUAGU UGUCGCAGGA GCCAAACUAA        50

AGUAUUAGCU UUAUUCGACA GGAGGCUCAC AACAGGC                     87

(2) INFORMATION FOR SEQ ID NO:252:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:252:

```
GGGAGAUAAG AAUAAACGCU CAACAACGGU AGCGGCCAGA ACGCGCCGAC            50

UGAUUUAGGC UUAUUCGACA GGAGGCUCAC AACAGGC                          87
```

(2) INFORMATION FOR SEQ ID NO:253:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:253:

```
GGGAGAUAAG AAUAAACGCU CAAUGCGAAG UACAAGACAA ACUUGUUUCG            50

ACAUUUAGCA UUGUUCGACA GGAGGCUCAC AACAGGC                          87
```

(2) INFORMATION FOR SEQ ID NO:254:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:254:

```
GGGAGAUAAG AAUAAACGCU CAACGCCGUC ACGAGGAUGA CCUCAGCGGA            50

AGGUUUAACG AUAUUCGACA GGAGGCUCAC AACAGGC                          87
```

(2) INFORMATION FOR SEQ ID NO:255:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:255:

GGGAGAUAAG AAUAAACGCU CAACGCAGAU AACGGUCUUU CCGUGUCUGA          50

UGUUUAACGA AGAUUCGACA GGAGGCUCAC AACAGGC                       87

(2) INFORMATION FOR SEQ ID NO:256:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:256:

GGGAGAUAAG AAUAAACGCU CAACGCGGAA CAAUAGAGGA UUGGGUCGGC          50

GAUUUAACGU UCAUUCGACA GGAGGCUCAC AACAGGC                       87

(2) INFORMATION FOR SEQ ID NO:257:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:257:

GGGAGAUAAG AAUAAACGCU CAACACUAGA UGGGAGAUCC UCAGGCUAGG          50

UGUUUAGGUU CAUUCGACAG GAGGCUCACA ACAGGC                        86

(2) INFORMATION FOR SEQ ID NO:258:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:258:

GGGAGAUAAG AAUAAACGCU CAAAUCCAGA UUGGAAGCAA UCCUGCUGGA          50

UUAUUAGCCU UAUUCGACAG GAGGCUCACA ACAGGC                        86

(2) INFORMATION FOR SEQ ID NO:259:

(i) SEQUENCE CHARACTERISTICS:
        (A) LENGTH: 56
        (B) TYPE: nucleic acid
        (C) STRANDEDNESS: single
        (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:259:

GGGAGACAAG AAUCCCACUG AUUCGGGGCC UUACUGAAAA GGGAGGCUCA          50

CAACAG                                                         56

(2) INFORMATION FOR SEQ ID NO:260:

(i) SEQUENCE CHARACTERISTICS:
           (A) LENGTH: 86
           (B) TYPE: nucleic acid
           (C) STRANDEDNESS: single
           (D) TOPOLOGY:linear (ix) FEATURE:

(ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:260:

GGGAGACAAG AAUAAACGCU CAAGCAACCU CGGACUAGAC UAACGACCUU          50

GUUUGACACU UAUUCGACAG GAGGCUCACA ACAGGC                        86

(2) INFORMATION FOR SEQ ID NO:261:

(i) SEQUENCE CHARACTERISTICS:
           (A) LENGTH: 87
           (B) TYPE: nucleic acid
           (C) STRANDEDNESS: single
           (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:261:

GGGAGACAAG AAUAAACGCU CAAUCAAUCU CGGACUAGAC UAACGACUUU          50

CGUUUGACGC UUAUUCGACA GGAGGCUCAC AACAGGC                       87

(2) INFORMATION FOR SEQ ID NO:262:

(i) SEQUENCE CHARACTERISTICS:
           (A) LENGTH: 86
           (B) TYPE: nucleic acid
           (C) STRANDEDNESS: single
           (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:262:

GGGAGACAAG AAUAAACGCU CAAGCAAUCU CGGACUAGAC UAACGACCUU          50

GUUUGACGCU GAUUCGACAG GAGGCUCACA ACAGGC                        86

(2) INFORMATION FOR SEQ ID NO:263:

(i) SEQUENCE CHARACTERISTICS:
        (A) LENGTH: 83
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:263:

AGACAAGAAU AAACGCUCAA CAAUCUCGGA CUAGACUAAC GACCUUGGUU        50

UGACGCUCAU UCGACAGGAG GCUCACAACA GGC                         83

(2) INFORMATION FOR SEQ ID NO:264:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:264:

GGGAGACAAG AAUAAACGCU CAAGCAACCU CGGACUAGAC UAACGACCUU        50

CGUUUGACGC UUAUUCGACA GGAGGCUCAC AACAGGC                     87

(2) INFORMATION FOR SEQ ID NO:265:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:265:

GGGAGACAAG AAUAAACGCU CAACCANNCU CGGACUANAC UACCCANCUU        50

CGUUNNACCC UUAUUCGACA GGAGGCUCAC AACAGGC                     87

(2) INFORMATION FOR SEQ ID NO:266:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:266:

GGGAGACAAG AAUAAACGCU CAAGCAAUCU CGGACUAGAC UAACGACUUC          50

GUUUGACGCU UAUUCGACAG GAGGCUCACA ACAGGC                         86

(2) INFORMATION FOR SEQ ID NO:267:

(i) SEQUENCE CHARACTERISTICS:
          (A) LENGTH: 86
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:267:

GGGAGACAAN AAUAAACGCU CAAGCAAUCU CGGAUUAGAC UAACKACUUC          50

GUUUGACACU UAUUCGACAG GAGGCUCACA ACAGGC                         86

(2) INFORMATION FOR SEQ ID NO:268:

(i) SEQUENCE CHARACTERISTICS:
          (A) LENGTH: 86
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:268:

GGGAGACAAG AAUAAACGCU CAAUCAAUCU CGGACUAGAC UAACGACCUU          50

GGUUGACGCU CAUUCGACAG GAGGCUCACA ACAGGC                         86

(2) INFORMATION FOR SEQ ID NO:269:

(i) SEQUENCE CHARACTERISTICS:
          (A) LENGTH: 86
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:269:

GGGAGACAAG AAUAAACGCU CAAGCAACCU CGGACUAGAC UAACGACCUU          50

GUUUGGCACU UAUUCGACAG GAGGCUCACA ACAGGC                         86

(2) INFORMATION FOR SEQ ID NO:270:

(i) SEQUENCE CHARACTERISTICS:
          (A) LENGTH: 87
          (B) TYPE: nucleic acid
          (C) STRANDEDNESS: single
          (D) TOPOLOGY:linear

```
    (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:270:

GGGAGACAAG AAUAAACGCU CAAGCAAUCU CGGACUAAAC UAACGACUUU         50

CGUUCGACGC UUAUUCGACA GGAGGCUCAC AACAGGC                      87

(2) INFORMATION FOR SEQ ID NO:271:

(i) SEQUENCE CHARACTERISTICS:
        (A) LENGTH: 86
        (B) TYPE: nucleic acid
        (C) STRANDEDNESS: single
        (D) TOPOLOGY: linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:271:

GGGAGACAAG AAUAAACGCU CAAGCAACCU CGGAUCAGAC UAACGACCUU         50

GGUUGACGCU UAUUCGACAG GAGGCUCACA ACAGGC                       86

(2) INFORMATION FOR SEQ ID NO:272:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:272:

GGGAGACAAG AAUAAACNCU CAAGCAACCU CGGAUUANAC UAACGACCUU         50

CNUUUGACGC UUAUUCGACA GGAGGCUCAC AACAGGC                      87

(2) INFORMATION FOR SEQ ID NO:273:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:273:

GGGAGACAAG AAUAAACGCU CAAGCAAUCU CGGACUAGAC UAACGACCUU         50

CGUUUGACGC UUAUUCGACA GGAGGCUCAC AACAGGC                      87
```

(2) INFORMATION FOR SEQ ID NO:274:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:274:

```
GGGAGACAAG AAUAAACGCU CAAGCAAUCU CGGACUARAC UAACGACCUU          50

CGUUUGACGC UUAUUCGACA GGAGGCUCAC AACAGGC                        87
```

(2) INFORMATION FOR SEQ ID NO:275:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:275:

```
GGGAGACAAG AAUAAACGCU CAAGCAACCU CGGACUAAAC UAACGACCUU          50

CGUUUGACGC UUAUUCGACA GGAGGCUCAC AACAGGC                        87
```

(2) INFORMATION FOR SEQ ID NO:276:

(i) SEQUENCE CHARACTERISTICS:
        (A) LENGTH: 88
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:276:

```
GGGAGACAAG AAUAAACGCU CAAGCAAACC UCGGACUAAA CUAACGACCU          50

UCGUUUGACG CUUAUUCGAC AGGAGGCUCA CAACAGGC                       88
```

(2) INFORMATION FOR SEQ ID NO:277:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:277:

GGGAGACAAK AAUAAACGCU CAAGCKAUCC CGGUACUANA CUAACGACCU          50

UGUUUGACGC UUAUUCGACA GGAGGCUCAC AACAGGC                       87

(2) INFORMATION FOR SEQ ID NO:278:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:278:

GGGAGACAAG AAUAAACUCU CAAGCAAUCU CGGACUAGAC UAACGACCUU          50

CGUUUGACGC UUAUUCGACA GGAGGCUCAC AACAGGC                       87

(2) INFORMATION FOR SEQ ID NO:279:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:279:

GGGAGACAAG AAUAAACGCU CAAUCAAUCU CGGACUAGAC UAACGACUUU          50

CGUUUGACGC UUAUUCGACA GGAGGCUCAC AACAGGC                       87

(2) INFORMATION FOR SEQ ID NO:280:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:280:

GGGAGACAAG AAUAAACGCU CAAKCAAUCU CGGACUAAAC UAACKACUUC          50

BUUUGACGCU UAUUCNACAG GAGGCUCACA ACAGGC                        86

(2) INFORMATION FOR SEQ ID NO:281:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:281:

GGGAGAUAAG AAUAAACGCU CAAKCAAUCU CGGACUAAAC UAACGACCUU           50

GUUUGACSCU UAUUCGACAG GAGGCUCACA UCAGGC                         86

(2) INFORMATION FOR SEQ ID NO:282:

(i) SEQUENCE CHARACTERISTICS:
              (A) LENGTH: 88
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:282:

GGGAGACAAG AAUAAACGCU CAAGCAAACC UCGGACUAAA CUAACGACCU           50

UCGUUUGACG CUUAUUCGAC AGGAGGCUCA CAACANGC                       88

(2) INFORMATION FOR SEQ ID NO:283:

(i) SEQUENCE CHARACTERISTICS:
              (A) LENGTH: 86
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:283:

GGGAGACAAG AAUAAACGCU CAAGCGAUCU CGGACUAAAC UAACGACUUC           50

GUUUGACGCU CAUUCGACAG GAGGCUCACA ACAUGC                         86

(2) INFORMATION FOR SEQ ID NO:284:

(i) SEQUENCE CHARACTERISTICS:
              (A) LENGTH: 87
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:284:

GGGAGACAAG AAUAAACGCU CAAGCAAUCU CGGACUANAC UAACNACYUU          50

CGUUUAACCC CCUUNCAANN GAAGGNCCCN ANNNGGC                        87

(2) INFORMATION FOR SEQ ID NO:285:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:285:

```
GGGAGACAAA AAUAAACGCU CAAGCAACCU CGGACUAAAC UAACGACCUU            50

CGUUUGACGC UUAUUCGACA GGAGGCUCAC AACAGGC                         87
```

(2) INFORMATION FOR SEQ ID NO:286:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:

(ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:286:

```
GGGAGACAAG AAUAAACGCU CAAGCAAUCU CGGACUANAC UAACGACCUU            50

CGUUUGACGC UUAUUCGACA GGAGGCUCAC AACAGGC                         87
```

(2) INFORMATION FOR SEQ ID NO:287:

(i) SEQUENCE CHARACTERISTICS:
        (A) LENGTH: 85
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:287:

```
GGGAGACAAG AAUAAACGCU CAAGCAACCU CGGACUAGAC UAACNACCUU            50

GUUUGACGCU AUUCGACAGG AGGCUCACAA CAGGC                           85
```

(2) INFORMATION FOR SEQ ID NO:288:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil

```
    (xi) SEQUENCE DESCRIPTION: SEQ ID NO:288:

GGGAGACAAG AAUAAACGCU CAACGACCCU GGCUCUAGAG UUCUCGUAUU           50

CGCUGUCGCA UGAUUCGACA GGAGGCUCAC AACAGGC                         87

(2) INFORMATION FOR SEQ ID NO:289:

(i) SEQUENCE CHARACTERISTICS:
         (A) LENGTH: 87
         (B) TYPE: nucleic acid
         (C) STRANDEDNESS: single
         (D) TOPOLOGY:linear (ix) FEATURE:

(ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:289:

GGGAGACAAG AAUAAACGCU CAACGCACAU GACCAGGCGC UACUGACUGA           50

RAUGUUGAAC UUAUUCGACA GGAGGCUCAC AACAGGC                         87

(2) INFORMATION FOR SEQ ID NO:290:

(i) SEQUENCE CHARACTERISTICS:
         (A) LENGTH: 87
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:290:

GGGAGACAAG AAUAAACGCU CAACGACCCU GGCUCUAAAR UUCUCGUAUU           50

CGCUGUCGCC UGAUUCGACA GGAGGCUCAC AACAGGC                         87

(2) INFORMATION FOR SEQ ID NO:291:

(i) SEQUENCE CHARACTERISTICS:
         (A) LENGTH: 88
         (B) TYPE: nucleic acid
         (C) STRANDEDNESS: single
         (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:291:

GGGAGACAAG AAUAAACGCU CAACUACCCA MGCCUCUAGA GUUCUCGUAU           50

UCGCUGUCGC AUGAUUCGAC AGGAGGCUCA CAACAGGC                        88

(2) INFORMATION FOR SEQ ID NO:292:

(i) SEQUENCE CHARACTERISTICS:
         (A) LENGTH: 87
         (B) TYPE: nucleic acid
         (C) STRANDEDNESS: single
         (D) TOPOLOGY:linear
```

```
        (ix) FEATURE:
             (D) OTHER INFORMATION:  All C's are 2'-F cytosine (ix) FEATURE:
             (D) OTHER INFORMATION:  All U's are 2'-F uracil (xi) SEQUENCE DESCRIPTION: SEQ ID NO:292:

GGGAGACAAC AAUAAACGCU CAACGACCCU GGCCCUARAG UUCUCGUAUU          50

CSCUGUCGCA UGAUUCGACA GGAGGCUCAC AACAGGC                       87

(2) INFORMATION FOR SEQ ID NO:293:

(i) SEQUENCE CHARACTERISTICS:
            (A) LENGTH: 87
            (B) TYPE: nucleic acid
            (C) STRANDEDNESS: single
            (D) TOPOLOGY:linear (ix) FEATURE:
             (D) OTHER INFORMATION:  All C's are 2'-F cytosine (ix) FEATURE:
             (D) OTHER INFORMATION:  All U's are 2'-F uracil (xi) SEQUENCE DESCRIPTION: SEQ ID NO:293:

GGGAGACAAG AAUAAACGCU CAACGACCCU GGCUCUARAG UUCUCGUAUU          50

CGCUGUCGCA UGAUUCGACA GGAGGCUCAC AACAGGC                       87

(2) INFORMATION FOR SEQ ID NO:294:

(i) SEQUENCE CHARACTERISTICS:
            (A) LENGTH: 87
            (B) TYPE: nucleic acid
            (C) STRANDEDNESS: single
            (D) TOPOLOGY:linear (ix) FEATURE:
             (D) OTHER INFORMATION:  All C's are 2'-F cytosine (ix) FEATURE:
             (D) OTHER INFORMATION:  All U's are 2'-F uracil (xi) SEQUENCE DESCRIPTION: SEQ ID NO:294:

GGGAGACAAG AAUAAACGCU CAACNACCCU GGCUCUAGAG UUCUCGUAUU          50

CGCUGUCGCA UGAUUCGACA GGAGGCUCAC AACAGGC                       87

(2) INFORMATION FOR SEQ ID NO:295:

(i) SEQUENCE CHARACTERISTICS:
            (A) LENGTH: 89
            (B) TYPE: nucleic acid
            (C) STRANDEDNESS: single
            (D) TOPOLOGY:linear (ix) FEATURE:
             (D) OTHER INFORMATION:  All C's are 2'-F cytosine (ix) FEATURE:
             (D) OTHER INFORMATION:  All U's are 2'-F uracil (xi) SEQUENCE DESCRIPTION: SEQ ID NO:295:

GGGAGACAAG AAUAAACGCU CAAAACUCGU UCAGCAUCUA CAAACUACUA          50

CAUUGAAGCA CCCUCGAACA GGGAAGGCUC ACAACAGGC                     89
```

(2) INFORMATION FOR SEQ ID NO:296:

(i) SEQUENCE CHARACTERISTICS:
        (A) LENGTH: 64
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:296:

AAGACACCWC WCCAAUUCUA AUAUACAGCA CUACAUGGCC UUCGACAGGA          50

GGCUCACAAC AGGC          64

(2) INFORMATION FOR SEQ ID NO:297:

(i) SEQUENCE CHARACTERISTICS:
        (A) LENGTH:84
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:297:

GGGAGACAAG AAUAAACGCU CAAAAGUACG GUGUCUACCA AACCGCAUCC          50

AUCACCGAUA UUCGACAGGA GGCUCACAAC AGGC          84

(2) INFORMATION FOR SEQ ID NO:298:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:298:

GGGAGACAAG AAUAAACGCU CAAAAUUUCA CCGAGGCAGA CGAACAUCAA          50

KUGCAGCUGC UAAUUCGACA GGAGGCUCAC AACAGGC          87

(2) INFORMATION FOR SEQ ID NO:299:

(i) SEQUENCE CHARACTERISTICS:
        (A) LENGTH: 85
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:299:

GGGAGACAAC AAUAAACGCU CAAACAAAUU CGUACWCACU UCKCGGAGGC    50

MGGGGUAYAU CUUCNACAGG AGGCUCACAA CAGGC    85

(2) INFORMATION FOR SEQ ID NO:300:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:300:

GGGAGACAAG AAUAAACGCU CAAACACUCA UAGAGUCCAA UUCAACGCGC    50

CAUUAUCUCA ARAUUCGACA GGAGGCUCAC AACAGGC    87

(2) INFORMATION FOR SEQ ID NO:301:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:301:

GGGAGACAAG AAUAAACGCU CAAACUCCYC UGCUAGACAA RCGGMCAKUG    50

CACNUCAACA AAUUUCGACA GGAGGCUCAC AACAGGC    87

(2) INFORMATION FOR SEQ ID NO:302:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:302:

UGGAGACAAG AAUAAACGCU CAAAGAGCCA UCCCUUAAAC GCAGCUACGG    50

AGGUCGUUCU UAUUUCGACA GGAGGCUCAC AACAGGC    87

(2) INFORMATION FOR SEQ ID NO:303:

(i) SEQUENCE CHARACTERISTICS:
        (A) LENGTH: 87
        (B) TYPE: nucleic acid
        (C) STRANDEDNESS: single
        (D) TOPOLOGY: linear

```
    (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:303:

GGGAGACAAG AAUAAACGCU CAAAKCAAAC AUUCUCAUAU AAAKAGCCAA               50

AAUAGACAAC CACUUCGACA GGAGGCUCAC AACAGGC                             87

(2) INFORMATION FOR SEQ ID NO:304:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:304:

UGGAGACAAC AAUAAACGCU CAAAGGCAUG CASCAAAAGC ACACCGAAAU               50

AUCUCCAAUC CCUUUCGACA GGAGGCUCAC AACAGGC                             87

(2) INFORMATION FOR SEQ ID NO:305:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:305:

GGGAGACAAG AAUAAACGCU CAAAGGCAUG AGUCCGCACA UAUGUGAACG               50

UGAGCACAUA AAUUUCGACA GGAGGCUCAC AACAGGC                             87

(2) INFORMATION FOR SEQ ID NO:306:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:306:

GGGAGACAAG AAUAAACGCU CAAAGUCGUC GCGCAUAUUG ACACAAUAAU               50

CGUGUCAUAA CCUUUCGACA GGAGGCUCAC AACAGGC                             87
```

(2) INFORMATION FOR SEQ ID NO:307:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:307:

GGGAGACAAA AAUAAACGCU CAAAUACUCG CGAUCGCAGC AUCAUCCCGC                50

CUCCUUGAAA CACUUCGACA GGAGGCUCAC AACAGGC                             87

(2) INFORMATION FOR SEQ ID NO:308:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:308:

GGGAGACAAG AAUAAACGCU CAAAUAGGAU GCCGCAUCGG UGUACACUCA                50

CACGCUAACC AAUUUCGACA GGAGGCUCAC AACAGGC                              87

(2) INFORMATION FOR SEQ ID NO:309:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:309:

GGGAGACACA AAUAAWCGCU CAAAUCCUUU AACGAUAGCA CAAUAGAAUU                50

AGACUCCAAC AAGUUCGACA GGAGGCUCAC AACAGGC                              87

(2) INFORMATION FOR SEQ ID NO:310:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:310:

GGGAGACAAG AAUAAACGCU CAAAUGUCGA CAUACAUAAA AUACGUCAAG　　　　50

UCUUGCGAUC GAUUUCGACA GGAGGCUCAC AACAGGC　　　　87

(2) INFORMATION FOR SEQ ID NO:311:

(i) SEQUENCE CHARACTERISTICS:
      (A) LENGTH: 80
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:311:

GGGAGACAAG AAUAAACGCU CAACAAGCCA UGCGUUAGUG CCCCUUCCAG　　　　50

UUCCCAUUCG ACAGGAGGCU CACAACAGGC　　　　80

(2) INFORMATION FOR SEQ ID NO:312:

(i) SEQUENCE CHARACTERISTICS:
      (A) LENGTH: 87
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:312:

GGGAGACAAU AAUAAACGCU CAACAACCCG GGCUCNANAN UUCUCGUAUC　　　　50

CCCUGUCNCN UUAUUCGACU GGANGCUCAC AACAGGN　　　　87

(2) INFORMATION FOR SEQ ID NO:313:

(i) SEQUENCE CHARACTERISTICS:
      (A) LENGTH: 88
      (B) TYPE: nucleic acid
      (C) STRANDEDNESS: single
      (D) TOPOLOGY:linear (ix) FEATURE:
      (D) OTHER INFORMATION: All C's are 2'-F cytosine (ix) FEATURE:
      (D) OTHER INFORMATION: All U's are 2'-F uracil
      (D) OTHER INFORMATION:

(xi) SEQUENCE DESCRIPTION: SEQ ID NO:313:

GGGAGACAAG AAUAAACGCU CAACAUGAAA AACUUUCUAU UCCGUAAAUC　　　　50

ACGUGAGUCG CUAGUUCGAC AGGAGGCUCA CAACAGGC　　　　88

(2) INFORMATION FOR SEQ ID NO:314:

(i) SEQUENCE CHARACTERISTICS:
      (A) LENGTH: 87
      (B) TYPE: nucleic acid
      (C) STRANDEDNESS: single
      (D) TOPOLOGY:linear

```
    (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:314:

GGGAGACAAG AAUAAACGCU CAACAUUGGC AGYWAABCMU CCAYCCAUAR          50

ACRCUCAACA AGUUUCGACA GGAGGCUCAC AACAGGC                        87

(2) INFORMATION FOR SEQ ID NO:315:

(i) SEQUENCE CHARACTERISTICS:
        (A) LENGTH: 89
        (B) TYPE: nucleic acid
        (C) STRANDEDNESS: single
        (D) TOPOLOGY: linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:315:

GGGAGACAAG AAUAAACGCU CAACCAAGGA GCUUCCUGGC ACCGUACCUA          50

CAUCGACCUG UUAUUCNAAC AGGAAGGCUC ACAACAGGC                      89

(2) INFORMATION FOR SEQ ID NO:316:

(i) SEQUENCE CHARACTERISTICS:
        (A) LENGTH: 87
        (B) TYPE: nucleic acid
        (C) STRANDEDNESS: single
        (D) TOPOLOGY: linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:316:

GGGAGACAAG AAUAAACGCU CAACCAWYCU CUSAYCAGAC UAACCACCYY          50

GUAUGAMCCU YAUUCCAAMG GAAGSYCMCA ACARGGV                        87

(2) INFORMATION FOR SEQ ID NO:317:

(i) SEQUENCE CHARACTERISTICS:
        (A) LENGTH: 84
        (B) TYPE: nucleic acid
        (C) STRANDEDNESS: single
        (D) TOPOLOGY: linear (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:317:

AGACAAGAAU AAACGCUCAA CCCAAUAUCA GUUGUCUCAA ACUGCGCUAC          50

UUCAUGCUUG UUCGACAGGA GGCUCACAAC AGGC                           84
```

(2) INFORMATION FOR SEQ ID NO:318:

(i) SEQUENCE CHARACTERISTICS:
        (A) LENGTH: 83
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:318:

```
AGACAAGAAU AAACNCUCAA CCCCAAACCU ACCCCUCUAU AUUCCUUCUC          50

GUAACCCAAU UCGACAGGAG GCUCACAACA GGC                            83
```

(2) INFORMATION FOR SEQ ID NO:319:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:319:

```
GGGAGACAAG AAUAAACGCU CAACCCCUCY YRGACUCCAU CAACAAMUCC          50

CCYCCUGACU CGUUCGACAG GAGGACGCAC AACAGGC                        87
```

(2) INFORMATION FOR SEQ ID NO:320:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:320:

```
GGGAGACAAG AAUAAACGCU CAAMCCGGUG CAUGUGCUAW AAUAACAUUC          50

GGCCAUUAUC CMAUUCUACA GGAGGCUCAN AACUNGC                        87
```

(2) INFORMATION FOR SEQ ID NO:321:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:321:

GGGAGACAAG AAUAAACGCU CAACCGUCCU CASAYYCCAC UWACGUCCAU           50

KWAUGAAAUW CACUCCAACA GGAGGCUCAC AACAGGC                         87

(2) INFORMATION FOR SEQ ID NO:322:

(i) SEQUENCE CHARACTERISTICS:
        (A) LENGTH: 85
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:322:

GGGAGACAAG AAUAAACGCU CAACCUAUCG UCGUCCUACA UAGAGCUAUC           50

CCUCGCUUCG CUUCGACAGG AGGCUCACAA CAGGC                           85

(2) INFORMATION FOR SEQ ID NO:323:

(i) SEQUENCE CHARACTERISTICS:
        (A) LENGTH: 88
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:323:

GGGAGACAAG AAUAAACGCU CAARCAAUCU CSGAAWMUCA CUACCCACUC           50

CCKUCUGACN CUCAUUCGAC AGGAGGCUCA CAACAGGC                        88

(2) INFORMATION FOR SEQ ID NO:324:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:324:

GGGAGACAAG AAUAAACGCU CAAGCAUCAG AACUCAAUUU CUUCAGCCAG           50

CGUGCUUACG ACAUUCGACA GGAGGCUCAC AACAGGC                         87

(2) INFORMATION FOR SEQ ID NO:325:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:325:

GGGAGACAAG AAUAAACGCU CAAGCAUUCA CAGUCGAUCC AAUUCCGGAA         50

CCUUAUCCAA CAAUUCGACA GGAGGCUCAC AACAGGC                      87

(2) INFORMATION FOR SEQ ID NO:326:

(i) SEQUENCE CHARACTERISTICS:
              (A) LENGTH: 87
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:326:

GGGAGACAAG AAUAAACGCU CAAGCCCCUU CUGGACGCCG CUAAGAUCUC         50

CCCCAACCCG AUAUUCGACA GGAGGCUCAC AACAGGC                      87

(2) INFORMATION FOR SEQ ID NO:327:

(i) SEQUENCE CHARACTERISTICS:
              (A) LENGTH: 87
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:327:

GGGAGACAAG AAUAAACGCU CAAGCGGGAU UUUCCNGAUC AUCCCACUGA         50

UUCGGGGCCU UACUUCGACA GGAGGCUCAC AACAGGC                      87

(2) INFORMATION FOR SEQ ID NO:328:

(i) SEQUENCE CHARACTERISTICS:
              (A) LENGTH: 87
              (B) TYPE: nucleic acid
              (C) STRANDEDNESS: single
              (D) TOPOLOGY: linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:328:

GGGAGACAAG AAUAAACGCU CAAGCGUAAU GAGCUGUGCC CGCGUUUAUG         50

AUCUAUAUCC UAAUUCGACA GGAGGCUCAC AACAGGC                      87

(2) INFORMATION FOR SEQ ID NO:329:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:

(ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:329:

```
GGGAGACAAG AAUAAACGCU CAAGCUAGUC AUCUGCCUAA CUCCUCACGA           50

GACCCAGCCG UACUUCGACA GGAGGCUCAC AACAGGC                         87
```

(2) INFORMATION FOR SEQ ID NO:330:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:330:

```
GGGAGACAAG AAUAAACGCU CAAGGAUGAA CAAUACCCCA UGCAGUCCAA           50

GUCCUGCUUU CACUUCGACA GGAGGCUCAC AACAGGC                         87
```

(2) INFORMATION FOR SEQ ID NO:331:

(i) SEQUENCE CHARACTERISTICS:
        (A) LENGTH: 88
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:331:

```
GGGAGACAAG AAUAAACGCU CAAGUGUACA CRAAGUCAGU UAGCGGACAG           50

UUUGCGCAGC CCGUUUCGAC AGGAGGCUCA CAACAGGC                        88
```

(2) INFORMATION FOR SEQ ID NO:332:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:   All C's are 2'-F cytosine (ix) FEATURE:
        (D) OTHER INFORMATION:   All U's are 2'-F uracil (xi) SEQUENCE DESCRIPTION: SEQ ID NO:332:

GGGAGACAAG AAUAAACGCU CAAGUSCAGG USUGACCACC UGWASGACCC          50

UGCCCACCCG UCAUUCGACA GGAGGCUCAC AACAGGC                        87

(2) INFORMATION FOR SEQ ID NO:333:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:333:

GGGAGACAAA AAUAAACGCU CAAGUUGCCC UCGCGAAUGU ACCCAUCGUA          50

CAGAACGGUC UAAUUCGACA GGAGGCUCAC AACAGGC                        87

(2) INFORMATION FOR SEQ ID NO:334:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:334:

GGGAGACAAG AAUAAACGCU CAAUAACACC CACCACUCRC GCAUGGCAUU          50

GUCVCCAAAU AACUUCGACA GGAGGCUCAC AACAGGC                        87

(2) INFORMATION FOR SEQ ID NO:335:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:335:

GGGAGACAAG AAUACCGGG CGAKCUACCC UGUACUGCCU                      50

CUUCCUUCAC AGCUUCGACA GGAGGCUCAC AACAGGC                        87

(2) INFORMATION FOR SEQ ID NO:336:

(i) SEQUENCE CHARACTERISTICS:
        (A) LENGTH: 86
        (B) TYPE: nucleic acid
        (C) STRANDEDNESS: single
        (D) TOPOLOGY:linear

```
        (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:336:

GGGAGACAAG AAUAAACGCU CAAUACGAAC AAAGGAACUC AGUCAAAAAC             50

AGCAGUGUAC CAUUCGACAG GAGGCUCACA ACAGGC                            86

(2) INFORMATION FOR SEQ ID NO:337:

(i) SEQUENCE CHARACTERISTICS:
              (A) LENGTH: 52
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:337:

GGGAGACAAGAAUAAACGCU CAAUCAACUU CGACAGGAGG CUCACAACAG              50

GC                                                                 52

(2) INFORMATION FOR SEQ ID NO:338:

(i) SEQUENCE CHARACTERISTICS:
              (A) LENGTH: 75
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:338:

GGGAGACAAG AAUAAACGCU CAAUCACGGU AAGGACCCAG AUUCUCCUCU             50

UCCCAACCUC GCAUUCGACA GGAGG                                        75

(2) INFORMATION FOR SEQ ID NO:339:

(i) SEQUENCE CHARACTERISTICS:
              (A) LENGTH: 87
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:339:

GGGAGACAAG AAUAAACGCU CAAUCAUGCU CACGACUAUU GCCAUAACGC             50

UAUCCACACA ACAUUCGACA GGAGGCUCAC AACAGGC                           87
```

(2) INFORMATION FOR SEQ ID NO:340:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:340:

GGGAGACAAG AAUAAACGCU CAAUCCAUGC AUGAUCGUAA GCUAUAAAGG                50

UGCGCAAACC UUGUUCGACA GGAGGCUCAC AACAGGC                              87

(2) INFORMATION FOR SEQ ID NO:341:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:341:

GGGAGACAAG AAUAAACGCU CAAUCGGUCU CAACCUACCC ACCCCAGUAA                50

GCAUGAGGCU ACAUUCGACA GGAGGCUCAC AACAGGC                              87

(2) INFORMATION FOR SEQ ID NO:342:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:342:

GGGAGACAAG AAUAAACGCU CAAUCGGCAA AGUCCUCUUA UAUACAGUCU                50

GCAAUCACUC AUUUUCGACA GGAGGCUCAC AACAGGC                              87

(2) INFORMATION FOR SEQ ID NO:343:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil

```
        (xi) SEQUENCE DESCRIPTION: SEQ ID NO:343:

GGGAGACAAG AAUAAACGCU CAAUCUAUGC AACAACGANC AUUCACUCCA            50

NCUAGGUWCA GGUUCGACAG GAGGCUCANA ACAGGC                           86

(2) INFORMATION FOR SEQ ID NO:344:

(i) SEQUENCE CHARACTERISTICS:
          (A) LENGTH: 87
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:344:

GGGAGACAAG AAUAAACGCU CAAUGCCCGG UACAAAUCUU UCUACACCAC            50

GAUCUCCCCU AUCUUCGACA GGAGGCUCAC AACAGGC                          87

(2) INFORMATION FOR SEQ ID NO:345:

(i) SEQUENCE CHARACTERISTICS:
          (A) LENGTH: 87
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:345:

GGGAGACAAG AAUAAACGCU CAAUGGGAUU GGGUCUUACA CGUUCACUCG            50

CUUAUCCUCC CAAUUCGACA GGAGGCUCAC AACAGGC                          87

(2) INFORMATION FOR SEQ ID NO:346:

(i) SEQUENCE CHARACTERISTICS:
          (A) LENGTH: 86
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil
          (D) OTHER INFORMATION:

(xi) SEQUENCE DESCRIPTION: SEQ ID NO:346:

GGGAGACAAG AAUAAACCUC AAUGUUACAA AACACAGACG CCGCGCUAAG            50

GUAUAUCCGC UGUUCGACAG GAGGCUCACA ACAGGC                           86

(2) INFORMATION FOR SEQ ID NO:347:

(i) SEQUENCE CHARACTERISTICS:
          (A) LENGTH: 87
          (B) TYPE: nucleic acid
          (C) STRANDEDNESS: single
          (D) TOPOLOGY:linear
```

(ix) FEATURE:
         (D) OTHER INFORMATION:   All C's are 2'-F cytosine (ix) FEATURE:
         (D) OTHER INFORMATION:   All U's are 2'-F uracil (xi) SEQUENCE DESCRIPTION: SEQ ID NO:347:

GGGAGACAAG AAUAAACGCU CAAUGUUAAU CAACUACAAU GCACUUGAGC         50

CAAACAACCG ACUUUCGACA GGAGGCUCAC AACAGGC                      87

(2) INFORMATION FOR SEQ ID NO:348:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
         (D) OTHER INFORMATION:   All C's are 2'-F cytosine (ix) FEATURE:
         (D) OTHER INFORMATION:   All U's are 2'-F uracil (xi) SEQUENCE DESCRIPTION: SEQ ID NO:348:

GGGAGACAAG AAUAAACGCU CAAUUCCAUU GGUUUGCCCU AUCGAGACCC         50

GUCCGCUGUU CCUUUCGACA GGAGGCUCAC AACAGGC                      87

(2) INFORMATION FOR SEQ ID NO:349:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
         (D) OTHER INFORMATION:   All C's are 2'-F cytosine (ix) FEATURE:
         (D) OTHER INFORMATION:   All U's are 2'-F uracil (xi) SEQUENCE DESCRIPTION: SEQ ID NO:349:

GGAGACAAGA AUAAACGCUC AAUUUCUUGU GAUGUCAGAA UGACCCUAGA         50

CUUACGUCCA AAUUCGACAG GAGGCUCACA ACAGGC                       86

(2) INFORMATION FOR SEQ ID NO:350:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
         (D) OTHER INFORMATION:

(ix) FEATURE:
         (D) OTHER INFORMATION:

(xi) SEQUENCE DESCRIPTION: SEQ ID NO:350:

GGGAGACAAG AAUAAACGCU CAAUUGACGC ACCCAUCGGC CCGUCCACUG         50

CUCCCCACCU AGUUUCGACA GGAGGCUCAC AACAGGC                      87

(2) INFORMATION FOR SEQ ID NO:351:

(i) SEQUENCE CHARACTERISTICS:
        (A) LENGTH: 85
        (B) TYPE: nucleic acid
        (C) STRANDEDNESS: single
        (D) TOPOLOGY:linear (ix) FEATURE:
        (D) OTHER INFORMATION:

(ix) FEATURE:
        (D) OTHER INFORMATION:

(xi) SEQUENCE DESCRIPTION: SEQ ID NO:351:

```
GGGAGACAAG AAUAAACGCU  CAACRGUAUC AUGAACUCCC ACGAACRCCA         50
CUGUUUUAAU UUUCGACAGG AGGCUCACAA CWGGC                          85
```

(2) INFORMATION FOR SEQ ID NO:352:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:352:

```
GGGAGACAAG AAUAAACGCU CAAGCGGGAU UUUCCUGAUC AUCCCACUGA          50
WUCGGGGCCU UACUUCGACA GGAGGCUCAC AACAGGC                        87
```

(2) INFORMATION FOR SEQ ID NO:353:

(i) SEQUENCE CHARACTERISTICS:
        (A) LENGTH: 87
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:353:

```
GGGAGACAAG AAUAAACGCU CAANAGUGGA UAACGUAUAG CCAAUUUUCU          50
CACUCGCCUC GUUUUCGACA GGAGGCUCAC AACAGGC                        87
```

(2) INFORMATION FOR SEQ ID NO:354:

(i) SEQUENCE CHARACTERISTICS:
        (A) LENGTH: 86
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:354:

GGGAGACAAA AAUAACGCUC AARAAAACCU ACCUUCGUAC AUUGGAUARA           50

AAAACGGCUC UUUUCGACAG GAGGCUCACA ACAGGC                          86

(2) INFORMATION FOR SEQ ID NO:355:

(i) SEQUENCE CHARACTERISTICS:
            (A) LENGTH: 87
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (ix) FEATURE:
            (D) OTHER INFORMATION:  N is a (mercaptoacetyl-glycyl-glycyl-
                amidyl)-6-hex-1-yl-moiety che (xi) SEQUENCE DESCRIPTION: SEQ ID NO:355:

NGGGAGACAA GAAUAAACGC UCAAUCAAUC UCGGACUAGA CUAACGACCU           50

UGGUUGACGC UCAUUCGACA GGAGGCUCAC AACAGGC                         87

(2) INFORMATION FOR SEQ ID NO:356:

(i) SEQUENCE CHARACTERISTICS:
            (A) LENGTH:39
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:356:

UCAAUCUCGG ACUAGACUAA CGACCUUGGU UGACGCUCA                       39

(2) INFORMATION FOR SEQ ID NO:357:

(i) SEQUENCE CHARACTERISTICS:
            (A) LENGTH: 63
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:357:

UCAAUCUCGG ACUAGACUAA CGACCUUGGU UGACGCUCAU UCGACAGGAG           50

GCUCACAACA GGC                                                   63

(2) INFORMATION FOR SEQ ID NO:358:

(i) SEQUENCE CHARACTERISTICS:
            (A) LENGTH: 62
            (B) TYPE: nucleic acid
            (C) STRANDEDNESS: single
            (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:358:

GGGAGACAAG AAUAAACGCU CAAUCAAUCU CGGACUAGAC UAACGACCUU            50

GGUUGACGCU CA                                                    62

(2) INFORMATION FOR SEQ ID NO:359:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:359:

UCAAUCAAUC UCGGACUAGA CUAACGACCU UGGUUGA                          37

(2) INFORMATION FOR SEQ ID NO:360:

(i) SEQUENCE CHARACTERISTICS:
        (A) LENGTH: 39
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (ix) FEATURE:
        (D) OTHER INFORMATION: N is a pentylamine (ix) FEATURE:
        (D) OTHER INFORMATION: Nucleotide number 39 is an inverted
            (3'3') phosphorodiester linkag (xi) SEQUENCE DESCRIPTION: SEQ ID NO:360:

NUCAAUCAAU CUCGGACUAG ACUAACGACC UUGGUUGAT                        39

(2) INFORMATION FOR SEQ ID NO:361:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (ix) FEATURE:
        (D) OTHER INFORMATION: All A's are 2'-OMe adenosine (ix) FEATURE:
        (D) OTHER INFORMATION: All G's are 2'-OMe guanosine (xi) SEQUENCE DESCRIPTION: SEQ ID NO:361:

UCAAUCAAUC UCGGACUAGA CUAACGACCU UGGUUGA                                    37

(2) INFORMATION FOR SEQ ID NO:362:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (ix) FEATURE:
        (D) OTHER INFORMATION:  A's at positions 3, 4, 7, 8, 15, 23,
            27 and 37 are 2'-OMe (ix) FEATURE:
        (D) OTHER INFORMATION:  G's at positions 13, 14, 26, 32, 33
            and 36 are 2'OMe (xi) SEQUENCE DESCRIPTION: SEQ ID NO:362:

UCAAUCAAUC UCGGACUAGA CUAACGACCU UGGUUGA                                    37

(2) INFORMATION FOR SEQ ID NO:363:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) FEATURE:
        (D) OTHER INFORMATION:  A's at positions 3, 4, 7, 8, 24, 27
            and 37 are 2'OMe (xi) FEATURE:
        (D) OTHER INFORMATION:  G's at positions 13, 14, 26, 32, 33
            and 36 are 2'-OMe (xi) SEQUENCE DESCRIPTION: SEQ ID NO:363:

UCAAUCAAUC UCGGACUAGA CUAACGACCU UGGUUGA                                    37

(2) INFORMATION FOR SEQ ID NO:364:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil
        (D) OTHER INFORMATION:  A's at positions 3, 4, 7, 8 and 37 are
            2'OMe (xi) FEATURE:
        (D) OTHER INFORMATION:  G's at positions 32,  33 and 36 are
            2'-OMe (xi) SEQUENCE DESCRIPTION: SEQ ID NO:364:

UCAAUCAAUC UCGGACUAGA CUAACGACCU UGGUUGA                                    37

(2) INFORMATION FOR SEQ ID NO:365:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION: U's at positions 1, 5, 11, 17, 22, 30,
             31, 34 and 35 2'-F uracil (ix) FEATURE:
         (D) OTHER INFORMATION:  U at position 9 is 5-bromouridine (xi) SEQUENCE DESCRIPTION: SEQ ID NO:365:

UCAAUCAAUC UCGGACUAGA CUAACGACCU UGGUUGA                                    37

(2) INFORMATION FOR SEQ ID NO:366:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION: U's at positions 1, 5, 11, 17, 22, 30,
             31, 34 and 35 2'-F uracil (ix) FEATURE:
         (D) OTHER INFORMATION:  U at position 16 is 5-bromouridine (xi) SEQUENCE DESCRIPTION: SEQ ID NO:366:

UCAAUCAAUC UCGGAUUAGA CUAACGACCU UGGUUGA                                    37

(2) INFORMATION FOR SEQ ID NO:367:

(i) SEQUENCE CHARACTERISTICS:
        (A) LENGTH: 37
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION: U's at positions 1, 5, 11, 17, 22, 30,
             31, 34 and 35 2'-F uracil (ix) FEATURE:
         (D) OTHER INFORMATION:  U at position 17 is 5-bromouridine (xi) SEQUENCE DESCRIPTION: SEQ ID NO:367:

UCAAUCAAUC UCGGACUAGA CUAACGACCU UGGUUGA                                    37

(2) INFORMATION FOR SEQ ID NO:368:

(i) SEQUENCE CHARACTERISTICS:
        (A) LENGTH: 37
        (B) TYPE: nucleic acid (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  U's at positions 1, 5, 11, 17, 30, 31,
                34 and 35 2'-F uracil (ix) FEATURE:
            (D) OTHER INFORMATION:  U at position 22 is 5-bromouridine (xi) SEQUENCE DESCRIPTION: SEQ ID NO:368:

UCAAUCAAUC UCGGACUAGA CUAACGACCU UGGUUGA                                    37

(2) INFORMATION FOR SEQ ID NO:369:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 18,
                20, 23, 24, 27 and 37 are 2'O (xi) FEATURE:
            (D) OTHER INFORMATION:  G's at positions 13, 14, 26, 32, 33
                and 36 are 2'-OMe guanosine (xi) SEQUENCE DESCRIPTION: SEQ ID NO:369:

UCAAUCAAUC UCGGACUAGA CUAACGACCU UGGUUGA                                    37

(2) INFORMATION FOR SEQ ID NO:370:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 18,
                24, 27 and 37 are 2'OMe adeno (xi) FEATURE:
            (D) OTHER INFORMATION:  G's at positions 13, 14, 19, 26, 32,
                33 and 36 are 2'-OMe guanosin (xi) SEQUENCE DESCRIPTION: SEQ ID NO:370:

UCAAUCAAUC UCGGACUAGA CUAACGACCU UGGUUGA                                    37

(2) INFORMATION FOR SEQ ID NO:371:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 18,
                24, 27 and 37 are 2'OMe adeno (xi) FEATURE:
            (D) OTHER INFORMATION:  G's at positions 13, 14, 26, 32, 33
                and 36 are 2'-OMe guanosine (xi) SEQUENCE DESCRIPTION: SEQ ID NO:371:

UCAAUCAAUC UCGGACUAGA CUAACGACCU UGGUUGA                                      37

(2) INFORMATION FOR SEQ ID NO:372:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 20,
                23, 24, 27 and 37 are 2'OMe a (xi) FEATURE:
            (D) OTHER INFORMATION:  G's at positions 13, 14, 26, 32, 33
                and 36 are 2'-OMe guanosine (xi) SEQUENCE DESCRIPTION: SEQ ID NO:372:

UCAAUCAAUC UCGGACUAGA CUAACGACCU UGGUUGA                                      37

(2) INFORMATION FOR SEQ ID NO:373:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 23,
                24, 27 and 37 are 2'OMe adeno (xi) FEATURE:
            (D) OTHER INFORMATION:  G's at positions 13, 14, 19, 26, 32,
                33 and 36 are 2'-OMe guanosin (xi) SEQUENCE DESCRIPTION: SEQ ID NO:373:

UCAAUCAAUC UCGGACUAGA CUAACGACCU UGGUUGA                                      37

(2) INFORMATION FOR SEQ ID NO:374:

(i) SEQUENCE CHARACTERISTICS:
            (A) LENGTH: 37
            (B) TYPE: nucleic acid
            (C) STRANDEDNESS: single
            (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil
            (D) OTHER INFORMATION:  A's at positions 3, 4, 7, 8, 15, 18,
                23, 24, 27 and 37 are 2'OMe a (xi) FEATURE:
   (D) OTHER INFORMATION: G's at positions 13, 14, 26, 32, 33
       and 36 are 2'-OMe guanosine (xi) SEQUENCE DESCRIPTION: SEQ ID NO:374:

UCAAUCAAUC UCGGACUAGA CUAACGACCU UGGUUGA                          37

(2) INFORMATION FOR SEQ ID NO:375:

(i) SEQUENCE CHARACTERISTICS:
       (A) LENGTH: 37
       (B) TYPE: nucleic acid
       (C) STRANDEDNESS: single
       (D) TOPOLOGY:linear (ix) FEATURE:
       (D) OTHER INFORMATION:  All C's are 2'-F cytosine (ix) FEATURE:
       (D) OTHER INFORMATION:  All U's are 2'-F uracil
       (D) OTHER INFORMATION:  A's at positions 3, 4, 7, 8, 15, 18,
           20, 23, 24, 27 and 37 are 2'O (xi) FEATURE:
       (D) OTHER INFORMATION: G's at positions 13, 14, 19, 26, 32,
           33 and 36 are 2'-OMe guanosin (xi) SEQUENCE DESCRIPTION: SEQ ID NO:375:

UCAAUCAAUC UCGGACUAGA CUAACGACCU UGGUUGA                          37

(2) INFORMATION FOR SEQ ID NO:376:

(i) SEQUENCE CHARACTERISTICS:
       (A) LENGTH: 37
       (B) TYPE: nucleic acid
       (C) STRANDEDNESS: single
       (D) TOPOLOGY:linear (ix) FEATURE:
       (D) OTHER INFORMATION:  All C's are 2'-F cytosine (ix) FEATURE:
       (D) OTHER INFORMATION:  All U's are 2'-F uracil
       (D) OTHER INFORMATION:  A's at positions 3, 4, 7, 8, 15, 18,
           23, 24, 27 and 37 are 2'OMe a (xi) FEATURE:
       (D) OTHER INFORMATION: G's at positions 13, 14, 19, 26, 32,
           33 and 36 are 2'-OMe guanosin (xi) SEQUENCE DESCRIPTION: SEQ ID NO:376:

UCAAUCAAUC UCGGACUAGA CUAACGACCU UGGUUGA                          37

(2) INFORMATION FOR SEQ ID NO:377:

(i) SEQUENCE CHARACTERISTICS:
       (A) LENGTH: 94
       (B) TYPE: nucleic acid
       (C) STRANDEDNESS: single
       (D) TOPOLOGY:linear (ix) FEATURE:
       (D) OTHER INFORMATION:  All C's are 2'-F cytosine (ix) FEATURE:
       (D) OTHER INFORMATION:  All U's are 2'-F uracil (xi) SEQUENCE DESCRIPTION: SEQ ID NO:377:

GGGAGACAAG AAUAAACGCU CAAAAACAAC CUCGGACUAG ACUAACGACC            50

UUGUUCGACG CUUAUUCGAC AGGAGGCUCA CAACAGGCAA GCUU                  94

(2) INFORMATION FOR SEQ ID NO:378:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:378:

```
GGGAGACAAG AAUAAACGCU CAAGCAAUCU CGGACUAGAC UAACGACCUU          50

CGUUUGACGC UUAUUCGACA GGAGGCUCAC AACAGGCAAG CUU                 93
```

(2) INFORMATION FOR SEQ ID NO:379:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:379:

```
GGGAGACAAG AAUAAACGCU CAAGCAACCU CGGACUAGAC UAACGACCUU          50

AGUUUGACGC UUAUUCGACA GGAGGCUCAC AACAGGCAAG CUU                 93
```

(2) INFORMATION FOR SEQ ID NO:380:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:380:

```
GGGAGACAAG AAUAAACGCU CAAGCAACCU CGGACUAGAC UAACGACCUU          50

CGUUUGACGC UUAUUCGACA GGAGGCUCAC AACAGGCAAG CUU                 93
```

(2) INFORMATION FOR SEQ ID NO:381:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:381:

GGGAGACAAG AAUAAACGCU CAAGCAAUCU CGGACUAGAC UAACGACCUC          50

GUUUGACGCU UAUUCGACAG GAGGCUCACA ACAGGCAAGC UU                  92

(2) INFORMATION FOR SEQ ID NO:382:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:382:

GGGAGACAAG AAUAAACGCU CAAGCAACCU CGGAUUAGAC UAACGACCUU          50

CGUUUGACGC UUAUUCGACA GGAGGCUCAC AACAGGCAAG CUU                 93

(2) INFORMATION FOR SEQ ID NO:383:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:383:

GGGAGACAAG AAUAAACGCU CAAGCAACCU CGGACUAGAC UAACGACCUU          50

GUUCGACGCU UAUUCGACAG GAGGCUCACA ACAGGCAAGC UU                  92

(2) INFORMATION FOR SEQ ID NO:384:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:384:

GGGAGACAAG AAUAAACGCU CAAGCAACCU CGGACUAGGC UAACGACCUU          50

GUUUGACACU UAUUCGACAG GAGGCUCACA ACAGGCAAGC UU                  92

(2) INFORMATION FOR SEQ ID NO:385:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:385:

GGGAGACAAG AAUAAACGCU CAAGCAACCU CGGACUAGAC UAACGACCUU            50

CGUUUGACGC UUAUUCGACA GGAGGCUCAC AACAGGCAAG CUU                   93

(2) INFORMATION FOR SEQ ID NO:386:

(i) SEQUENCE CHARACTERISTICS:
              (A) LENGTH: 92
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:386:

GGGAGACAAG AAUAAACGCU CAAGCAAUCU CGGACUAGAC UAACGACUUC            50

GCUUGACGCU CAUUCGACAG GAGGCUCACA ACAGGCAAGC UU                    92

(2) INFORMATION FOR SEQ ID NO:387:

(i) SEQUENCE CHARACTERISTICS:
              (A) LENGTH: 92
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:387:

GGGAGACAAG AAUAAACGCU CAAGCAAUCU CGGACUAGAC UAACGACCUU            50

GUUUGACGCC UAUUCGACAG GAGGCUCACA ACAGGCAAGC UU                    92

(2) INFORMATION FOR SEQ ID NO:388:

(i) SEQUENCE CHARACTERISTICS:
              (A) LENGTH: 92
              (B) TYPE: nucleic acid
              (C) STRANDEDNESS: single
              (D) TOPOLOGY:linear (ix) FEATURE:
              (D) OTHER INFORMATION:   All C's are 2'-F cytosine (ix) FEATURE:
              (D) OTHER INFORMATION:   All U's are 2'-F uracil (xi) SEQUENCE DESCRIPTION: SEQ ID NO:388:

GGGAGACAAG AAUAAACGCU CAAGCAAUCU CGGACUAGAC UAACGACCUU            50

CGUUUGACGC UUAUUCGACA GGAGGCUCAC AACAGGCAAG CU                    92

(2) INFORMATION FOR SEQ ID NO:389:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:389:

GGGAGACAAG AAUAAACGCU CAACGACCCU GGCUCUAGAG UUCUCGUAUU      50

CGCUGUCGCA UGAUUCGACA GGAGGCUCAC AACAGGCAAG CU      92

(2) INFORMATION FOR SEQ ID NO:390:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:390:

GGGAGACAAG AAUAAACGCU CAAGGCUAGA UCUACAGAAG GACUAGAACC      50

CCAAAAGCGA CAAUUCGACA GGAGGCUCAC AACAGGCAAG CUU      93

(2) INFORMATION FOR SEQ ID NO:391:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:391:

GGGAGACAAG AAUAAACGCU CAAGGCUAGA UCUACAGACG GACUAGAACC      50

CCAAAAGCGA CAAUUCGACA GGAGGCUCAC AACAGGCAAG CUU      93

(2) INFORMATION FOR SEQ ID NO:392:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:392:

GGGAGACAAG AAUAAACGCU CAAGGCUAGA UCUACAGACG GACUAGAACC            50

CCAAAAGCGA CAAUUCGACA GGAGGCUCAC AACAGGCAAG CUU                  93

(2) INFORMATION FOR SEQ ID NO:393:

(i) SEQUENCE CHARACTERISTICS:
          (A) LENGTH: 54
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:393:

GGGAGACAAG AAUAAACGCU CAAGGCUAGA UCUAUAGACG GACUAGAACC            50

CCAA                                                             54

(2) INFORMATION FOR SEQ ID NO:394:

(i) SEQUENCE CHARACTERISTICS:
          (A) LENGTH: 93
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:394:

GGGAGACAAG AAUAAACGCU CAAGGCUAGA UCUACAGACG GACUAGAACC            50

CCAAAAGCGA CAAUUCGACA GGAGGCUCAC AACAGGCAAG CUU                  93

(2) INFORMATION FOR SEQ ID NO:395:

(i) SEQUENCE CHARACTERISTICS:
          (A) LENGTH: 93
          (B) TYPE: nucleic acid
          (C) STRANDEDNESS: single
          (D) TOPOLOGY:linear (ix) FEATURE:
          (D) OTHER INFORMATION:  All C's are 2'-F cytosine (ix) FEATURE:
          (D) OTHER INFORMATION:  All U's are 2'-F uracil (xi) SEQUENCE DESCRIPTION: SEQ ID NO:395:

GGGAGACAAG AAUAAACGCU CAAGGCUAGA UCUACAGACG GACUAGAACC            50

CCAAAAGCGA CAAUUCGACA GGAGGCUCAC AACAGGCAAG CUU                  93

(2) INFORMATION FOR SEQ ID NO:396:

(i) SEQUENCE CHARACTERISTICS:
          (A) LENGTH: 93
          (B) TYPE: nucleic acid
          (C) STRANDEDNESS: single
          (D) TOPOLOGY:linear

```
       (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:396:

GGGAGACAAG AAUAAACGCU CAAGGNUAGA UCUACAGACA GACUAGAACC              50

CCAAAAGUGA CAAUUCGACA GGAGGCUCAC AACAGGCAAG CUU                    93

(2) INFORMATION FOR SEQ ID NO:397:

(i) SEQUENCE CHARACTERISTICS:
           (A) LENGTH: 93
           (B) TYPE: nucleic acid
           (C) STRANDEDNESS: single
           (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:397:

GGGAGACAAG AAUAAACGCU CAACGUUGAG AGCAACCUGU CGAUCCCGGA              50

GCAGACUAAC GAUUUCGACA GGAGGCUCAC AACAGGCAAG CUU                    93

(2) INFORMATION FOR SEQ ID NO:398:

(i) SEQUENCE CHARACTERISTICS:
           (A) LENGTH: 93
           (B) TYPE: nucleic acid
           (C) STRANDEDNESS: single
           (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:398:

GGGAGACAAG AAUAAACGCU CAACGUUCAG AGCAACCUGU CGAUCCCGGA              50

GCAGACUAAC GAUUUCGACA GGAGGCUCAC AACAGGCAAG CUU                    93

(2) INFORMATION FOR SEQ ID NO:399:

(i) SEQUENCE CHARACTERISTICS:
           (A) LENGTH: 93
           (B) TYPE: nucleic acid
           (C) STRANDEDNESS: single
           (D) TOPOLOGY:linear (ix) FEATURE:
            (D) OTHER INFORMATION:  All C's are 2'-F cytosine (ix) FEATURE:
            (D) OTHER INFORMATION:  All U's are 2'-F uracil (xi) SEQUENCE DESCRIPTION: SEQ ID NO:399:

GGGAGACAAG AAUAAACGCU CAAGUGUUGG AGCUCUUGAU UGGAAAAGUA              50

GAGCAAAUCG AAAUUCGACA GGAGGCUCAC AACAGGCAAG CUU                    93
```

(2) INFORMATION FOR SEQ ID NO:400:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:400:

GGGAGACAAG AAUAAACGCU CAAGUGUUGG AGCUCUUGAU UGGAAAAGUA            50

GAGCAAAUCG AAAUUCGACA GGAGGCUCAC AACAGGCAAG CUU                  93

(2) INFORMATION FOR SEQ ID NO:401:

(i) SEQUENCE CHARACTERISTICS:
        (A) LENGTH: 94
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:401:

GGGAGACAAG AAUAAACGCU CAAAAAAUCG UCACCCCUCC GGUCCUCACA            50

UGACAGCAUG AACAUUCGAC AGGAGGCUCA CAACAGGCAA GCUU                 94

(2) INFORMATION FOR SEQ ID NO:402:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:402:

GGGAGACAAG AAUAAACGCU CAAAAAGCUA GAUCAGCAGU GAACGACUAC            50

AAGUGCAUAG UAUUCGACAG GAGGCUCACA ACAGGCAAG CUU                   92

(2) INFORMATION FOR SEQ ID NO:403:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:403:

GGGAGACAAG AAUAAACGCU CAAAACCGGA GAGCCCGAAC CACCGGUAGC          50

AUCCGCAUCA UACUUCGACA GGAGGCUCAC AACAGGCAAG CUU                93

(2) INFORMATION FOR SEQ ID NO:404:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:404:

GGGAGACAAG AAUAAACGCU CAAAAUAUAG CCCUGCGAUC UUAGCCCAAC          50

UUCCUCAAAG CUUUUCGACA GGAGGCUCAC AACAGGCAAG CUU                93

(2) INFORMATION FOR SEQ ID NO:405:

(i) SEQUENCE CHARACTERISTICS:
        (A) LENGTH:92
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:405:

GGGAGACAAG AAUAAACGCU CAAACCAGAA AGAAGCUCA AAACCUUUGC           50

UUGAUCGACA CAUUCGACAG GAGGCUCACA ACAGGCAAGC UU                 92

(2) INFORMATION FOR SEQ ID NO:406:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:406:

GGGAGACAAG AAUAAACGCU CAAACCGAUC GAUAUGACUC GACAUGUCGA          50

UGCACAAAGU AACUUCGACA GGAGGCUCAC AACAGGCAAG CUU                93

(2) INFORMATION FOR SEQ ID NO:407:

(i) SEQUENCE CHARACTERISTICS:
        (A) LENGTH: 93
        (B) TYPE: nucleic acid
        (C) STRANDEDNESS: single
        (D) TOPOLOGY:linear -continued

```
    (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:407:

GGGAGACAAG AAUAAACGCU CAAACCUUAU ACCAUCCUGU CUCAACCAUA         50

CUCUGAUACA CAAUUCGACA GGAGGCUCAC AACAGGCAAG CUU                93

(2) INFORMATION FOR SEQ ID NO:408:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:408:

GGGAGACAAG AAUAAACGCU CAAAGAUGAA UAAUGACCCA CAACUGACCC         50

AGCGAUACUA UAAUUCGACA GGAGGCUCAC AACAGGCAAG CUU                93

(2) INFORMATION FOR SEQ ID NO:409:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:409:

GGGAGACAAG AAUAAACGCU CAAAGCUGCC AGACACAAUC CGGUGGCAGU         50

CCGAUAAAUA CACUUCGACA GGAGGCUCAC AACAGGCAAG CUU                93

(2) INFORMATION FOR SEQ ID NO:410:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:410:

GGGAGACAAG AAUAAACGCU CAAAGGCCCA AGAUGUACAC ACGGUCACGU         50

CCUACAUACU ACAUUCGACA GGAGGCUCAC AACAGGCAAG CUU                93
```

(2) INFORMATION FOR SEQ ID NO:411:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:411:

GGGAGACAAG AAUAAACGCU CAAAGUCCAC GCUGCGUGUG CUCCAGCAUA          50

CGACUCUUAA GCUUCGACA GGAGGCUCAC AACAGGCAAG CUU                  93

(2) INFORMATION FOR SEQ ID NO:412:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:412:

GGGAGACAAG AAUAAACGCU CAAAGUGUGA ACUCCUAAAC CCCUCCGGAC          50

AGAUAACACG GACUUCGACA GGAGGCUCAC AACAGGCAAG CUU                 93

(2) INFORMATION FOR SEQ ID NO:413:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:413:

GGGAGACAAG AAUAAACGCU CAAAUCUCGA CCUCGGUCGG CCCUUCCCGA          50

AGCCGUGUAU AUCUUCGACA GGAGGCUCAC AACAGGCAAG CUU                 93

(2) INFORMATION FOR SEQ ID NO:414:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil -continued (xi) SEQUENCE DESCRIPTION: SEQ ID NO:414:

GGGAGACAAG AAUAAACGCU CAAAUGAAGC UGAUGCACCA UUAUCAACAC          50

CACCCUACGU UACUUCGACA GGAGGCUCAC AACAGGCAAG CUU                93

(2) INFORMATION FOR SEQ ID NO:415:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:415:

GGGAGACAAG AAUAAACGCU CAAAUUAUGG AUAUACGAGA CCCACCCUCC          50

UCUCUAGCGU ACAUUCGACA GGAGGCUCAC AACAGGCAAG CUU                93

(2) INFORMATION FOR SEQ ID NO:416:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:416:

GGGAGACAAG AAUAAACGCU CAACAACUAA UACCGCUAAA AGACUGCAGC          50

CUCAGUACAC AAAUUCGACA GGAGGCUCAC AACAGGCAAG CUU                93

(2) INFORMATION FOR SEQ ID NO:417:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:417:

GGGAGACAAG AAUAAACGCU CAACAACAUA CUCAACUACC ACGAAGCAAA          50

CUGCGUAAAC CACUUCGACA GGAGGCUCAC AACAGGCAAG CUU                93

(2) INFORMATION FOR SEQ ID NO:418:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:418:

GGGAGACAAG AAUAAACGCU CAACACACCC UAAAUCACCA UCCACUGGCC            50

GUCACCAAUA ACUUCGACAG GAGGCUCACA ACAGGCAAGC UU                   92

(2) INFORMATION FOR SEQ ID NO:419:

(i) SEQUENCE CHARACTERISTICS:
        (A) LENGTH: 92
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:419:

GGGAGACAAG AAUAAACGCU CAACCCCAAU GUACGAGCCA GUACCAAGCC            50

ACCACGAUAU GUUUCGACAG GAGGCUCAAA ACAGGCAAGC UU                   92

(2) INFORMATION FOR SEQ ID NO:420:

(i) SEQUENCE CHARACTERISTICS:
        (A) LENGTH: 93
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:420:

GGGAGACAAG AAUAAACGCU CAACCCCGUA UCUCUUCGAC AGCCCCCUCU            50

UCCUCCAACC ACAUUCGACA GGAGGCUCAC AACAGGCAAG CUU                  93

(2) INFORMATION FOR SEQ ID NO:421:

(i) SEQUENCE CHARACTERISTICS:
        (A) LENGTH: 93
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:421:

GGGAGACAAG AAUAAACGCU CAACUCAACU GGAAACCACG GGAUGACAAC            50

CGUCCAUUGC AAUUUCGACA GGAGGCUCAC AACAGGCAAG CUU                  93

(2) INFORMATION FOR SEQ ID NO:422:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:422:

```
GGGAGACAAG AAUAAACGCU CAAGACCUAU UUCAACCUGU GCCUGAUCAC          50

CUAAAGUUUG CCUUUCGACA GGAGGCUCAC AACAGGCAAG CUU                 93
```

(2) INFORMATION FOR SEQ ID NO:423:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:423:

```
GGGAGACAAG AAUAAACGCU CAAGAGACUC AUUAAGCGCC CGCCGUUGAA          50

CGUCACCCCU AUCUUCGACA GGAGGCUCAC AACAGGCAAG CUU                 93
```

(2) INFORMATION FOR SEQ ID NO:424:

(i) SEQUENCE CHARACTERISTICS:
        (A) LENGTH: 94
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:424:

```
GGGAGACAAG AAUAAACGCU CAAGCACCCC AGCAAAAAUC CGAUCCAAAC          50

CACACUCCCA AAACUUCGAC AGGAGGCUCA CAACAGGCAA GCUU                94
```

(2) INFORMATION FOR SEQ ID NO:425:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:425:

GGGAGACAAG AAUAAACGCU CAAGGAUCUU ACUCAGCCCC UGUUUCAACA                50

AUCCAUGCUC CAGUUCGACA GGAGGCUCAC AACAGGCAAG CUU                       93

(2) INFORMATION FOR SEQ ID NO:426:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:426:

NGGAGACACG AGUANACGCU CAAGGNUNUG CACACAUAGC CAACCNGACC                50

NUUGNUUAAU UCAUUCGACA GGAGGCUCAC AACAGGCAAG CUU                       93

(2) INFORMATION FOR SEQ ID NO:427:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:427:

GGGAGACAAG AAUAAACGCU CAAGGGAUCA AAAUCCAAAC GCGUUAACCG                50

UUAAUACACU UAUUUCGACA GGAGGCUCAC AACAGGCAAG CUU                       93

(2) INFORMATION FOR SEQ ID NO:428:

(i) SEQUENCE CHARACTERISTICS:
        (A) LENGTH: 92
        (B) TYPE: nucleic acid
        (C) STRANDEDNESS: single
        (D) TOPOLOGY:linear (ix) FEATURE:

(ix) FEATURE:
        (D) OTHER INFORMATION:  All C's are 2'-F cytosine (ix) FEATURE:
        (D) OTHER INFORMATION:  All U's are 2'-F uracil (xi) SEQUENCE DESCRIPTION: SEQ ID NO:428:

GGGAGACAAG AAUAAACGCU CAAGUCCUGA CUACUAACAU UGCCCGUGAC                50

CCAUUGCCUU ACUUCGACAG GAGGCUCACA ACAGGCAAGC UU                        92

(2) INFORMATION FOR SEQ ID NO:429:

(i) SEQUENCE CHARACTERISTICS:
        (A) LENGTH: 93
        (B) TYPE: nucleic acid
        (C) STRANDEDNESS: single
        (D) TOPOLOGY:linear

```
        (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:429:

GGGAGACAAG AAUAAACGCU CAAUAACACA AUGUAAGUCC UUCGAUCACA            50

CCUAAUUAGA UCAUUCGACA GGAGGCUCAC AACAGGCAAG CUU                   93

(2) INFORMATION FOR SEQ ID NO:430:

(i) SEQUENCE CHARACTERISTICS:
              (A) LENGTH: 93
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:430:

GGGAGACAAG AAUAAACGCU CAAUACCCCA CACUCCUGAU CACCCCCAUU            50

ACUUUCUAUA UACUUCGACA GGAGGCUCAC AACAGGCAAG CUU                   93

(2) INFORMATION FOR SEQ ID NO:431:

(i) SEQUENCE CHARACTERISTICS:
              (A) LENGTH: 93
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:431:

GGGAGACAAG AAUAAACGCU CAAUAGGGAC UAACGCUGUG UGCUACAGGC            50

CCCCCAAACA UCAUUCGACA GGAGGCUCAC AACAGGCAAG CUU                   93

(2) INFORMATION FOR SEQ ID NO:432:

(i) SEQUENCE CHARACTERISTICS:
              (A) LENGTH: 93
              (B) TYPE: nucleic acid
              (C) STRANDEDNESS: single
              (D) TOPOLOGY:linear (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:432:

GGGAGACAAG AAUAAACGCU CAAUCAAACA GCCUGGAUAC CUCUCUCCCU            50

AUCCCCUCAC UUAUUCGACA GGAGGCUCAC AACAGGCAAG CUU                   93
```

(2) INFORMATION FOR SEQ ID NO:433:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:433:

GGGAGACAAG AAUAAACGCU CAAUCGAUAC UAGAUCCUAU UGCAGACGUA         50

ACGUUGCUUU AAGUUCGACA GGAGGCUCAC AACAGGCAAG CUU               93

(2) INFORMATION FOR SEQ ID NO:434:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:434:

GGGAGACAAG AAUAAACGCU CAAUCGGCCA GCAUCAAGGA CAUCACUUAC         50

ACCUAGUACC UACUUCGACA GGAGGCUCAC AACAGGCAAG CUU               93

(2) INFORMATION FOR SEQ ID NO:435:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:435:

GGGAGACAAG AAUAAACGCU CAAUCUACCA CACGCUUCCC GAACGACCUC         50

CCAAUUAACU CGAUUCGACA GGAGGCUCAC AACAGGCAAG CUU               93

(2) INFORMATION FOR SEQ ID NO:436:

(i) SEQUENCE CHARACTERISTICS:
        (A) LENGTH: 91
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:436:

GGGAGACAAG AAUAAACGCU CAAUCUCACA GUUGAAGUAA UCACCAUCGC          50

CAUACAAACU AUUCGACAGG AGGCUCACAA CAGGCAAGCU U                  91

(2) INFORMATION FOR SEQ ID NO:437:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:437:

GGGAGACAAG AAUAAACGCU CAAUGAUAGA AGCCAAAAGC GCCGUUUGCG          50

ACGAUCACCU UAUUUCGACA GGAGGCUCAC AACAGGCAAG CUU                93

(2) INFORMATION FOR SEQ ID NO:438:

(i) SEQUENCE CHARACTERISTICS:
        (A) LENGTH: 94
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:438:

GGGAGACAAG AAUAAACGCU CAAUGAUGUG CCGCGGCCCA ACCACAAUAA          50

UCGCACUCUU ACAUUCGACA GGAGGCUUCA CAACAGGCAA GCUU               94

(2) INFORMATION FOR SEQ ID NO:439:

(i) SEQUENCE CHARACTERISTICS:
        (A) LENGTH: 93
        (B) TYPE: nucleic acid
        (C) STRANDEDNESS: single
        (D) TOPOLOGY:linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:439:

GGGAGACAAG AAUAAACGCU CAAUUAGCAA CCAAGCAUCC GUUAAUAAGC          50

GGAAAAGACA CGAUUCGACA GGAGGCUCAC AACAGGCAAG CUU                93

(2) INFORMATION FOR SEQ ID NO:440:

(i) SEQUENCE CHARACTERISTICS:
        (A) LENGTH: 93
        (B) TYPE: nucleic acid
        (C) STRANDEDNESS: single
        (D) TOPOLOGY:linear -continued

```
    (ix) FEATURE:
         (D) OTHER INFORMATION:  All C's are 2'-F cytosine (ix) FEATURE:
         (D) OTHER INFORMATION:  All U's are 2'-F uracil (xi) SEQUENCE DESCRIPTION: SEQ ID NO:440:

GGGAGACAAG AAUAAACGCU CAANGNUAAC GCUUUACCUC UCCCAANCNU          50

CAAACAGGAA UUAUUCGACA GGAGGCUCAC AACAGGCAAG CUU                93
```

What is claimed is:

1. A method for identifying a nucleic acid ligand to a blood vessel comprising:
   a) preparing a candidate mixture of nucleic acid sequences;
   b) contacting said candidate mixture of nucleic acids with said blood vessel, wherein nucleic acids having an increased affinity to the blood vessel relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acid sequences with relatively higher affinity and specificity for binding to said blood vessel, whereby a nucleic acid ligand of said blood vessel may be identified.

2. The method of claim 1 further comprising:
   e) repeating steps b), c) and d).

3. The method of claim 1 wherein said candidate mixture is comprised of single-stranded nucleic acids.

4. The method of claim 3 wherein said single-stranded nucleic acids are ribonucleic acids.

5. The method of claim 3 wherein said single-stranded nucleic acids are deoxyribonucleic acids.

6. The method of claim 1 wherein said blood vessel is selected from the group consisting of arteries, veins and capillaries.

7. A nucleic acid ligand to a blood vessel identified according to the method of claim 1.

8. The nucleic acid ligand of claim 7 wherein said candidate mixture is comprised of single-stranded nucleic acids.

9. The nucleic acid ligand of claim 7 wherein said single-stranded nucleic acids are deoxyribonucleic acids.

10. The nucleic acid ligand of claim 7 wherein said single-stranded nucleic acids are ribonucleic acids.

11. The nucleic acid ligand of claim 7 wherein said ligand is a RNA ligand selected from the group consisting of the nucleotide sequences set forth in Table 10 (SEQ ID NOS: 242–258).

12. The nucleic acid ligand of claim 7 wherein said blood vessel is selected from the group consisting of arteries, veins and capillaries.

13. The nucleic acid ligand of claim 12 wherein said blood vessel is an artery.

14. The nucleic acid ligand of claim 13 wherein said ligand is a RNA ligand to an atherosclerotic lesion or plaque in said artery selected from the group consisting of the nucleotide sequences SEQ ID NOS: 260–440.

15. The nucleic acid ligand of claim 7 wherein said ligand further comprises a label.

16. The nucleic acid ligand of claim 7 wherein said ligand comprises a complexing agent.

17. The nucleic acid ligand of claim 16 wherein said complexing agent comprises a label.

18. The nucleic acid ligand of claim 17 wherein label is 99'm-Tc.

19. The nucleic acid ligand of claim 18 having the structure:

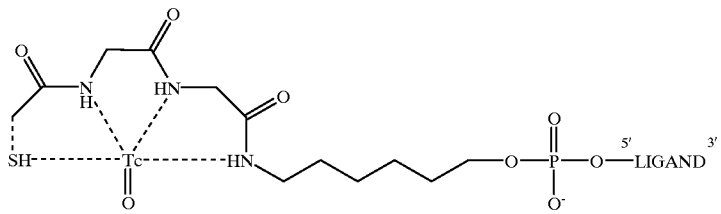

Wherein the ligand has the nucleotide sequence 5'-gggagacaagaauaaacgcucaaUCAAUCUCGGACUAGAC-UAACGACCUUGGUUGACGCUCAuucgacaggaggcucac-aacagga-3' (SEQ ID NO:354) (SEQ ID NO:355).

20. A purified and isolated non-naturally occurring nucleic acid ligand to a blood vessel.

21. The purified and isolated non-naturally occurring nucleic acid ligand of claim 20 wherein said blood vessel is selected from the group consisting of arteries, veins and capillaries.

* * * * *